(12) United States Patent
Foley

(10) Patent No.: US 8,063,083 B2
(45) Date of Patent: Nov. 22, 2011

(54) METHOD FOR TREATING NON-HODGKIN'S LYMPHOMA

(75) Inventor: Kevin Foley, Waltham, MA (US)

(73) Assignee: Synta Pharmaceuticals Corp., Lexington, MA (US)

(*) Notice: Subject to any disclaimer, the term of this patent is extended or adjusted under 35 U.S.C. 154(b) by 326 days.

(21) Appl. No.: 11/807,199

(22) Filed: May 25, 2007

(65) Prior Publication Data

US 2008/0004276 A1 Jan. 3, 2008

Related U.S. Application Data

(60) Provisional application No. 60/808,341, filed on May 25, 2006.

(51) Int. Cl.
*A61K 31/4196* (2006.01)
*A61P 35/00* (2006.01)

(52) U.S. Cl. .......................................................... 514/383
(58) Field of Classification Search .................... 514/383
See application file for complete search history.

(56) References Cited

U.S. PATENT DOCUMENTS

| | | | | |
|---|---|---|---|---|
| 6,080,772 A * | 6/2000 | Tang et al. | ...... | 514/370 |
| 6,858,598 B1 * | 2/2005 | McKearn et al. | ...... | 514/183 |
| 7,247,734 B2 * | 7/2007 | Drysdale et al. | ...... | 548/364.1 |
| 7,825,148 B2 * | 11/2010 | Ying et al. | ...... | 514/383 |
| 2005/0267185 A1 * | 12/2005 | Marino et al. | ...... | 514/383 |
| 2006/0167070 A1 * | 7/2006 | Ying et al. | ...... | 514/383 |
| 2007/0066831 A1 * | 3/2007 | MacDonald et al. | ...... | 548/262.2 |
| 2007/0155809 A1 * | 7/2007 | Ying et al. | ...... | 514/383 |
| 2011/0009397 A1 | 1/2011 | Ying | | |
| 2011/0105749 A1 | 5/2011 | Ying | | |

FOREIGN PATENT DOCUMENTS

| | | | |
|---|---|---|---|
| WO | WO 2005/000300 A1 * | 1/2005 | |
| WO | WO 2006/047631 | * | 5/2006 |
| WO | WO 2006/055760 A1 | 5/2006 | |
| WO | WO 2007/139951 A2 | 12/2007 | |
| WO | WO 2007/139960 A2 | 12/2007 | |
| WO | WO 2008/021364 | 2/2008 | |

OTHER PUBLICATIONS

Mitisades et al. HSP90 molecular chaperone a novel therapeutic target for B-cell lymphomas and multiple myeloma. Annals of Oncology. 2002; 13 (Suppl 2): 168, abstract # 601.*

Lee et al. Late relapse in patients with diffuse large-cell lymphoma treated with MACOP-B. J Clin Oncol. 1997;15(5):1745-1753; abstract only.*

Dias, S. et al., "VEGF$_{165}$ Promotes Survival of Leukemic Cells by Hsp90-Mediated Induction of Bcl-2 Expression and Apoptosis Inhibition," *Blood*, 99(7):2532-2540 (2002).

Valbuena, J.R. et al., "Expression of Heat-Shock Protein-90 in Non-Hodgkin's Lymphomas," *Modern Pathology*, 18:1343-1349 (2005).

Rostom, S.A.F., et al., "Polysubstituted Pyrazoles, Part 5.[1] Synthesis of New 1-(4-chlorophenyl)-4-hydroxy-1*H*-pyrazole-3-carboxylic acid hydrazide analogs and some derived ring systems. A Novel Class of Potential Antitumor and Anti-HCV Agents,"*European Journal of Medicinal Chemistry*, vol. 38, pp. 959-974 (2003).

* cited by examiner

*Primary Examiner* — Sharmila G. Landau
*Assistant Examiner* — Kortney L Klinkel
(74) *Attorney, Agent, or Firm* — McCarter & English LLP; Steven G. Davis

(57) ABSTRACT

The present invention relates to methods of inhibiting the activity of Hsp90 in a subject in need thereof and methods for treating non-Hodgkin's lymphoma, in a subject in need thereof.

11 Claims, 6 Drawing Sheets

METHOD FOR TREATING NON-HODGKIN'S LYMPHOMA

RELATED APPLICATIONS

This application claims the benefit of U.S. Provisional Application No. 60/808,341, filed on May 25, 2006. The entire teachings of the above applications are incorporated herein by reference.

FIELD OF THE INVENTION

The invention relates to a method of inhibiting the activity of Hsp90 in a subject in need thereof and methods for treating non-Hodgkin's lymphoma.

BACKGROUND OF THE INVENTION

Although tremendous advances have been made in elucidating the genomic abnormalities that cause malignant cancer cells, currently available chemotherapy remains unsatisfactory, and the prognosis for the majority of patients diagnosed with cancer remains dismal. Most chemotherapeutic agents act on a specific molecular target thought to be involved in the development of the malignant phenotype. However, a complex network of signaling pathways regulate cell proliferation, and the majority of malignant cancers are facilitated by multiple genetic abnormalities in these pathway. Therefore, it is unlikely that a therapeutic agent that acts on one molecular target will be fully effective in curing a patient who has cancer.

Heat shock proteins (HSPs) are a class of chaperone proteins that are up-regulated in response to elevated temperature and other environmental stresses, such as ultraviolet light, nutrient deprivation, and oxygen deprivation. HSPs act as chaperones to other cellular proteins (called client proteins) and facilitate their proper folding and repair, and aid in the refolding of misfolded client proteins. There are several known families of HSPs, each having its own set of client proteins. The Hsp90 family is one of the most abundant HSP families, accounting for about 1-2% of proteins in a cell that is not under stress and increasing to about 4-6% in a cell under stress. Inhibition of Hsp90 results in degradation of its client proteins via the ubiquitin proteasome pathway. Unlike other chaperone proteins, the client proteins of Hsp90 are mostly protein kinases or transcription factors involved in signal transduction, and a number of its client proteins have been shown to be involved in the progression of cancer. Examples of Hsp90 client proteins that have been implicated in the progression of cancer are described below.

Her-2 is a transmembrane tyrosine kinase cell surface growth factor receptor that is expressed in normal epithelial cells. Her2 has an extracellular domain that interacts with extracellular growth factors and an internal tyrosine kinase portion that transmits the external growth signal to the nucleus of the cell. Her2 is overexpressed in a significant proportion of malignancies, such as breast cancer, ovarian cancer, prostate cancer, and gastric cancers, and is typically associated with a poor prognosis.

c-Kit is a membrane receptor protein tyrosine kinase which binds Stem Cell Factor (SCF) to its extraellular domain. c-Kit is involved in the development of melanocytes, mast, germ and hematopoietic cells, and there is evidence that it plays a role in several types of cancer including leukemias, mast cell tumors, small cell lung cancer, testicular cancer, cancers of the gastointesinal tract and cancers of the central nervous system.

c-Met is a receptor tyrosine kinase that is encoded by the Met protooncogene and transduces the biological effects of hepatocyte growth factor (HGF), which is also referred to as scatter factor (SF). Jiang et al., *Crit. Rev. Oncol. Hemtol.* 29: 209-248 (1999), the entire teachings of which are incorporated herein by reference. c-Met and HGF are expressed in numerous tissues, although their expression is normally confined predominantly to cells of epithelial and mesenchymal origin, respectively. c-Met and HGF are required for normal mammalian development and have been shown to be important in cell migration, cell proliferation and survival, morphogenic differentiation, and organization of 3-dimensional tubular structures (e.g., renal tubular cells, gland formation, etc.). The c-Met receptor has been shown to be expressed in a number of human cancers. c-Met and its ligand, HGF, have also been shown to be co-expressed at elevated levels in a variety of human cancers (particularly sarcomas). However, because the receptor and ligand are usually expressed by different cell types, c-Met signaling is most commonly regulated by tumor-stroma (tumor-host) interactions. Furthermore, c-Met gene amplification, mutation, and rearrangement have been observed in a subset of human cancers. Families with germine mutations that activate c-Met kinase are prone to multiple kidney tumors as well as tumors in other tissues. Numerous studies have correlated the expression of c-Met and/or HGF/SF with the state of disease progression of different types of cancer (including lung, colon, breast, prostate, liver, pancreas, brain, kidney, ovaries, stomach, skin, and bone cancers). Furthermore, the overexpression of c-Met or HGF have been shown to correlate with poor prognosis and disease outcome in a number of major human cancers including lung, liver, gastric, and breast.

Akt kinase is a serine/threonine kinase which is a downstream effector molecule of phosphoinositide 3-kinase and is involved in protecting the cell from apoptosis. Akt kinase is thought to be involved in the progression of cancer because it stimulates cell proliferation and suppresses apoptosis.

Cdk4/cyclin D complexes are involved in phosphorylation of retinoblastoma protein which is an essential step in progression of a cell through the G1 phase of the cell cycle. Disruption of Hsp90 activity has been shown to decrease the half life of newly synthesized Cdk4.

Raf-1 is a MAP 3-kinase (MAP3K) which when activated can phosphorylate and activate the serine/threonine specific protein kinases ERK1 and ERK2. Activated ERKs play an important role in the control of gene expression involved in the cell division cycle, apoptosis, cell differentiation and cell migration.

The transforming protein of Rous sarcoma virus, v-src, is a prototype of an oncogene family that induces cellular transformation (i.e., tumorogenesis) by non-regulated kinase activity. Hsp90 has been shown to complex with v-scr and inhibit its degradation.

The BCR-ABL fusion protein associated with chronic myelogenous leukemia and in a subset of patients with acute lymphoblastic leukemia. The fusion protein is a consequence of exchange of genetic material from the long arms of chromosomes 9 and 22 and results in unregulated tyrosine kinase activity. BCR-ABL exists as a complex with Hsp90 and is rapidly degraded when the action of Hsp90 is inhibited.

Hsp90 is required to maintain steroid hormone receptors in a conformation capable of binding hormone with high affinity. Inhibition of the action of Hsp90 therefore is expected to be useful in treating hormone-associated malignancies such as breast cancer.

p53 is a tumor suppressor protein that causes cell cycle arrest and apoptosis. Mutation of the p53 gene is found in about half of all human cancers making it one of the most common genetic alterations found in cancerous cells. In addition, p53 mutation is associated with a poor prognosis. Wild-type p53 has been shown to interact with Hsp90, but mutated p53 forms a more stable association than wild-type p53 as a result of its misfolded conformations. A stronger interaction with Hsp90 protects the mutated protein from normal proteolytic degradation and prolongs its half-life. In a cell that is heterozygous for mutated and wild-type p53, inhibition of the stabilizing effect of Hsp90 causes mutant p53 to be degraded and restores the normal transcriptional activity of wild-type p53.

Hif-1α (is a hypoxia-inducible transcription factor that is up-regulated under low oxygen conditions. Under normal oxygen conditions Hif-1α associates with Von Hippel-Lindau (VHL) tumor suppressor protein and is degraded. Low oxygen conditions inhibits this association and allows Hif-1α to accumulate and complex with Hif-1β to form an active transcription complex that associates with hypoxia-response elements to activate the transcription of vascular endothelial growth factor (VEGF). Increased Hif-1α is associated with increased metastasis and a poor prognosis.

Hsp90 has been shown by mutational analysis to be necessary for the survival of normal eukaryotic cells. However, Hsp90 is over expressed in many tumor types indicating that it may play a significant role in the survival of cancer cells and that cancer cells may be more sensitive to inhibition of Hsp90 than normal cells. In particular, Hsp90 has been shown to be overexpressed in a number of B-cell and T-cell Non-Hodgkin's Lymphomas (NHL). For example, in a survey of 412 cases of NHL in B-cell NHL, Hsp90 was found to be moderately to strongly over expressed in all cases of Burkitt's lymphoma (5/5, 100%), and in a subset of follicular lymphoma (17/28, 61%), diffuse large B-cell lymphoma (27/46, 59%), nodal marginal zone B-cell lymphoma (6/16, 38%), plasma cell neoplasms (14/39, 36%), small lymphocytic lymphoma/chronic lymphocytic leukemia (3/9, 33%), mantle cell lymphoma (12/38, 32%), and lymphoplamacytic lymphoma/Waldenstrom macroglobulinemia (3/10, 30%). In addition, in T-cell NHL, Hsp90 was found to be moderately to strongly over expressed in a subset of anaplastic large-cell lymphoma (14/24, 58%), precursor-T-cell lymphoblastic leukemia/lymphoma (20/65, 31%), unspecified peripheral T-cell lymphoma (8/43, 23%), and angioimmunoblastic T-cell lymphoma (2/17, 12%). (See Valbuena, et al., *Modern Pathology* (2005), 18:1343-1349, the entire teachings of which are incorporated herein by reference.)

Cancer cells typically have a large number of mutated and overexpressed oncoproteins that are dependent on Hsp90 for folding. In addition, because the environment of a tumor is typically hostile due to hypoxia, nutrient deprivation, acidosis, etc., tumor cells may be especially dependent on Hsp90 for survival. Since inhibition of Hsp90 causes simultaneous inhibition of a number of oncoproteins, as well as hormone receptors and transcription factors, it is an attractive target for an anti-cancer agent. In fact, benzoquinone ansamycins, a family of natural products that inhibit Hsp90, has shown evidence of therapeutic activity in clinical trials.

Although promising, benzoquinone ansamycins, and their derivatives, suffer from a number of limitations. For example, they have low oral bioavailability, and their limited solubility makes them difficult to formula. In addition, they are metabolized by polymorphic cytochrome P450 CYP3A4 and are a substrate for P-glycoprotein export pump involved in the development of multidrug resistance. Therefore, a need exist for new therapeutics that improve the prognosis of cancer patients and that reduces or overcomes the limitations of currently used anti-cancer agents.

SUMMARY OF THE INVENTION

The present invention provides novel compounds which inhibit the activity of Hsp90 and are useful in the treatment of proliferative disorders, such as cancer. In particular, the compounds of the invention are useful for treating cancers in which Hsp90 is up-regulated, such as non-Hodgkin's lymphoma. The present invention also provides new uses for previously disclosed compounds.

In one embodiment, the present invention provides compounds having the formula (I):

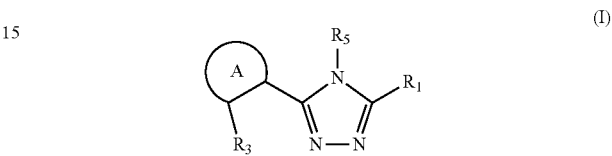

(I)

and tautomers, pharmaceutically acceptable salts, solvates, clathrates, and prodrugs thereof. In formula (I), ring A is an aryl or a heteroaryl, wherein the aryl or the heteroaryl are optionally further substituted with one or more substituents in addition to $R_3$;

$R_1$ is —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —OC(O)$NR_{10}R_{11}$, —SC(O)$NR_{10}R_{11}$, —$NR_7C(O)NR_{10}R_{11}$, —OC(O)$R_7$, —SC(O)$R_7$, —$NR_7C(O)R_7$, —OC(O)$OR_7$, —SC(O)$OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R^{11}$, —$SCH_2C(O)NR_{10}R_{11}$, —$NR_7CH_2C(O)NR_{10}R_{11}$, —$OS(O)_pR_7$, —$SS(O)_pR_7$, —$S(O)_pOR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —OC(S)$R_7$, —SC(S)$R_7$, —$NR_7C(S)R_7$, —OC(S)$OR_7$, —SC(S)$OR_7$, —$NR_7C(S)OR_7$, —OC(S)$NR_{10}R_{11}$, —SC(S)$NR_{10}R_{11}$, —$NR_7C(S)NR_{10}R_{11}$, —OC($NR_8$)$R_7$, —SC($NR_8$)$R_7$, —$NR_7C(NR_8)R_7$, —OC($NR_8$)$OR_7$, —SC($NR_8$)$OR_7$, —$NR_7C(NR_8)OR_7$, —OC($NR_8$)$NR_{10}R_{11}$, —SC($NR_8$)$NR_{10}R_{11}$, —$NR_7C(NR_8)NR_{10}R_{11}$, —OP(O)$(OR7)_2$, or —SP(O)$(OR_7)_2$;

$R_3$ is —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —OC(O)$NR_{10}R_{11}$, —SC(O)$NR_{10}R_{11}$, —$NR_7C(O)NR_{10}R_{11}$, —OC(O)$R_7$, —SC(O)$R_7$, —$NR_7C(O)R_7$, —OC(O)$OR_7$, —SC(O)$OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$S(O)_pOR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —OC(S)$R_7$, —SC(S)$R_7$, —$NR_7C(S)R_7$, —OC(S)$OR_7$, —SC(S)$OR_7$, —$NR_7C(S)OR_7$, —OC(S)$NR_{10}R_{11}$, —SC(S)$NR_{10}R_{11}$, —$NR_7C(S)NR_{10}R_{11}$, —OC($NR_8$)$R_7$, —SC($NR_8$)$R_7$, —$NR_7C(NR_8)R_7$, —OC($NR_8$)$OR_7$, —SC($NR_8$)$OR_7$, —$NR_7C(NR_8)OR_7$, —OC($NR_8$)$NR_{10}R_{11}$, —SC($NR_8$)$NR_{10}R_{11}$, —$NR_7C(NR_8)NR_{10}R_{11}$, —C(O)OH, —C(O)$NHR_8$, —C(O)SH, —S(O)OH, —S(O)$_2$OH, —S(O)$NHR_8$, —S(O)$_2NHR_8$, —OP(O)$(OR_7)_2$, or —SP(O)$(OR_7)_2$;

$R_5$ is an optionally substituted heteroaryl or an optionally substituted 8 to 14 membered aryl;

$R_7$ and $R_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{10}$ and $R_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{26}$ is a lower alkyl;

p, for each occurrence, is, independently, 0, 1 or 2; and m, for each occurrence, is independently, 1, 2, 3, or 4.

In one embodiment, ring A of the compounds of formula (I) is not a substituted [1,2,3]triazole, and/or compounds represented by formula (I) do not include 3-(2,4-dihydroxy-phenyl)-4-(7-naphthalen-1-yl)-5-mercapto-triazole.

The present invention also provides compounds having the formula (II):

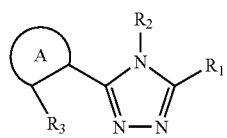

(II)

and tautomers, pharmaceutically acceptable salts, solvates, clathrates, and prodrugs thereof. In formula (II), ring A, $R_1$, and $R_3$ are defined as for formula (I); and $R_2$ is a substituted phenyl, wherein the phenyl group is substituted with:
  i) one substituent selected from nitro, cyano, a haloalkoxy, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxylalkyl, alkoxyalkyl, guanadino, —NR$_{10}$R$_{11}$, —O—R$_{20}$, —C(O)R$_7$, —C(O)OR$_{20}$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$, or
  ii) two to five substituents selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, —F, —Br, —I, cyano, nitro, guanadino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$; and $R_{20}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl.

In one embodiment, compounds represented by formula (II) do not include 3-(2,4-dihydroxy-phenyl)-4-(7-naphthalen-1-yl)-5-mercapto-triazole, 3-(2,4-dihydroxyphenyl)-4-(2,5-dimethoxyphenyl)-5-mercapto-triazole, 3-(1-phenyl-5-amino-pyrazol-4-yl)-4-(2,4-dichlorophenyl)-5-mercapto-triazole, or 3-(2-hydroxy-phenyl)-4-(2,4-dimethylphenyl)-5-mercapto-triazole.

The present invention also provides compounds having the formula (III):

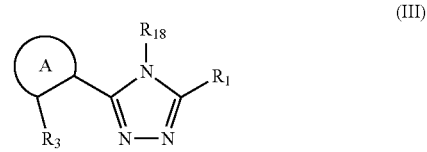

(III)

and tautomers, pharmaceutically acceptable salts, solvates, clathrates, and prodrugs thereof. In formula (III), ring A, $R_1$, and $R_3$ are defined as for formula (I); and $R_{18}$ is an optionally substituted cycloalkyl, and optionally substituted cycloalkenyl, or a substituted alkyl, wherein the alkyl group is substituted with one or more substituents independently selected from the group consisting of an optionally substituted alkynyl, an optionally substituted cycloalkyl, an optionally substituted cycloalkenyl, an optionally substituted heteroaryl, an optionally substituted aralkyl, an optionally substituted heteraralkyl, halo, cyano, nitro, guanadino, a haloalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$;

In one embodiment, compounds represented by formula (III) do not include compounds in which $R_{18}$ is not cyclohexyl.

The invention also provides compounds represented by formula (IV) or formula (V):

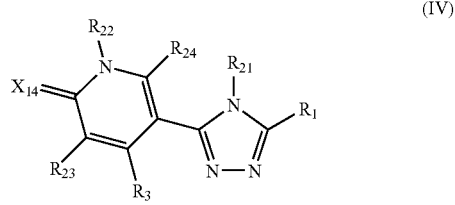

(IV)

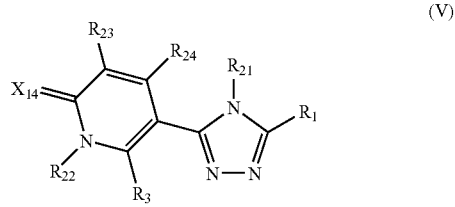

(V)

and tautomers, pharmaceutically acceptable salts, solvates, clathrates, and prodrugs thereof. In formulas (IV) and (V), $R_1$ and $R_3$ are defined as for formula (I); and $X_{14}$ is O, S, or $NR_7$;

$R_{21}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{22}$, for each occurrence, is independently a substituent selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, a haloalkyl, —C(O)$R_7$, —C(O)O$R_7$, —OC(O)$R_7$, —C(O)N$R_{10}R_{11}$, —N$R_8$C(O)$R_7$, —S(O)$_p R_7$, —S(O)$_p$O$R_7$, or —S(O)$_p$N$R_{10}R_{11}$; and $R_{23}$ and $R_{24}$, for each occurrence, are independently a substituent selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, halo, cyano, nitro, guanadino, a haloalkyl, a heteroalkyl, —N$R_{10}R_{11}$, —O$R_7$, —C(O)$R_7$, —C(O)O$R_7$, —OC(O)$R_7$, —C(O)N$R_{10}R_{11}$, —N$R_8$C(O)$R_7$, —S$R_7$, —S(O)$_p R_7$, —OS(O)$_p R_7$, —S(O)$_p$O$R_7$, —N$R_8$S(O)$_p R_7$, or —S(O)$_p$N$R_{10}R_{11}$.

In one embodiment, the present invention is an Hsp90 inhibitor represented by structural formula (VI):

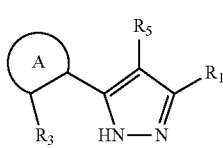

(VI)

or a tautomer, pharmaceutically acceptable salt, solvate, clathrate, or a prodrug thereof. In formula (VI):

ring A is an aryl or a heteroaryl, wherein the aryl or the heteroaryl are optionally further substituted with one or more substituents in addition to $R_3$;

$R_1$ is —OH, —SH, —N$R_7$H, —O$R_{26}$, —S$R_{26}$, —NH$R_{26}$, —O(CH$_2$)$_m$OH, —O(CH$_2$)$_m$SH, —O(CH$_2$)$_m$N$R_7$H, —S(CH$_2$)$_m$OH, —S(CH$_2$)$_m$SH, —S(CH$_2$)$_m$N$R_7$H, —OC(O)N$R_{10}R_{11}$, —SC(O)N$R_{10}R_{11}$, —N$R_7$C(O)N$R_{10}R_{11}$, —OC(O)$R_7$, —SC(O)$R_7$, —N$R_7$C(O)$R_7$, —OC(O)O$R_7$, —SC(O)O$R_7$, —N$R_7$C(O)O$R_7$, —OCH$_2$C(O)$R_7$, —SCH$_2$C(O)$R_7$, —N$R_7$CH$_2$C(O)$R_7$, —OCH$_2$C(O)O$R_7$, —SCH$_2$C(O)O$R_7$, —N$R_7$CH$_2$C(O)O$R_7$, —OCH$_2$C(O)N$R_{10}R_{11}$, —SCH$_2$C(O)N$R_{10}R_{11}$, —N$R_7$CH$_2$C(O)N$R_{10}R_{11}$, —OS(O)$_p R_7$, —SS(O)$_p R_7$, —S(O)$_p$O$R_7$, —N$R_7$S(O)$_p R_7$, —OS(O)$_p$N$R_{10}R_{11}$, —SS(O)$_p$N$R_{10}R_{11}$, —N$R_7$S(O)$_p$N$R_{10}R_{11}$, —OS(O)$_p$O$R_7$, —SS(O)$_p$O$R_7$, —N$R_7$S(O)$_p$O$R_7$, —OC(S)$R_7$, —SC(S)$R_7$, —N$R_7$C(S)$R_7$, —OC(S)O$R_7$, —SC(S)O$R_7$, —N$R_7$C(S)O$R_7$, —OC(S)N$R_{10}R_{11}$, —SC(S)N$R_{10}R_{11}$, —N$R_7$C(S)N$R_{10}R_{11}$, —OC(N$R_8$)$R_7$, —SC(N$R_8$)$R_7$, —N$R_7$C(N$R_8$)$R_7$, —OC(N$R_8$)O$R_7$, —SC(N$R_8$)O$R_7$, —N$R_7$C(N$R_8$)O$R_7$, —OC(N$R_8$)N$R_{10}R_{11}$, —SC(N$R_8$)N$R_{10}R_{11}$, —N$R_7$C(N$R_8$)N$R_{10}R_{11}$, —NR$_7$C(NR$_8$)NR$_{10}$R$_{11}$, —OP(O)(OR$_7$)$_2$, or —SP(O)(OR$_7$)$_2$;

$R_3$ is —OH, —SH, —N$R_7$H, —O$R_{26}$, —S$R_{26}$, —NH$R_{26}$, —O(CH$_2$)$_m$OH, —O(CH$_2$)$_m$SH, —O(CH$_2$)$_m$N$R_7$H, —S(CH$_2$)$_m$OH, —S(CH$_2$)$_m$SH, —S(CH$_2$)$_m$N$R_7$H, —OC(O)N$R_{10}R_{11}$, —SC(O)N$R_{10}R_{11}$, —N$R_7$C(O)N$R_{10}R_{11}$, —OC(O)$R_7$, —SC(O)$R_7$, —N$R_7$C(O)$R_7$, —OC(O)O$R_7$, —SC(O)O$R_7$, —N$R_7$C(O)O$R_7$, —OCH$_2$C(O)$R_7$, —SCH$_2$C(O)$R_7$, —N$R_7$CH$_2$C(O)$R_7$, —OCH$_2$C(O)O$R_7$, —SCH$_2$C(O)O$R_7$, —N$R_7$CH$_2$C(O)O$R_7$, —OCH$_2$C(O)N$R_{10}R_{11}$, —SCH$_2$C(O)N$R_{10}R_{11}$, —N$R_7$CH$_2$C(O)N$R_{10}$, $R_{11}$, —OS(O)$_p R_7$, —SS(O)$_p R_7$, —S(O)$_p$O$R_7$, —N$R_7$S(O)$_p R_7$, —OS(O)$_p$N$R_{10}R_{11}$, —SS(O)$_p$N$R_{10}R_{11}$, —N$R_7$S(O)$_p$N$R_{10}R_{11}$, —OS(O)$_p$O$R_7$, —SS(O)$_p$O$R_7$, —N$R_7$S(O)$_p$O$R_7$, —OC(S)$R_7$, —SC(S)$R_7$, —N$R_7$C(S)$R_7$, —OC(S)O$R_7$, —SC(S)O$R_7$, —N$R_7$C(S)O$R_7$, —OC(S)N$R_{10}R_{11}$, —SC(S)N$R_{10}R_{11}$, —N$R_7$C(S)N$R_{10}R_{11}$, —OC(N$R_8$)$R_7$, —SC(N$R_8$)$R_7$, —N$R_7$C(N$R_8$)$R_7$, —OC(N$R_8$)O$R_7$, —SC(N$R_8$)O$R_7$, —N$R_7$C(N$R_8$)O$R_7$, —OC(N$R_8$)N$R_{10}R_{11}$, —SC(N$R_8$)N$R_{10}R_{11}$, —N$R_7$C(N$R_8$)N$R_{10}R_{11}$, —C(O)OH, —C(O)NH$R_8$, —C(O)SH, —S(O)OH, —S(O)$_2$OH, —S(O)NH$R_8$, —S(O)$_2$NH$R_8$, —OP(O)(OR$_7$)$_2$, or —SP(O)(OR$_7$)$_2$;

$R_5$ is an optionally substituted heteroaryl or an optionally substituted 8 to 14-membered aryl;

$R_7$ and $R_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{10}$ and $R_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{26}$ is a lower alkyl;

p, for each occurrence, is, independently, 0, 1 or 2; and m, for each occurrence, is independently, 1, 2, 3, or 4.

In another embodiment of the present invention, the Hsp90 inhibitor is represented by structural formula (VII):

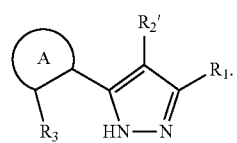

(VII)

In formula (VII), $R_2$' is an optionally substituted phenyl group. Preferably, $R_2$' is substituted with one or more group represented by $R_{30}$, wherein $R_{30}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —N$R_{10}R_{11}$, —O$R_7$, —C(O)$R_7$, —C(O)O$R_7$, —C(S)$R_7$, —C(O)S$R_7$, —C(S)S$R_7$, —C(S)O$R_7$, —C(S)N$R_{10}R_{11}$, —C(N$R_8$)O$R_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$. The remainder of the variables in structural formula (VII) have values defined above with reference to structural formula (VI).

In another embodiment of the present invention, the Hsp90 inhibitor is represented by structural formula (VIII):

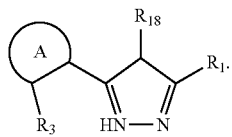

(VIII)

In formula (VIII), R$_{18}$ is an optionally substituted cycloalkyl, and optionally substituted cycloalkenyl, or a substituted alkyl, wherein the alkyl group is substituted with one or more substituents independently selected from the group consisting of an optionally substituted alkynyl, an optionally substituted cycloalkyl, an optionally substituted cycloalkenyl, an optionally substituted heteroaryl, an optionally substituted aralkyl, an optionally substituted heteraralkyl, halo, cyano, nitro, guanadino, a haloalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$. The remainder of the variables in structural formula (VIII) have values defined above with reference to structural formula (VI).

In one embodiment, the present invention is an Hsp90 inhibitor represented by structural formula (IX):

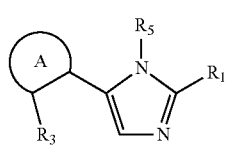

(IX)

or a tautomer, pharmaceutically acceptable salt, solvate, clathrate, or a prodrug thereof. In formula (IX):

ring A is an aryl or a heteroaryl, wherein the aryl or the heteroaryl are optionally further substituted with one or more substituents in addition to R$_3$;

R$_1$ is —OH, —SH, —NR$_7$H, —OR$_{26}$, —SR$_{26}$, —NHR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP(O)(OR$_7$)$_2$;

R$_3$ is —OH, —SH, —NR$_7$H, —OR$_{26}$, —SR$_{26}$, —NHR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)OH, —C(O)NHR$_8$, —C(O)SH, —S(O)OH, —S(O)$_2$OH, —S(O)NHR$_8$, —S(O)$_2$NHR$_8$, —OP(O)(OR$_7$)$_2$, or —SP(O)(OR$_7$)$_2$;

R$_5$ is an optionally substituted heteroaryl or an optionally substituted 8 to 14-membered aryl;

R$_7$ and R$_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$_{10}$ and R$_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{10}$ and R$_{11}$, taken together with the nitrogen to which they are attached, form an optionally substituted heterocyclyl or an optionally substituted heteroaryl;

R$_{26}$ is a lower alkyl;

p, for each occurrence, is, independently, 0, 1 or 2; and m, for each occurrence, is independently, 1, 2, 3, or 4.

In another embodiment of the present invention, the Hsp90 inhibitor is represented by structural formula (X):

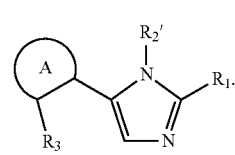

(X)

In formula (X), R$_2$' is an optionally substituted phenyl group. Preferably, R$_2$' is substituted with one or more group represented by R$_{30}$, wherein R$_{30}$, for each occurrence, are independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$. The remainder of the variables in structural formula (X) have values defined above with reference to structural formula (IX).

In another embodiment of the present invention, the Hsp90 inhibitor is represented by structural formula (XI):

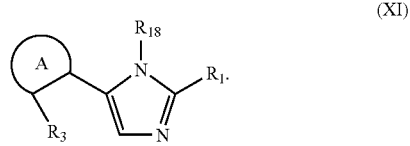

(XI)

In formula (XI), R$_{18}$ is an optionally substituted cycloalkyl, and optionally substituted cycloalkenyl, or a substituted alkyl, wherein the alkyl group is substituted with one or more substituents independently selected from the group consisting of an optionally substituted alkynyl, an optionally substituted cycloalkyl, an optionally substituted cycloalkenyl, an optionally substituted heteroaryl, an optionally substituted aralkyl, an optionally substituted heteraralkyl, halo, cyano, nitro, guanadino, a haloalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$. The remainder of the variables in structural formula (XI) have values defined above with reference to structural formula (IX).

In another embodiment, the present invention is a method of inhibiting Hsp90 in a mammal in need of such treatment. The method comprises administering to the mammal an effective amount of an Hsp90 inhibitor disclosed herein.

In another embodiment, the present invention is a method of inhibiting Hsp90 in a cell. The method comprises administering to the cell an effective amount of an Hsp90 inhibitor disclosed herein.

In another embodiment, the present invention is a method of treating a proliferative disorder in a mammal comprising administering an effective amount of an Hsp90 inhibitor disclosed herein.

In another embodiment, the present invention is a method of treating cancer in a mammal. The method comprises administering to the mammal an effective amount of an Hsp90 inhibitor disclosed herein.

In another embodiment, the present invention is directed to a method of treating a non-Hodgkin's lymphoma, comprising administering to the mammal an effective amount of an Hsp90 inhibitor disclosed herein. In one aspect, the non-Hodgkin's lymphoma is a B-cell non-Hodgkin's lymphoma. Examples of B-cell non-Hodgkin's lymphoma include Burkitt's lymphoma, follicular lymphoma, diffuse large B-cell lymphoma, nodal marginal zone B-cell lymphoma, plasma cell neoplasms, small lymphocytic lymphoma/chronic lymphocytic leukemia, mantle cell lymphoma, and lymphoplamacytic lymphoma/Waldenstrom macroglobulinemia. In another aspect, the non-Hodgkin's lymphoma is T-cell non-Hodgkin's lymphoma. Examples of T-cell non-Hodgkin's lymphoma include anaplastic large-cell lymphoma, precursor-T-cell lymphoblastic leukemia/lymphoma, unspecified peripheral T-cell lymphoma, and angioimmunoblastic T-cell lymphoma.

In another embodiment of the present invention is a pharmaceutical composition comprising an Hsp90 inhibitor disclosed herein and a pharmaceutically acceptable carrier. The pharmaceutical compositions can be used in therapy, e.g., to inhibit Hsp90 activity in a mammal in need of such inhibition, to treat a mammal with a proliferative disorder, or to treat a mammal with cancer, for example a non-Hodgkin's lymphoma.

In another embodiment of the present invention is the use of an Hsp90 inhibitor disclosed herein for the manufacture of a medicament for inhibiting Hsp90 in a mammal in need of such inhibition or for treating a mammal with cancer, such as a non-Hodgkin's lymphoma.

The compounds shown in Tables 5, 6, and 7, or compounds of any formula herein, or tautomers, pharmaceutically acceptable salts, solvates, clathrates, hydrates, polymorphs or prodrugs thereof, inhibit the activity of Hsp90 and, thereby cause the degradation of Hsp90 client proteins. Hsp90 is necessary for the survival of normal eukaryotic cells. However, Hsp90 is over expressed in many tumor types, such as non-Hodgkin's lymphoma, indicating that it may play a significant role in the survival of cancer cells and that cancer cells may be more sensitive to inhibition of Hsp90 than normal cells. Thus, the compounds shown in Table 5, 6, or 7, or compounds of any formula herein, or tautomers, pharmaceutically acceptable salts, solvates, clathrates, hydrates, polymorphs or prodrugs thereof, are useful treating proliferative disorders such as cancer.

Although chemotherapeutic agents initially cause tumor regression, most agents that are currently used to treat cancer target only one pathway to tumor progression. Therefore, in many instances, after treatment with one or more chemotherapeutic agents, a tumor develops multidrug resistance and no longer responses positively to treatment. One of the advantages of inhibiting Hsp90 activity is that several of its client proteins, which are mostly protein kinases or transcription factors involved in signal transduction, have been shown to be involved in the progression of cancer. Thus, inhibition of Hsp90 provides a method of short circuiting several pathways for tumor progression simultaneously. Therefore, treatment of cancers with an Hsp90 inhibitor of the invention either alone, or in combination with other chemotherapeutic agents, is more likely to result in regression or elimination of the cancer, and less likely to result in the development of more aggressive multidrug resistant cancers than other currently available therapies.

DETAILED DESCRIPTION OF THE INVENTION

Figure 1:
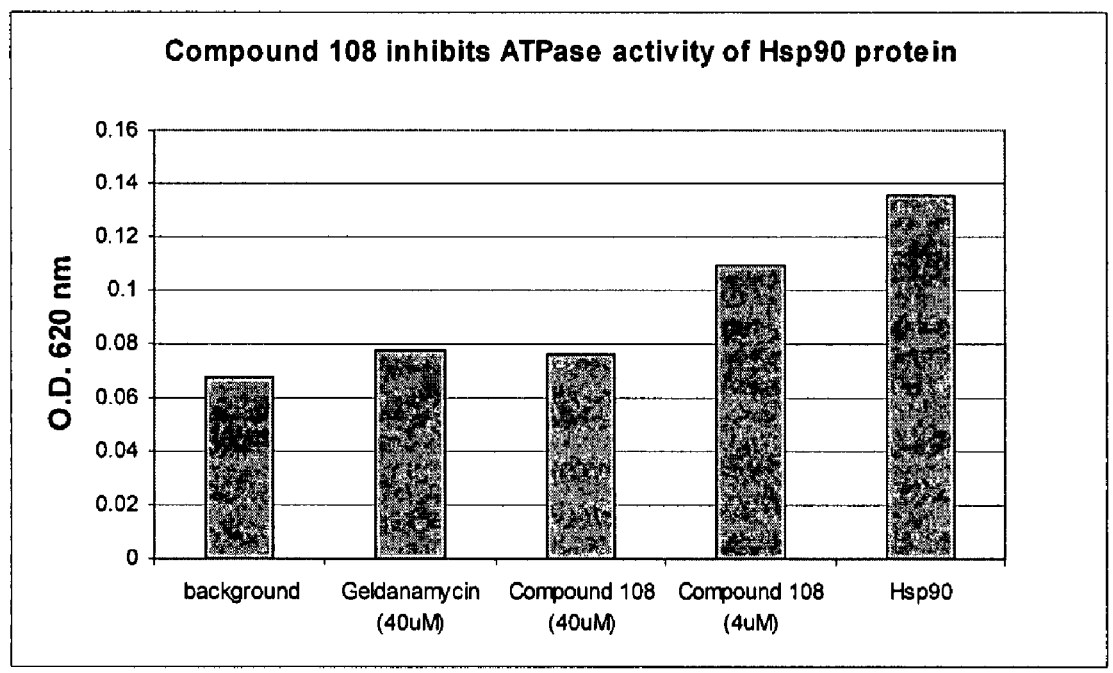
FIG. 1 is a graph showing the ATPase activity of Hsp90 when untreated, when treated with 40 mM of Geldanamycin, a known Hsp90 inhibitor as a positive control, and when treated with 40 µM or 4 µM of Compound 108 of the invention.

The present invention provides compounds and uses of said compounds. The present invention encompasses the use of the compounds of the invention to inhibit Hsp90 activity and for the treatment of a proliferative disorder, such as cancer, and in particular non-Hodgkins lymphoma. The present invention encompasses the use of compounds of the invention to slow or stop the growth of cancerous cells or to reduce or eliminate cancerous cells in a mammal.

In certain embodiments, the compounds of the invention can be used in combination with other chemotherapeutic agents and may help to prevent or reduce the development of multidrug resistant cancerous cells in a mammal. In this embodiment, the compounds of the invention may allow a reduced efficacious amount of a second chemotherapeutic agent given to a mammal, because compounds of the invention should inhibit the development of multidrug resistant cancerous cells.

A. TERMINOLOGY

Unless otherwise specified, the below terms used herein are defined as follows:

As used herein, the term "alkyl" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. The term "$(C_1$-$C_6)$alkyl" means a saturated straight chain or branched non-cyclic hydrocarbon having from 1 to 6 carbon atoms. Representative $(C_1$-$C_6)$alkyl groups are those shown above having from 1 to 6 carbon atoms. Alkyl groups included in compounds of this invention may be optionally substituted with one or more substituents.

As used herein, the term "alkenyl" means a saturated straight chain or branched non-cyclic hydrocarbon having from 2 to 10 carbon atoms and having at least one carbon-carbon double bond. Representative straight chain and branched $(C_2$-$C_{10})$alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups may be optionally substituted with one or more substituents.

As used herein, the term "alkynyl" means a saturated straight chain or branched non-cyclic hydrocarbon having from 2 to 10 carbon atoms and having at least one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkynyl groups may be optionally substituted with one or more substituents.

As used herein, the term "cycloalkyl" means a saturated, mono- or polycyclic alkyl radical having from 3 to 20 carbon atoms. Representative cycloalkyls include cyclopropyl, 1-methylcyclopropyl, cyclobutyl, cyclopentyl, cyclohexyl, cycloheptyl, cyclooctyl, cyclononyl, -cyclodecyl, octahydropentalenyl, and the like. Cycloalkyl groups may be optionally substituted with one or more substituents.

As used herein, the term "cycloalkenyl" means a mono- or poly-cyclic non-aromatic alkyl radical having at least one carbon-carbon double bond in the cyclic system and from 3 to 20 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl, 1,2,3,4,5,8-hexahydronaphthalenyl and the like. Cycloalkenyl groups may be optionally substituted with one or more substituents.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, an "alkoxy" is an alkyl group which is attached to another moiety via an oxygen linker.

As used herein, an "haloalkoxy" is an haloalkyl group which is attached to another moiety via an oxygen linker.

As used herein, the term an "aromatic ring" or "aryl" means a hydrocarbon monocyclic or polycyclic radical in which at least one ring is aromatic. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Aryl groups may be optionally substituted with one or more substituents. In one embodiment, the aryl group is a monocyclic ring, wherein the ring comprises 6 carbon atoms, referred to herein as "($C_6$)aryl."

As used herein, the term "aralkyl" means an aryl group that is attached to another group by a ($C_1$-$C_6$)alkylene group. Representative aralkyl groups include benzyl, 2-phenylethyl, naphth-3-yl-methyl and the like. Aralkyl groups may be optionally substituted with one or more substituents.

As used herein, the term "alkylene" refers to an alkyl group that has two points of attachment. The term "($C_1$-$C_6$)alkylene" refers to an alkylene group that has from one to six carbon atoms. Straight chain ($C_1$-$C_6$)alkylene groups are preferred. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like. Alkylene groups may be optionally substituted with one or more substituents.

As used herein, the term "heterocyclyl" means a monocyclic (typically having 3- to 10-members) or a polycyclic (typically having 7- to 20-members) heterocyclic ring system which is either a saturated ring or a unsaturated non-aromatic ring. A 3- to 10-membered heterocycle can contain up to 5 heteroatoms; and a 7- to 20-membered heterocycle can contain up to 7 heteroatoms. Typically, a heterocycle has at least on carbon atom ring member. Each heteroatom is independently selected from nitrogen, which can be oxidized (e.g., N(O)) or quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents. Only stable isomers of such substituted heterocyclic groups are contemplated in this definition.

As used herein, the term "heteroaromatic", "heteroaryl" or like terms means a monocyclic or polycyclic heteroaromatic ring comprising carbon atom ring members and one or more heteroatom ring members. Each heteroatom is independently selected from nitrogen, which can be oxidized (e.g., N(O)) or quaternized; oxygen; and sulfur, including sulfoxide and sulfone. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings. Heteroaryl groups may be optionally substituted with one or more substituents.

As used herein, the term "($C_5$)heteroaryl" means an aromatic heterocyclic ring of 5 members, wherein at least one carbon atom of the ring is replaced with a heteroatom such as, for example, oxygen, sulfur or nitrogen. Representative ($C_5$) heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like.

As used herein, the term "($C_6$)heteroaryl" means an aromatic heterocyclic ring of 6 members, wherein at least one carbon atom of the ring is replaced with a heteroatom such as, for example, oxygen, nitrogen or sulfur. Representative ($C_6$) heteroaryls include pyridyl, pyridazinyl, pyrazinyl, triazinyl, tetrazinyl and the like.

As used herein, the term "heteroaralkyl" means a heteroaryl group that is attached to another group by a ($C_1$-$C_6$) alkylene. Representative heteroaralkyls include 2-(pyridin-4-yl)-propyl, 2-(thien-3-yl)-ethyl, imidazol-4-yl-methyl and the like. Heteroalkyl groups may be optionally substituted with one or more substituents.

As used herein, the term "halogen" or "halo" means —F, —Cl, —Br or —I.

Suitable substituents for an alkyl, alkylene, alkenyl, alkynyl, cycloalkyl, cycloalkenyl, heterocyclyl, aryl, aralkyl, heteroaryl, and heteroaralkyl groups include any substituent which will form a stable compound of the invention. Examples of substituents for an alkyl, alkylene, alkenyl, alkynyl, cycloalkyl, cycloalkenyl, heterocyclyl, aryl, aralkyl, heteroaryl, and heteroarylalkyl include an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_{28}$R$_{29}$, —C(S)NR$_{28}$R$_{29}$, —C(NR$_{32}$)NR$_{28}$R$_{29}$, —NR$_{30}$C(O)R$_{31}$, —NR$_{30}$C(S)R$_{31}$, —NR$_{30}$C(NR$_{32}$)R$_{31}$, halo, —OR$_{30}$, cyano, nitro, haloalkoxy, —C(O)R$_{30}$, —C(S)R$_{30}$, —C(NR$_{32}$)R$_{30}$, —NR$_{28}$R$_{29}$, —C(O)OR$_{30}$, —C(S)OR$_{30}$, —C(NR$_{32}$)OR$_{30}$, —OC(O)R$_{30}$, —OC(S)R$_{30}$, —OC(NR$_{32}$)R$_{30}$, —NR$_{30}$C(O)NR$_{28}$R$_{29}$, —NR$_{30}$C(S)NR$_{28}$R$_{29}$, —NR$_{30}$C(NR$_{32}$)NR$_{28}$R$_{29}$, —OC(O)NR$_{28}$R$_{29}$, —OC(S)NR$_{28}$R$_{29}$, —OC(NR$_{32}$)NR$_{28}$R$_{29}$, —NR$_{30}$C(O)OR$_{31}$, —NR$_{30}$C(S)OR$_{31}$, —NR$_{30}$C(NR$_{32}$)OR$_{31}$, —S(O)$_h$R$_{30}$, —OS(O)$_p$R$_{30}$, —NR$_3$OS(O)$_p$R$_{30}$, —S(O)$_p$NR$_{28}$R$_{29}$, —OS(O)$_p$NR$_{28}$R$_{29}$, or —NR$_3$OS(O)$_p$NR$_{28}$R$_{29}$, wherein R$_{28}$ and R$_{29}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{28}$ and R$_{29}$ taken together with the nitrogen to which they are attached is optionally substituted heterocyclyl or optionally substituted heteroaryl.

R$_{30}$ and R$_{31}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; and R$_{32}$, for each occurrence is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, —C(O)R$_{30}$, —C(O)NR$_{28}$R$_{29}$, —S(O)$_p$R$_{30}$, or —S(O)$_p$NR$_{28}$R$_{29}$; and h is 0, 1 or 2.

In addition, alkyl, cycloalkyl, alkylene, a heterocyclyl, and any saturated portion of a alkenyl, cycloalkenyl, alkynyl, aralkyl, and heteroaralkyl groups, may also be substituted with =O, =S, =N—R$_{32}$.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, the term "lower" refers to a group having up to four atoms. For example, a "lower alkyl" refers to an alkyl radical having from 1 to 4 carbon atoms, "lower alkoxy" refers to "—O—(C$_1$-C$_4$)alkyl and a "lower alkenyl" or "lower alkynyl" refers to an alkenyl or alkynyl radical having from 2 to 4 carbon atoms, respectively.

Unless indicated otherwise, the compounds of the invention containing reactive functional groups (such as (without limitation) carboxy, hydroxy, thiol, and amino moieties) also include protected derivatives thereof. "Protected derivatives" are those compounds in which a reactive site or sites are blocked with one or more protecting groups. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxycarbonyl (Fmoc). Examples of suitable thiol protecting groups include benzyl, tert-butyl, acetyl, methoxymethyl and the like. Other suitable protecting groups are well known to those of ordinary skill in the art and include those found in T. W. Greene, Protecting Groups in Organic Synthesis, John Wiley & Sons, Inc. 1981.

As used herein, the term "compound(s) of this invention" and similar terms refers to a compound of formula (I) through (LXXII) and Tables 5, 6, and 7, or a pharmaceutically acceptable salt, solvate, clathrate, hydrate, polymorph or prodrug thereof, and also include protected derivatives thereof.

The compounds of the invention may contain one or more chiral centers and/or double bonds and, therefore, exist as stereoisomers, such as double-bond isomers (i.e., geometric isomers), enantiomers, or diastereomers. According to this invention, the chemical structures depicted herein, including the compounds of this invention, encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, that further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of formula (I) through (LXXII) and Tables 5, 6, and 7 that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of formula (I) through (LXXII), and Tables 5, 6, and 7, that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as improved water solubility, improved circulating half-life in the blood (e.g., because of reduced metabolism of the prodrug), improved uptake, improved duration of action, or improved onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, "Hsp90" includes each member of the family of heat shock proteins having a mass of about 90-kilo Daltons. For example, in humans the highly conserved Hsp90 family includes cytosolic Hsp90α and Hsp90β isoforms, as well as GRP94, which is found in the endoplasmic reticulum, and HSP75/TRAP1, which is found in the mitochondrial matrix.

As used herein, a "proliferative disorder" or a "hyperproliferative disorder," and other equivalent terms, means a disease or medical condition involving pathological growth of cells. Proliferative disorders include cancer, smooth muscle cell proliferation, systemic sclerosis, cirrhosis of the liver, adult respiratory distress syndrome, idiopathic cardiomyopathy, lupus erythematosus, retinopathy, e.g., diabetic retinopathy or other retinopathies, cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, desmoid tumors.

Smooth muscle cell proliferation includes hyperproliferation of cells in the vasculature, for example, intimal smooth muscle cell hyperplasia, restenosis and vascular occlusion, particularly stenosis following biologically- or mechanically-mediated vascular injury, e.g., vascular injury associated with angioplasty. Moreover, intimal smooth muscle cell hyperplasia can include hyperplasia in smooth muscle other than the vasculature, e.g., bile duct blockage, bronchial airways of the lung in patients with asthma, in the kidneys of patients with renal interstitial fibrosis, and the like.

Non-cancerous proliferative disorders also include hyperproliferation of cells in the skin such as psoriasis and its varied clinical forms, Reiter's syndrome, pityriasis rubra pilaris, and hyperproliferative variants of disorders of keratinization (e.g., actinic keratosis, senile keratosis), scleroderma, and the like.

In a preferred embodiment, the proliferative disorder is cancer. Cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1 (murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic)cell line); neutrophilic leukemia; eosinophilic leukemia; monocytic leukemia (e.g., as exemplified by the THP-1 (acute) cell line); myelomonocytic leukemia; Naegeli-type myeloid leukemia; and nonlymphocytic leukemia. Other examples of leukemias are described in Chapter 60 of *The Chemotherapy Sourcebook*, Michael C. Perry Ed., Williams & Williams (1992) and Section 36 of *Holland Frie Cancer Medicine* 5th Ed., Bast et al. Eds., B. C. Decker Inc. (2000). The entire teachings of the preceding references are incorporated herein by reference.

In one embodiment, the disclosed method is believed to be particularly effective in treating subject with non-solid tumors such as multiple myeloma. In another embodiment, the disclosed method is believed to be particularly effective against T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line); monocytic leukemia (e.g., as exemplified by the THP-1 (acute) cell line); and lymphoma (e.g., as exemplified by the U937 cell line).

In a preferred embodiment, the disclosed methods are particularly useful for treating cancers in which Hsp90 is up-regulated, such as in non-Hodgkin's lymphomas. Lymphomas are generally classified as either Hodgkin's disease (HD) or non-Hodgkin's lymphomas (NHL). NHL differs from HD by the absence of Reed-Sternberg cells. The course of NHL is less predictable than HD and is more likely to spread to areas beyond the lymph nodes. NHL can be further divided into B-cell NHL and T-cell NHL each of which can be further categorized into a variety of different subtypes. For example, B-cell NHL includes Burkitt's lymphoma, follicular lymphoma, diffuse large B-cell lymphoma, nodal marginal zone B-cell lymphoma, plasma cell neoplasms, small lymphocytic lymphoma/chronic lymphocytic leukemia, mantle cell lymphoma, extranodal marginal zone B-cell lymphoma, and lymphoplamacytic lymphoma/Waldenstrom macroglobulinemia. T-cell NHL include anaplastic large-cell lymphoma, precursor-T-cell lymphoblastic leukemia/lymphoma, unspecified peripheral T-cell lymphoma, acute lymphoblastic leukemia/lymphoma, angioimmunoblastic T-cell lymphoma, and mycosis fungoides. Without wishing to be bound by any theory, it is believed that the compounds of the invention are useful for treating NHLs, including B-cell and T-cell NHLs, since Hsp90 is upregulated in many NHLs.

Some of the disclosed methods can be particularly effective at treating subjects whose cancer has become "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

As used herein, the term "pharmaceutically acceptable salt," is a salt formed from, for example, an acid and a basic group of one of the compounds of formula (I) through (LXXII) and Tables 5, 6, and 7. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of formula (I) through (LXXII) and Tables 5, 6, and 7 having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of formula (I) through (LXXII) and Tables 5, 6, and 7 having a basic functional group, such as an amine functional group, and a pharmaceutically acceptable inorganic or organic acid. Suitable acids include, but are not limited to, hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the term "pharmaceutically acceptable solvate," is a solvate formed from the association of one or more pharmaceutically acceptable solvent molecules to one of the compounds of formula (I) through (LXXII) and Tables 5, 6, and 7. The term solvate includes hydrates (e.g., hemihydrate, monohydrate, dihydrate, trihydrate, tetrahydrate, and the like).

A pharmaceutically acceptable carrier may contain inert ingredients which do not unduly inhibit the biological activity of the compounds. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

As used herein, the term "effective amount" refers to an amount of a compound of this invention which is sufficient to reduce or ameliorate the severity, duration, progression, or onset of a proliferative disorder, prevent the advancement of a proliferative disorder, cause the regression of a proliferative, prevent the recurrence, development, onset or progression of a symptom associated with a proliferative disorder, or enhance or improve the prophylactic or therapeutic effect(s) of another therapy. The precise amount of compound administered to a subject will depend on the mode of administration, the type and severity of the disease or condition and on the characteristics of the subject, such as general health, age, sex, body weight and tolerance to drugs. It will also depend on the degree, severity and type of cell proliferation, and the mode of administration. The skilled artisan will be able to determine appropriate dosages depending on these and other factors. When co-administered with other agents, e.g., when co-administered with an anti-cancer agent, an "effective amount" of the second agent will depend on the type of drug used.

Suitable dosages are known for approved agents and can be adjusted by the skilled artisan according to the condition of the subject, the type of condition(s) being treated and the amount of a compound of the invention being used. In cases where no amount is expressly noted, an effective amount should be assumed.

Non-limiting examples of an effective amount of a compound of the invention are provided herein below. In a specific embodiment, the invention provides a method of preventing, treating, managing, or ameliorating a proliferative disorder or one or more symptoms thereof, said methods comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention once every day, preferably, once every 2 days, once every 3 days, once every 4 days, once every 5 days, once every 6 days, once every 7 days, once every 8 days, once every 10 days, once every two weeks, once every three weeks, or once a month.

The dosages of a chemotherapeutic agents other than compounds of the invention, which have been or are currently being used to prevent, treat, manage, or ameliorate a proliferative disorder, or one or more symptoms thereof, can be used in the combination therapies of the invention. Preferably, dosages lower than those which have been or are currently being used to prevent, treat, manage, or ameliorate a proliferative disorder, or one or more symptoms thereof, are used in the combination therapies of the invention. The recommended dosages of agents currently used for the prevention, treatment, management, or amelioration of a proliferative disorder, or one or more symptoms thereof, can obtained from any reference in the art including, but not limited to, Hardman et al., eds., 1996, Goodman & Gilman's The Pharmacological Basis Of Basis Of Therapeutics 9$^{th}$ Ed, Mc-Graw-Hill, N.Y.; Physician's Desk Reference (PDR) 57$^{th}$ Ed., 2003, Medical Economics Co., Inc., Montvale, N.J., which are incorporated herein by reference in its entirety.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a compound of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating" -refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

As used herein, the terms "prevent", "prevention" and "preventing" refer to the reduction in the risk of acquiring or developing a given proliferative disorder, or the reduction or inhibition of the recurrence or a proliferative disorder. In one embodiment, a compound of the invention is administered as a preventative measure to a patient, preferably a human, having a genetic predisposition to any of the disorders described herein.

As used herein, the terms "therapeutic agent" and "therapeutic agents" refer to any agent(s) which can be used in the treatment, management, or amelioration of a proliferative disorder or one or more symptoms thereof. In certain embodiments, the term "therapeutic agent" refers to a compound of the invention. In certain other embodiments, the term "therapeutic agent" refers does not refer to a compound of the invention. Preferably, a therapeutic agent is an agent which is known to be useful for, or has been or is currently being used for the treatment, management, prevention, or amelioration a proliferative disorder or one or more symptoms thereof.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a proliferative disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, management or treatment of a proliferative disorder. In addition, a synergistic effect can result in improved efficacy of agents in the prevention, management or treatment of a proliferative disorder. Finally, a synergistic effect of a combination of therapies (e.g., a combination of prophylactic or therapeutic agents) may avoid or reduce adverse or unwanted side effects associated with the use of either therapy alone.

As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

As used herein, the term "in combination" refers to the use of more than one therapies (e.g., one or more prophylactic and/or therapeutic agents). The use of the term "in combination" does not restrict the order in which therapies (e.g., prophylactic and/or therapeutic agents) are administered to a subject with a proliferative disorder. A first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject with a proliferative disorder, such as cancer.

As used herein, the terms "therapies" and "therapy" can refer to any protocol(s), method(s), and/or agent(s) that can be used in the prevention, treatment, management, or amelioration of a proliferative disorder or one or more symptoms thereof.

A used herein, a "protocol" includes dosing schedules and dosing regimens. The protocols herein are methods of use and include prophylactic and therapeutic protocols.

As used herein, the terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., one or more prophylactic or therapeutic agents) to "manage" a disease so as to prevent the progression or worsening of the disease.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

As used herein, a racemic mixture means about 50% of one enantiomer and about 50% of is corresponding enantiomer relative to a chiral center in the molecule. The invention encompasses all enantiomerically-pure, enantiomerically-enriched, diastereomerically pure, diastereomerically enriched, and racemic mixtures of the compounds of the invention.

Enantiomeric and diastereomeric mixtures can be resolved into their component enantiomers or diastereomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

The compounds of the invention are defined herein by their chemical structures and/or chemical names. Where a compound is referred to by both a chemical structure and a chemical name, and the chemical structure and chemical name conflict, the chemical structure is determinative of the compound's identity.

When administered to a patient, e.g., to a non-human animal for veterinary use or for improvement of livestock, or to a human for clinical use, the compounds of the invention are administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, the compounds of the invention are purified via conventional techniques. As used herein, "purified" means that when isolated, the isolate contains at least 95%, preferably at least 98%, of a compound of the invention by weight of the isolate either as a mixture of stereoisomers or as a diastereomeric or enantiomeric pure isolate. An "isolated agent" can be a synthetic or naturally occurring molecule having a molecular weight of about 1000 daltons or less, or a natural product having a molecular weight of greater than 1000 daltons. For example, an isolated agent can be an antibody, or fragment thereof, or an antibiotic.

As used herein, a composition that is "substantially free" of a compound means that the composition contains less than about 20% by weight, more preferably less than about 10% by weight, even more preferably less than about 5% by weight, and most preferably less than about 3% by weight of the compound.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

B. THE COMPOUNDS OF THE INVENTION

The present invention encompasses compounds having formula (I) through (LXXII), or any embodiment thereof, or a compound shown in Table 5, 6, or 7, and tautomers, pharmaceutically acceptable salts, solvates, clathrates, hydrates, polymorphs and prodrugs thereof. In one aspect, the invention provides compounds of formula (I) as set forth below:

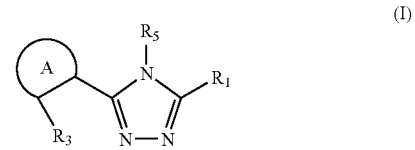

(I)

and tautomers, pharmaceutically acceptable salts, solvates, clathrates, and prodrugs thereof, wherein ring A, $R_1$, $R_3$ and $R_5$ are defined as above.

Compounds of formula (I) inhibit the activity of Hsp90 and are particularly useful for treating or preventing proliferative disorders, such as cancer. In addition, compounds of formula (I) are particularly useful in treating cancer when given in combination with other anti-cancer agent.

In one embodiment, in the compounds of formula (I), $R_5$ is an optionally substituted naphthyl.

In another embodiment, in the compounds of formula (I), $R_5$ is represented by the following formula:

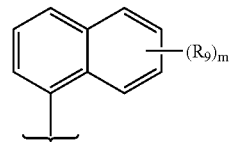

wherein:

$R_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$; or two R$_9$ groups taken together with the carbon atoms to which they are attached form a fused ring; and m is zero or an integer from 1 to 7, wherein R$_7$, R$_8$, R$_{10}$, R$_{11}$, and p are defined as above.

In another embodiment, in the compounds represented by formula (I), R$_5$ is represented by one of the following formulas:

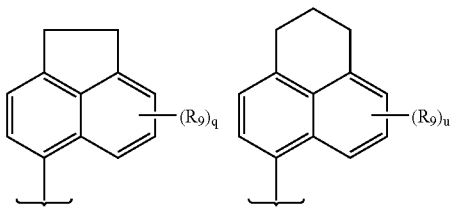

wherein R$_9$ is defined as above;

q is zero or an integer from 1 to 7; and u is zero or an integer from 1 to 8.

In another embodiment, in the compounds represented by formula (I), R$_5$ is selected from the group consisting of:

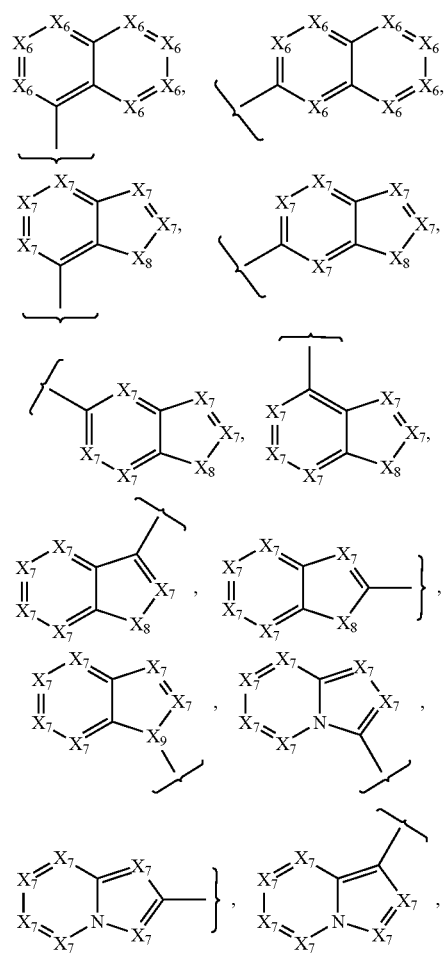

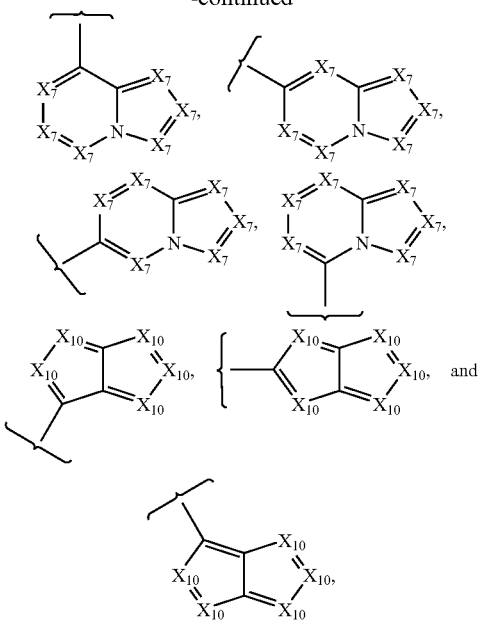

wherein:

X$_6$, for each occurrence, is independently CH, CR$_9$, N, N(O), N$^+$(R$_{17}$), provided that at least three X$_6$ groups are independently selected from CH and CR$_9$;

X$_7$, for each occurrence, is independently CH, CR$_9$, N, N(O), N$^+$(R$_{17}$), provided that at least three X$_7$ groups are independently selected from CH and CR$_9$;

X$_8$, for each occurrence, is independently CH$_2$, CHR$_9$, CR$_9$R$_9$, O, S, S(O)$_p$, NR$_7$, or NR$_{17}$;

X$_9$, for each occurrence, is independently N or CH;

X$_{10}$, for each occurrence, is independently CH, CR$_9$, N, N(O), N$^+$(R$_{17}$), provided that at least one X$_{10}$ is selected from CH and CR$_9$;

R$_{17}$, for each occurrence, is independently —H, an alkyl, an aralkyl, —C(O)R$_7$, —C(O)OR$_7$, or —C(O)NR$_{10}$R$_{11}$; wherein R$_7$, R$_9$, R$_{10}$, R$_{11}$ and p are defined as above.

In another embodiment, in the compounds represented by formula (I), R$_5$ is an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl, an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b]pyridinyl, an optionally substituted 1H-imidazo[4,5-c]pyridinyl, an optionally substituted 3H-imidazo[4,5-c]pyridinyl, an optionally substituted pyridopyrdazinyl, and optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo[b]thienyl.

In another embodiment, in the compounds represented by formula (I), $R_5$ is an optionally substituted indolyl. Preferably, $R_5$ is an indolyl represented by the following structural formula:

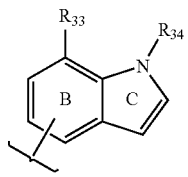

wherein:
$R_{33}$ is —H, a halo, lower alkyl, a lower alkoxy, a lower haloalkyl, a lower haloalkoxy, and lower alkyl sulfanyl;
$R_{34}$ is H, a lower alkyl, or a lower alkylcarbonyl; and
Ring B and Ring C are optionally substituted with one or more substituents.

In another embodiment, in the compounds represented by formula (I), $R_5$ is selected from the group consisting of:

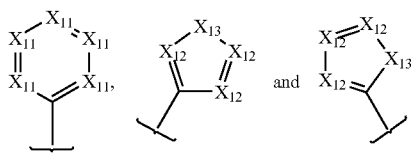

wherein:
$X_{11}$, for each occurrence, is independently CH, $CR_9$, N, N(O), or $N^+(R_{17})$, provided that at least one $X_{11}$ is N, N(O), or $N^+(R_{17})$ and at least two $X_{11}$ groups are independently selected from CH and $CR_9$;
$X_{12}$, for each occurrence, is independently CH, $CR_9$, N, N(O), $N^+(R_{17})$, provided that at least one $X_{12}$ group is independently selected from CH and $CR_9$;
$X_{13}$, for each occurrence, is independently O, S, $S(O)_p$, $NR_7$, or $NR_{17}$; wherein $R_7$, $R_9$ and $R_{17}$ are defined as above.

In another embodiment, in compounds represented by formula (I), or any of the embodiments of formula (I) in which particular groups are disclosed, the compound is represented by formula (XII):

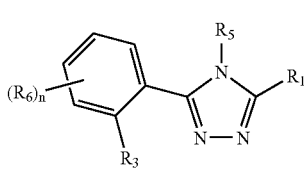

wherein $R_1$, $R_3$, and $R_5$ are defined as above; and
$R_6$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, —$NR_{10}R_{11}$, —$OR_7$, —C(O)$R_7$, —C(O)$OR_7$, —OC(O)$R_7$, —C(O)$NR_{10}R_{11}$, —$NR_8$C(O)$R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$; and
n is zero of an integer from 1 to 4, wherein $R_7$, $R_8$, $R_{10}$, $R_{11}$, and p are defined as above.

In another embodiment, in compounds represented by formula (I), or any of the embodiments of formula (I) in which particular groups are disclosed, the compound is represented by structural formula (XIII):

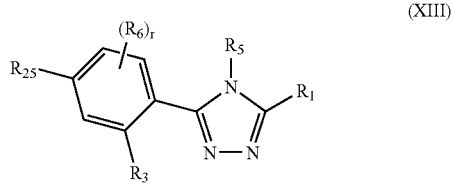

wherein $R_1$, $R_3$, $R_5$, and $R_6$ are defined as above; and
$R_{25}$ is a halo, a haloalkyl, a haloalkoxy, a heteroalkyl, —OH, —SH, —$NHR_7$, —$(CH_2)_kOH$, —$(CH_2)_kSH$, —$(CH_2)_kNR_7H$, —$OCH_3$, —$SCH_3$, —$NHCH_3$, —$OCH_2CH_2OH$, —$OCH_2CH_2SH$, —$OCH_2CH_2NR_7H$, —$SCH_2CH_2OH$, —$SCH_2CH_2SH$, —$SCH_2CH_2NR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$;
k is 1, 2, 3, or 4; and
r is zero or an integer from 1 to 3, wherein $R_7$, $R_8$, $R_{10}$, $R_{11}$, and p are defined as above.

In another embodiment, in compounds represented by formula (I), or any of the embodiments of formula (I) in which particular groups are disclosed, $R_1$ and $R_3$ are each, independently, —OH, —SH, or —$NHR_7$.

In another embodiment, in compounds represented by formula (I), or any of the embodiments of formula (I) in which particular groups are disclosed, the compound is represented by structural formula (XIV):

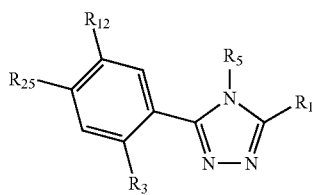
(XIV)

wherein $R_1$, $R_3$, $R_5$, and $R_{25}$ are defined as above; and $R_{12}$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$, wherein $R_7$, $R_8$, $R_{10}$, $R_{11}$, and p are defined as above. In a preferred embodiment, $R_1$ is —SH or —OH; $R_3$ and $R_{25}$ are —OH; $R_{12}$ is a lower alkyl, lower alkoxy, a lower alkyl sulfanyl, or —$NR_{10}R_{11}$; and $R_9$, for each occurrence, is independently selected from the group consisting of —OH, —SH, halo, a lower haloalkyl, cyano, a lower alkyl, a lower alkoxy, and a lower alkyl sulfanyl.

In another embodiment, in compounds represented by formula (I), or any of the embodiments of formula (I) in which particular groups are disclosed, the compound is represented by one of the following structural formulas:

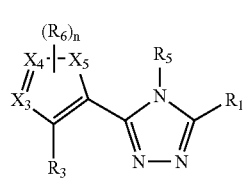
(XV)

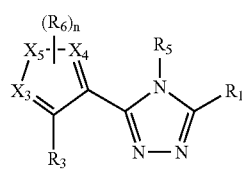
(XVI)

wherein $R_1$, $R_3$, $R_5$, $R_6$ and n are as defined above; and $X_3$ and $X_4$ are each, independently, N, N(O), $N^+(R_{17})$, CH or $CR_6$; and $X_5$ is O, S, $NR_{17}$, CH═CH, CH═$CR_6$, $CR_6$═CH, $CR_6$═$CR_6$, CH═N, $CR_6$═N, CH═N(O), $CR_6$═N(O), N═CH, N═$CR_6$, N(O)═CH, N(O)═$CR_6$, $N^+(R_{17})$═CH, $N^+(R_{17})$═$CR_6$, CH═$N^+(R_{17})$, $CR_6$═$N^+(R_{17})$, or N═N; wherein $R_{17}$ is defined as above.

In another embodiment, in compounds represented by formula (I), or any of the embodiments of formula (I) in which particular groups are disclosed, the compound is selected from the group consisting of:

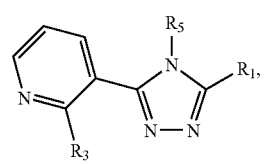
(XVIIa)

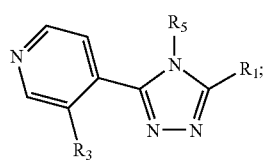
(XVIIb)

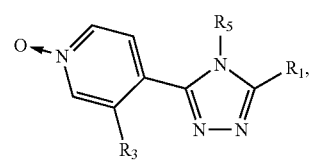
(XVIIc)

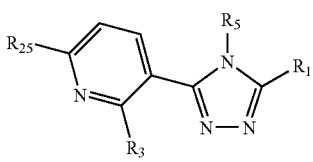
(XVIId)

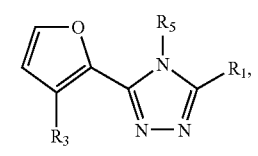
(XVIIe)

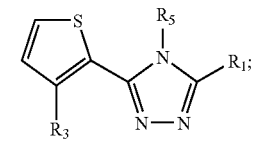
(XVIIf)

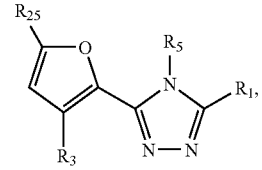
(XVIIg)

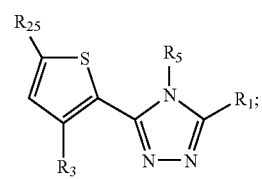
(XVIIh)

-continued

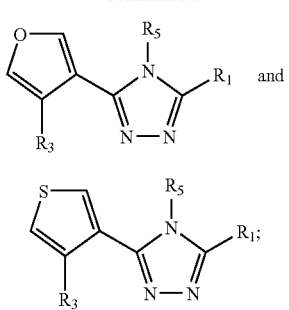

wherein R$_1$, R$_3$, R$_5$, and R$_{25}$ are defined as above.

In another aspect, the invention provides compounds of formula (II) as set forth below:

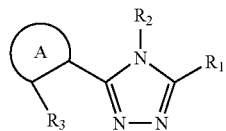

and tautomers, pharmaceutically acceptable salts, solvates, clathrates, and prodrugs thereof, wherein ring A, R$_1$ and R$_3$ are defined as above; and R$_2$ is a substituted phenyl, wherein the phenyl group is substituted with:
  i) one substituent selected from nitro, cyano, a haloalkoxy, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxylalkyl, alkoxyalkyl,
    guanadino, —NR$_{10}$R$_{11}$, —O—R$_{20}$, —C(O)R$_7$, —C(O)OR$_{20}$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$, or
  ii) two to five substituents selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, —F, —Br, —I, cyano, nitro, guanadino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$;
    R$_{20}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteralkyl;
    p, for each occurrence, is, independently, 0, 1 or 2.

Compounds of formula (II) inhibit the activity of Hsp90 and are particularly useful for treating or preventing proliferative disorders, such as cancer. In addition, compounds of formula (II) are particularly useful in treating cancer when given in combination with other anti-cancer agent.

In one embodiment, the compounds represented by formula (II) do not include 3-(2,4-dihydroxy-phenyl)-4-(7-naphthalen-1-yl)-5-mercapto-triazole, 3-(2,4-dihydroxyphenyl)-4-(2,5-dimethoxyphenyl)-5-mercapto-triazole, 3-(1-phenyl-5-amino-pyrazol-4-yl)-4-(2,4-dichlorophenyl)-5-mercapto-triazole, and 3-(2-hydroxy-phenyl)-4-(2,4-dimethylphenyl)-5-mercapto-triazole.

In another embodiment, in compounds represented by formula (II), or any of the embodiments of formula (II) in which particular groups are disclosed, the compound is represented by structural formula (XVIII):

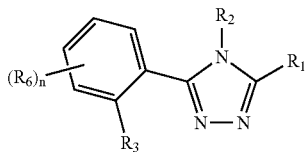

wherein R$_1$, R$_2$, R$_3$, R$_6$, and n are defined as above.

In another embodiment, in compounds represented by formula (II), or any of the embodiments of formula (II) in which particular groups are disclosed, the compound is represented by structural formula (XIX):

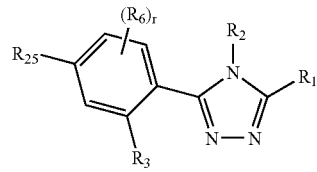

wherein R$_1$, R$_2$, R$_3$, R$_6$, R$_{25}$ and r are defined as above.

In another embodiment, in compounds represented by formula (II), or any of the embodiments of formula (II) in which particular groups are disclosed, R$_1$ and R$_3$ are each, independently, —OH, —SH, or —NHR$_7$.

In another embodiment, in compounds represented by formula (II), or any of the embodiments of formula (II) in which particular groups are disclosed, the compound is represented by structural formula (XX):

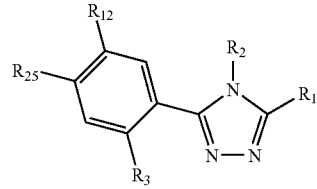

wherein R$_1$, R$_2$, R$_3$, R$_{12}$ and R$_{25}$ are defined as above. In a preferred embodiment, R$_1$ is —SH or —OH; R$_3$ and R$_{25}$ are —OH; R$_{12}$ is a lower alkyl, lower alkoxy, a lower alkyl sulfanyl, or —NR$_{10}$R$_{11}$; and R$_9$, for each occurrence, is independently selected from the group consisting of —OH, —SH, halo, a lower haloalkyl, cyano, a lower alkyl, a lower alkoxy, and a lower alkyl sulfanyl.

In another embodiment, in compounds represented by formula (II), or any of the embodiments of formula (II) in which particular groups are disclosed, the compound is represented by one of the following structural formulas:

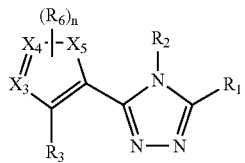
(XXI)

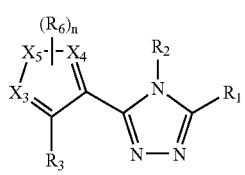
(XXII)

wherein $R_1$, $R_2$, $R_3$, $R_6$, $X_3$, $X_4$, $X_5$ and n are defined as above.

In another embodiment, in compounds represented by formula (II), or any of the embodiments of formula (II) in which particular groups are disclosed, the compound is selected from the group consisting of:

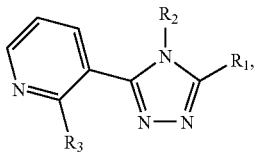
(XXIIIa)

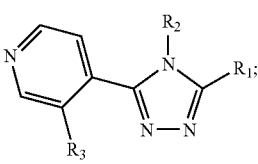
(XXIIIb)

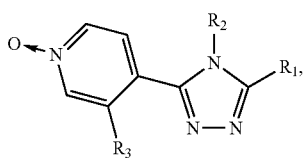
(XXIIIc)

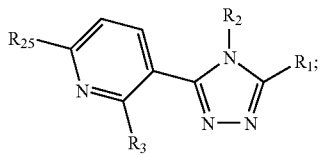
(XXIIId)

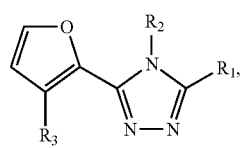
(XXIIIe)

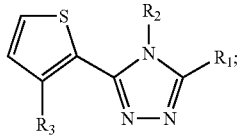
(XXIIIf)

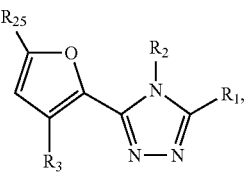
(XXIIIg)

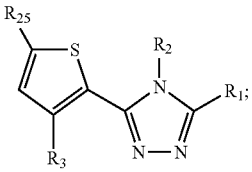
(XXIIIh)

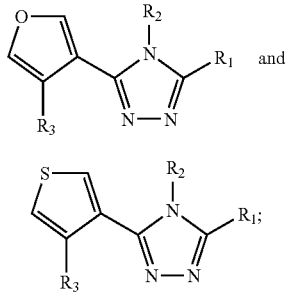
(XXIIIi) and (XXIIIj)

wherein $R_1$, $R_2$, $R_3$, and $R_{25}$ are defined as above.

In another aspect, the invention provides compounds of formula (III) as set forth below:

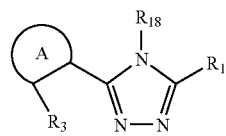
(III)

and tautomers, pharmaceutically acceptable salts, solvates, clathrates, and prodrugs. In formula (III), ring A, $R_1$, and $R_3$ are defined as above; and $R_{18}$ is an optionally substituted cycloalkyl, and optionally substituted cycloalkenyl, or a substituted alkyl, wherein the alkyl group is substituted with one or more substituents independently selected from the group consisting of an optionally substituted alkynyl, an optionally substituted cycloalkyl, an optionally substituted cycloalkenyl, an optionally substituted heteroaryl, an optionally substituted aralkyl, an optionally substituted heteraralkyl, halo, cyano, nitro, guanadino, a haloalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$, wherein $R_7$, $R_8$, $R_{10}$, $R_{11}$, and p are defined as above.

Compounds of formula (III) inhibit the activity of Hsp90 and are particularly useful for treating or preventing proliferative disorders, such as cancer. In addition, compounds of formula (III) are particularly useful in treating cancer when given in combination with other anti-cancer agent.

In one embodiment, in formula (III) R$_{18}$ is not cyclohexyl.

In another embodiment, in formula (III) R$_{18}$ is an optionally substituted cycloalkyl or an optionally substituted cycloalkenyl.

In another embodiment, in formula (III) R$_{18}$ is a substituted alkyl.

In another embodiment, in compounds represented by formula (III), or any of the embodiments of formula (III) in which particular groups are disclosed, the compound is represented by structural formula (XXIV):

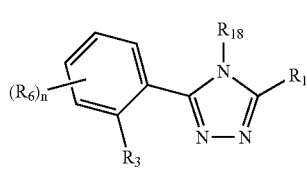

(XXIV)

wherein R$_1$, R$_3$, R$_6$, R$_{18}$, and n are defined as above.

In another embodiment, in compounds represented by formula (III), or any of the embodiments of formula (III) in which particular groups are disclosed, the compound is represented by structural formula (XXV):

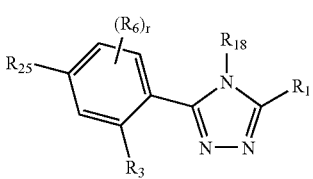

(XXV)

wherein R$_1$, R$_3$, R$_6$, R$_{18}$, R$_{25}$ and r are defined as above.

In another embodiment, in compounds represented by formula (III), or any of the embodiments of formula (III) in which particular groups are disclosed, R$_1$ and R$_3$ are each, independently, —OH, —SH, or —NHR$_7$.

In another embodiment, in compounds represented by formula (III), or any of the embodiments of formula (III) in which particular groups are disclosed, the compound is represented by structural formula (XXVI):

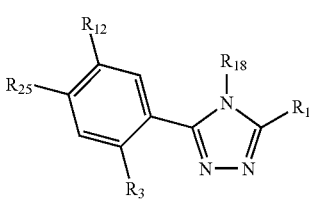

(XXVI)

wherein R$_1$, R$_3$, R$_{12}$, R$_{18}$, and R$_{25}$ are defined as above. In a preferred embodiment, R$_1$ is —SH or —OH; R$_3$ and R$_{25}$ are —OH; and R$_{12}$ is a lower alkyl, lower alkoxy, a lower alkyl sulfanyl, or —NR$_{10}$R$_{11}$.

In another embodiment, in compounds represented by formula (III), or any of the embodiments of formula (III) in which particular groups are disclosed, the compound is represented by one of the following structural formulas:

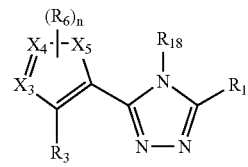

(XXVII)

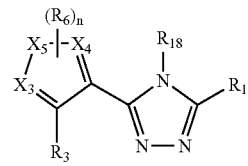

(XXVIII)

wherein R$_1$, R$_3$, R$_6$, R$_{18}$, X$_3$, X$_4$, X$_5$, and n are defined as above.

In another embodiment, in compounds represented by formula (III), or any of the embodiments of formula (III) in which particular groups are disclosed, the compound is selected from the group consisting of:

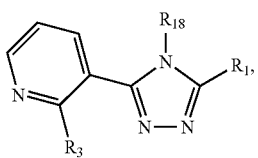

(XXIXa)

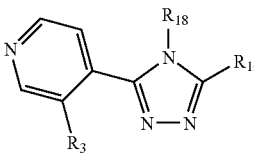

(XXIXb)

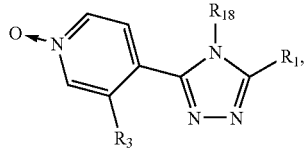

(XXIXc)

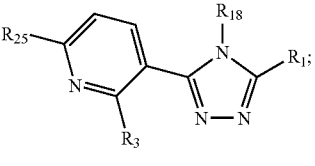

(XXIXd)

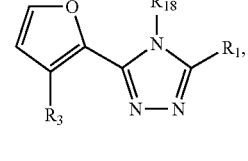

(XXIXe)

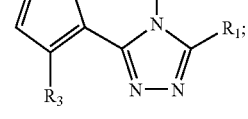

(XXIXf)

-continued

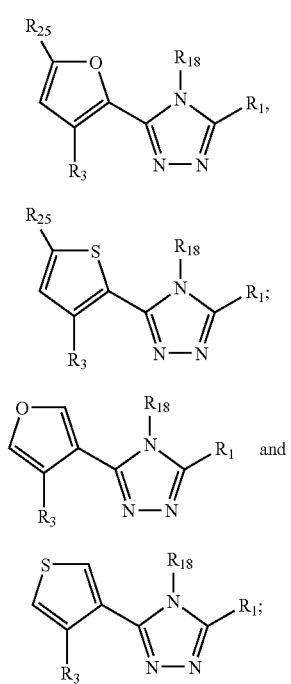

wherein $R_1$, $R_3$, $R_{18}$, and $R_{25}$ are defined as above.

In another aspect, the invention provides compounds of formula (IV) or (V) as set forth below:

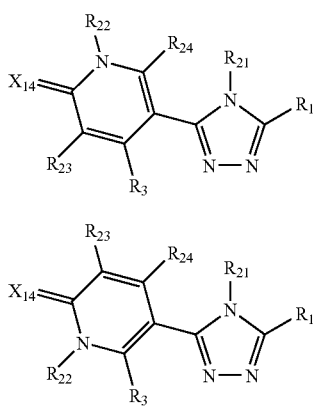

and tautomers, pharmaceutically acceptable salts, solvates, clathrates, and prodrugs thereof. In formulas (IV) and (V), $R_1$ and $R_3$ are as defined above; and $X_{14}$ is O, S, or $NR_7$;

$R_{21}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{22}$, for each occurrence, is independently a substituent selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, a haloalkyl, —C(O)$R_7$, —C(O)O$R_7$, —OC(O)$R_7$, —C(O)N$R_{10}R_{11}$, —N$R_8$C(O)$R_7$, —S(O)$_p R_7$, —S(O)$_p$O$R_7$, or —S(O)$_p$N$R_{10}R_{11}$; and $R_{23}$ and $R_{24}$, for each occurrence, are independently a substituent selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, halo, cyano, nitro, guanadino, a haloalkyl, a heteroalkyl, —N$R_{10}R_{11}$, —O$R_7$, —C(O)$R_7$, —C(O)O$R_7$, —OC(O)$R_7$, —C(O)N$R_{10}R_{11}$, —N$R_8$C(O)$R_7$, —S$R_7$, —S(O)$_p R_7$, —OS(O)$_p R_7$, —S(O)$_p$O$R_7$, —N$R_8$S(O)$_p R_7$, or —S(O)$_p$N$R_{10}R_{11}$;

wherein $R_7$, $R_8$, $R_{10}$, $R_{11}$ and p are defined as above.

In one embodiment, in formulas (IV) and (V), $R_{21}$ is an optionally substituted alkyl, an optionally substituted cycloalkyl, an optionally substituted aryl or an optionally substituted heteroaryl.

In another embodiment, in the formulas (IV) and (V), $R_1$ is —OH, —SH, or —NH$R_7$.

In another embodiment, in the formulas (IV) and (V), $R_{22}$ is an alkyl, an aralkyl, —C(O)$R_7$, —C(O)O$R_7$, or —C(O)N$R_{10}R_{11}$.

In another embodiment, in the formulas (IV) and (V), $X_{14}$ is O.

Compounds of formula (IV) or (V) inhibit the activity of Hsp90 and are particularly useful for treating or preventing proliferative disorders, such as cancer. In addition, compounds of formula (IV) or (V) are particularly useful in treating cancer when given in combination with other anti-cancer agent.

In another embodiment, the invention provides compounds represented by formula (XXX):

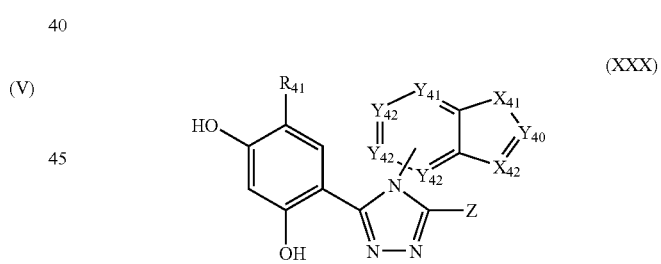

and tautomers, pharmaceutically acceptable salts, solvates, clathrates, and prodrugs thereof, wherein:

$X_{41}$ is O, S, or $NR_{42}$;
$X_{42}$ is $CR_{44}$ or N;
$Y_{40}$ is N or $CR_{43}$;
$Y_{41}$ is N or $CR_{45}$;
$Y_{42}$, for each occurrence, is independently N, C or $CR_{46}$;
Z is OH, SH, or $NHR_7$;
$R_{41}$ is —H, —OH, —SH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, haloalkyl, a heteroalkyl, an alkoxy or cycloalkoxy, a haloalkoxy, —N$R_{10}R_{11}$, —O$R_7$, —C(O)$R_7$, —C(O)O$R_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)R_7$, —$OC(NR_8)R_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$;

$R_{42}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, a haloalkyl, a heteroalkyl, —$C(O)R_7$, —$(CH_2)_mC(O)OR_7$, —$C(O)OR_7$, —$OC(O)R_7$, —$C(O)NR_{10}R_{11}$, —$S(O)_pR_7$, —$S(O)_pOR_7$, or —$S(O)_pNR_{10}R_{11}$;

$R_{43}$ and $R_{44}$ are, independently, —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, —$S(O)_pNR_{10}R_{11}$, or $R_{43}$ and $R_{44}$ taken together with the carbon atoms to which they are attached form an optionally substituted cycloalkenyl, an optionally substituted aryl, an optionally substituted heterocyclyl, or an optionally substituted heteroaryl;

$R_{45}$ is —H, —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, or —$NR_7C(NR_8)NR_{10}R_{11}$;

$R_{46}$, for each occurrence, is independently selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$;

$R_7$, $R_8$, $R_{10}$, $R_{11}$, $R_{26}$, p, and m are defined as above.

In one embodiment, in formula (XXX), $X_{41}$ is $NR_{42}$ and $X_{42}$ is $CR_{44}$.

In another embodiment, in formula (XXX), $X_{41}$ is $NR_{42}$ and $X_{42}$ is N.

In another embodiment, in formula (XXX), $R_{41}$ is selected from the group consisting of —H, lower alkyl, lower alkoxy, lower cycloalkyl, and lower cycloalkoxy.

In another embodiment, in formula (XXX), $R_{41}$ is selected from the group consisting of —H, methyl, ethyl, propyl, isopropyl, cyclopropyl, methoxy, ethoxy, propoxy, and cyclopropoxy.

In another embodiment, in formula (XXX), $X_{41}$ is $NR_{42}$, and $R_{42}$ is selected from the group consisting of —H, a lower alkyl, a lower cycloalkyl, —$C(O)N(R_{27})_2$, and —$C(O)OH$, wherein $R_{27}$, for each occurrence, is independently is —H or a lower alkyl.

In another embodiment, in formula (XXX), $X_{41}$ is $NR_{42}$, and $R_{42}$ is selected from the group consisting of —H, methyl, ethyl, n-propyl, isopropyl, cyclopropyl, n-butyl, sec-butyl, tert-butyl, n-pentyl, n-hexyl, —$C(O)OH$, —$(CH_2)_mC(O)OH$, —$CH_2OCH_3$, —$CH_2CH_2OCH_3$, and —$C(O)N(CH_3)_2$.

In one embodiment, $Y_{40}$ is $CR_{43}$. Preferably, $Y_{40}$ is $CR_{43}$ and $R_{43}$ is H or a lower alkyl.

In another embodiment, in formula (XXX), $R_{43}$ and $R_{44}$ are, independently, selected from the group consisting of —H, methyl, ethyl, propyl, isopropyl, cyclopropyl, methoxy, ethoxy, propoxy, and cyclopropoxy.

In another embodiment, in formula (XXX), $X_{42}$ is $CR_{44}$; Y is $CR_{43}$; and $R_{43}$ and $R_{44}$ together with the carbon atoms to which they are attached form a cycloalkenyl, an aryl, heterocyclyl, or heteroaryl ring. In one aspect of this embodiment, $R_{43}$ and $R_{44}$ together with the carbon atoms to which they are attached form a $C_5$-$C_8$ cycloalkenyl or a $C_5$-$C_8$ aryl.

In another embodiment, in formula (XXX), $R_{45}$ is selected from the group consisting of —H, —OH, —SH, —$NH_2$, a lower alkoxy, a lower alkyl amino, and a lower dialkyl amino.

In another embodiment, in formula (XXX), $R_{45}$ is selected from the group consisting of —H, —OH, methoxy and ethoxy.

In another embodiment, in formula (XXX), $X_{41}$ is O.

In another embodiment, the compound is selected from the group consisting of:

3-(2,4-dihydroxy-5-ethyl-phenyl)-4-(2-methyl-7-methoxy-benzofuran-4-yl)-5-mercapto-[1,2,4]triazole, 3-(2,4-dihydroxy-5-ethyl-phenyl)-4-(benzofuran-5-yl)-5-mercapto-[1,2,4]triazole, 3-(2,4-dihydroxy-5-ethyl-phenyl)-4-(2-methyl-1,3-benzoxaz-5-yl)-5-mercapto-[1,2,4]triazole, and tautomers, pharmaceutically acceptable salts, solvates, clathrates, and prodrugs thereof.

In another embodiment, in formula (XXX), Z is —OH.

In another embodiment, the compound is selected from the group consisting of:

3-(2,4-dihydroxy-5-ethyl-phenyl)-4-(1,3-dimethyl-indol-5-yl)-5-hydroxy-[1,2,4]triazole, 3-(2,4-dihydroxy-5-isopropyl-phenyl)-4-(1,3-dimethyl-indol-5-yl)-5-hydroxy-[1,2,4]triazole, 3-(2,4-dihydroxy-5-isopropyl-phenyl)-4-(1-methyl-indol-5-yl)-5-hydroxy-[1,2,4]triazole, 3-(2,4-dihydroxy-5-isopropyl-phenyl)-4-(1-isopropyl-indol-4-yl)-5-hydroxy-[1,2,4]triazole, and tautomers, pharmaceutically acceptable salts, solvates, clathrates, and prodrugs thereof.

In another embodiment, Z is —SH.

In another embodiment, the compound is selected from the group consisting of:

3-(2,4-dihydroxy-5-isopropyl-phenyl)-4-(1-methyl-indazol-5-yl)-5-mercapto-[1,2,4]triazole, 3-(2,4-dihydroxy-5-isopropyl-phenyl)-4-(1-methyl-indazol-6-yl)-5-mercapto-[1,2,4]triazole, and tautomers, pharmaceutically acceptable salts, solvates, clathrates, and prodrugs thereof.

Compounds of formula (XXX) inhibit the activity of Hsp90 and are particularly useful for treating or preventing proliferative disorders, such as cancer. In addition, compounds of formula (XXX) are particularly useful in treating cancer when given in combination with other anti-cancer agent.

In another aspect, the invention provides compounds represented by formula (XXXI):

(XXXI)

and tautomers, pharmaceutically acceptable salts, solvates, clathrates, and prodrugs thereof, wherein:

$Z_1$ is —OH or —SH;

$X_{42}$, $R_{41}$, $R_{42}$, $R_{43}$, and $R_{45}$ are defined as above.

In one embodiment, in formula (XXXI), $Z_1$ is —OH.

In another embodiment, in formula (XXXI), $Z_1$ is —SH.

In another embodiment, in formula (XXXI), $R_{41}$ is selected from the group consisting of —H, lower alkyl, lower alkoxy, lower cycloalkyl, and lower cycloalkoxy.

In another embodiment, in formula (XXXI), $R_{41}$ is selected from the group consisting of —H, methyl, ethyl, propyl, isopropyl, cyclopropyl, methoxy, ethoxy, propoxy, and cyclopropoxy.

In another embodiment, in formula (XXXI), $R_{42}$ is selected from the group consisting of lower alkyl, lower cycloalkyl, —C(O)N($R_{27}$)$_2$, or —C(O)OH, wherein $R_{27}$, for each occurrence, is independently is —H or a lower alkyl.

In another embodiment, in formula (XXXI), $R_{42}$ is selected from the group consisting of —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, and —C(O)N(CH$_3$)$_2$.

In another embodiment, $R_{43}$ is H or a lower alkyl.

In another embodiment, in formula (XXXI), $X_{42}$ is $CR_{44}$, and $R_{43}$ and $R_{44}$ are, independently, selected from the group consisting of —H, methyl, ethyl, propyl, isopropyl, cyclopropyl, methoxy, ethoxy, propoxy, and cyclopropoxy.

In another embodiment, in formula (XXXI), $X_{42}$ is $CR_{44}$, and $R_{43}$ and $R_{44}$, taken together with the carbon atoms to which they are attached, form a cycloalkenyl, aryl, heterocyclyl, or heteroaryl ring. Preferably, in this embodiment, $R_{43}$ and $R_{44}$, taken together with the carbon atoms to which they are attached, form a $C_5$-$C_8$ cycloalkenyl or a $C_5$-$C_8$ aryl.

In another embodiment, in formula (XXXI), $R_{45}$ is selected from the group consisting of —H, —OH, —SH, —NH$_2$, a lower alkoxy, a lower alkyl amino, and a lower dialkyl amino.

In another embodiment, in formula (XXXI), $R_{45}$ is selected from the group consisting of —H, —OH, methoxy, and ethoxy.

In another embodiment, in formula (XXXI), $X_{43}$ is $CR_{44}$.

In another embodiment, the compound is selected from the group consisting of:

3-(2,4-dihydroxyphenyl)-4-(1-ethyl-indol-4-yl)-5-mercapto-[1,2,4]triazole, 3-(2,4-dihydroxyphenyl)-4-(1-isopropyl-indol-4-yl)-5-mercapto-[1,2,4]triazole, 3-(2,4-dihydroxyphenyl)-4-(indol-4-yl)-5-mercapto-[1,2,4]triazole, 3-(2,4-dihydroxyphenyl)-4-(1-methoxyethyl-indol-4-yl)-5-mercapto-[1,2,4]triazole, 3-(2,4-dihydroxy-5-ethyl-phenyl)-4-(1-isopropyl-indol-4-yl)-5-mercapto-[1,2,4]triazole, 3-(2,4-dihydroxyphenyl)-4-(1-dimethylcarbamoyl-indol-4-yl)-5-mercapto-[1,2,4]triazole, 3-(2,4-dihydroxy-5-ethyl-phenyl)-4-(1-propyl-indol-4-yl)-5-mercapto-[1,2,4]triazole, 3-(2,4-dihydroxy-5-ethyl-phenyl)-4-(1,2,3-trimethyl-indol-5-yl)-5-mercapto-[1,2,4]triazole, 3-(2,4-dihydroxy-5-ethyl-phenyl)-4-(2,3-dimethyl-indol-5-yl)-5-mercapto-[1,2,4]triazole, 3-(2,4-dihydroxy-5-ethyl-phenyl)-4-(1-acetyl-2,3-dimethyl-indol-5-yl)-5-mercapto-[1,2,4]triazole, 3-(2,4-dihydroxy-5-ethyl-phenyl)-4-(1-isopropyl-7-methoxy-indol-4-yl)-5-mercapto-[1,2,4]triazole, 3-(2,4-dihydroxy-5-ethyl-phenyl)-4-(1-propyl-2,3-dimethyl-indol-5-yl)-5-mercapto-[1,2,4]triazole, 3-(2,4-dihydroxy-5-ethyl-phenyl)-4-(N-methyl-tetrahydrocarbozol-7-yl)-5-mercapto-[1,2,4]triazole, 3-(2,4-dihydroxy-5-ethyl-phenyl)-4-(N-methyl-cyclononan[a]indol-5-yl)-5-mercapto-[1,2,4]triazole, 3-(2,4-dihydroxy-5-ethyl-phenyl)-4-(1-n-butyl-indol-4-yl)-5-mercapto-[1,2,4]triazole, 3-(2,4-dihydroxy-5-ethyl-phenyl)-4-(1-n-pentyl-indol-4-yl)-5-mercapto-[1,2,4]triazole, 3-(2,4-dihydroxy-5-ethyl-phenyl)-4-(1-n-hexyl-indol-4-yl)-5-mercapto-[1,2,4]triazole, 3-(2,4-dihydroxy-5-cyclopropyl-phenyl)-4-(1-(1-methylcyclopropyl)-indol-4-yl)-5-mercapto-[1,2,4]triazole, 3-(2,4-dihydroxy-5-cyclopropyl-phenyl)-4-(1-isopropyl-7-methoxy-indol-4-yl)-5-mercapto-[1,2,4]triazole, 3-(2,4-dihydroxy-5-cyclopropyl-phenyl)-4-(1,2,3-trimethyl-indol-5-yl)-5-mercapto-[1,2,4]triazole, 3-(2,4-dihydroxy-5-ethyl-phenyl)-4-(1-isopropyl-7-methoxy-indol-4-yl)-5-mercapto-[1,2,4]triazole disodium salt, 3-(2,4-dihydroxy-5-tert-butyl-phenyl)-4-(1-isopropyl-7-methoxy-indol-4-yl)-5-mercapto-[1,2,4]triazole, 3-(2,4-dihydroxy-5-cyclopropyl-phenyl)-4-(1-propyl-7-methoxy-indol-4-yl)-5-mercapto-[1,2,4]triazole, 3-(2,4-dihydroxy-5-ethyl-phenyl)-4-(1-methyl-3-ethyl-indol-5-yl)-5-mercapto-[1,2,4]triazole, 3-(2,4-dihydroxy-5-ethyl-phenyl)-4-(1,3-dimethyl-indol-5-yl)-5-mercapto-[1,2,4]triazole, 3-(2,4-dihydroxy-5-isopropyl-phenyl)-4-(1-isopropyl-7-methoxy-indol-4-yl)-5-mercapto-[1,2,4]triazole, 3-(2,4-dihydroxy-5-ethyl-phenyl)-4-(1-methyl-3-isopropyl-indol-5-yl)-5-mercapto-[1,2,4]triazole, 3-(2,4-dihydroxy-5-ethyl-phenyl)-4-(N-ethyl-carbozol-7-yl)-5-mercapto-[1,2,4]triazole, 3-(2,4-dihydroxy-5-ethyl-phenyl)-4-(1-isopropyl-7-hydroxy-indol-4-yl)-5-mercapto-[1,2,4]triazole, 3-(2,4-dihydroxy-5-ethyl-phenyl)-4-(1-isopropyl-7-ethoxy-indol-4-yl)-5-mercapto-[1,2,4]triazole, 3-(2,4-dihydroxy-5-ethyl-phenyl)-4-(1,2-dimethyl-indol-5-yl)-5-mercapto-[1,2,4]triazole, 3-(2,4-dihydroxy-5-ethyl-phenyl)-4-(N-methyl-indol-5-yl)-5-mercapto-[1,2,4]triazole,
3-(2,4-dihydroxy-5-isopropyl-phenyl)-4-(1,3-dimethyl-indol-5-yl)-5-mercapto-[1,2,4]triazole,
3-(2,4-dihydroxy-5-cyclopropyl-phenyl)-4-(1,3-dimethyl-indol-5-yl)-5-mercapto-[1,2,4]triazole,
3-(2,4-dihydroxy-5-cyclopropyl-phenyl)-4-(1-methyl-indol-5-yl)-5-mercapto-[1,2,4]triazole,
3-(2,4-dihydroxy-5-isopropyl-phenyl)-4-(1H-indol-5-yl)-5-mercapto-[1,2,4]triazole,
3-(2,4-dihydroxy-5-ethyl-phenyl)-4-(1,2-dimethyl-indol-5-yl)-5-mercapto-[1,2,4]triazole,
3-(2,4-dihydroxy-5-isopropyl-phenyl)-4-(1-ethyl-indol-5-yl)-5-mercapto-[1,2,4]triazole,
3-(2,4-dihydroxy-5-isopropyl-phenyl)-4-(1-propyl-indol-5-yl)-5-mercapto-[1,2,4]triazole, and tautomers, pharmaceutically acceptable salts, solvates, clathrates, and prodrugs thereof.

In another embodiment, in formula (XXXI), $X_{42}$ is N.

In another embodiment, the compound is selected from the group consisting of
3-(2,4-dihydroxy-5-ethyl-phenyl)-4-(1-ethyl-benzimidazol-4-yl)-5-mercapto-[1,2,4]triazole,
3-(2,4-dihydroxy-5-ethyl-phenyl)-4-(1-ethyl-benzimidazol-4-yl)-5-mercapto-[1,2,4]triazole HCL salt,
3-(2,4-dihydroxy-5-ethyl-phenyl)-4-(2-methyl-3-ethyl-benzimidazol-5-yl)-5-mercapto-[1,2,4]triazole,
3-(2,4-dihydroxy-5-ethyl-phenyl)-4-(1-ethyl-2-methyl-benzimidazol-5-yl)-5-mercapto-[1,2,4]triazole,
3-(2,4-dihydroxy-5-isopropyl-phenyl)-4-(1-methyl-2-trifluoromethyl-benzimidazol-5-yl)-5-mercapto-[1,2,4]triazole, and tautomers, pharmaceutically acceptable salts, solvates, clathrates, and prodrugs thereof.

Compounds of formula (XXXI) inhibit the activity of Hsp90 and are particularly useful for treating or preventing proliferative disorders, such as cancer. In addition, compounds of formula (XXXI) are particularly useful in treating cancer when given in combination with other anti-cancer agent.

In another aspect, the invention provides compounds represented by formula (XXXII):

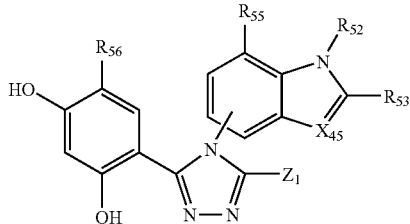

(XXXII)

and tautomers, pharmaceutically acceptable salts, solvates, clathrates, and prodrugs thereof, wherein:

$X_{45}$ is $CR_{54}$ or N;
$Z_1$ is —OH or —SH;
$R_{52}$ is selected from the group consisting of —H, methyl, ethyl, n-propyl, isopropyl, n-butyl, n-pentyl, n-hexyl, —(CH$_2$)$_2$OCH$_3$, —CH$_2$C(O)OH, and —C(O)N(CH$_3$)$_2$;
$R_{53}$ and $R_{54}$ are each, independently, —H, methyl, ethyl, or isopropyl; or $R_{53}$ and $R_{54}$ taken together with the carbon atoms to which they are attached form a phenyl, cyclohexenyl, or cyclooctenyl ring;
$R_{55}$ is selected from the group consisting of —H, —OH, —OCH$_3$, and —OCH$_2$CH$_3$; and
$R_{56}$ is selected from the group consisting of —H, methyl, ethyl, isopropyl, and cyclopropyl.

In one embodiment, in formula (XXXII), $Z_1$ is —OH.
In another embodiment, in formula (XXXII), $Z_1$ is —SH.
In another embodiment, in formula (XXXII), $R_{53}$ is H or a lower alkyl.
In another embodiment, in formula (XXXII), $X_{45}$ is $CR_{54}$. Preferably, $R_{54}$ is H or a lower alkyl.
In another embodiment, $X_{45}$ is N.

In another embodiment, the compound is 3-(2,4-dihydroxy-5-isopropyl-phenyl)-4-(N-methyl-indol-5-yl)-5-mercapto-[1,2,4]triazole.

Compounds of formula (XXXII) inhibit the activity of Hsp90 and are particularly useful for treating or preventing proliferative disorders, such as cancer. In addition, compounds of formula (XXXII) are particularly useful in treating cancer when given in combination with other anti-cancer agent.

In another aspect, the invention provides compounds represented by formula (XXXIII):

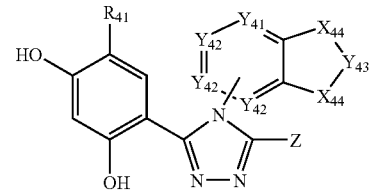

(XXXIII)

and tautomers, pharmaceutically acceptable salts, solvates, clathrates, and prodrugs thereof, wherein, $X_{44}$, for each occurrence, is independently, O, NR$_4$ or C(R$_{46}$)$_2$;
$Y_{43}$ is NR$_{42}$ or C(R$_{46}$)$_2$;
$Y_{41}$, $Y_{42}$, Z, $R_{41}$, $R_{42}$, and $R_{46}$ are defined as above.

In one embodiment, in formula (XXXIII), $R_{41}$ is selected from the group consisting of —H, lower alkyl, lower alkoxy, lower cycloalkyl, and lower cycloalkoxy.

In another embodiment, in formula (XXXIII), $R_{41}$ is selected from the group consisting of —H, methyl, ethyl, propyl, isopropyl, cyclopropyl, methoxy, ethoxy, propoxy, and cyclopropoxy.

In another embodiment, in formula (XXXIII), $R_{42}$ is selected from the group consisting of —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, and —C(O)N(CH$_3$)$_2$.

In another embodiment, in formula (XXXIII), $Y_{41}$ is $CR_{45}$. Preferably, $R_{45}$ is H, a lower alkoxy, or —OH.

In another embodiment, in formula (XXXIII), $Y_{42}$ is CH.
In another embodiment, in formula (XXXIII), $Y_{43}$ is CH$_2$.
In another embodiment, in formula (XXXIII), $Y_{43}$ is NR$_{42}$, wherein $R_{42}$ is H or a lower alkyl.

In another embodiment, in formula (XXXIII), one of $X_{44}$ is NR$_{42}$ and the other is CH$_2$ or C(R$_6$)$_2$. Preferably, one of $X_{44}$ is NR$_{42}$ and the other is CH$_2$.

In another embodiment, in formula (XXXIII), Z is —OH.
In another embodiment, Z is —SH.

Compounds of formula (XXXIII) inhibit the activity of Hsp90 and are particularly useful for treating or preventing proliferative disorders, such as cancer. In addition, compounds of formula (XXXIII) are particularly useful in treating cancer when given in combination with other anti-cancer agent.

In another aspect, the invention provides compounds represented by formula (XXXIV):

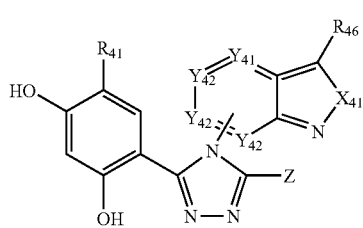

(XXXIV)

and tautomers, pharmaceutically acceptable salts, solvates, clathrates, and prodrugs thereof, wherein:

$X_{41}, Y_{41}, Y_{42}, Z, R_7, R_8, R_{10}, R_{11}, R_4, R_{46}$, and p are defined as above.

In one embodiment, in formula (XXXIV), $R_{41}$ is selected from the group consisting of —H, lower alkyl, lower alkoxy, lower cycloalkyl, and lower cycloalkoxy.

In another embodiment, in formula (XXXIV), $R_{41}$ is selected from the group consisting of —H, methyl, ethyl, propyl, isopropyl, cyclopropyl, methoxy, ethoxy, propoxy, and cyclopropoxy.

In another embodiment, in formula (XXXIV), $X_{41}$ is $NR_{42}$. Preferably, $R_{42}$ is selected from the group consisting of —H, methyl, ethyl, n-propyl, isopropyl, cyclopropyl, n-butyl, sec-butyl, tert-butyl, n-pentyl, n-hexyl, —C(O)OH, —$(CH_2)_m$C(O)OH, —$CH_2OCH_3$, —$CH_2CH_2OCH_3$, and —C(O)N$(CH_3)_2$. More preferably, $R_{42}$ is H or a lower alkyl.

In another embodiment, in formula (XXXIV), $X_{41}$ is O.

In another embodiment, in formula (XXXIV), $X_{41}$ is S.

In another embodiment, in formula (XXXIV), $Y_{41}$ is $CR_{45}$. Preferably, $R_{45}$ is H, a lower alkoxy, or —OH.

In another embodiment, in formula (XXXIV), $Y_{42}$ is CH.

In another embodiment, in formula (XXXIV), $R_{46}$ is H or a lower alkyl.

In one embodiment, the compound is 3-(2,4-dihydroxy-5-isopropyl-phenyl)-4-(2-methyl-indazol-6-yl)-5-mercapto-[1,2,4]triazole.

Compounds of formula (XXXIV) inhibit the activity of Hsp90 and are particularly useful for treating or preventing proliferative disorders, such as cancer. In addition, compounds of formula (XXXIV) are particularly useful in treating cancer when given in combination with other anti-cancer agent.

In one embodiment the present invention provides compounds having formula (I) as described above or a tautomer, pharmaceutically acceptable salt, solvate, clathrate or a prodrug thereof.

In another embodiment, the compounds of the present invention can be represented by structural formula (XXXV):

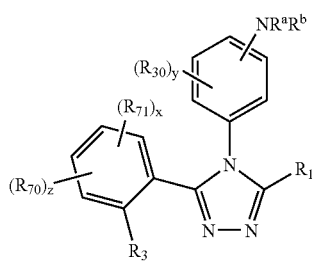

(XXXV)

or a tautomer, pharmaceutically acceptable salt, solvate, clathrate or a prodrug thereof.

In formula (XXXV), $R_1$ is —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NROR_{11}$, —$NR_7CH_2C(O)NR_{10}R_{11}$, —$OS(O)_pR_7$, —$SS(O)_pR_7$, —$S(O)_pOR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$OP(O)(OR_7)_2$, or —$SP(O)(OR_7)_2$. Preferably, $R_1$ is —OH, —SH, —$NHR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$, —$SC(S)OR_7$—$OC(S)NR_{10}R_{11}$, —$SC(S)NR_{10}R_{11}$, —$OC(NR_8)R_7$, —$SC(NR_8)R_7$, —$OC(NR_8)OR_7$, —$SC(NR_8)OR_7$, —$OP(O)(OR_7)_2$ or —$SP(O)(OR_7)_2$. More preferably, $R_1$ is —OH, —SH, or —$NHR_7$. Even more preferably, $R_1$, is —SH or —OH;

$R_3$ is —OH, —SH, —$NR_7H$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$S(O)_pOR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —C(O)OH, —$C(O)NHR_8$, —C(O)SH, —S(O)OH, —$S(O)_2OH$, —$S(O)NHR_8$, —$S(O)_2NHR_8$, —$OP(O)(OR_7)_2$, or —$SP(O)(OR_7)_2$. In another embodiment, —$OR_{26}$ and —$SR_{26}$, are additional values for $R_3$. Preferably, $R_3$ is —OH, —SH, —$NHR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$, —$SC(S)OR_7$, —$OC(S)NR_{10}R_{11}$, —$SC(S)NR_{10}R_{11}$, —$OC(NR_8)R_7$—$SC(NR_8)R_7$, —$OC(NR_8)OR_7$, —$SC(NR_8)OR_7$, —$OP(O)(OR_7)_2$ or —$SP(O)(OR_7)_2$. More preferably, $R_3$ is —OH, —SH, or —$NHR_7$. Even more preferably, $R_3$ is —SH or —OH;

$R_{70}$ for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$. Preferably, $R_{70}$ for each occurrence, is independently an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$. More preferably, $R_{70}$ for each occurrence, is independently a C1-C6 alkyl, a C1-C6 haloalkyl, a C1-C6 alkoxy, a C1-C6 haloalkoxy, a C1-C6 alkyl sulfanyl or a C3-C6 cycloalkyl. Even more preferably, $R_{70}$ for each occurrence, is independently cyclopropyl or isopropyl;

$R_7$ and $R_8$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl. Preferably, $R_7$ and $R_8$, for each occurrence, is independently —H, C1-C3 alkyl, C1-C6 cycloalkyl, an optionally substituted aryl or an optionally substituted heteroaryl. More preferably, $R_7$ and $R_8$, for each occurrence, is independently —H or C1-C3 alkyl.

$R_{10}$ and $R_{11}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl. Preferably, $R_{10}$ and $R_{11}$, for each occurrence, is independently —H, C1-C3 alkyl, C1-C6 cycloalkyl, an optionally substituted aryl or an optionally substituted heteroaryl. More preferably, $R_{10}$ and $R_{11}$, for each occurrence, is independently —H or C1-C3 alkyl.

Alternatively, $R_{10}$ and $R_{11}$, taken together with the nitrogen to which they are attached, form an optionally substituted heterocyclyl or an optionally substituted heteroaryl. Preferably $R_{10}$ and $R_{11}$, taken together with the nitrogen to which they are attached, form an optionally substituted imidazolyl, pyrrolyl, pyrazolyl, triazolyl, tetrazolyl, pyridinyl, pyrazinyl, pyrimidinyl, pyridazinyl, oxazolyl, iosoxazolyl, oxadiazolyl, thiazolyl, isothiazolyl, thiadiazolyl, pyrrolidinyl, piperidinyl, morpholinyl, pyrazinyl, thiomorpholinyl, pyrrolidinyl, piperidinyl, pyranzinyl, thiomorpholinyl, tetrahydroquinolinyl or tetrahydroisoquinolinyl. More preferably $R_{10}$ and $R_{11}$, taken together with the nitrogen to which they are attached, form an optionally substituted pyrrolidinyl, piperidinyl, piperazinyl, tetrahydroisoquinolinyl, morpholinyl or pyrazolyl.

$R_{71}$ for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$. Preferably $R_{71}$ for each occurrence, is independently —OH, —SH, —$NHR_7$, —$(CH_2)_kOH$, —$(CH_2)_kSH$, —$(CH_2)_kNR_7H$, —$OCH_3$, —$SCH_3$, —$NHCH_3$, —$OCH_2CH_2OH$, —$OCH_2CH_2SH$, —$OCH_2CH_2NR_7H$, $SCH_2CH_2OH$, —$SCH_2CH_2SH$, —$SCH_2CH_2NR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$. More preferably, $R_{71}$ for each occurrence, is independently —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$. Even more preferably, R$_7$) for each occurrence, is independently —SH or —OH;

R$_{26}$ is a C1-C6 alkyl;

R$_{30}$ for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_7$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$. Preferably R$_{30}$ for each occurrence, is independently an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —OR$_7$, —SR$_7$, —NR$_{10}$R$_{11}$, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, or —S(O)$_p$R$_7$. More preferably, R$_{30}$ for each occurrence, is independently a hydrogen, —OH, —SH, halogen, cyano, a C1-C6 alkyl, C1-C6 haloalkyl, C1-C6 alkoxy, C1-C6 haloalkoxy or C1-C6 alkyl sulfanyl. Even more preferably, R$_{30}$ for each occurrence, is independently a hydrogen, methyl, ethyl, propyl, isopropyl, methoxy or ethoxy;

R$_{35}$ is —H, a C1-C4 alkyl or a C1-C4 acyl;

R$^a$ and R$^b$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or heteroaryl, an optionally substituted aralkyl. Preferably, R$^a$ and R$^b$ for each occurrence, is independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl. More preferably, R$^a$ and R$^b$ for each occurrence, is independently a hydrogen, methyl, ethyl, propyl, isopropyl.

Alternatively, R$^a$ and R$^b$, taken together with the nitrogen to which they are attached, form an optionally substituted heteroaryl or heterocyclyl. Preferably, R$^a$ and R$^b$ taken together with the nitrogen to which they are attached form a substituted or unsubstituted nonaromatic, nitrogen-containing heterocyclyl. More preferably, R$^a$ and R$^b$ taken together with the nitrogen to which they are attached, are:

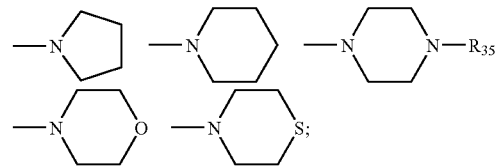

k is 1, 2, 3 or 4;

p, for each occurrence, is independently, 0, 1 or 2;

m, for each occurrence, is independently, 1, 2, 3 or 4;

z and y for each occurrence, is independently an integer from 0 to 4. Preferably z and y for each occurrence, is independently 0, 1, or 2. More preferably z and y for each occurrence, is independently 0 or 1; and x is 0 or 1, provided that z+x is less than or equal to 4.

In a first preferred embodiment, the values for the variables in formula (IV) are as described in the following paragraphs;

R$_{70}$, R$_{71}$ and R$_{30}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_7$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$. Preferably, R$_{70}$ and R$_{30}$ are as just described and R$_{71}$ is —OH, —SH, —NHR$_7$, —(CH$_2$)$_k$OH, —(CH$_2$)$_k$SH, —(CH$_2$)$_k$NR$_7$H, —OCH$_3$, —SCH$_3$, —NHCH$_3$, —OCH$_2$CH$_2$OH, —OCH$_2$CH$_2$SH, —OCH$_2$CH$_2$NR$_7$H, —SCH$_2$CH$_2$OH, —SCH$_2$CH$_2$SH, —SCH$_2$CH$_2$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, or —S(O)$_p$R$_7$;

k is 1, 2, 3, or 4;

z and y for each occurrence, is independently an integer from 0 to 4;

x is 0 or 1, provided that n+x less than or equal to 4; and the values and preferred values for the remainder of the variables in formula (IV) are as described immediately above.

In a second preferred embodiment, the present invention provides compounds represented by structural formula (XXXVI):

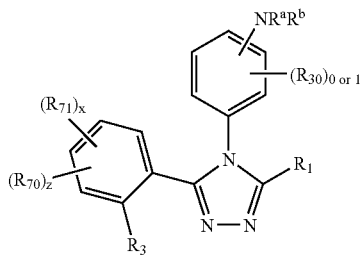

(XXXVI)

The values and preferred values for the variables in formula (XXXVI) are as described above for formula (XXXV). Alternatively, the values and preferred values for the variables in formula (XXXVI) are as described in the first preferred embodiment for formula (XXXV) immediately above.

In a third preferred embodiment, the present invention provides compounds represented by structural formula (XXXVII):

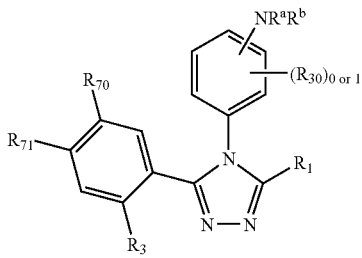

(XXXVII)

or a tautomer, pharmaceutically acceptable salt, solvate, clathrate or a prodrug thereof.

The values and preferred values for the variables in formula (XXXVII) are as described above for formula (XXXV). Preferably, the values and preferred values for the variables in formula (XXXVII) are as described for formula (XXXVI). More preferably, the values for the variables in formula (XXXVII) are described in the following paragraphs:

R$_{30}$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —OR$_7$, —SR$_7$, —NR$_{10}$R$_{11}$, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, or —S(O)$_p$R$_7$; and the values and preferred values for the remainder of the variables are as described above for formula (XXXV). Preferably, the values and preferred values for the variables in formula (XXXVII) are as described for formula (XXXVI).

More preferably for formula (XXXVII), R$_{70}$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —OR$_7$, —SR$_7$, —NR$_{10}$R$_{11}$, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, or —S(O)$_p$R$_7$; the values for R$_{30}$ are as described in the preceding paragraph; and the values and preferred values for the remainder of the variables are as described above for formula (XXXV). Preferably, the values and preferred values for the variables in formula (XXXVII) are as described for formula (XXXVI).

In a fourth preferred embodiment, the present invention provides compounds represented by a structural formula selected from formulas (XXXVIII) and (XXXIX)

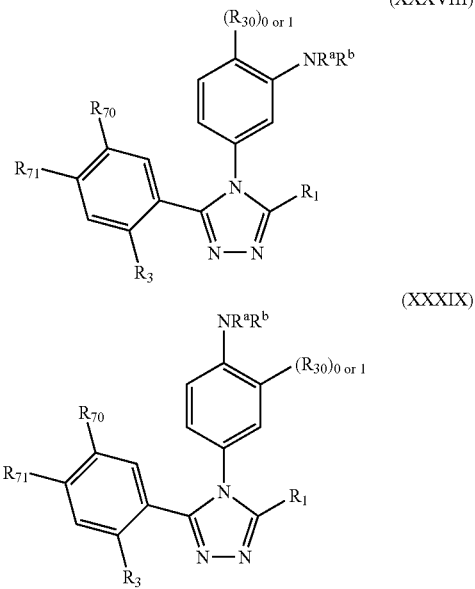

or a tautomer, pharmaceutically acceptable salt, solvate, clathrate or a prodrug thereof.

The values and preferred values for formulas (XXXVIII) and (XXXIX) are as described above for formula (XXXV). Preferably, the values and preferred values for formulas (XXXVIII) and (XXXIX) are as described above for formula (XXXVII). More preferably, the values for the variables in formulas (XXXVIII) and (XXXIX) are described in the following paragraphs:

$R_1$, $R_3$ or $R_{71}$, are each independently —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$. Preferably, $R_1$ and $R_3$ are each, independently, —OH, —SH, or —NHR$_7$ and $R_{71}$ is as just described; and the values and preferred values for the remainder of the variables are as described above for formula (XXXV) or formula (XXXVII).

In a first more preferred embodiment for formulas (XXXVIII) and (XXXIX), $R_1$, $R_3$ and $R_{71}$ are as described in the immediately preceeding two paragraphs: and $R^a$ and $R^b$ are each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or $R^a$ and $R^b$ taken together with the nitrogen to which they are attached form a substituted or unsubstituted nonaromatic, nitrogen-containing heterocyclyl; and the values and preferred values for the remainder of the variables are as described above for formula (XXXVII).

In a second more preferred embodiment for formulas (XXXVIII) and (XXXIX), $R_{70}$ is a C1-C6 alkyl, a C1-C6 haloalkyl, a C1-C6 alkoxy, a C1-C6 haloalkoxy, a C1-C6 alkyl sulfanyl or a C3-C6 cycloalkyl; and the values and preferred values for the remainder of the variables are as described above for first more preferred embodiment for formulas (XXXVIII) and (XXXIX).

In a third more preferred embodiment for formulas (XXXVIII) and (XXXIX):

$R_1$ and $R_3$ are each, independently, —OH, —SH, or —NHR$_7$;

$R_{70}$ is a C1-C6 alkyl, a C1-C6 haloalkyl, a C1-C6 alkoxy, a C1-C6 haloalkoxy, a C1-C6 alkyl sulfanyl or a C3-C6 cycloalkyl;

$R_{71}$ is —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$;

$R_{30}$ is —OH, —SH, halogen, cyano, a C1-C6 alkyl, C1-C6 haloalkyl, C1-C6 alkoxy, C1-C6 haloalkoxy or C1-C6 alkyl sulfanyl. Preferably, $R_{30}$ is methyl, ethyl, propyl, isopropyl, methoxy or ethoxy;

$R^a$ and $R^b$ are each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or $R^a$ and $R^b$ taken together with the nitrogen to which they are attached form a substituted or unsubstituted nonaromatic, nitrogen-containing heterocyclyl; and the values and preferred values for the remainder of the variables are as described above for formula (XXXVII).

In a fourth more preferred embodiment for formulas (XXXVIII) and (XXXIX):

$R_1$, $R_3$ and $R_{71}$ for each occurance, is independently —SH or —OH;

$R_{70}$ is cyclopropyl or isopropyl; and the remainder of the variables are as described for the third more preferred embodiment for formulas (XXXVIII) and (XXXIX). More preferably $R_{30}$ is methyl, ethyl, propyl, isopropyl, methoxy or ethoxy. Even more preferably, $R_{30}$ is methyl, ethyl, propyl, isopropyl, methoxy or ethoxy and $R^a$ and $R^b$ are each independently a hydrogen, methyl, ethyl, propyl, isopropyl, or taken together with the nitrogen to which they are attached, are:

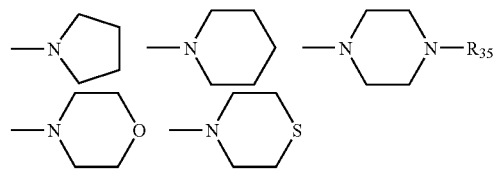

wherein $R_{35}$ is —H, a C1-C4 alkyl or a C1-C4 acyl; and the values and preferred values for the remainder of the variables are as described above for formula (XXXVII).

In another preferred embodiment, the present invention is a compound represented by formula (XXXV), (XXXVI), (XXXVII), (XXXVIII) or (XXXIX), wherein $R_1$, $R_3$ and $R_{71}$ are —SH or —OH and $R_6$ is cyclopropyl or isopropyl and the remainder of the variables are as described for Formula (XXXV), (XXXVI), (XXXVII), (XXXVIII) or (XXXIX), respectively.

In another embodiment, the present invention provides compounds represented by a structural formula selected from formulas (XL) and (XLI):

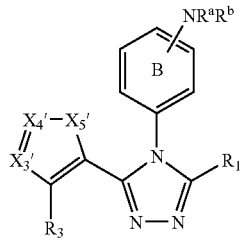
(XL)

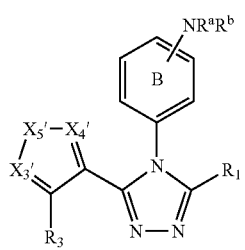
(XLI)

or a tautomer, pharmaceutically acceptable salt, solvate, clathrate or a prodrug thereof.

In formulas (XL) and (XLI), ring B is further optionally substituted with one or more substituents in addition to —$NR^aR^b$. Preferably ring B is substituted with $(R_{30})_y$, where y is 0, 1, 2, 3 or 4, preferably y is 0 or 1;

$R_1$ is —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$S(O)_pOR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, $SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, or —$NR_7C(NR_8)NR_{10}R_{11}$, —$OP(O)(OR_7)_2$ or —$SP(O)(OR_7)_2$. Preferably, $R_1$ is —OH, —SH, —$HNR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$—$SC(S)OR_7$—$OC(S)NR_{10}R_{11}$, —$SC(S)NR_{10}R_{11}$, —$OC(NR_8)R_7$, —$SC(NR_8)R_7$—$OC(NR_8)OR_7$, —$SC(NR_8)OR_7$, —$OP(O)(OR_7)_2$ or —$SP(O)(OR_7)_2$. More preferably, $R_1$ is —OH, —SH, or —$NHR_7$. Even more preferably, $R_1$ is —SH or —OH;

$R_3$ is —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$S(O)_pOR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, $SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)OH$, —$C(O)NHR_8$, —$C(O)SH$, —$S(O)OH$, —$S(O)_2OH$, —$S(O)NHR_8$, —$S(O)_2NHR_8$, —$OP(O)(OR_7)_2$, or —$SP(O)(OR_7)_2$. Preferably, $R_3$ is —OH, —SH, —$HNR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$, —$SC(S)OR_7$—$OC(S)NR_{10}R_{11}$, —$SC(S)NR_{10}R_{11}$, —$OC(NR_8)R_7$, —$SC(NR_8)R_7$, —$OC(NR_8)OR_7$, —$SC(NR_8)OR_7$, —$OP(O)(OR_7)_2$ or —$SP(O)(OR_7)_2$. More preferably, $R_3$ is —OH, —SH, or —$NHR_7$. Even more preferably, $R_3$ is —SH or —OH;

$R_{70}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7(O)_pNR_{10}R_{11}$, —$NR_7S(O)_pOR_7$, —$S(O)_pNR_{10}R_{11}$, —$SS(O)_pR_7$, —$SS(O)_pOR_7$ or —$SS(O)_pNR_{10}R_{11}$. Preferably, $R_{70}$ is for each occurrence, is independently an optionally substituted C1-C6 alkyl, an optionally substituted C3-C6 cycloalkyl, an optionally substituted C3-C6 cycloalkenyl, an optionally substituted heterocyclyl, a halo, a haloalkyl, a haloalkoxy, a heteroalkyl, an alkoxy, an alkylsulfanyl, —OH, —SH, —$NHR_7$, —$(CH_2)_kOH$, —$(CH_2)_kSH$, —$(CH_2)_kNR_7H$, —$OCH_3$, —$SCH_3$, —$NHCH_3$, —$OCH_2CH_2OH$, —$OCH_2CH_2SH$, —$OCH_2CH_2NR_7H$, —$SCH_2CH_2OH$, —$SCH_2CH_2SH$, —$SCH_2CH_2NR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, —S(O)$_p$R$_7$, —OP(O)(OR$_7$)$_2$ or —SP(O)(OR$_7$)$_2$. More preferably, R$_{70}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, —OH, —SH, —HNR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$. Even more preferably, R$_{70}$ is for each occurrence, is independently a C1-C6 alkyl, a C1-C6 haloalkyl, a C1-C6 alkoxy, a C1-C6 haloalkoxy, a C1-C6 alkyl sulfanyl or a C3-C6 cycloalkyl. Still more preferably, R$_{70}$ for each occurrence, is independently a cyclopropyl or isopropyl;

R$_7$ and R$_8$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl. Preferably, R$_7$ and R$_8$, for each occurrence, is independently —H, C1-C3 alkyl, C1-C6 cycloalkyl, an optionally substituted aryl or an optionally substituted heteroaryl. More preferably, R$_7$ and R$_8$, for each occurrence, is independently —H or C1-C3 alkyl;

R$_{10}$ and R$_{11}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl. Preferably, R$_{10}$ and R$_{11}$, for each occurrence, is independently —H, C1-C3 alkyl, C1-C6 cycloalkyl, an optionally substituted aryl or an optionally substituted heteroaryl. More preferably, R$_{10}$ and R$_{11}$, for each occurrence, is independently —H or C1-C3 alkyl;

alternatively, R$_{10}$ and R$_{11}$, taken together with the nitrogen to which they are attached, form an optionally substituted heterocyclyl or an optionally substituted heteroaryl. Preferably R$_{10}$ and R$_{11}$, taken together with the nitrogen to which they are attached, form an optionally substituted imidazolyl, pyrrolyl, pyrazolyl, triazolyl, tetrazolyl, pyridinyl, pyrazinyl, pyrimidinyl, pyridazinyl, oxazolyl, iosoxazolyl, oxadiazolyl, thiazolyl, isothiazolyl, thiadiazolyl, pyrrolidinyl, piperidinyl, morpholinyl, pyrazinyl, thiomorpholinyl, pyrrolidinyl, piperidinyl, pyranzinyl, thiomorpholinyl, tetrahydroquinolinyl or tetrahydroisoquinolinyl. More preferably R$_{10}$ and R$_{11}$, taken together with the nitrogen to which they are attached, form an optionally substituted pyrrolidinyl, piperidinyl, piperazinyl, tetrahydroisoquinolinyl, morpholinyl or pyrazolyl;

R$_{17}$, for each occurrence, is independently an alkyl or an aralkyl. Preferably R$_{17}$ for each occurrence is independently a C1-C6 alkyl;

R$_{26}$ is a C1-C6 alkyl;

R$_{30}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanadino, a haloalkyl, a heteroalkyl, alkoxy, haloalkoxy, —H, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$^{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, or —SS(O)$_p$NR$_{10}$R$_{11}$. Preferably R$_{30}$ for each occurrence, is independently an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —OR$_7$, —SR$_7$, —NR$_{10}$R$_{11}$, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$ or —S(O)$_p$R$_7$. More preferably, R$_{30}$ for each occurrence, is independently a hydrogen, —OH, —SH, halogen, cyano, a C1-C6 alkyl, C1-C6 haloalkyl, C1-C6 alkoxy, C1-C6 haloalkoxy or C1-C6 alkyl sulfanyl. Even more preferably, R$_{30}$ for each occurrence, is independently a hydrogen, methyl, ethyl, propyl, isopropyl, methoxy or ethoxy;

R$^a$ and R$^b$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or heteroaryl, an optionally substituted aralkyl. Preferably, R$^a$ and R$^b$ for each occurrence, is independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl. More preferably, R$^a$ and R$^b$ for each occurrence, is independently a hydrogen, methyl, ethyl, propyl, isopropyl;

Alternatively, R$^a$ and R$^b$, taken together with the nitrogen to which they are attached, form an optionally substituted heteroaryl or heterocyclyl. Preferably, R$^a$ and R$^b$ taken together with the nitrogen to which they are attached form a substituted or unsubstituted nonaromatic, nitrogen-containing heterocyclyl. More preferably, $R^a$ and $R^b$ taken together with the nitrogen to which they are attached, are:

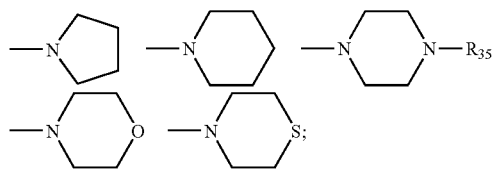

$X_3'$ and $X_4'$ are each, independently, N, N(O), N$^+$(R$_{17}$), CH or CR$_{70}$;

$X_5'$ is O, S, NR$_{17}$, CH$_2$, CH(R$_{70}$), C(R$_{70}$)$_2$, CH=CH, CH=CR$_{70}$, CR$_{70}$=CH, CR$_{70}$=CR$_{70}$, CH=N, CR$_{70}$=N, CH=N(O), CR$_{70}$=N(O), N=CH, N=CR$_{70}$, N(O)=CH, N(O)=CR$_{70}$, N$^+$(R$_{17}$)=CH, N$^+$(R$_{17}$)=CR$_{70}$, CH=N$^+$(R$_{17}$), CR$_{70}$=N$^+$(R$_{17}$), or N=N, provided that at least one $X_3'$, $X_4'$ or $X_5'$ is a heteroatom;

k is 1, 2, 3, or 4;

p, for each occurrence, is independently, 0, 1 or 2; and m, for each occurrence, is independently, 1, 2, 3, or 4.

In a fifth preferred embodiment, the present invention provides a compound represented by a structural formula selected from formulas (XLII) and (XLIII):

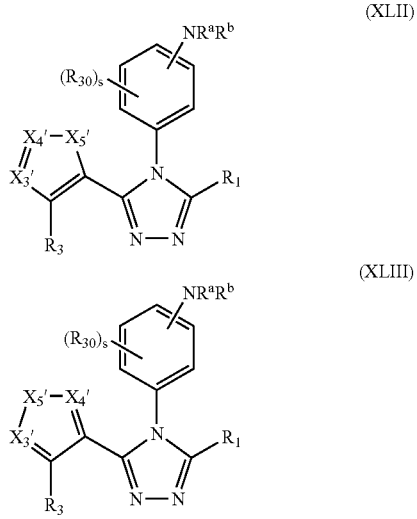

or a tautomer, pharmaceutically acceptable salt, solvate, clathrate or a prodrug thereof.

Preferably the values and preferred values for formulas (XLII) and (XLIII) are as described above for formulas (XL) and (XLI), and more preferably:

$R_{70}$ is for each occurrence, is independently an optionally substituted C1-C6 alkyl, an optionally substituted C3-C6 cycloalkyl, an optionally substituted C3-C6 cycloalkenyl, an optionally substituted heterocyclyl, a halo, a haloalkyl, a haloalkoxy, a heteroalkyl, an alkoxy, an alkylsulfanyl, —OH, —SH, —NHR$_7$, —(CH$_2$)$_k$OH, —(CH$_2$)$_k$SH, —(CH$_2$)$_k$NR$_7$H, —OCH$_3$, —SCH$_3$, —NHCH$_3$, —OCH$_2$CH$_2$OH, —OCH$_2$CH$_2$SH, —OCH$_2$CH$_2$NR$_7$H, —SCH$_2$CH$_2$OH, —SCH$_2$CH$_2$SH, —SCH$_2$CH$_2$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, —S(O)$_p$R$_7$, —OP(O)(OR$_7$)$_2$ or —SP(O)(OR$_7$)$_2$;

$R_{30}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$R$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$ or —SS(O)$_p$NR$_{10}$R$_{11}$;

s is 0, 1, 2, 3 or 4;

k is 1, 2, 3, or 4; and the values and preferred values for the remainder of the variables are as described above for formulas (XL) and (XLI).

In a sixth preferred embodiment, the present invention provides a compound represented by a structural formula selected from formulas (XLIV) and (XLV):

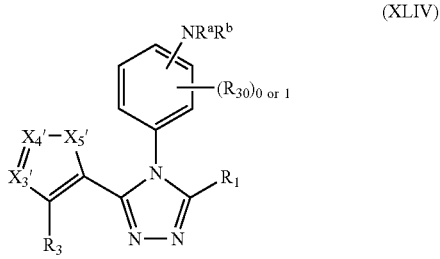

-continued (XLV)

or a tautomer, pharmaceutically acceptable salt, solvate, clathrate or a prodrug thereof.

The values and preferred values for formulas (XLIV) and (XLV) are as described above for formulas (XL) and (XLI). Preferably the values and preferred values for formulas (XLIV) and (XLV) are as described for formulas (XLII) and (XLIII). More preferably, the values for formulas (XLIV) and (XLV) are described in the following paragraphs:

$R_{30}$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$; and the values and preferred values for the remainder of the variables are as described above for formulas (XLIV) and (XLV) are as described above for formulas (XL) and (XLI). Preferably the values and preferred values for the remainder of the variables in formulas (XLIV) and (XLV) are as described for formulas (XLII) and (XLIII).

In a seventh more preferred embodiment, the present invention provides a compound represented by a structural formula selected from formulas (XLVI)-(XLIX):

(XLVI)

(XLVII)

(XLVIII)

(XLIX)

or a tautomer, pharmaceutically acceptable salt, solvate, clathrate or a prodrug thereof.

The values and preferred values for formulas (XLVI)-(XLIX) are as described above for formulas (XL) and (XLI). Preferably the values and preferred values for formulas (XLVI)-(XLIX) are as described above for formulas (XLIV) and (XLV). More preferably, the values for formulas (XLVI)-(XLIX) are provided below in the following paragraphs:

$R_1$ and $R_3$ are each independently —OH, —SH, —$HNR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$—$OC(S)OR_7$, —$SC(S)OR_7$—$OC(S)NR_{10}R_{11}$, —$SC(S)NR_{10}R_{11}$, —$OC(NR_8)R_7$, —$SC(NR_8)R_7$, —$OC(NR_8)OR_7$, —$SC(NR_8)OR_7$, —$OP(O)(OR_7)_2$ or —$SP(O)(OR_7)_2$; and $R_{70}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, —OH, —SH, —$HNR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$, —$SC(S)OR_7$, —$OC(S)NR_{10}R_{11}$, —$SC(S)NR_{10}R_{11}$, —$OC(NR_8)R_7$, —$SC(NR_8)R_7$, —$OC(NR_8)OR_7$, —$SC(NR_8)OR_7$, —$OP(O)(OR_7)_2$ or —$SP(O)(OR_7)_2$; and the values and preferred values for the remainder of the variables are as described for formulas (XLIV) and (XLV).

Still more preferably for formulas (XLVI)-(XLIX), $R_1$, $R_3$ and $R_{70}$ are as described in the immediately preceeding paragraphs; and $R^a$ and $R^b$ are each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or $R^a$ and $R^b$ taken together with the nitrogen to which they are attached form a substituted or unsubstituted nonaromatic, nitrogen-containing heterocyclyl; and the values and preferred values for the remainder of the variables are as described for formulas (XLIV) and (XLV).

Still more preferably for formulas (XLVI)-(XLIX), $R_1$, $R_3$, $R_6$, $R^a$ and $R^b$ are as described in the immediately preceeding paragraphs; and $R_{70}$ is a C1-C6 alkyl, a C1-C6 haloalkyl, a C1-C6 alkoxy, a C1-C6 haloalkoxy, a C1-C6 alkyl sulfanyl or a C3-C6 cycloalkyl; and the values and preferred values for the remainder of the variables are as described above for formulas (XL) and (XLI). More preferably, the values and preferred values for the remainder of the variables are as described above for formulas (XLIV) and (XLV).

In an eighth preferred embodiment, the present invention provides a compound represented by a structural formula selected from formulas (La)-(Lp):

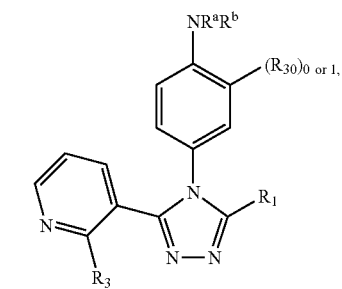
(La)

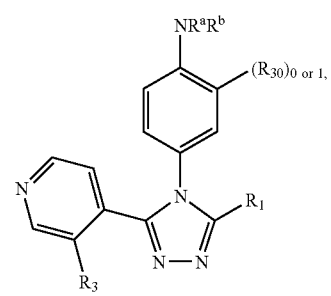
(Lb)

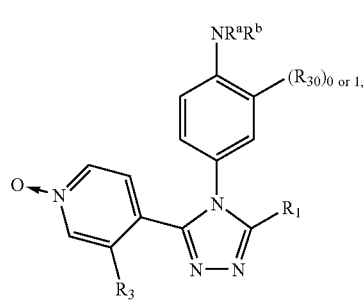
(Lc)

-continued

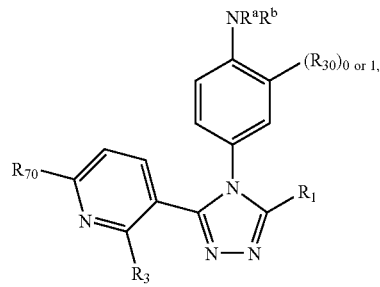
(Ld)

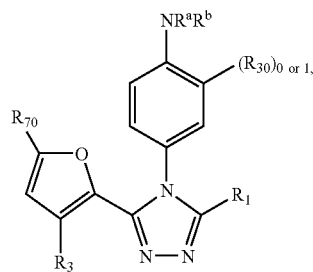
(Le)

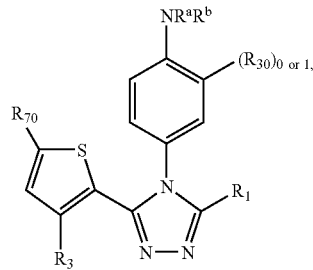
(Lf)

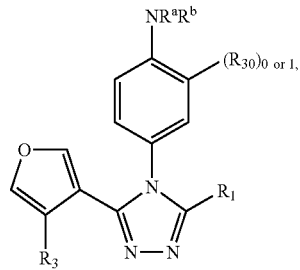
(Lg)

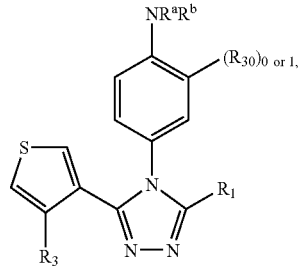
(Lh)

-continued

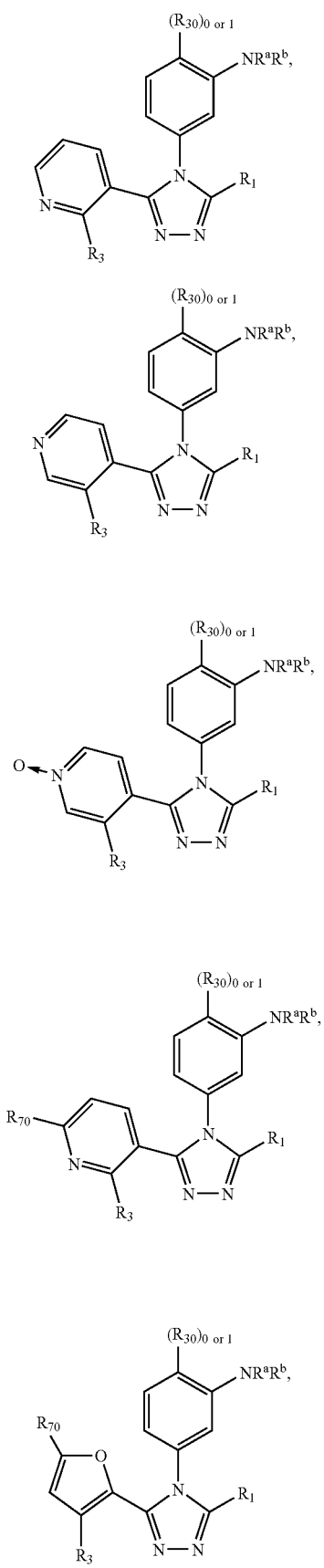

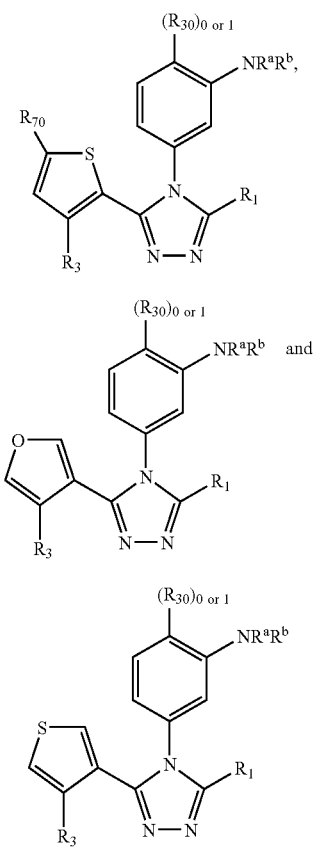

or a tautomer, pharmaceutically acceptable salt, solvate, clathrate or a prodrug thereof.

The values and preferred values for formulas (La) through (Lp) are as described above for formulas (XL) and (XLI). Preferably the values and preferred values for formulas (La)-(Lp) are as described for formulas (XLVI)-(XLIX). More preferably, $R_1$ and $R_3$ are each, independently, —OH, —SH, or —NHR$_7$. Even more preferable, $R_1$ and $R_3$ are each, independently, —OH, —SH, or —NHR$_7$; and $R_{30}$ is —OH, —SH, halogen, cyano, a C1-C6 alkyl, $C_1$-$C_6$ haloalkyl, C1-C6 alkoxy, C1-C6 haloalkoxy or C1-C6 alkyl sulfanyl (preferably methyl, ethyl, propyl, isopropyl, methoxy or ethoxy). Even more preferably, $R_1$ and $R_3$ for each occurrence, is independently —SH or —OH; $R_{70}$ is cyclopropyl or isopropyl; and $R_{30}$ is —OH, —SH, halogen, cyano, a C1-C6 alkyl, C1-C6 haloalkyl, C1-C6 alkoxy, C1-C6 haloalkoxy or C1-C6 alkyl sulfanyl (preferably methyl, ethyl, propyl, isopropyl, methoxy or ethoxy). Even more preferably yet, $R_1$, $R_3$, $R_{70}$ and $R_{30}$ are as just described and $R^a$ and $R^b$ are each independently a hydrogen, methyl, ethyl, propyl, isopropyl, or taken together with the nitrogen to which they are attached, are:

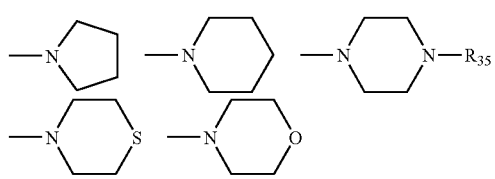

$R_{35}$ is —H, a C1-C4 alkyl or a C1-C4 acyl; and
the values and preferred values for the remainder of the variables are as defined for formulas (XLVI)-(XLIX).

In another embodiment the compounds of the present invention are represented by a structural formula selected from formulas (LIa) and (LIb):

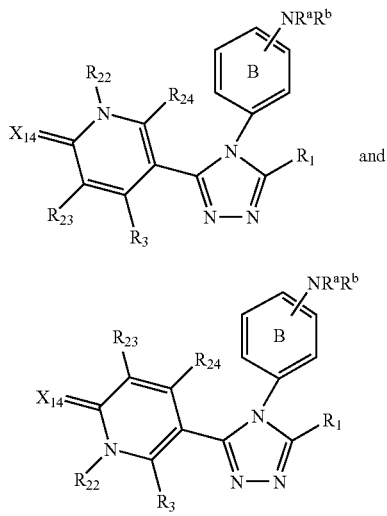

or a tautomer, pharmaceutically acceptable salt, solvate, clathrate or a prodrug thereof.

In formulas (LIa) and (LIb), ring B is further optionally substituted with one or more substituents in addition to —NR$^a$R$^b$. Preferably ring B is further substituted with (R$_{30}$)$_s$ where s is 0, 1, 2, 3 or 4, preferably s is 0 or 1;

R$_1$ is —OH, —SH, —NR$_7$H, —OR$_{26}$, —SR$_{26}$, —NHR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{15}$, —OP(O)(OR$_7$)$_2$ or —SP(O)(OR$_7$)$_2$. Preferably, R$_1$ is —OH, —SH, —HNR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$—OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$. More preferably, R$_1$ is —OH, —SH, or —NHR$_7$. Even more preferably, R$_1$ is —SH or —OH;

R$_3$ is —OH, —SH, —NR$_7$H, —OR$_{26}$, —SR$_{26}$, —NHR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{13}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)OH, —C(O)NHR$_8$, —C(O)SH, —S(O)OH, —S(O)$_2$OH, —S(O)NHR$_8$, —S(O)$_2$NHR$_8$, —OP(O)(OR$_7$)$_2$, or —SP(O)(OR$_7$)$_2$. Preferably, R$_3$ is —OH, —SH, —HNR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$. More preferably, R$_3$ is —OH, —SH, or —NHR$_7$. Even more preferably, R$_3$ is —SH or —OH;

R$_7$ and R$_8$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl. Preferably, R$_7$ and R$_8$, for each occurrence, is independently —H, C1-C3 alkyl, C1-C6 cycloalkyl, an optionally substituted aryl or an optionally substituted heteroaryl. More preferably, R$_7$ and R$_8$, for each occurrence, is independently —H or C1-C3 alkyl;

R$_{10}$ and R$_{11}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl. Preferably, R$_{10}$ and R$_{11}$, for each occurrence, is independently —H, C1-C3 alkyl, C1-C6 cycloalkyl, an optionally substituted aryl or an optionally substituted heteroaryl. More preferably, R$_{10}$ and R$_{11}$, for each occurrence, is independently —H or C1-C3 alkyl;

Alternatively, R$_{10}$ and R$_{11}$, taken together with the nitrogen to which they are attached, form an optionally substituted heterocyclyl or an optionally substituted heteroaryl. Preferably R$_{10}$ and R$_{11}$, taken together with the nitrogen to which they are attached, form an optionally substituted imidazolyl, pyrrolyl, pyrazolyl, triazolyl, tetrazolyl, pyridinyl, pyrazinyl, pyrimidinyl, pyridazinyl, oxazolyl, iosoxazolyl, oxadiazolyl, thiazolyl, isothiazolyl, thiadiazolyl, pyrrolidinyl, piperidinyl, morpholinyl, pyrazinyl, thiomorpholinyl, pyrrolidinyl, piperidinyl, pyranzinyl, thiomorpholinyl, tetrahydroquinolinyl or tetrahydroisoquinolinyl. More preferably R$_{10}$ and R$_{11}$, taken together with the nitrogen to which they are attached, form an optionally substituted pyrrolidinyl, piperidinyl, piperazinyl, tetrahydroisoquinolinyl, morpholinyl or pyrazolyl;

R$_{22}$, for each occurrence, is independently —H, an optionally substituted alky, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl, a haloalkyl, —C(O)R$_7$, —C(O)OR$_7$, —OC(O)R$_7$, —C(O)NR$_{10}$R$_{11}$, —NR$_8$C(O)R$_7$, —S(O)$_p$R$_7$, —S(O)$_p$OR$_7$, or —S(O)$_p$NR$_{10}$R$_{11}$. Preferably, R$_{22}$ is —H, an alkyl, an aralkyl, —C(O)R$_7$, —C(O)OR$_7$, or —C(O)NR$_{10}$R$_{11}$;

R$_{23}$ and R$_{24}$, for each occurrence, is independently —H, an optionally substituted alky, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl, halo, cyano, nitro, guanadino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$. Preferably, R$_{23}$ and R$_{24}$ for each occurrence is independently —H;

R$_{26}$ is a C1-C6 alkyl;

R$^a$ and R$^b$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or heteroaryl, an optionally substituted aralkyl. Preferably, R$^a$ and R$^b$ for each occurrence, is independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl. More preferably, R$^a$ and R$^b$ for each occurrence, is independently a hydrogen, methyl, ethyl, propyl or isopropyl;

Alternatively, R$^a$ and R$^b$, taken together with the nitrogen to which they are attached, form an optionally substituted heteroaryl or heterocyclyl. Preferably, R$^a$ and R$^b$ taken together with the nitrogen to which they are attached form a substituted or unsubstituted nonaromatic, nitrogen-containing heterocyclyl. More preferably, R$^a$ and R$^b$ taken together with the nitrogen to which they are attached, are:

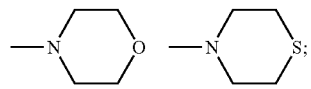

X$_{14}$ is O, S, or NR$_7$. Preferably, X$_{14}$ is O;

p, for each occurrence, is independently, 0, 1 or 2; and m, for each occurrence, is independently, 1, 2, 3, or 4.

Preferably for the compound represented by formulas (LIa) and (LIb), R$_1$ is —OH, —SH, or —NHR$_7$; and R$_{22}$ is —H, an alkyl, an aralkyl, —C(O)R$_7$, —C(O)OR$_7$, or —C(O)NR$_{10}$R$_{11}$. More preferably, R$_1$ is —OH, —SH, or —NHR$_7$; R$_{22}$ is —H, an alkyl, an aralkyl, —C(O)R$_7$, —C(O)OR$_7$, or —C(O)NR$_{10}$R$_{11}$; and X$_{14}$ is O. The values and preferred values for the remainder of the variables are as described above.

In one embodiment, a compound of the present invention is represented by the structural formulas (VI)-(VIII):

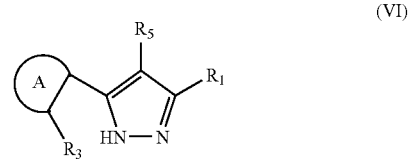

(VI)

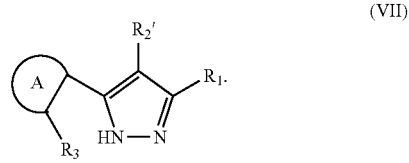

(VII)

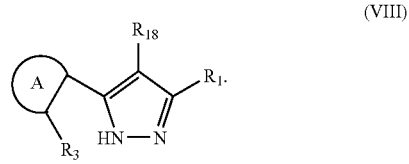

(VIII)

In formulas (VI-VIII):

ring A is an aryl or a heteroaryl, optionally further substituted with one or more substituents in addition to R$_3$. Preferably, Ring A is represented one of the following structural formulas:

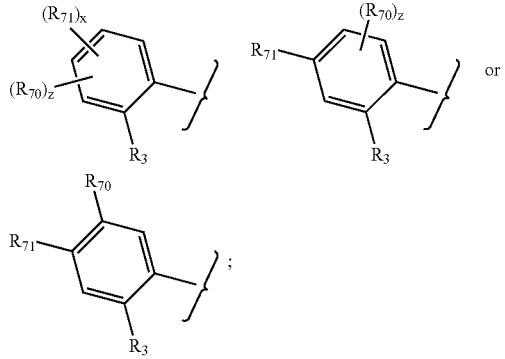

where z is 0, 1, 2, 3 or 4; x is 0 or 1; and z+x is less than or equal to 4.

R$_1$ is —OH, —SH, —NR$_7$H, —OR$_{26}$, —SR$_{26}$, —NHR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP $O)(OR_7)_2$. Preferably, $R_1$ is —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$—SC(O)OR$_7$, —OS(O)$_p$R$_7$, —S(O)$_p$OR$_7$, —SS(O)$_p$R$_7$, —OS(O)$_p$OR$_7$—SS(O)$_p$OR$_7$, —SS(O)$_p$SR$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$. More preferably, $R_1$ is —OH, —SH, or —NHR$_7$. Even more preferably, $R_1$, is —SH or —OH;

$R_2'$ is an optionally substituted phenyl group. Preferably, $R_2'$ is substituted with one or more group represented by $R_{30}$, wherein $R_{30}$, for each occurrence, are independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$. More preferably, $R_2'$ is an optionally substituted indolyl group or a phenyl group substituted with NR$_{10}$R$_{11}$, and optionally with at least one other substitutent represented by $R_{30}$;

$R_3$ is —OH, —SH, —NR$_7$H, —NHR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)OH, —C(O)NHR$_8$, —C(O)SH, —S(O)OH, —S(O)$_2$OH, —S(O)NHR$_8$, —S(O)$_2$NHR$_8$, —OP(O)(OR$_7$)$_2$, or —SP(O)(OR$_7$)$_2$. In another embodiment, —OR$_{26}$ and —SR$_{26}$, are additional values for $R_3$. Preferably, $R_3$ is —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$—SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$. More preferably, $R_3$ is —OH, —SH, or —NHR$_7$. Even more preferably, $R_3$ is —SH or —OH;

$R_5$ is an optionally substituted heteroaryl; an optionally substituted 6 to 14-membered aryl.

$R_{70}$, for each occurrence, is independently, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, an alkoxy or cycloalkoxy, a haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$R$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$. Preferably, $R_{70}$ is selected from the group consisting of —H, C1-C6 alkyl, C1-C6 alkoxy, C1-C6 cycloalkyl, and C1-C6 cycloalkoxy, more preferably from the group consisting of —H, methyl, ethyl, propyl, isopropyl, cyclopropyl, methoxy, ethoxy, propoxy, and cyclopropoxy.

$R_{71}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$.

$R_7$ and $R_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{10}$ and $R_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{18}$ is an optionally substituted cycloalkyl, and optionally substituted cycloalkenyl, or a substituted alkyl, wherein the alkyl group is substituted with one or more substituents independently selected from the group consisting of an optionally substituted alkynyl, an optionally substituted cycloalkyl, an optionally substituted cycloalkenyl, an optionally substituted heteroaryl, an optionally substituted aralkyl, an optionally substituted heteraralkyl, halo, cyano, nitro, guanadino, a haloalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$;

$R_{26}$ is a lower alkyl;

p, for each occurrence, is, independently, 0, 1 or 2; and m, for each occurrence, is independently, 1, 2, 3, or 4.

$R_5$ in structural formula (VI) is preferably represented by the following structural formula:

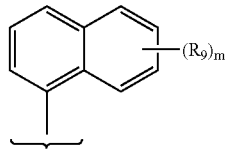

wherein:

$R_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$; or two $R_9$ groups taken together with the carbon atoms to which they are attached form a fused ring; and m is zero or an integer from 1 to 7.

More preferably, substituent $R_5$ in structural formula (VI) is represented by one of the following structural formulas:

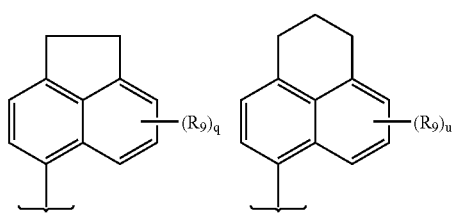

wherein:

$R_9$ is as defined as above, q is zero or an integer from 1 to 7 and u is zero or an integer from 1 to 8.

In another alternative, $R_5$ in structural formula (VI) is represented by the following structural formula:

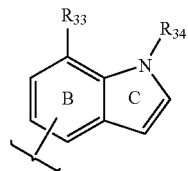

wherein:

$R_{33}$ is —H, a halo, lower alkyl, a lower alkoxy, a lower haloalkyl, a lower haloalkoxy, and lower alkyl sulfanyl; $R_{34}$ is H, a lower alkyl, or a lower alkylcarbonyl; and ring B and ring C are optionally substituted with one or more substituents.

In another alternative, $R_5$ in structural formula (VI) is selected from a group listed in Table 1.

TABLE 1

| # | $R_5$ |
|---|---|
| 1 | ![structure with X6] |
| 2 | ![structure with X7] |
| 3 | ![structure with X6] |
| 4 | ![structure with X7] |
| 5 | ![structure with X7, X8] |
| 6 | ![structure with X7] |
| 7 | ![structure with X7, X8] |

TABLE 1-continued

| # | R$_5$ |
|---|---|
| 8 | (structure) |
| 9 | (structure) |
| 10 | (structure) |
| 11 | (structure) |
| 12 | (structure) |
| 13 | (structure) |
| 14 | (structure) |
| 15 | (structure) |
| 16 | (structure) |
| 17 | (structure) |
| 18 | (structure) |
| 19 | (structure) |

In the structural formulas of Table 1:

$X_6$, for each occurrence, is independently CH, CR$_9$, N, N(O), N$^+$(R$_{17}$), provided that at least three X$_6$ groups are independently selected from CH$_1$ and CR$_9$;

$X_7$, for each occurrence, is independently CH$_1$, CR$_9$, N, N(O), N$^+$(R$_{17}$), provided that at least three X$_7$ groups are independently selected from CH$_1$ and CR$_9$;

$X_8$, for each occurrence, is independently CH$_2$, CHR$_9$, CR$_9$R$_9$, O, S, S(O)$_p$, NR$_7$, or NR$_{17}$;

$X_9$, for each occurrence, is independently N or CH;

$X^{10}$, for each occurrence, is independently CH$_1$, CR$_9$, N, N(O), N$^+$(R$_{17}$), provided that at least one X$_{10}$ is selected from Cl$_1$ and CR$_9$;

R$_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$; or two R$_9$ groups taken together with the carbon atoms to which they are attached form a fused ring; and R$_{17}$, for each occurrence, is independently —H, an alkyl, an aralkyl, —C(O)R$_7$, —C(O)OR$_7$, or —C(O)NR$_{10}$R$_{11}$.

Preferred R$_5$ groups from Table 1 are selected from the group consisting of an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl, an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b]pyridinyl, an optionally substituted 1H-imidazo[4,5-c]pyridinyl, an optionally substituted 3H-imidazo[4,5-c]pyridinyl, an optionally substituted pyridopyrdazinyl, and optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo[b]thienyl.

In another alternative, $R_5$ in structural formula (VI) is selected from the group consisting of:

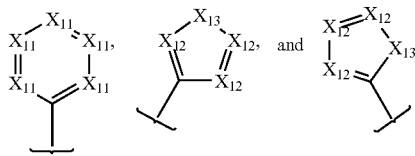

wherein:

$X_{11}$, for each occurrence, is independently CH, $CR_9$, N, N(O), or $N^+(R_{17})$, provided that at least one $X_{11}$ is N, N(O), or $N^+(R_{17})$ and at least two $X_{11}$ groups are independently selected from CH and $CR_9$;

$X_{12}$, for each occurrence, is independently CH, $CR_9$, N, N(O), $N^+(R_{17})$, provided that at least one $X_{12}$ group is independently selected from CH and $CR_9$;

$X_{13}$, for each occurrence, is independently O, S, $S(O)_p$, $NR_7$, or $NR_{17}$;

$R_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a hydroxyalkyl, alkoxyalkyl, haloalkyl, a heteroalkyl, $-NR_{10}R_{11}$, $-OR_7$, $-C(O)R_7$, $-C(O)OR_7$, $-OC(O)R_7$, $-C(O)NR_{10}R_{11}$, $-NR_8C(O)R_7$, $-SR_7$, $-S(O)_pR_7$, $-OS(O)_pR_7$, $-S(O)_pOR_7$, $-NR_8S(O)_pR_7$, or $-S(O)_pNR_{10}R_{11}$; or two $R_9$ groups taken together with the carbon atoms to which they are attached form a fused ring; and $R_{17}$, for each occurrence, is independently an alkyl or an aralkyl. The remainder of the variables have values defined above with reference to structural formula (I).

In a preferred embodiment, the compound of the invention is represented by structural formula (LII):

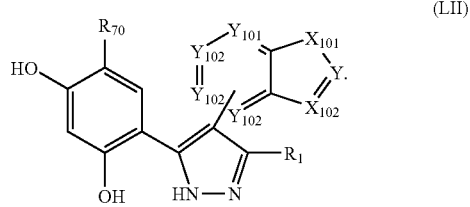

(LII)

In structural formula (LII):

$X_{101}$ is O, S, or $NR_{102}$ and $X_{102}$ is $CR_{104}$ or N. Preferably, $X_{101}$ is $NR_{102}$ and $X_{102}$ is $CR_{104}$. Alternatively, $X_{101}$ is $NR_{102}$ and $X_{102}$ is N;

Y, for each occurrence, is independently N or $CR_{103}$;

$Y_{101}$ is N or $CR_{105}$;

$Y_{102}$ is N, C or $CR_{106}$;

$R_1$ is —OH, —SH, or $NHR_7$. Preferably, $R_1$ is —OH or —SH;

$R_{70}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, an alkoxy, cycloalkoxy, a haloalkoxy, $-NR_{10}R_{11}$, $-OR_7$, $-C(O)R_7$, $-C(O)OR_7$, $-C(S)R_7$, $-C(O)SR_7$, $-C(S)SR_7$, $-C(S)OR_7$, $-C(S)NR_{10}R_{11}$, $-C(NR_8)OR_7$, $-C(NR_8)R_7$, $-C(NR_8)NR_{10}R_{11}$, $-C(NR_8)SR_7$, $-OC(O)R_7$, $-OC(O)OR_7$, $-OC(S)OR_7$, $-OC(NR_8)OR_7$, $-SC(O)R_7$, $-SC(O)OR_7$, $-SC(NR_8)OR_7$, $-OC(S)R_7$, $-SC(S)R_7$, $-SC(S)OR_7$, $-OC(O)NR_{10}R_{11}$, $-OC(S)NR_{10}R_{11}$, $-OC(NR_8)NR_{10}R_{11}$, $-SC(O)NR_{10}R_{11}$, $-SC(NR_8)NR_{10}R_{11}$, $-SC(S)NR_{10}R_{11}$, $-OC(NR_8)R_7$, $-SC(NR_8)R_7$, $-C(O)NR_{10}R_{11}$, $-NR_8C(O)R_7$, $-NR_7C(S)R_7$, $-NR_7C(S)OR_7$, $-NR_7C(NR_8)R_7$, $-NR_7C(O)OR_7$, $-NR_7C(NR_8)OR_7$, $-NR_7C(O)NR_{10}R_{11}$, $-NR_7C(S)NR_{10}R_{11}$, $-NR_7C(NR_8)NR_{10}R_{11}$, $-SR_7$, $-S(O)_pR_7$, $-OS(O)_pR_7$, $-OS(O)_pOR_7$, $-OS(O)_pNR_{10}R_{11}$, $-S(O)_pOR_7$, $-NR_8S(O)_pR_7$, $-NR_7S(O)_pNR_{10}R_{11}$, $-NR_7S(O)_pOR_7$, $-S(O)_pNR_{10}R_{11}$, $-SS(O)_pR_7$, $-SS(O)_pOR_7$, $-SS(O)_pNR_{10}R_{11}$, $-OP(O)(OR_7)_2$, or $-SP(O)(OR_7)_2$. Preferably, $R_{70}$ is selected from the group consisting of —H, C1-C6 alkyl, C1-C6 alkoxy, C1-C6 cycloalkyl, and C1-C6 cycloalkoxy, more preferably from the group consisting of —H, methyl, ethyl, propyl, isopropyl, cyclopropyl, methoxy, ethoxy, propoxy, and cyclopropoxy;

$R_{102}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, a haloalkyl, a heteroalkyl, $-C(O)R_7$, $-(CH_2)_mC(O)OR_7$, $-C(O)OR_7$, $-OC(O)R_7$, $-C(O)NR_{10}R_{11}$, $-S(O)_pR_7$, $-S(O)_pOR_7$, or $-S(O)_pNR_{10}R_{11}$; preferably, $R_{102}$ is selected from the group consisting of —H, a C1-C6 alkyl, a C1-C6 cycloalkyl, $-C(O)N(R_{27})_2$, and $-C(O)OH$, wherein $R_{27}$, for each occurrence, is independently is —H or a lower alkyl;

$R_{103}$ and $R_{104}$ are, independently, —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, $-C(O)R_7$, $-C(O)OR_7$, $-OC(O)R_7$, $-C(O)NR_{10}R_{11}$, $-NR_8C(O)R_7$, $-SR_7$, $-S(O)_pR_7$, $-OS(O)_pR_7$, $-S(O)_pOR_7$, $-NR_8S(O)_pR_7$, $-S(O)_pNR_{10}R_{11}$, or $R_{103}$ and $R_{104}$ taken together with the carbon atoms to which they are attached form an optionally substituted cycloalkenyl, an optionally substituted aryl, an optionally substituted heterocyclyl, or an optionally substituted heteroaryl; preferably, $R_{103}$ and $R_{104}$ are independently, selected from the group consisting of —H, methyl, ethyl, propyl, isopropyl, cyclopropyl, methoxy, ethoxy, propoxy, and cyclopropoxy;

$R_{105}$ is —H, —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, or —$NR_7C(NR_8)NR_{10}R_{11}$; preferably, $R_{105}$ is selected from the group consisting of —H, —OH, —SH, —$NH_2$, a C1-C6 alkoxy, a C1-C6 alkyl amino, and a C1-C6 dialkyl amino, more preferably from the group consisting of —H, —OH, methoxy and ethoxy; and $R_{106}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$.

The remainder of the variables of the compounds of structural formula (LII) has values defined above with reference to structural formula (VI).

In one preferred set of values for the variables of the Hsp90 inhibitor represented by formula (LII), $X_{101}$ is $NR_{102}$, $R_{102}$ is selected from the group consisting of —H, a C1-C6 alkyl, a C1-C6 cycloalkyl, —$C(O)N(R_{27})_2$, and —$C(O)OH$, each $R_{27}$, for each occurrence, is independently is —H or a lower alkyl, and the values for the remainder of the variables are as described above for formula (LII).

In a second preferred set of values for the variables of the Hsp90 inhibitor represented by formula (LII), $X_{101}$ is $NR_{102}$, $R_{102}$ is selected from the group consisting of —H, methyl, ethyl, n-propyl, isopropyl, cyclopropyl, n-butyl, sec-butyl, tert-butyl, n-pentyl, n-hexyl, —$C(O)OH$, —$(CH_2)_mC(O)OH$, —$CH_2OCH_3$, —$CH_2CH_2OCH_3$, and —$C(O)N(CH_3)_2$ and the values for the remainder of the variables are as described above for formula (LII).

In third preferred set of values for the variables of the Hsp90 inhibitor represented by formula (LII), $X_{102}$ is $CR_{104}$; Y is $CR_{103}$; and $R_{103}$ and $R_{104}$ together with the carbon atoms to which they are attached form a cycloalkenyl, an aryl, heterocyclyl, or heteroaryl ring. Preferably, $R_{103}$ and $R_{104}$ together with the carbon atoms to which they are attached form a $C_5$-$C_8$ cycloalkenyl or a $C_5$-$C_8$ aryl and the values for the remainder of the variables are as described above for formula (LII).

In fourth preferred set of values for the variables of the Hsp90 inhibitor represented by formula (LII), $R_1$ is —OH or —SH and the values for the remainder of the variables are as described above for formula (LII).

In another preferred embodiment, the Hsp90 inhibitor of the invention is represented by structural formula (LIII):

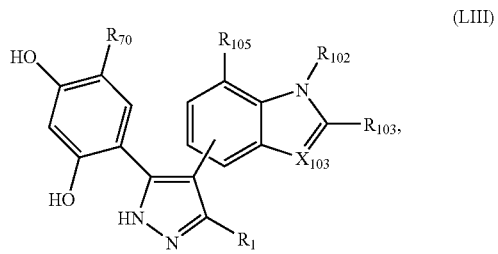

(LIII)

where $X_{103}$ is $CR_{104}$ or N and the remainder of the variables is defined above with reference with structural formulas (LII).

In another preferred embodiment, the Hsp90 inhibitor of the invention is represented by a structural formula selected from formulas (LIVa)-(LIVi):

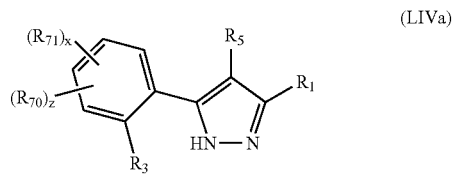

(LIVa)

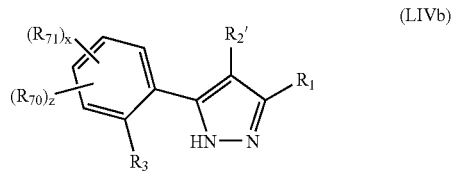

(LIVb)

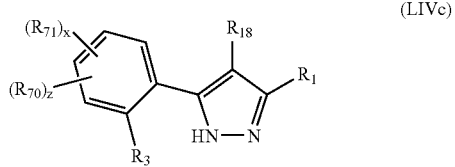

(LIVc)

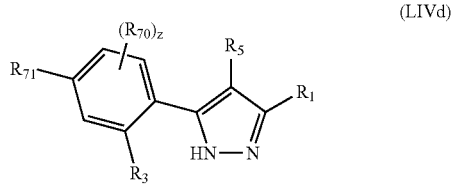

(LIVd)

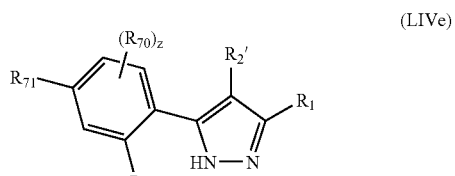

(LIVe)

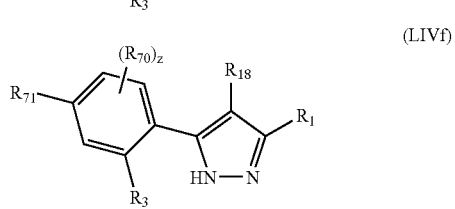

(LIVf)

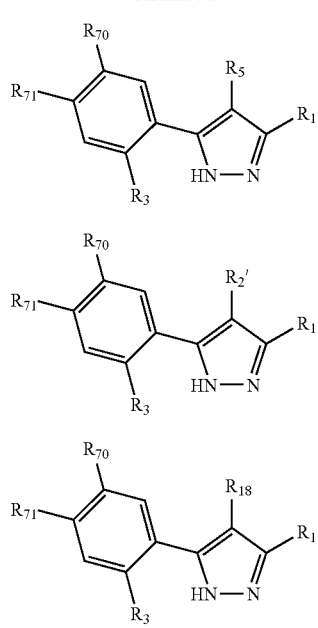

(LIVg)

(LIVh)

(LIVi)

The values for the variables in structural formulas (LIVa)-(LIVi) are as described in structural formulas (VI), (VII), and (VIII).

In one preferred set of values for the variables of the Hsp90 inhibitor represented by structural formulas (LIVa)-(LIVi):

$R_5$ is as described for structural formula (VI), (VII), and (VIII) or a structural formula from Table 1;

$R_{70}$ and $R_{71}$, for each occurrence, are independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$;

z in structural formula (LIVa)-(LIVc) is zero or an integer from 1 to 4; z in structural formula (LIVd)-(LIVf) is zero or an integer from 1 to 3;

x is 0 or 1;

z+x in structural formula (LIVa)-(LIVc) is less than or equal to 4; and the remainder of the variables in formulas (LIVa)-(LIVi) have values defined above with reference to structural formula (VI), (VII) and (VIII).

A second preferred set of values for the variables of the Hsp90 inhibitor represented by structural formula (LIVa)-(LIVc) is provided in the following paragraphs:

$R_{71}$ is a halo, a haloalkyl, a haloalkoxy, a heteroalkyl, —OH, —SH, —$NHR_7$, —$(CH_2)_kOH$, —$(CH_2)_kSH$, —$(CH_2)_kNR_7H$, —$OCH_3$, —$SCH_3$, —$NHCH_3$, —$OCH_2CH_2OH$, —$OCH_2CH_2SH$, —$OCH_2CH_2NR_7H$, —$SCH_2CH_2OH$, —$SCH_2CH_2SH$, —$SCH_2CH_2NR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$; and k is 1, 2, 3, or 4; and $R_1$, $R_3$, $R_{70}$ and the remainder of the variables are as described in the first preferred set of values for the variables in structural formulas (LIVa)-(LIVc). Preferably, $R_1$ and $R_3$ are each, independently, —OH, —SH, or —$NHR_7$.

A third preferred set of values for the variables of the Hsp90 inhibitor represented by formula (LIVa)-(LIVc) is provided in the following paragraphs:

$R_1$, and $R_3$ are each, independently, —OH, —SH, or —$NHR_7$;

$R_{70}$ is an optionally substituted alkyl or cycloalkyl, an optionally substituted alkenyl, an optionally substituted alkynyl, cyano, halo, nitro, an optionally substituted cycloalkyl, haloalkyl, alkoxy, haloalkoxy, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$ and $R_1$, and $R_3$ and the remainder of the variables are as described in the second preferred set of values for the variables in structural formulas (LIVa)-(LIVc).

In a fourth preferred set of values for the variables of Structural Formulas (LIVa)-(LIVc):

$R_1$ is —SH or —OH;

$R_3$ and $R_{71}$ are —OH;

$R_{70}$ is a C1-C6 alkyl, a C3-C6 cycloalkyl, a C1-C6 alkoxy, a C1-C6 haloalkoxy, a C1-C6 alkyl sulfanyl, or —$NR_{10}R_{11}$; and The remainder of the variables are as defined in Structural Formula (VI)-(VIII).

In another preferred embodiment, the Hsp90 inhibitor is represented by a structural formula selected from formulas (LVa)-(LVf):

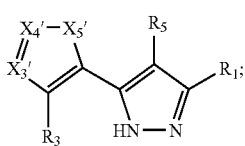
(LVa)

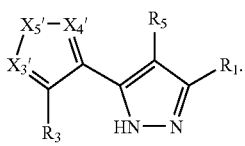
(LVb)

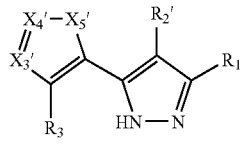
(LVc)

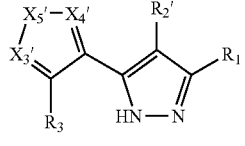
(LVd)

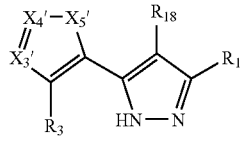
(LVe)

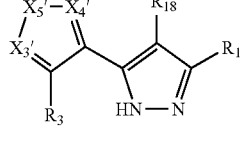
(LVf)

In formulas (LVa) and (LVb):

$R_5$ is as described for structural formula (VI) or a structural formula from Table 1;

$X_3'$ and $X_4'$ are each, independently, N, N(O), $N^+(R_{17})$, CH or $CR_{70}$;

$X_5'$ is O, S, $NR_{17}$, $CH_2$, $CH(R_{70})$, $C(R_{70})_2$, CH=CH, CH=$CR_{70}$, $CR_{70}$=CH, $CR_{70}$=$CR_{70}$=$CR_{70}$, CH=N, $CR_{70}$=N, CH=N(O), $CR_{70}$=N(O), N=CH, N=$CR_{70}$, N(O)=CH, N(O)=$CR_{70}$, $N^+(R_{17})$=CH, $N^+(R_{17})$=$CR_{70}$, CH=$N^+(R_{17})$, $CR_{70}$=$N^+(R_{17})$, or N=N, provided that at least one $X_3'$, $X_4'$ or $X_5'$ is a heteroatom;

$R_{70}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanadino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$;

$R_{17}$, for each occurrence, is independently an alkyl or an aralkyl; and n is zero or an integer from 1 to 4; and the remainder of the variables has values defined above with reference to structural formulas (VI), (VII), and (VIII).

Preferably, Hsp90 inhibitor of structural formulas (LVa)-(LVf) are selected from Table 2a-c.

TABLE 2a

| Number | Compound |
|---|---|
| 1. | 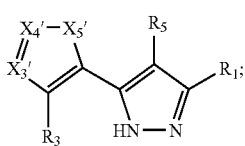 |
| 2. | 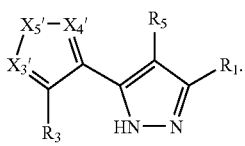 |
| 3. | 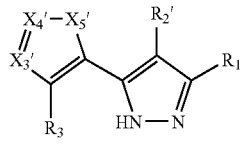 |
| 4. | 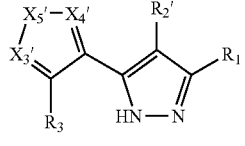 |
| 5. | 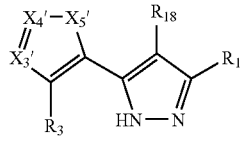 |
| 6. | 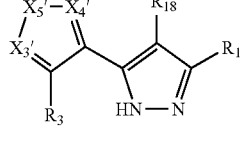 |

TABLE 2a-continued

| Number | Compound |
|---|---|
| 7. | thiophen-2-yl pyrazole with R5, R1, R3, HN-N |
| 8. | furan (R70) pyrazole with R5, R1, R3, HN-N |
| 9. | thiophene (R70) pyrazole with R5, R1, R3, HN-N |
| 10. | thiophen-3-yl pyrazole with R5, R1, R3, HN-N |

TABLE 2b

| Number | Compound |
|---|---|
| 1. | pyridin-3-yl pyrazole with R2', R1, R3, HN-N |
| 2. | pyridin-3-yl pyrazole with R2', R1, R3, HN-N |
| 3. | pyridine N-oxide pyrazole with R2', R1, R3, HN-N |
| 4. | pyridine (R70) pyrazole with R2', R1, R3, HN-N |

TABLE 2b-continued

| Number | Compound |
|---|---|
| 5. | furan-3-yl pyrazole with R2', R1, R3, HN-N |
| 6. | furan-2-yl pyrazole with R2', R1, R3, HN-N |
| 7. | thiophen-2-yl pyrazole with R2', R1, R3, HN-N |
| 8. | furan (R70) pyrazole with R2', R1, R3, HN-N |
| 9. | thiophene (R70) pyrazole with R2', R1, R3, HN-N |
| 10. | thiophen-3-yl pyrazole with R2', R1, R3, HN-N |

TABLE 2c

| Number | Compound |
|---|---|
| 1. | pyridin-3-yl pyrazole with $R_{18}$, $R_1$, $R_3$, HN-N |
| 2. | pyridine N-oxide pyrazole with $R_{18}$, $R_1$, $R_3$, HN-N |
| 3. | furan-2-yl pyrazole with $R_{18}$, $R_1$, $R_3$, HN-N |

TABLE 2c-continued

| Number | Compound |
|---|---|
| 4. | 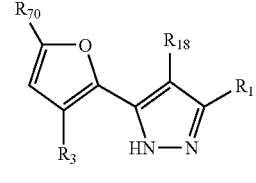 |
| 5. | 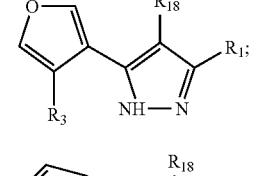 |
| 6. | 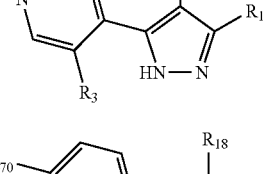 |
| 7. | 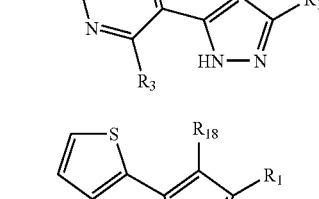 |
| 8. | 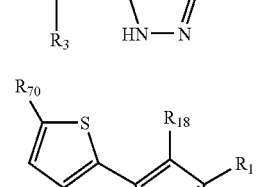 |
| 9. | 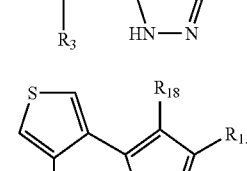 |
| 10. | 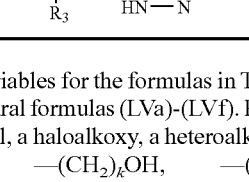 |

The values for the variables for the formulas in Tables 2a-c are as defined for structural formulas (LVa)-(LVf). Preferably, $R_{70}$ is a halo, a haloalkyl, a haloalkoxy, a heteroalkyl, —OH, —SH, —NHR$_7$, —(CH$_2$)$_k$OH, —(CH$_2$)$_k$SH, —(CH$_2$)$_k$NR$_7$H, —OCH$_3$, —SCH$_3$, —NHCH$_3$, —OCH$_2$CH$_2$OH, —OCH$_2$CH$_2$SH, —OCH$_2$CH$_2$NR$_7$H, —SCH$_2$CH$_2$OH, —SCH$_2$CH$_2$SH, —SCH$_2$CH$_2$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, or —S(O)$_p$R$_7$; and k is 1, 2, 3, or 4.

In another preferred embodiment, the Hsp90 inhibitor of the present invention is represented by structural formula (LVI):

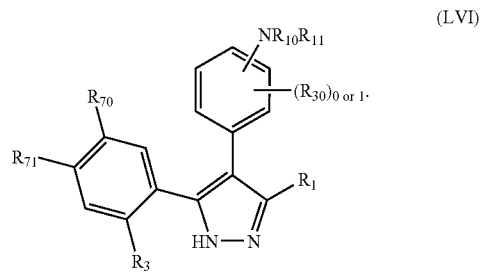

(LVI)

$R_{70}$ and $R_{71}$, for each occurrence, are independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$. Preferably, R$_{70}$ is selected from an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —OR$_7$, —SR$_7$, —NR$_{10}$R$_{11}$, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, or —S(O)$_p$R$_7$ and R$_{71}$ is as just described. The values for the remainder of the variables are as described for structural formulas (VI), (VII), and (VIII).

In another preferred embodiment, the Hsp90 inhibitors is represented by structural formula (LVIIa) or (LVIIb):

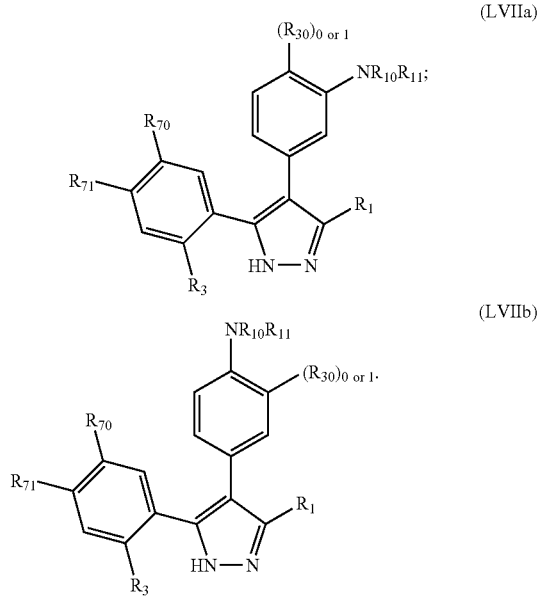

The variables in formulas (LVIIa) and (LVIIb) are defined above with reference to formula (LVI).

A first preferred set of values for the variables of structural formula (LVIIa) and (LVIIb) is provided in the following paragraph:

R$_1$, R$_3$ or R$_{71}$, are each independently selected from —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$—SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$, and p, R$_{70}$, R$_7$, R$_8$, R$_{10}$, R$_{11}$, and R$_{30}$ are as described for structural formula (LVI). Preferably, when R$_1$, R$_3$ and R$_{71}$, have these values, R$_{10}$ and R$_{11}$ are preferably each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or R$_{10}$ and R$_{11}$ taken together with the nitrogen to which they are attached form a substituted or unsubstituted nonaromatic, nitrogen-containing heterocyclyl; and p, R$_{70}$, R$_7$, and R$_{30}$ are as described for structural formula (LVI). More preferably, when R$_1$, R$_3$, R$_{10}$, R$_{11}$, and R$_{71}$ have these values, R$_{70}$ is preferably a C1-C6 alkyl, a C1-C6 haloalkyl, a C1-C6 alkoxy, a C1-C6 haloalkoxy, a C1-C6 alkyl sulfanyl or a C3-C6 cycloalkyl; and p, R$_7$, R$_8$ and R$_{30}$ are as described for structural formula (LVI).

A second preferred set of values for the variables of structural formula (LVIIa) and (LVIIb) is provided in the following paragraph:

R$_1$ and R$_3$ are each independently —OH or —SH; R$_{70}$ is preferably a C1-C6 alkyl, a C1-C6 haloalkyl, a C1-C6 alkoxy, C1-C6 haloalkoxy, a C1-C6 alkyl sulfanyl or a C3-C6 cycloalkyl; R$_{10}$ and R$_{11}$ are preferably each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or R$_{10}$ and R$_{11}$ taken together with the nitrogen to which they are attached form a substituted or unsubstituted nonaromatic, nitrogen-containing heterocyclyl; R$_{71}$ is —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$—OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$—SC(NR$_8$)OR$_7$, —OP(O)(OR$_7$)$_2$ or —SP(O)(OR$_7$)$_2$; and p, R$_7$ R$_8$ and R$_{30}$ are as described for structural formula (LVI). Preferably, R$_{30}$ is a —OH, —SH, halogen, cyano, a C1-C6 alkyl, C1-C6 haloalkyl, C1-C6 alkoxy, C1-C6 haloalkoxy or C1-C6 alkyl sulfanyl and the remainder of the variables are as just described.

A third preferred set of values for the variables of structural formula (LVIIa) and (LVIIb) is provided in the following paragraph:

R$_1$, R$_3$ and R$_{71}$, are independently —SH or —OH; R$_{70}$ is cyclopropyl or isopropyl; R$_{10}$ and R$_{11}$ are each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or R$_{10}$ and R$_{11}$ taken together with the nitrogen to which they are attached form a substituted or unsubstituted nonaromatic, nitrogen-containing heterocyclyl; and R$_{30}$ is —OH, —SH, halogen, cyano, a C1-C6 alkyl, C1-C6 haloalkyl, C1-C6 alkoxy, C1-C6 haloalkoxy or C1-C6 alkyl sulfanyl. Preferably, R$_{30}$ is a methyl, ethyl, propyl, isopropyl, methoxy or ethoxy. More preferably, R$_1$, R$_3$, R$_{70}$, R$_{71}$, and R$_{30}$ are as just described and R$_{10}$ and R$_{11}$ are each independently a hydrogen, methyl, ethyl, propyl, isopropyl, or taken together with the nitrogen to which they are attached, are:

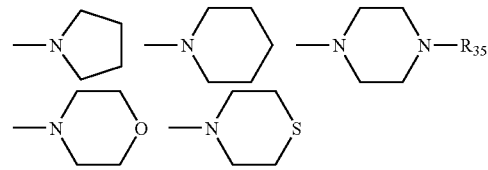

wherein R$_{35}$ is —H, a C1-C4 alkyl or a C1-C4 acyl.

In another preferred embodiment, the Hsp90 inhibitor is represented by structural formulas (LVIIIa) or (LVIIIb):

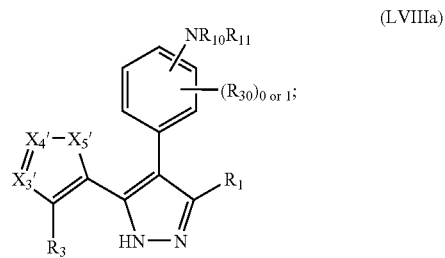

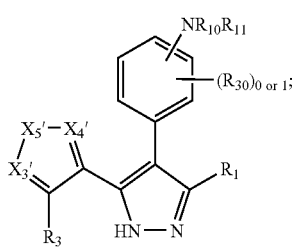

(LVIIIb)

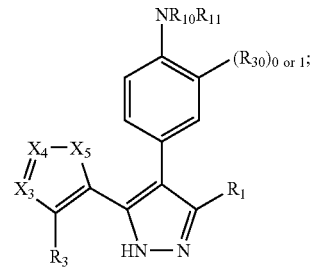

(LIXa)

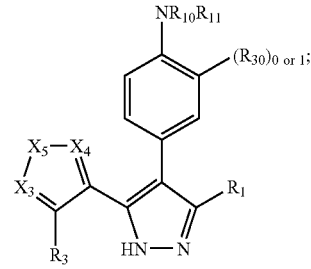

(LIXb)

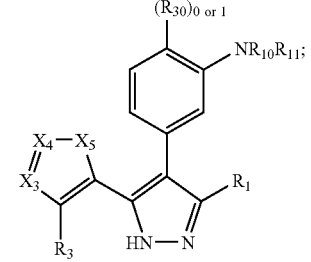

(LIXc)

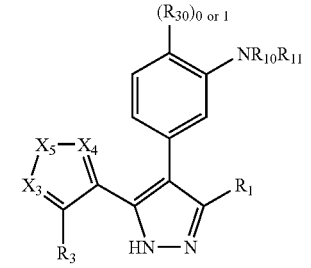

(LIXa)

The values for the variables in structural formulas (LVIIIa) and (LVIIIb) are as described for structural formulas (LVc) and (LVd). Preferably, $R_{30}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$—$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$. More preferably, $R_{30}$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$.

In another preferred embodiment, the Hsp90 inhibitor is represented by a structural formula selected from formulas (LIXa)-(LIXd):

The values of the variables in structural formulas (LIXa)-(LIXd) are defined above with reference to structural formulas (LVIIIa) and (LVIIIb).

A first preferred set of values for the variables in structural formulas (LIXa)-(LIXd) are as described in the following paragraphs:

$R_1$ and $R_3$ are each independently —OH or —SH, —$HNR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$, —$SC(S)OR_7$, —$OC(S)NR_{10}R_{11}$, —$SC(S)NR_{10}R_{11}$, —$OC(NR_8)R_7$, —$SC(NR_8)R_7$, —$OC(NR_8)OR_7$, —$SC(NR_8)OR_7$, —$OP(O(OR_7)_2$ or —$SP(O)(OR_7)_2$;

$R_{70}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, —OH, —SH, —$HNR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$. Preferably, R$_{70}$ is a C1-C6 alkyl, a C1-C6 haloalkyl, a C1-C6 alkoxy, a C1-C6 haloalkoxy, a C1-C6 alkyl sulfanyl or a C3-C6 cycloalkyl; and R$_{10}$ and R$_{11}$ and the remainder of the variables in structural formulas (LIXa)-(LIXd) are as described for structural formulas (LVIIIa) and (LVIIIb). Preferably, R$_{10}$ and R$_{11}$ are each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or R$_{10}$ and R$_{11}$ taken together with the nitrogen to which they are attached form a substituted or unsubstituted nonaromatic, nitrogen-containing heterocyclyl.

In another preferred embodiment, the Hsp90 inhibitor is represented by a structural formula selected from formulas (LXa)-(LXp):

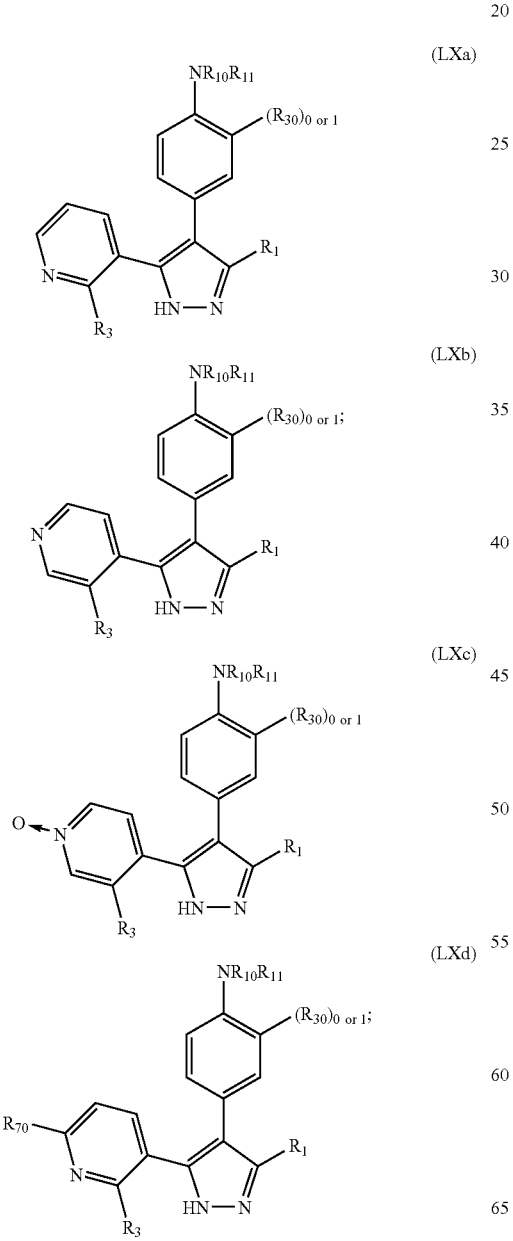
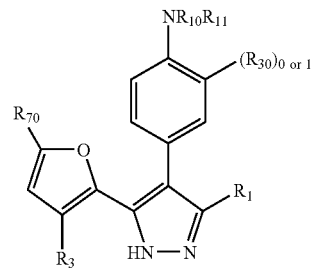
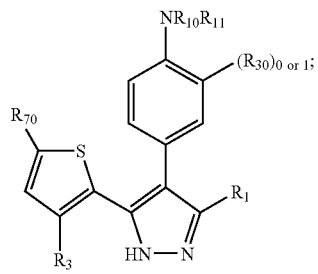
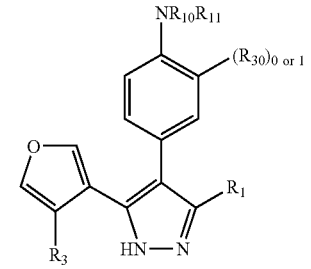
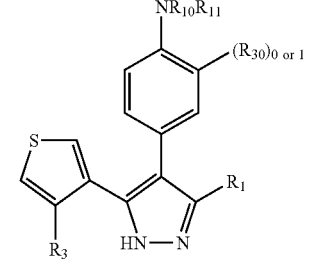
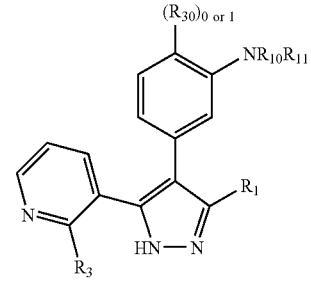

(LXj) 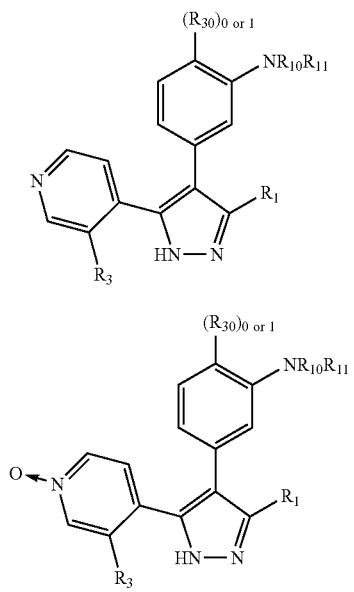

(LXk)

(LXl)

(LXm)

(LXn)

(LXo) 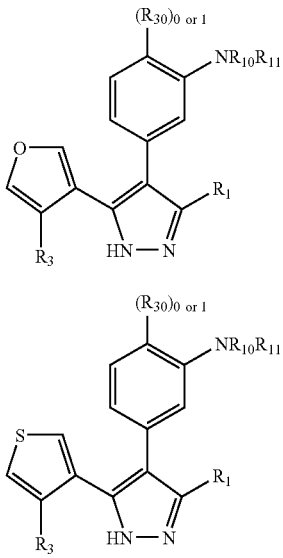

(LXp)

The values of the variables in structural formulas (LXa)-(LXp) are defined above with reference to structural formulas (XIXa)-(XIXd).

A first preferred set of values for the variables in structural formulas (LX) are as described in the following paragraphs:

$R_1$ and $R_3$ are each independently —OH or —SH, or —HNR$_7$;

$R_{70}$, is a C1-C6 alkyl, a C1-C6 haloalkyl, a C1-C6 alkoxy, a C1-C6 haloalkoxy, a C1-C6 alkyl sulfanyl or a C3-C6 cycloalkyl;

$R_{10}$ and $R_{11}$ and the remainder of the variables in structural formulas (LXa)-(LXp) are as described for structural formulas (LVIIIa) and (LVIIIb). Preferably, $R_{10}$ and $R_{11}$ are each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or $R_{10}$ and $R_{11}$ taken together with the nitrogen to which they are attached form a substituted or unsubstituted nonaromatic, nitrogen-containing heterocyclyl; and $R_{30}$ and the remainder of the variables in structural formulas (LXa)-(LXp) are as described for structural formulas (LIXa)-(LIXd). Preferably, $R_{30}$ is —OH, —SH, halogen, cyano, a C1-C6 alkyl, C1-C6 haloalkyl, C1-C6 alkoxy, C1-C6 haloalkoxy or C1-C6 alkyl sulfanyl.

A second preferred set of values for the variables in structural formulas (LXa)-(LXp) are as described in the following paragraphs:

$R_1$ and $R_3$ are independently —SH or —OH;

$R_{70}$ is cyclopropyl or isopropyl;

$R_{10}$ and $R_{11}$ are each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or $R_{10}$ and $R_{11}$ taken together with the nitrogen to which they are attached form a substituted or unsubstituted nonaromatic, nitrogen-containing heterocyclyl;

$R_{30}$ is —OH, —SH, halogen, cyano, a C1-C6 alkyl, C1-C6 haloalkyl, C1-C6 alkoxy, C1-C6 haloalkoxy or C1-C6 alkyl sulfanyl. Preferably, $R_{30}$ is a methyl, ethyl, propyl, isopropyl, methoxy or ethoxy; and the remainder of the variables are as described for formulas (LVIIIa) and (LVIIIb). More preferably, $R_{10}$ and $R_{11}$ are each independently a hydrogen, methyl, ethyl, propyl, isopropyl, or taken together with the nitrogen to which they are attached, are:

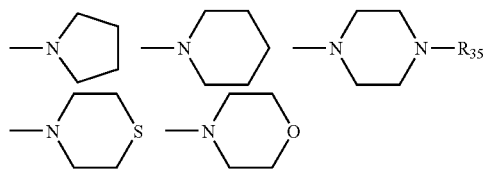

wherein $R_{35}$ is —H, a C1-C4 alkyl or a C1-C4 acyl.

In another embodiment, the Hsp90 inhibitor of the present invention is represented by structural formulas (LXIa) or (LXIb):

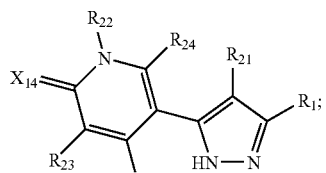
(LXIa)

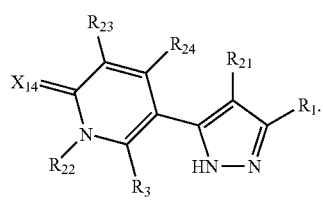
(LXIb)

In formulas (LXIa) and (LXIb):
$X_{14}$ is O, S, or $NR_7$. Preferably, $X_{14}$ is O;
$R_1$ is —OH, —SH, —$NR_7$H, —$OR_{26}$, —$SR_{26}$, —$NHR_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP(O)(OR$_7$)$_2$. Preferably, $R_1$ is —OH, —SH, or —$NHR_7$;

$R_3$ is —OH, —SH, —$NR_7$H, —$OR_{26}$, —$SR_{26}$, —$NHR_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)OH, —C(O)NHR$_8$, —C(O)SH, —S(O)OH, —S(O)$_2$OH, —S(O)NHR$_8$, —S(O)$_2$NHR$_8$, —OP(O)(OR$_7$)$_2$, or —SP(O)(OR$_7$)$_2$;

$R_7$ and $R_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{10}$ and $R_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{21}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl. Preferably, $R_{21}$ is an optionally substituted alkyl, an optionally substituted cycloalkyl, an optionally substituted aryl or an optionally substituted heteroaryl. Alternatively, $R_{21}$ is

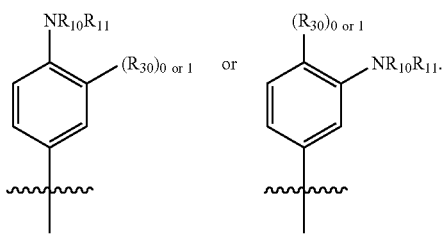

wherein
$R_{10}$ and $R_{11}$, is defined as above; and
$R_{30}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C (NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$;

z and q are independently an integer from 0 to 4; and x is 0 or 1, provided that z+x less than or equal to 4.

R$_{22}$, for each occurrence, is independently a substituent selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, a haloalkyl, —C(O)R$_7$, —C(O)OR$_7$, —OC(O)R$_7$, —C(O)NR$_{10}$R$_{11}$, —NR$_8$C(O)R$_7$, —S(O)$_p$R$_7$, —S(O)$_p$OR$_7$, or —S(O)$_p$NR$_{10}$R$_{11}$. Preferably, R$_{22}$ is an alkyl, an aralkyl, —C(O)R$_7$, —C(O)OR$_7$, or —C(O)NR$_{10}$R$_{11}$; and R$_{23}$ and R$_{24}$, for each occurrence, are independently a substituent selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, halo, cyano, nitro, guanadino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$;

R$_{26}$ is a lower alkyl;

p, for each occurrence, is, independently, 0, 1 or 2; and m, for each occurrence, is independently, 1, 2, 3, or 4.

In one embodiment, a compound of the present invention is represented by a structural formula selected from formulas (IX), (X) and (XI):

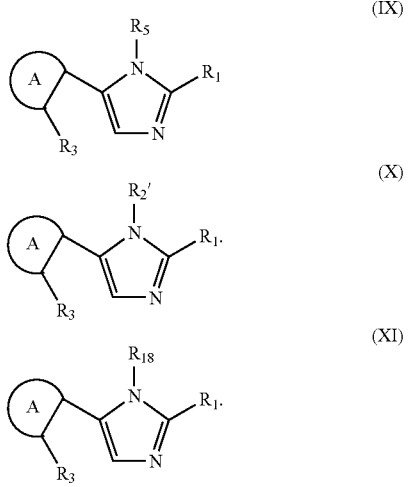

In formulas (IX)-(XI):

ring A is an aryl or a heteroaryl, optionally further substituted with one or more substituents in addition to R$_3$. Preferably, Ring A is represented one of the following structural formulas:

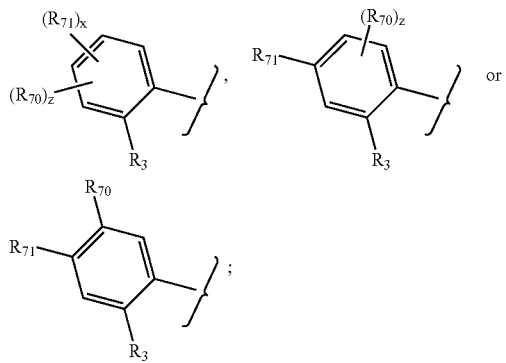

wherein z is 0, 1, 2, 3 or 4; x is 0 or 1; and z+x is less than or equal to 4.

R$_1$ is —OH, —SH, —NR$_7$H, —OR$_{26}$, —SR$_{26}$, —NHR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP(O)(OR$_7$)$_2$. Preferably, R$_1$ is —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$. More preferably, R$_1$ is —OH, —SH, or —NHR$_7$. Even more preferably, R$_1$, is —SH or —OH;

R$_2$' is an optionally substituted phenyl group. Preferably, R$_2$' is substituted with one or more group represented by R$_{30}$, wherein R$_{30}$, for each occurrence, are independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C —S(S)NR₁₀R₁₁, —NR₇C(NR₈)NR₁₀R₁₁, —SR₇, —S(O)ₚR₇, —OS(O)ₚR₇, —OS(O)ₚOR₇, —OS(O)ₚNR₁₀R₁₁, —S(O)ₚOR₇, —NR₈S(O)ₚR₇, —NR₇S(O)ₚNR₁₀R₁₁, —NR₇S(O)ₚOR₇, —S(O)ₚNR₁₀R₁₁, —SS(O)ₚR₇, —SS(O)ₚOR₇,—SS(O)ₚNR₁₀R₁₁, —OP(O)(OR₇)₂, or —SP(O)(OR₇)₂. More preferably, $R_2'$ is an optionally substituted indolyl group or a phenyl group substituted with NR₁₀R₁₁, and optionally with at least one other substituent represented by $R_{30}$;

$R_3$ is —OH, —SH, —NR₇H, —NHR₂₆, —O(CH₂)ₘOH, —O(CH₂)ₘSH, —O(CH₂)ₘNR₇H, —S(CH₂)ₘOH, —S(CH₂)ₘSH, —S(CH₂)ₘNR₇H, —OC(O)NR₁₀R₁₁, —SC(O)NR₁₀R₁₁, —NR₇C(O)NR₁₀R₁₁, —OC(O)R₇, —SC(O)R₇, —NR₇C(O)R₇, —OC(O)OR₇, —SC(O)OR₇, —NR₇C(O)OR₇, —OCH₂C(O)R₇, —SCH₂C(O)R₇, —NR₇CH₂C(O)R₇, —OCH₂C(O)OR₇, —SCH₂C(O)OR₇, —NR₇CH₂C(O)OR₇, —OCH₂C(O)NR₁₀R₁₁, —SCH₂C(O)NR₁₀R₁₁, —NR₇CH₂C(O)NR₁₀R₁₁, —OS(O)ₚR₇, —SS(O)ₚR₇, —S(O)ₚOR₇, —NR₇S(O)ₚR₇, —OS(O)ₚNR₁₀R₁₁, —SS(O)ₚNR₁₀R₁₁, —NR₇S(O)ₚNR₁₀R₁₁, —OS(O)ₚOR₇, —SS(O)ₚOR₇, —NR₇S(O)ₚOR₇, —OC(S)R₇, —SC(S)R₇, —NR₇C(S)R₇, —OC(S)OR₇, —SC(S)OR₇, —NR₇C(S)OR₇, —OC(S)NR₁₀R₁₁, —SC(S)NR₁₀R₁₁, —NR₇C(S)NR₁₀R₁₁, —OC(NR₈)R₇, —SC(NR₈)R₇, —NR₇C(NR₈)R₇, —OC(NR₈)OR₇, —SC(NR₈)OR₇, —NR₇C(NR₈)OR₇, —OC(NR₈)NR₁₀R₁₁, —SC(NR₈)NR₁₀R₁₁, —NR₇C(NR₈)NR₁₀R₁₁, —C(O)OH, —C(O)NHR₈, —C(O)SH, —S(O)OH, —S(O)₂OH, —S(O)NHR₈, —S(O)₂NHR₈, —OP(O)(OR₇)₂, or —SP(O)(OR₇)₂. In another embodiment, —OR₂₆ and —SR₂₆, are additional values for $R_3$. Preferably, $R_3$ is —OH, —SH, —NHR₇, —OC(O)NR₁₀R₁₁, —SC(O)NR₁₀R₁₁, —OC(O)R₇, —SC(O)R₇, —OC(O)OR₇, —SC(O)OR₇, —OS(O)ₚR₇, —S(O)ₚOR₇, —SS(O)ₚR₇, —OS(O)ₚOR₇, —SS(O)ₚOR₇, —OC(S)R₇, —SC(S)R₇, —OC(S)OR₇, —SC(S)OR₇, —OC(S)NR₁₀R₁₁, —SC(S)NR₁₀R₁₁, —OC(NR₈)R₇, —SC(NR₈)R₇, —OC(NR₈)OR₇, —SC(NR₈)OR₇, —OP(O)(OR₇)₂ or —SP(O)(OR₇)₂. More preferably, $R_3$ is —OH, —SH, or —NHR₇. Even more preferably, $R_3$ is —SH or —OH.

$R_5$ is an optionally substituted heteroaryl; an optionally substituted 6 to 14-membered aryl.

$R_{70}$, for each occurrence, is independently, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, an alkoxy or cycloalkoxy, a haloalkoxy, —NR₁₀R₁₁, —OR₇, —C(O)R₇, —C(O)OR₇, —C(S)R₇, —C(O)SR₇, —C(S)SR₇, —C(S)OR₇, —C(S)NR₁₀R₁₁, —C(NR₈)OR₇, —C(NR₈)R₇, —C(NR₈)NR₁₀R₁₁, —C(NR₈)SR₇, —OC(O)R₇, —OC(O)OR₇, —OC(S)OR₇, —OC(NR₈)OR₇, —SC(O)R₇, —SC(O)OR₇, —SC(NR₈)OR₇, —OC(S)R₇, —SC(S)R₇, —SC(S)OR₇, —OC(O)NR₁₀R₁₁, —OC(S)NR₁₀R₁₁, —OC(NR₈)NR₁₀R₁₁, —SC(O)NR₁₀R₁₁, —SC(NR₈)NR₁₀R₁₁, —SC(S)NR₁₀R₁₁, —OC(NR₈)R₇, —SC(NR₈)R₇, —C(O)NR₁₀R₁₁, —NR₈C(O)R₇, —NR₇C(S)R₇, —NR₇C(S)OR₇, —NR₇C(NR₈)R₇, —NR₇C(O)OR₇, —NR₇C(NR₈)OR₇, —NR₇C(O)NR₁₀R₁₁, —NR₇C(S)NR₁₀R₁₁, —NR₇C(NR₈)NR₁₀R₁₁, —SR₇, —S(O)ₚR₇, —OS(O)ₚR₇, —OS(O)ₚOR₇, —OS(O)ₚNR₁₀R₁₁, —S(O)ₚOR₇, —NR₈S(O)ₚR₇, —NR₇S(O)ₚNR₁₀R₁₁, —NR₇S(O)ₚOR₇, —S(O)ₚNR₁₀R₁₁, —SS(O)ₚR₇, —SS(O)ₚOR₇, —SS(O)ₚNR₁₀R₁₁, —OP(O)(OR₇)₂, or —SP(O)(OR₇)₂. Preferably, $R_{70}$ is selected from the group consisting of —H, C1-C6 alkyl, C1-C6 alkoxy, C1-C6 cycloalkyl, and C1-C6 cycloalkoxy, more preferably from the group consisting of —H, methyl, ethyl, propyl, isopropyl, cyclopropyl, methoxy, ethoxy, propoxy, and cyclopropoxy.

$R_{71}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —NR₁₀R₁₁, —OR₇, —C(O)R₇, —C(O)OR₇, —C(S)R₇, —C(O)SR₇, —C(S)SR₇, —C(S)OR₇, —C(S)NR₁₀R₁₁, —C(NR₈)OR₇, —C(NR₈)R₇, —C(NR₈)NR₁₀R₁₁, —C(NR₈)SR₇, —OC(O)R₇, —OC(O)OR₇, —OC(S)OR₇, —OC(NR₈)OR₇, —SC(O)R₇, —SC(O)OR₇, —SC(NR₈)OR₇, —OC(S)R₇, —SC(S)R₇, —SC(S)OR₇, —OC(O)NR₁₀R₁₁, —OC(S)NR₁₀R₁₁, —OC(NR₈)NR₁₀R₁₁, —SC(O)NR₁₀R₁₁, —SC(NR₈)NR₁₀R₁₁, —SC(S)NR₁₀R₁₁, —OC(NR₈)R₇, —SC(NR₈)R₇, —C(O)NR₁₀R₁₁, —NR₈C(O)R₇, —NR₇C(S)R₇, —NR₇C(S)OR₇, —NR₇C(NR₈)R₇, —NR₇C(O)OR₇, —NR₇C(NR₈)OR₇, —NR₇C(O)NR₁₀R₁₁, —NR₇C(S)NR₁₀R₁₁, —NR₇C(NR₈)NR₁₀R₁₁, —SR₇, —S(O)ₚR₇, —OS(O)ₚR₇, —OS(O)ₚOR₇, —OS(O)ₚNR₁₀R₁₁, —S(O)ₚOR₇, —NR₈S(O)ₚR₇, —NR₇S(O)ₚNR₁₀R₁₁, —NR₇S(O)ₚOR₇, —S(O)ₚNR₁₀R₁₁, —SS(O)ₚR₇, —SS(O)ₚOR₇, —SS(O)ₚNR₁₀R₁₁, —OP(O)(OR₇)₂, or —SP(O)(OR₇)₂.

$R_7$ and $R_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{10}$ and $R_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{18}$ is an optionally substituted cycloalkyl, and optionally substituted cycloalkenyl, or a substituted alkyl, wherein the alkyl group is substituted with one or more substituents independently selected from the group consisting of an optionally substituted alkynyl, an optionally substituted cycloalkyl, an optionally substituted cycloalkenyl, an optionally substituted heteroaryl, an optionally substituted aralkyl, an optionally substituted heteraralkyl, halo, cyano, nitro, guanadino, haloalkyl, —NR₁₀R₁₁, —OR₇, —C(O)R₇, —C(O)OR₇, —OC(O)R₇, —C(O)NR₁₀R₁₁, —NR₈C(O)R₇, —SR₇, —S(O)ₚR₇, —OS(O)ₚR₇, —S(O)ₚOR₇, —NR₈S(O)ₚR₇, or —S(O)ₚNR₁₀R₁₁;

$R_{26}$ is a lower alkyl;

p, for each occurrence, is, independently, 0, 1 or 2; and m, for each occurrence, is independently, 1, 2, 3, or 4.

$R_5$ in structural formula (IX) is preferably represented by the following structural formula:

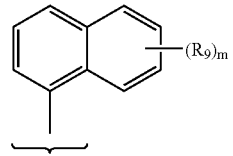

wherein:

R₉, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —NR₁₀R₁₁, —OR₇, —C(O)R₇, —C(O)OR₇, —OC(O)R₇, —C(O)NR₁₀R₁₁, —NR₈C(O)R₇, —SR₇, —S(O)ₚR₇, —OS(O)ₚR₇, —S(O)ₚOR₇, —NR₈S(O)ₚR₇, or —S(O)ₚNR₁₀R₁₁; or two R₉ groups taken together with the carbon atoms to which they are attached form a fused ring, and m is zero or an integer from 1 to 7. More preferably, substituent R₅ is represented by one of the following structural formulas:

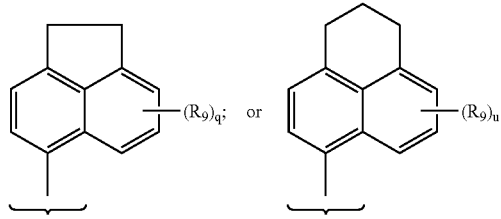

wherein:

R₉ is as defined as above; q is zero or an integer from 1 to 7; and u is zero or an integer from 1 to 8. The remainder of the variables have values defined above with reference to structural formula (IX).

In another alternative, R₅ in structural formula (IX) is represented by the following structural formula:

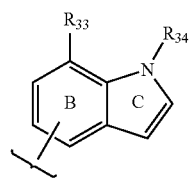

wherein:

R₃₃ is —H, a halo, lower alkyl, a lower alkoxy, a lower haloalkyl, a lower haloalkoxy, and lower alkyl sulfanyl; R₃₄ is H, a lower alkyl, or a lower alkylcarbonyl; and ring B and ring C are optionally substituted with one or more substituents. The remainder of the variables have values defined above with reference to structural formula (IX).

In another alternative, R₅ in structural formula (IX) is selected from a group listed in Table 3.

TABLE 3

| Number | Substituent R₅ |
|---|---|
| 1 | |
| 2 | |
| 3 | |
| 4 | |
| 5 | |
| 6 | |
| 7 | |
| 8 | |
| 9 | |
| 10 | |
| 11 | |

TABLE 3-continued

| Number | Substituent R$_5$ |
|---|---|
| 12 | |
| 13 | |
| 14 | |
| 15 | |
| 16 | |
| 17 | |
| 18 | |
| 19 | |

In the structural formulas of Table 3:

$X_6$, for each occurrence, is independently CH, CR$_9$, N, N(O), N$^+$(R$_{17}$), provided that at least three $X_6$ groups are independently selected from CH and CR$_9$;

$X_7$, for each occurrence, is independently CH, CR$_9$, N, N(O), N$^+$(R$_{17}$), provided that at least three $X_7$ groups are independently selected from CH and CR$_9$;

$X_8$, for each occurrence, is independently CH$_2$, CHR$_9$, CR$_9$R$_9$, O, S, S(O)$_p$, NR$_7$, or NR$_{17}$;

$X_9$, for each occurrence, is independently N or CH;

$X_{10}$, for each occurrence, is independently CH, CR$_9$, N, N(O), N$^+$(R$_{17}$), provided that at least one $X_{10}$ is selected from CH and CR$_9$;

R$_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$; or two R$_9$ groups taken together with the carbon atoms to which they are attached form a fused ring; and R$_{17}$, for each occurrence, is independently —H, an alkyl, an aralkyl, —C(O)R$_7$, —C(O)OR$_7$, or —C(O)NR$_{10}$R$_{11}$.

Preferred R$_5$ groups from Table 3 are selected from the group consisting of an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl, an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b]pyridinyl, an optionally substituted 1H-imidazo[4,5-c]pyridinyl, an optionally substituted 3H-imidazo[4,5-c]pyridinyl, an optionally substituted pyridopyrdazinyl, and optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo[b]thienyl.

In another alternative, R$_5$ in structural formula (IX) is selected from the group consisting of:

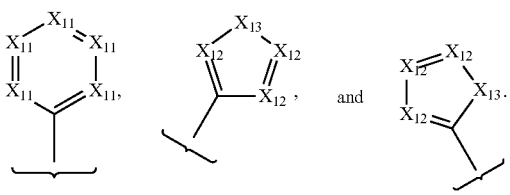

wherein:

$X_{11}$, for each occurrence, is independently CH, $CR_9$, N, N(O), or $N^+(R_{17})$, provided that at least one $X_{11}$ is N, N(O), or $N^+(R_{17})$ and at least two $X_{11}$ groups are independently selected from CH and $CR_9$;

$X_{12}$, for each occurrence, is independently CH, $CR_9$, N, N(O), $N^+(R_{17})$, provided that at least one $X_{12}$ group is independently selected from CH and $CR_9$;

$X_{13}$, for each occurrence, is independently O, S, $S(O)_p$, $NR_7$, or $NR_{17}$;

$R_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a hydroxyalkyl, alkoxyalkyl, haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$; or two $R_9$ groups taken together with the carbon atoms to which they are attached form a fused ring; and $R_{17}$, for each occurrence, is independently an alkyl or an aralkyl. The remainder of the variables have values defined above with reference to structural formula (IX).

In a preferred embodiment, the compound of the invention is represented by structural formula (LXII):

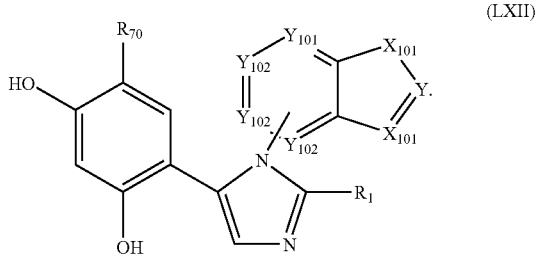

(LXII)

In structural formula (LXII):

$X_{101}$ is O, S, or $NR_{102}$ and $X_{102}$ is $CR_{104}$ or N. Preferably, $X_{101}$ is $NR_{102}$ and $X_{102}$ is $CR_{104}$. Alternatively, $X_{101}$ is $NR_{102}$ and $X_{102}$ is N;

Y, for each occurrence, is independently N or $CR_{103}$;

$Y_{101}$ is N or $CR_{105}$;

$Y_{102}$ is N, C or $CR_{106}$;

$R_1$ is OH, SH, or $NHR_7$. Preferably, $R_1$ is —OH or —SH;

$R_{70}$ is —H, —OH, —SH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, an alkoxy or cycloalkoxy, a haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$. Preferably, $R_{70}$ is selected from the group consisting of —H, C1-C6 alkyl, C1-C6 alkoxy, C1-C6 cycloalkyl, and C1-C6 cycloalkoxy, more preferably from the group consisting of —H, methyl, ethyl, propyl, isopropyl, cyclopropyl, methoxy, ethoxy, propoxy, and cyclopropoxy;

$R_{102}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, a haloalkyl, a heteroalkyl, —$C(O)R_7$, —$(CH_2)_mC(O)OR_7$, —$C(O)OR_7$, —$OC(O)R_7$, —$C(O)NR_{10}R_{11}$, —$S(O)_pR_7$, —$S(O)_pOR_7$, or —$S(O)_pNR_{10}R_{11}$; preferably, $R_{102}$ is selected from the group consisting of —H, a C1-C6 alkyl, a C1-C6 cycloalkyl, —$C(O)N(R_{27})_2$, and —$C(O)OH$, wherein $R_{27}$, for each occurrence, is independently is —H or a lower alkyl;

$R_{103}$ and $R_{104}$ are, independently, —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, —$S(O)_pNR_{10}R_{11}$, or $R_{103}$ and $R_{104}$ taken together with the carbon atoms to which they are attached form an optionally substituted cycloalkenyl, an optionally substituted aryl, an optionally substituted heterocyclyl, or an optionally substituted heteroaryl; preferably, $R_{103}$ and $R_{104}$ are independently, selected from the group consisting of —H, methyl, ethyl, propyl, isopropyl, cyclopropyl, methoxy, ethoxy, propoxy, and cyclopropoxy;

$R_{105}$ is —H, —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, or —$NR_7C(NR_8)NR_{10}R_{11}$; preferably, $R_{105}$ is selected from the group consisting of —H, —OH, —SH, —$NH_2$, a C1-C6 alkoxy, a C1-C6 alkyl amino, and a C1-C6 dialkyl amino, more preferably from the group consisting of —H, —OH, methoxy and ethoxy; and $R_{106}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$.

The remainder of the variables of the compounds of structural formula (LXII) has values defined above with reference to structural formula (IX).

In one preferred set of values for the variables of the Hsp90 inhibitor represented by formula (LXII), $X_{101}$ is $NR_{102}$, $R_{102}$ is selected from the group consisting of —H, a C1-C6 alkyl, a C1-C6 cycloalkyl, —$C(O)N(R_{27})_2$, and —$C(O)OH$, wherein $R_{27}$, for each occurrence, is independently is —H or a lower alkyl and the values for the remainder of the variables are as described above for formula (LXII).

In a second preferred set of values for the variables of the Hsp90 inhibitor represented by formula (LXII), $X_{101}$ is $NR_{102}$, $R_{102}$ is selected from the group consisting of —H, methyl, ethyl, n-propyl, isopropyl, cyclopropyl, n-butyl, sec-butyl, tert-butyl, n-pentyl, n-hexyl, —$C(O)OH$, —$(CH_2)_mC(O)OH$, —$CH_2OCH_3$, —$CH_2CH_2OCH_3$, and —$C(O)N(CH_3)_2$ and the values for the remainder of the variables are as described above for formula (LXII).

In third preferred set of values for the variables of the Hsp90 inhibitor represented by formula (LXII), $X_{102}$ is $CR_{104}$; Y is $CR_{103}$; and $R_{103}$ and $R_{104}$ together with the carbon atoms to which they are attached form a cycloalkenyl, an aryl, heterocyclyl, or heteroaryl ring. Preferably, $R_{103}$ and $R_{104}$ together with the carbon atoms to which they are attached form a $C_5$-$C_8$ cycloalkenyl or a $C_5$-$C_8$ aryl and the values for the remainder of the variables are as described above for formula (LXII).

In fourth preferred set of values for the variables of the Hsp90 inhibitor represented by formula (LXII), $R_1$ is —OH or —SH and the values for the remainder of the variables are as described above for formula (LXII).

In another preferred embodiment, the Hsp90 inhibitor of the invention is represented by structural formula (LXIII):

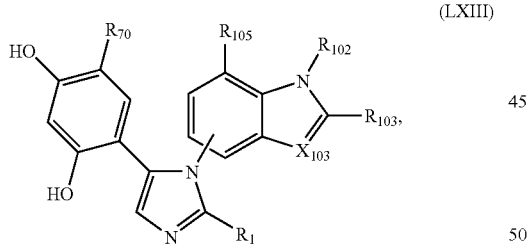

(LXIII)

where $X_{103}$ is $CR_{104}$ or N and the remainder of the variables is defined above with reference with structural formulas (LXII).

In another preferred embodiment, the Hsp90 inhibitor of the invention is represented by structural formula selected from (LXIVa)-(LXIVi):

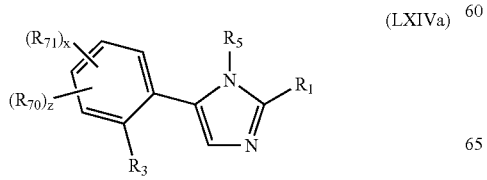

(LXIVa)

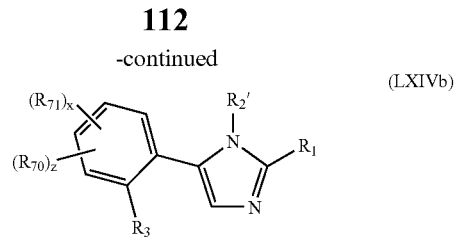

(LXIVb)

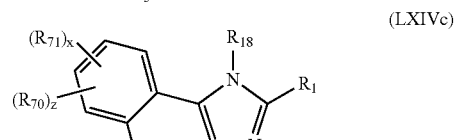

(LXIVc)

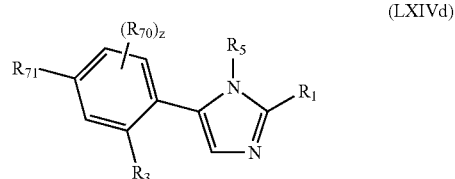

(LXIVd)

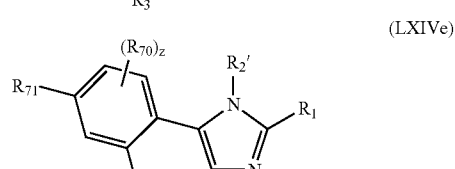

(LXIVe)

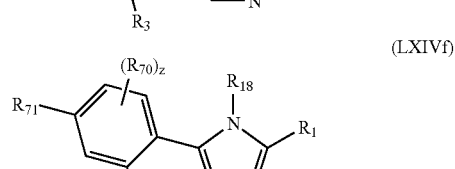

(LXIVf)

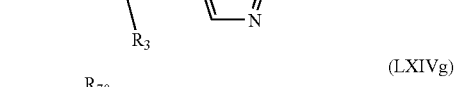

(LXIVg)

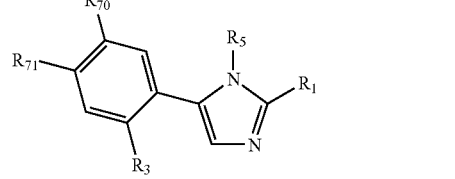

(LXIVh)

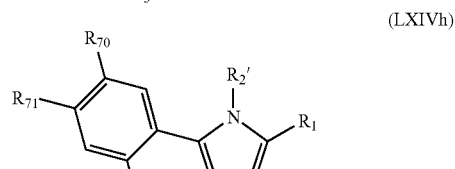

(LXIVi)

The values for the variables in structural formulas (LXIVa)-(LXIVi) are as described in structural formula (IX), (X), and (XI).

In one preferred set of values for the variables of the Hsp90 inhibitor represented by structural formulas (VIa-c)-(VIIIa-c):

$R_5$ is as described for structural formula (IX), (LXII), (LXIII) or a structural formula from Table 1;

$R_{70}$ and $R_{71}$, for each occurrence, are independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$;

z in structural formula (VIa-c) is zero or an integer from 1 to 4; z in structural formula (VIIa-c) is zero or an integer from 1 to 3;

x is 0 or 1;

z+x in structural formula (LXIVa)-(LXIVc) is less than or equal to 4; and the remainder of the variables in formulas (LXIVa)-(LXIVi) have values defined above with reference to structural formula (IX), (X), and (XI).

A second preferred set of values for the variables of the Hsp90 inhibitor represented by structural formula (LXIVa)-(LXIVi) is provided in the following paragraphs:

$R_{71}$ is a halo, a haloalkyl, a haloalkoxy, a heteroalkyl, —OH, —SH, —$NHR_7$, —$(CH_2)_kOH$, —$(CH_2)_kSH$, —$(CH_2)_kNR_7H$, —$OCH_3$, —$SCH_3$, —$NHCH_3$, —$OCH_2CH_2OH$, —$OCH_2CH_2SH$, —$OCH_2CH_2NR_7H$, —$SCH_2CH_2OH$, —$SCH_2CH_2SH$, —$SCH_2CH_2NR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$; and k is 1, 2, 3, or 4; and $R_1$, $R_3$, $R_{70}$ and the remainder of the variables are as described in the first preferred set of values for the variables in structural formulas (LXIVa)-(LXIVi). Preferably, $R_1$ and $R_3$ are each, independently, —OH, —SH, or —$NHR_7$.

A third preferred set of values for the variables of the Hsp90 inhibitor represented by formula (LXIVa)-(LXIVi) is provided in the following paragraphs:

$R_1$ and $R_3$ are each, independently, —OH, —SH, or —$NHR_7$;

$R_{70}$ is an optionally substituted alkyl or cycloalkyl, an optionally substituted alkenyl, an optionally substituted alkynyl, cyano, halo, nitro, an optionally substituted cycloalkyl, haloalkyl, alkoxy, haloalkoxy, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$ and $R_1$ and $R_3$ and the remainder of the variables are as described in the second preferred set of values for the variables in structural formulas (LXIVa)-(LXIVi).

In a fourth preferred set of values for the variables of Structural Formulas (LXIVa)-(LXIVi):

$R_1$ is —SH or —OH;

$R_3$ and $R_{25}$ are —OH;

$R_{70}$ is a C1-C6 alkyl, a C3-C6 cycloalkyl, a C1-C6 alkoxy, a C1-C6 haloalkoxy, a C1-$C_6$ alkyl sulfanyl, or —$NR_{10}R_{11}$; and The remainder of the variables are as defined in Structural Formula (IX), (X), and (XI).

In another preferred embodiment, the Hsp90 inhibitor is represented by a structural formula selected from (LXVa)-LXVf):

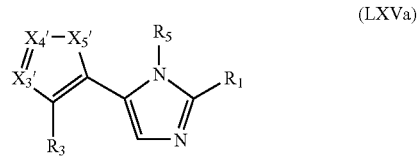

(LXVa)

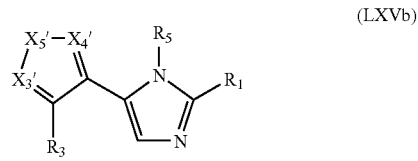

(LXVb)

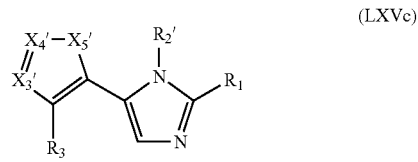

(LXVc)

-continued (LXVd)

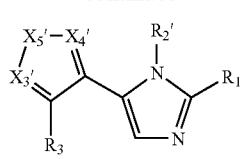

(LXVe)

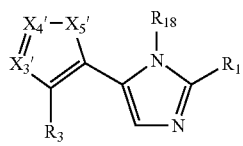

(LXVf)

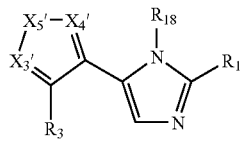

In formulas (LXVa) and (LXVb):

$R_5$ is as described for structural formula (IX), (LXII), or (LXIII), or a structural formula from Table 1;

$X_3'$ and $X_4'$ are each, independently, N, N(O), N⁺($R_{17}$), CH or $CR_{70}$;

$X_5'$ is O, S, $NR_{17}$, $CH_2$, $CH(R_{70})$, $C(R_{70})_2$, CH═CH, CH═$CR_{70}$, $CR_{70}$═CH, $CR_{70}$═$CR_{70}$, CH═N, $CR_{70}$═N, CH═N(O), $CR_{70}$═N(O), N═CH, N═$CR_{70}$, N(O)═CH, N(O)═$CR_{70}$, N⁺($R_{17}$)═CH, N⁺($R_{17}$)═$CR_{70}$, CH═N⁺($R_{17}$), $CR_{70}$═N⁺($R_{17}$), or N═N, provided that at least one $X_3'$, $X_4'$ or $X_5'$ is a heteroatom;

$R_{70}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$;

$R_{17}$, for each occurrence, is independently an alkyl or an aralkyl; and n is zero or an integer from 1 to 4; and the remainder of the variables has values defined above with reference to structural formulas (IX), (X), and (XI).

Preferably, Hsp90 inhibitor of structural formulas (LXVa)-LXVf) are selected from Table 4a-c.

TABLE 4a

| Number | Compound |
|---|---|
| 1. | ![structure with pyridine, $R_5$, $R_1$, $R_3$] |
| 2. | ![structure] |
| 3. | ![structure with O←N, $R_5$, $R_1$, $R_3$] |
| 4. | ![structure with $R_{70}$, $R_5$, $R_1$, $R_3$] |
| 5. | ![structure with furan, $R_5$, $R_1$, $R_3$] |
| 6. | ![structure with furan, $R_5$, $R_1$, $R_3$] |
| 7. | ![structure with thiophene, $R_5$, $R_1$, $R_3$] |
| 8. | ![structure with $R_{70}$, furan, $R_5$, $R_1$, $R_3$] |
| 9. | ![structure with $R_{70}$, thiophene, $R_5$, $R_1$, $R_3$] |

TABLE 4a-continued

| Number | Compound |
|---|---|
| 10. | (thiophene-imidazole structure with R5, R1, R3) |

TABLE 4b

| Number | Compound |
|---|---|
| 1. | (pyridine-imidazole structure with R2', R1, R3) |
| 2. | (pyridine-imidazole structure with R2', R1, R3) |
| 3. | (pyridine N-oxide-imidazole structure with R2', R1, R3) |
| 4. | (pyridine-imidazole structure with R70, R2', R1, R3) |
| 5. | (furan-imidazole structure with R2', R1, R3) |
| 6. | (furan-imidazole structure with R2', R1, R3) |
| 7. | (thiophene-imidazole structure with R2', R1, R3) |
| 8. | (furan-imidazole structure with R70, R2', R1, R3) |

TABLE 4b-continued

| Number | Compound |
|---|---|
| 9. | (thiophene-imidazole structure with R70, R2', R1, R3) |
| 10. | (thiophene-imidazole structure with R2', R1, R3) |

TABLE 4c

| Number | Compound |
|---|---|
| 1. | (pyridine-imidazole structure with R18, R1, R3) |
| 2. | (pyridine N-oxide-imidazole structure with R18, R1, R3) |
| 3. | (furan-imidazole structure with R18, R1, R3) |
| 4. | (furan-imidazole structure with R70, R18, R1, R3) |
| 5. | (furan-imidazole structure with R18, R1, R3) |
| 6. | (pyridine-imidazole structure with R18, R1, R3) |

TABLE 4c-continued

| Number | Compound |
|---|---|
| 7. | 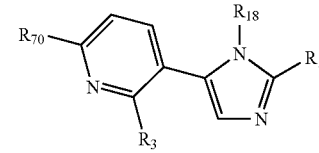 |
| 8. | 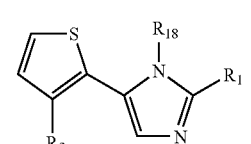 |
| 9. | 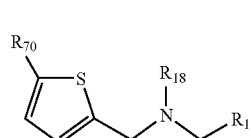 |
| 10. | 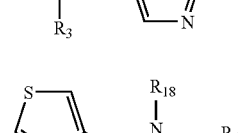 |

The values for the variables for the formulas in Tables 4a-c are as defined for structural formulas (LXVa)-(LXVf). Preferably, $R_{70}$ is a halo, a haloalkyl, a haloalkoxy, a heteroalkyl, OH, —SH, —$NHR_7$, —$(CH_2)_kOH$, —$(CH_2)_kSH$, —$(CH_2)_kNR_7H$, —$OCH_3$, —$SCH_3$, —$NHCH_3$, —$OCH_2CH_2OH$, —$OCH_2CH_2SH$, —$OCH_2CH_2NR_7H$, —$SCH_2CH_2OH$, —$SCH_2CH_2SH$, —$SCH_2CH_2NR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$; and k is 1, 2, 3, or 4.

In another preferred embodiment, the Hsp90 inhibitor of the present invention is represented by structural formula (LXVI):

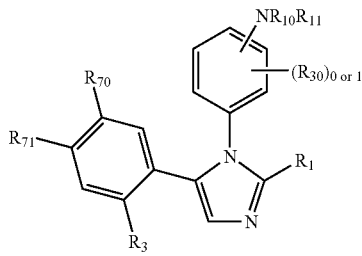

$R_{70}$ and $R_{71}$, for each occurrence, are independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)$ $OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_9C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$. Preferably, $R_{70}$ is selected from an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)$ $OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$ and $R_{71}$ is as just described. The values for the remainder of the variables are as described for structural formulas (IX), (X), and (XI).

In another preferred embodiment, the Hsp90 inhibitors are represented by structural formula (LXVIIa) or (LXVIIb):

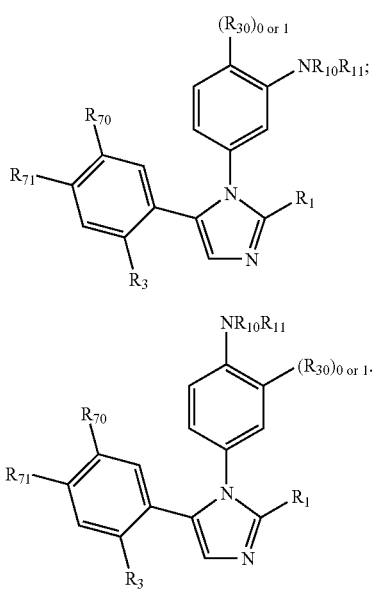

(LXVIIa)

(LXVIIb)

The variables in formulas (LXVIIa) and (LXVIIb) are defined above with reference to formula (LXVI).

A first preferred set of values for the variables of structural formula (LXVIIa) and (LXVIIb) is provided in the following paragraph:

$R_1$, $R_3$ or $R_{71}$, are each independently selected from —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$, and p, $R_{70}$, $R_7$, $R_9$, $R_{10}$, $R_{11}$, and $R_{30}$ are as described for structural formula (LXVI). Preferably, when $R_1$, $R_3$ and $R_{71}$, have these values, $R_{10}$ and $R_{11}$ are preferably each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or $R_{10}$ and $R_{11}$ taken together with the nitrogen to which they are attached form a substituted or unsubstituted nonaromatic, nitrogen-containing heterocyclyl; and p, $R_{70}$, $R_7$, and $R_{30}$ are as described for structural formula (LXVI). More preferably, when $R_1$, $R_3$, $R_{10}$, $R_{11}$, and $R_{71}$ have these values, $R_{70}$ is preferably a C1-C6 alkyl, a C1-C6 haloalkyl, a C1-C6 alkoxy, a C1-C6 haloalkoxy, a C1-C6 alkyl sulfanyl or a C3-C6 cycloalkyl; and p, $R_7$, $R_8$ and $R_{30}$ are as described for structural formula (LXVI).

A second preferred set of values for the variables of structural formula (LXVIIa) and (LXVIIb) is provided in the following paragraph:

$R_1$ and $R_3$ are each independently —OH, —SH; $R_{70}$ is preferably a C1-C6 alkyl, a C1-C6 haloalkyl, a C1-C6 alkoxy, a C1-C6 haloalkoxy, a C1-C6 alkyl sulfanyl or a C3-C6 cycloalkyl; $R_{10}$ and $R_{11}$ are preferably each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or $R_{10}$ and $R_{11}$ taken together with the nitrogen to which they are attached form a substituted or unsubstituted nonaromatic, nitrogen-containing heterocyclyl; $R_{71}$ is —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$—SS(O)$_p$OR$_7$, —OC(S)R$_7$, —SC(S)R$_7$, —OC(S)OR$_7$—SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$; and p, $R_7$, $R_8$ and $R_{30}$ are as described for structural formula (LXVI). Preferably, $R_{30}$ is —OH, —SH, halogen, cyano, a C1-C6 alkyl, C1-C6 haloalkyl, C1-C6 alkoxy, C1-C6 haloalkoxy or C1-C6 alkyl sulfanyl and the remainder of the variables are as just described.

A third preferred set of values for the variables of structural formula (LXVIIa) and (LXVIIb) is provided in the following paragraph:

$R_1$, $R_3$ and $R_{71}$, are independently —SH or —OH; $R_{70}$ is cyclopropyl or isopropyl; $R_{10}$ and $R_{11}$ are each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or $R_{10}$ and $R_{11}$ taken together with the nitrogen to which they are attached form a substituted or unsubstituted nonaromatic, nitrogen-containing heterocyclyl; and $R_{30}$ is —OH, —SH, halogen, cyano, a C1-C6 alkyl, C1-C6 haloalkyl, C1-C6 alkoxy, C1-C6 haloalkoxy or C1-C6 alkyl sulfanyl. Preferably, $R_{30}$ is a methyl, ethyl, propyl, isopropyl, methoxy or ethoxy. More preferably, $R_1$, $R_3$, $R_{70}$, $R_{71}$, and $R_{30}$ are as just described and $R_{10}$ and $R_{11}$ are each independently a hydrogen, methyl, ethyl, propyl, isopropyl, or taken together with the nitrogen to which they are attached, are:

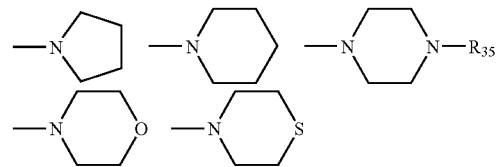

wherein $R_{35}$ is —H, a C1-C4 alkyl or a C1-C4 acyl.

In another preferred embodiment, the Hsp90 inhibitor is represented by structural formulas (LXVIIIa) or (LXVIIIb):

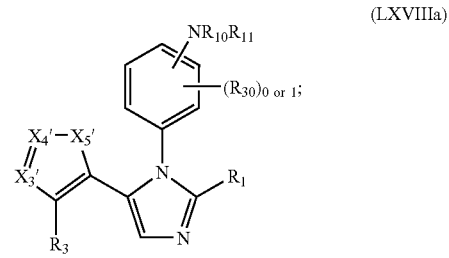

(LXVIIIa)

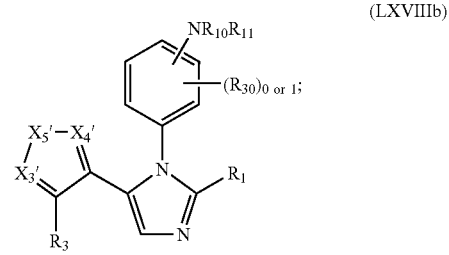

(LXVIIIb)

The values for the variables in structural formulas (LXVIIIa) and (LXVIIIb) are as described for structural formulas (LXVc) and (LXVd). Preferably, $R_{30}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_7C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$. More preferably, $R_{30}$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$.

In another preferred embodiment, the Hsp90 inhibitor is represented by a structural formula selected from formulas (LXIXa)-(LXIXd):

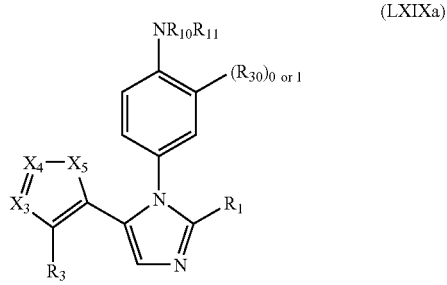
(LXIXa)

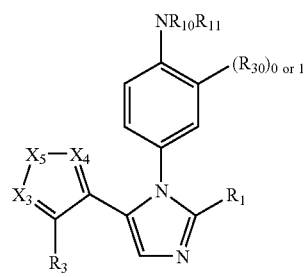
(LXIXb)

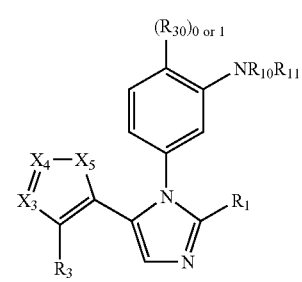
(LXIXc)

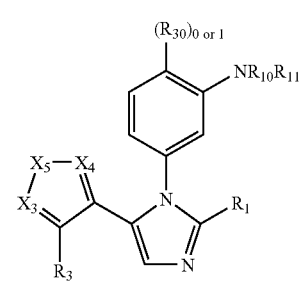
(LXIXd)

The values of the variables in structural formulas (LXIXa)-(LXIXd) are defined above with reference to structural formulas (LXVIIIa) and (LXVIIIb).

A first preferred set of values for the variables in structural formulas (LXIXa)-(LXIXd) are as described in the following paragraphs:

$R_1$ and $R_3$ are each independently —OH, —SH, —$HNR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$, —$SC(S)OR_7$, —$OC(S)NR_{10}R_{11}$, —$SC(S)NR_{10}R_{11}$, —$OC(NR_8)R_7$, —$SC(NR_8)R_7$, —$OC(NR_8)OR_7$, —$SC(NR_8)OR_7$, —$OP(O)(OR_7)_2$ or —$SP(O)(OR_7)_2$;

$R_{70}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, —OH, —SH, —$HNR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$, —$SC(S)OR_7$, —$OC(S)NR_{10}R_{11}$, —$SC(S)NR_{10}R_{11}$, —$OC(NR_8)R_7$, —$SC(NR_8)R_7$, —$OC(NR_8)OR_7$, —$SC(NR_8)OR_7$, —$OP(O)(OR_7)_2$ or —$SP(O)(OR_7)_2$. Preferably, $R_{70}$ is a C1-C6 alkyl, a C1-C6 haloalkyl, a C1-C6 alkoxy, a C1-C6 haloalkoxy, a C1-C6 alkyl sulfanyl or a C3-C6 cycloalkyl; and $R_{10}$ and $R_{11}$ and the remainder of the variables in structural formulas (LXIXa)-(LXIXd) are as described for structural formulas (LXVIIIa) and (LXVIIIb). Preferably, $R_{10}$ and $R_{11}$ are each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or $R_{10}$ and $R_{11}$ taken together with the nitrogen to which they are attached form a substituted or unsubstituted nonaromatic, nitrogen-containing heterocyclyl.

In another preferred embodiment, the Hsp90 inhibitor is represented by a structural formula selected form formulas (LXXa)-(LXXp):

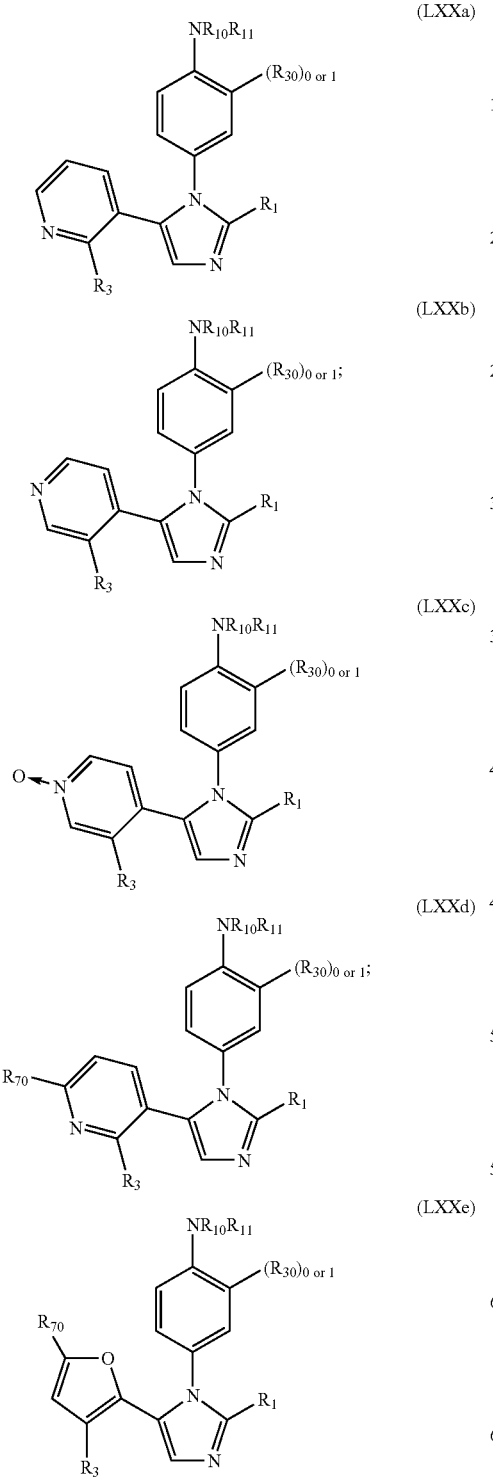

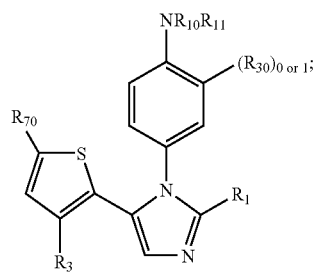

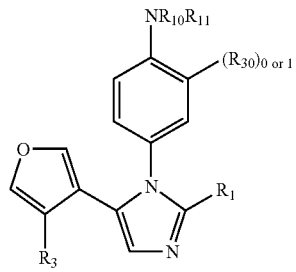

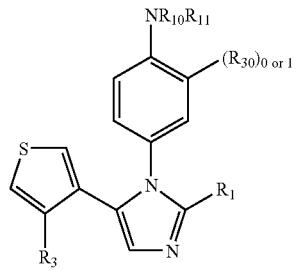

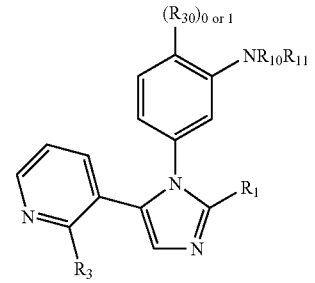

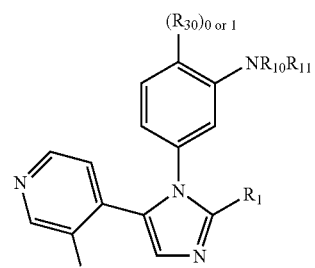

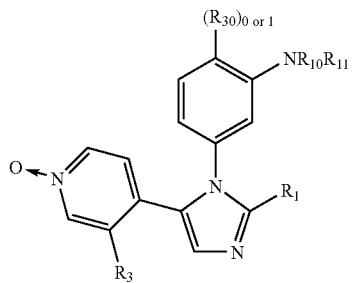
(LXXk)

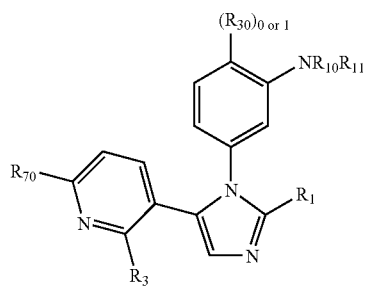
(LXXl)

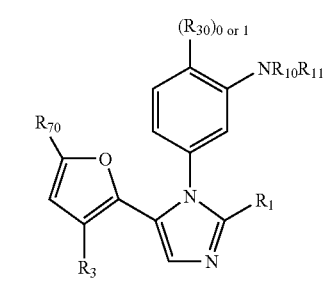
(LXXm)

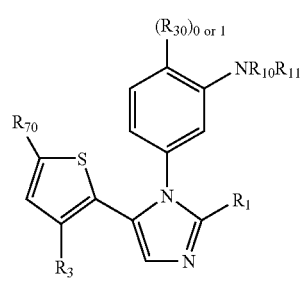
(LXXn)

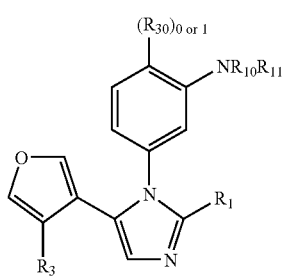
(LXXo)

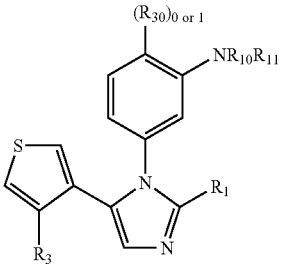
(LXXp)

The values of the variables in structural formulas (LXXa)-(LXXp) are defined above with reference to structural formulas (LXIXa)-(LXIXd).

A first preferred set of values for the variables in structural formulas (XIVa-p) are as described in the following paragraphs:

$R_1$, and $R_3$ are each independently —OH, —SH, —HNR$_7$;

$R_{70}$, is a C1-C6 alkyl, a C1-C6 haloalkyl, a C1-C6 alkoxy, a C1-C6 haloalkoxy, a C1-C6 alkyl sulfanyl or a C3-C6 cycloalkyl;

$R_{10}$ and $R_{11}$ and the remainder of the variables in structural formulas (LXXa)-(LXXp) are as described for structural formulas (LXVIIIa) and (LXVIIIb). Preferably, $R_{10}$ and $R_{11}$ are each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or $R_{10}$ and $R_{11}$ taken together with the nitrogen to which they are attached form a substituted or unsubstituted nonaromatic, nitrogen-containing heterocyclyl; and $R_{30}$ and the remainder of the variables in structural formulas (LXXa)-(LXXp) are as described for structural formulas (LXIXa)-(LXIXd). Preferably, $R_{30}$ is —OH, —SH, halogen, cyano, a C1-C6 alkyl, C1-C6 haloalkyl, C1-C6 alkoxy, C1-C6 haloalkoxy or C1-C6 alkyl sulfanyl.

A second preferred set of values for the variables in structural formulas (LXXa)-(LXXp) are as described in the following paragraphs:

$R_1$ and $R_3$ are independently —SH or —OH;

$R_{70}$ is cyclopropyl or isopropyl;

$R_{10}$ and $R_{11}$ are each independently a hydrogen, a C1-C6 straight or branched alkyl, optionally substituted by —OH, —CN, —SH, amino, a C1-C6 alkoxy, alkylsulfanyl, alkylamino, dialkylamino or a cycloalkyl; or $R_{10}$ and $R_{11}$ taken together with the nitrogen to which they are attached form a substituted or unsubstituted nonaromatic, nitrogen-containing heterocyclyl;

$R_{30}$ is —OH, —SH, halogen, cyano, a C1-C6 alkyl, C1-C6 haloalkyl, C1-C6 alkoxy, C1-C6 haloalkoxy or C1-C6 alkyl sulfanyl. Preferably, $R_{30}$ is a methyl, ethyl, propyl, isopropyl, methoxy or ethoxy; and the remainder of the variables are as described for formulas (LXVIIIa) and (LXVIIIb). More preferably, $R_{10}$ and $R_{11}$ are each independently a hydrogen, methyl, ethyl, propyl, isopropyl, or taken together with the nitrogen to which they are attached, are:

-continued

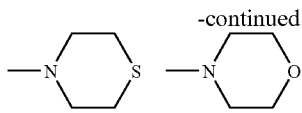

wherein $R_{35}$ is —H, a C1-C4 alkyl or a C1-C4 acyl.

In another embodiment, the Hsp90 inhibitor of the present invention is represented by structural formulas (LXXI) and (LXXII):

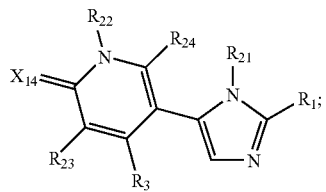

(LXXI)

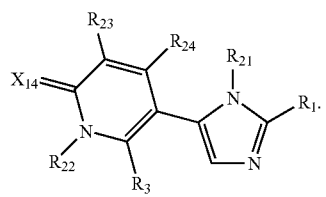

(LXXII)

In formulas (LXXI) and (LXXII):

$X_{14}$ is O, S, or $NR_7$. Preferably, $X_{14}$ is O;

$R_1$ is —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —OC(O)$NR_{10}R_{11}$, —SC(O)$NR_{10}R_{11}$, —$NR_7C(O)NR_{10}R_{11}$, —OC(O)$R_7$, —SC(O)$R_7$, —$NR_7C(O)R_7$, —OC(O)$OR_7$, —SC(O)$OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$S(O)_pOR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —OC(S)$R_7$, —SC(S)$R_7$, —$NR_7C(S)R_7$, —OC(S)$OR_7$, —SC(S)$OR_7$, —$NR_7C(S)OR_7$, —OC(S)$NR_{10}R_{11}$, —SC(S)$NR_{10}R_{11}$, —$NR_7C(S)NR_{10}R_{11}$, —OC($NR_8$)$R_7$, —SC($NR_8$)$R_7$, —$NR_7C(NR_8)R_7$, —OC($NR_8$)$OR_7$, —SC($NR_8$)$OR_7$, —$NR_7C(NR_8)OR_7$, —OC($NR_8$)$NR_{10}R_{11}$, —SC($NR_8$)$NR_{10}R_{11}$, —$NR_7C(NR_8)NR_{10}R_{11}$, —OP(O)($OR_7$)$_2$, or —SP(O)($OR_7$)$_2$. Preferably, $R_1$ is —OH, —SH, or —$NHR_7$;

$R_3$ is —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —OC(O)$NR_{10}R_{11}$, —SC(O)$NR_{10}R_{11}$, —$NR_7C(O)NR_{10}R_{11}$, —OC(O)$R_7$, —SC(O)$R_7$, —$NR_7C(O)R_7$, —OC(O)$OR_7$, —SC(O)$OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$S(O)_pOR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —OC(S)$R_7$, —SC(S)$R_7$, —$NR_7C(S)R_7$, —OC(S)$OR_7$, —SC(S)$OR_7$, —$NR_7C(S)OR_7$, —OC(S)$NR_{10}R_{11}$, —SC(S)$NR_{10}R_{11}$, —$NR_7C(S)NR_{10}R_{11}$, —OC($NR_8$)$R_7$, —SC($NR_8$)$R_7$, —$NR_7C(NR_8)R_7$, —OC($NR_8$)$OR_7$, —SC($NR_8$)$OR_7$, —$NR_7C(NR_8)OR_7$, —OC($NR_8$)$NR_{10}R_{11}$, —SC($NR_8$)

$NR_{10}R_{11}$, —$NR_7C(NR_8)NR_{10}R_{11}$, —C(O)OH, —C(O)$NHR_8$, —C(O)SH, —S(O)OH, —S(O)$_2$OH, —S(O)$NHR_8$, —S(O)$_2NHR_8$, —OP(O)($OR_7$)$_2$, or —SP(O)($OR_7$)$_2$;

$R_7$ and $R_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{10}$ and $R_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{21}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl. Preferably, $R_{21}$ is an optionally substituted alkyl, an optionally substituted cycloalkyl, an optionally substituted aryl or an optionally substituted heteroaryl. Alternatively, $R_{21}$ is

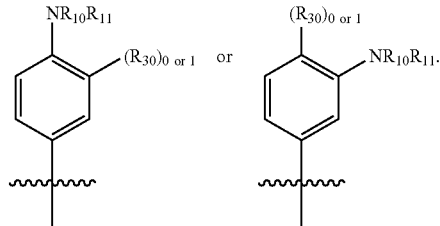

wherein $R_{10}$ and $R_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or heteroaryl, an optionally substituted aralkyl; or $R_{10}$ and $R_{11}$, taken together with the nitrogen to which they are attached, form an optionally substituted heteroaryl or heterocyclyl; and $R_{30}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, alkoxy, haloalkoxy, —$NR_{10}R_{11}$, —$OR_7$, —C(O)$R_7$, —C(O)$OR_7$, —C(S)$R_7$, —C(O)$SR_7$, —C(S)$SR_7$, —C(S)$OR_7$, —C(S)$NR_{10}R_{11}$, —C($NR_8$)$OR_7$, —C($NR_8$)$R_7$, —C($NR_8$)$NR_{10}R_{11}$, —C($NR_8$)$SR_7$, —OC(O)$R_7$, —OC(O)$OR_7$, —OC(S)$OR_7$, —OC($NR_8$)$OR_7$, —SC(O)$R_7$, —SC(O)$OR_7$, —SC($NR_8$)$OR_7$, —OC(S)$R_7$, —SC(S)$R_7$, —SC(S)$OR_7$, —OC(O)$NR_{10}R_{11}$, —OC(S)$NR_{10}R_{11}$, —OC($NR_8$)$NR_{10}R_{11}$, —SC(O)$NR_{10}R_{11}$, —SC($NR_8$)$NR_{10}R_{11}$, —SC(S)

$NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$;

z and q are independently an integer from 0 to 4; and x is 0 or 1, provided that z+x less than or equal to 4.

$R_{22}$, for each occurrence, is independently —H or an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, a haloalkyl, —$C(O)R_7$, —$C(O)OR_7$, —$OC(O)R_7$, —$C(O)NR_{10}R_{11}$, —$NR_8C(O)R_7$, —$S(O)_pR_7$, —$S(O)_pOR_7$, or —$S(O)_pNR_{10}R_{11}$. Preferably, $R_{22}$ is —H, an alkyl, an aralkyl, —$C(O)R_7$, —$C(O)OR_7$, or —$C(O)NR_{10}R_{11}$; and $R_{23}$ and $R_{24}$, for each occurrence, are independently —H, a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, halo, cyano, nitro, guanadino, a haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$;

$R_{26}$ is a lower alkyl;

p, for each occurrence, is, independently, 0, 1 or 2; and m, for each occurrence, is independently, 1, 2, 3, or 4.

i) Exemplary Compounds of the Invention

Exemplary triazole compounds of the invention are depicted in Table 5 below, including tautomers, pharmaceutically acceptable salts, solvates, clathrates, hydrates, polymorphs or prodrugs thereof.

TABLE 5

| No. | Structure | Tautomeric Structure | Name |
| --- | --- | --- | --- |
| 1 | 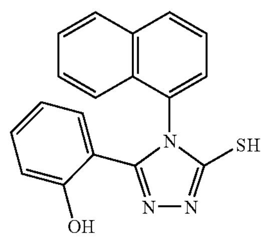 |  | 3-(2-Hydroxyphenyl)-4-(naphthalen-1-yl)-5-mercapto-triazole |
| 2 | 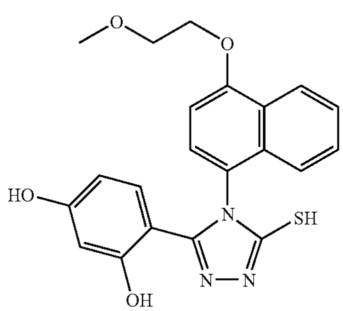 |  | 3-(2,4-Dihydroxyphenyl)-4-[4-(2-methoxyethoxy)-naphthalen-1-yl]-5-mercapto-triazole |
| 3 | 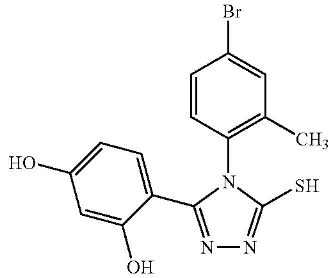 |  | 3-(2,4-Dihydroxyphenyl)-4-(2-methyl-4-bromophenyl)-5-mercapto-triazole |

TABLE 5-continued

| No. | Structure | Tautomeric Structure | Name |
|---|---|---|---|
| 4 | 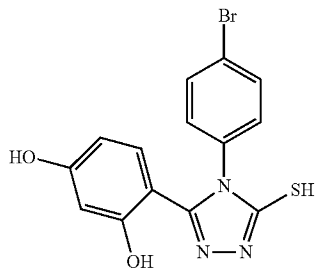 | | 3-(2,4-Dihydroxyphenyl)-4-(4-bromophenyl)-5-mercapto-triazole |
| 5 | 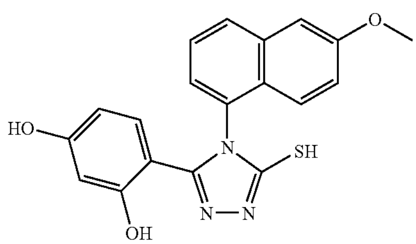 | | 3-(3,4-Dihydroxyphenyl)-4-(6-methoxy-naphthalen-1-yl)-5-mercapto-triazole |
| 6 | 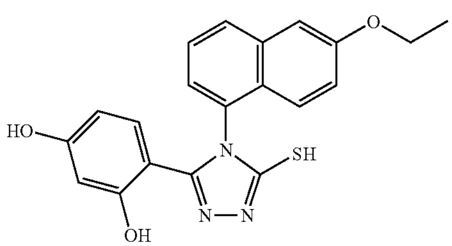 | | 3-(3,4-Dihydroxyphenyl)-4-(6-ethoxy-naphthalen-1-yl)-5-mercapto-triazole |
| 7 | 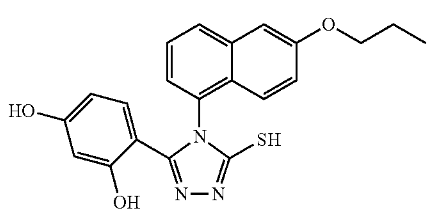 | | 3-(3,4-Dihydroxyphenyl)-4-(6-propoxy-naphthalen-1-yl)-5-mercapto-triazole |
| 8 | 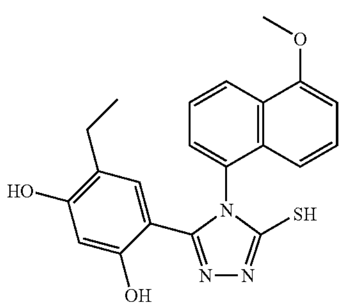 | | 3-(2,4-Dihydroxy-5-ethyl-phenyl)-4-(5-methoxy-naphthalen-1-yl)-5-mercapto-triazole |
| 9 | 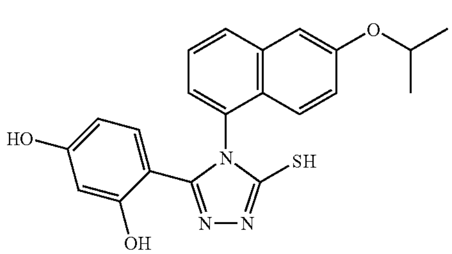 | | 3-(3,4-Dihydroxyphenyl)-4-(6-isopropoxy-naphthalen-1-yl)-5-mercapto-triazole |

TABLE 5-continued

| No. | Structure | Tautomeric Structure | Name |
|---|---|---|---|
| 10 | 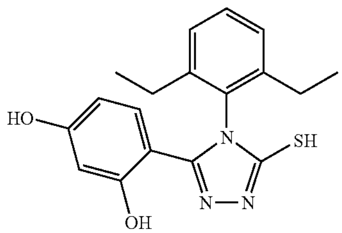 | | 3-(2,4-Dihydroxyphenyl)-4-(2,6-diethylphenyl)-5-mercapto-triazole |
| 11 | 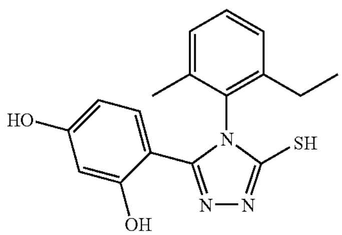 | | 3-(2,4-Dihydroxyphenyl)-4-(2-methy-6-ethylphenyl)-5-mercapto-triazole |
| 12 | 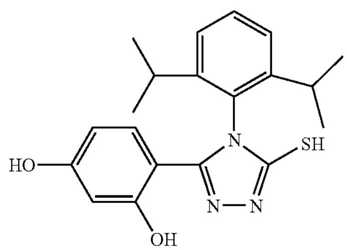 | | 3-(2,4-Dihydroxyphenyl)-4-(2,6-diisopropylphenyl)-5-mercapto-triazole |
| 13 | 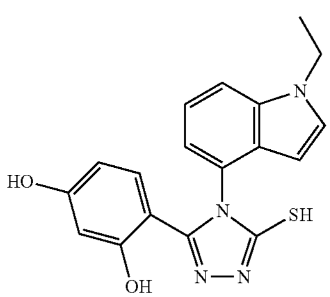 | | 3-(2,4-Dihydroxyphenyl)-4-(1-ethyl-indol-4-yl)-5-mercapto-triazole |
| 14 | 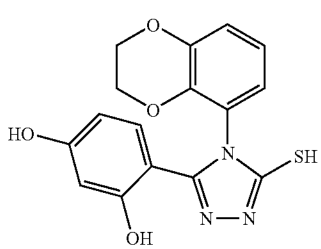 | | 3-(2,4-Dihydroxyphenyl)-4-(2,3-dihydro-benzo[1,4]dioxin-5-yl)-5-mercapto-triazole |
| 15 | 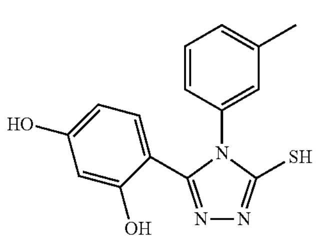 | | 3-(2,4-Dihydroxyphenyl)-4-(3-methylphenyl)-5-mercapto-triazole |

TABLE 5-continued

| No. | Structure | Tautomeric Structure | Name |
|---|---|---|---|
| 16 | 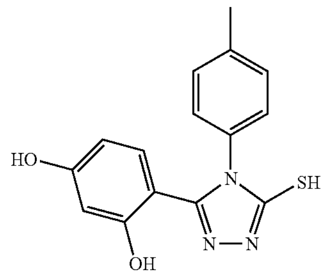 | | 3-(2,4-Dihydroxyphenyl)-4-(4-methylphenyl)-5-mercapto-triazole |
| 17 | 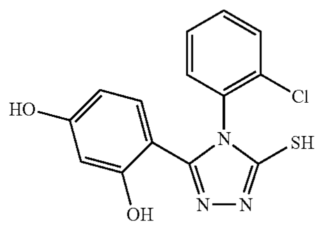 | | 3-(2,4-Dihydroxyphenyl)-4-(2-chlorophenyl)-5-mercapto-triazole |
| 18 | 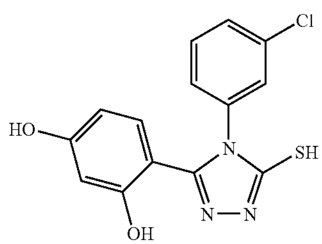 | | 3-(2,4-Dihydroxyphenyl)-4-(3-chlorophenyl)-5-mercapto-triazole |
| 19 | 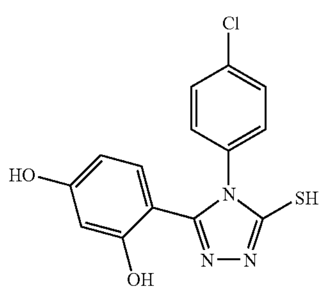 | | 3-(2,4-Dihydroxyphenyl)-4-(4-chlorophenyl)-5-mercapto-triazole |
| 20 | 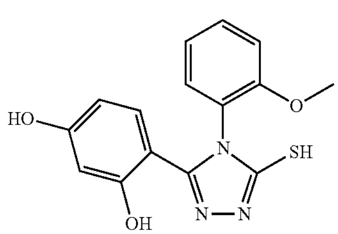 | | 3-(2,4-Dihydroxyphenyl)-4-(2-methoxyphenyl)-5-mercapto-triazole |
| 21 | 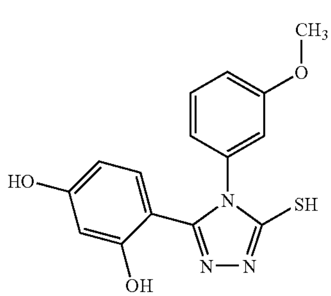 | | 3-(2,4-Dihydroxyphenyl)-4-(3-methoxyphenyl)-5-mercapto-triazole |

TABLE 5-continued

| No. | Structure | Tautomeric Structure | Name |
|---|---|---|---|
| 22 | 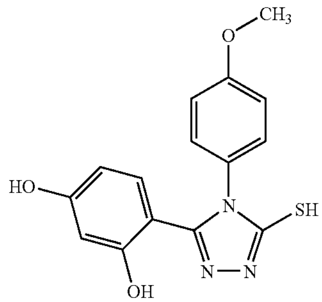 | | 3-(2,4-Dihydroxy-phenyl)-4-(4-methoxyphenyl)-5-mercapto-triazole |
| 23 | 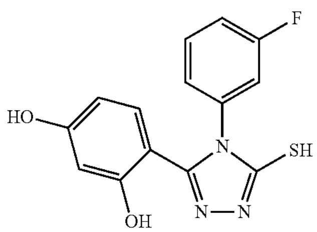 | | 3-(2,4-Dihydroxy-phenyl)-4-(3-fluorophenyl)-5-mercapto-triazole |
| 24 | 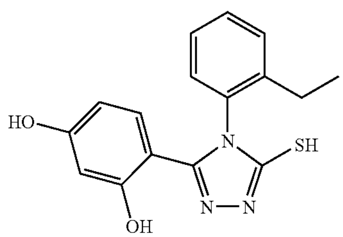 | | 3-(2,4-Dihydroxy-phenyl)-4-(2-ethylphenyl)-5-mercapto-triazole |
| 25 | 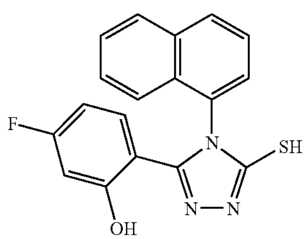 | | 3-(2-Hydroxy-4-fluorophenyl)-4-(naphthalen-1-yl)-5-mercapto-triazole |
| 26 | 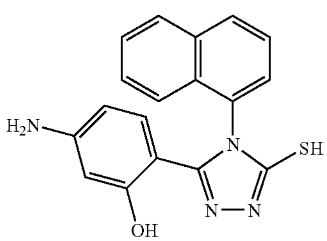 | | 3-(2-Hydroxy-4-aminophenyl)-4-(naphthalen-1-yl)-5-mercapto-triazole |
| 27 | 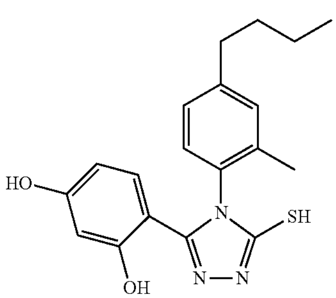 | | 3-(2,4-Dihydroxy-phenyl)-4-(2-methyl-4-butyl-phenyl)-5-mercapto-triazole |

TABLE 5-continued

| No. | Structure | Tautomeric Structure | Name |
|---|---|---|---|
| 28 | 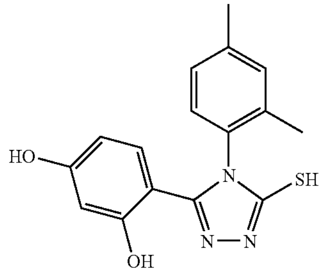 | | 3-(2,4-Dihydroxyphenyl)-4-(2,4-dimethylphenyl)-5-mercapto-triazole |
| 29 | 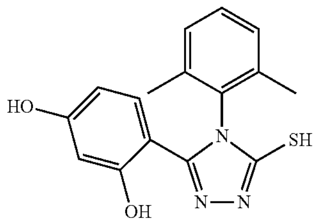 | | 3-(2,4-Dihydroxyphenyl)-4-(2,6-dimethylphenyl)-5-mercapto-triazole |
| 30 | 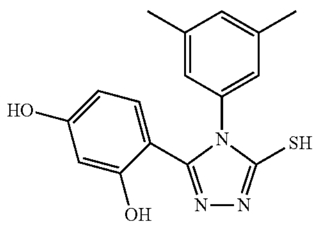 | | 3-(2,4-Dihydroxyphenyl)-4-(2,6-dimethylphenyl)-5-mercapto-triazole |
| 31 | 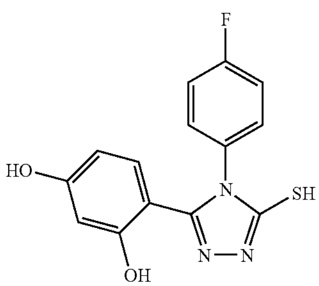 | | 3-(2,4-Dihydroxyphenyl)-4-(4-fluorophenyl)-5-mercapto-triazole |
| 32 | 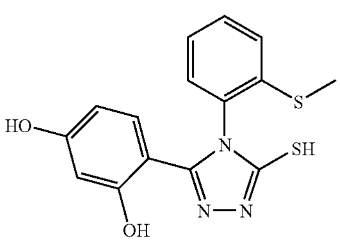 | | 3-(2,4-Dihydroxyphenyl)-4-(2-methylsulfanylphenyl)-5-mercapto-triazole |
| 33 | 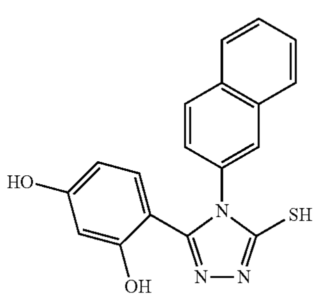 | | 3-(2,4-Dihydroxyphenyl)-4-(naphthalene-2-yl)-5-mercapto-triazole |

TABLE 5-continued

| No. | Structure | Tautomeric Structure | Name |
|---|---|---|---|
| 34 | 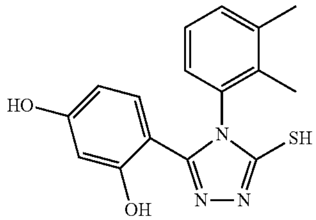 | | 3-(2,4-Dihydroxyphenyl)-4-(2,3-dimethyl-phenyl)-5-mercapto-triazole |
| 35 | 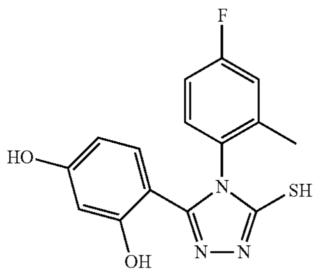 | | 3-(2,4-Dihydroxy-phenyl)-4-(2-methyl-4-fluorophenyl)-5-mercapto-triazole |
| 36 | 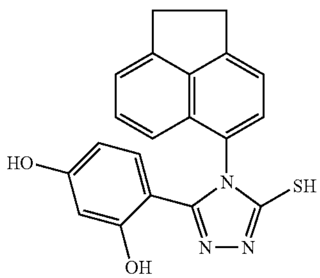 | | 3-(2,4-Dihydroxy-phenyl)-4-(acenaphthalen-5-yl)-5-mercapto-triazole |
| 37 | 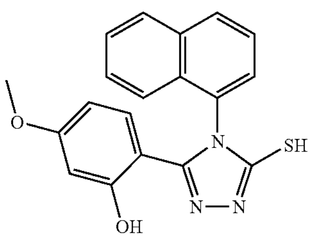 | | 3-(2-Hydroxy-4-methoxy-phenyl)-4-(naphthalen-1-yl)-5-mercapto-triazole |
| 38 | 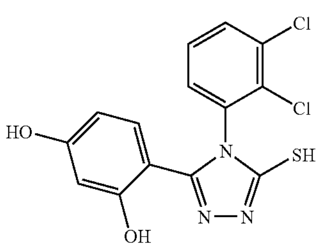 | | 3-(2,4-Dihydroxy-phenyl)-4-(2,3-dichloro-phenyl)-5-mercapto-triazole |
| 39 | 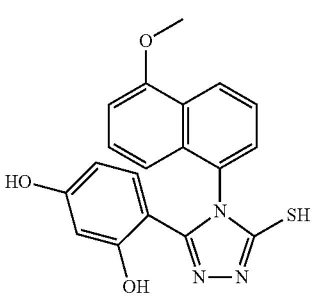 | | 3-(2,4-Dihydroxy-phenyl)-4-(5-methoxy-naphthalen-1-yl)-5-mercapto-triazole |

TABLE 5-continued

| No. | Structure | Tautomeric Structure | Name |
|---|---|---|---|
| 40 | 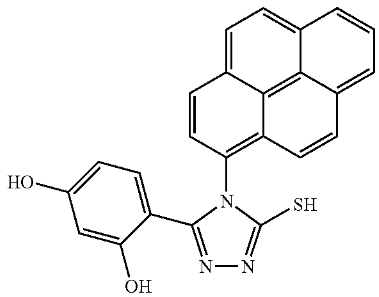 | | 3-(2,4-Dihydroxy-phenyl)-4-(pyren-1-yl)-5-mercapto-triazole |
| 41 | 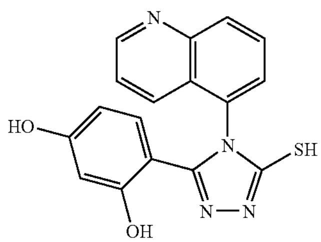 | | 3-(2,4-Dihydroxy-phenyl)-4-(quinolin-5-yl)-5-mercapto-triazole |
| 42 | 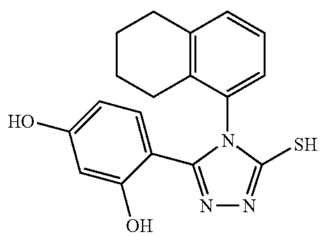 | | 3-(2,4-Dihydroxy-phenyl)-4-(1,2,3,4-tetrahydronaphthalen-5-yl)-5-mercapto-triazole |
| 43 | 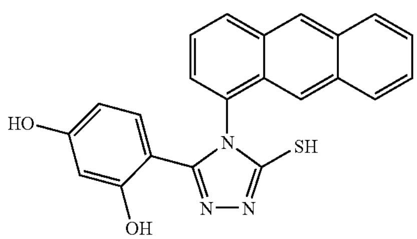 | | 3-(2,4-Dihydroxy-phenyl)-4-(anthracen-1-yl)-5-mercapto-triazole |
| 44 | 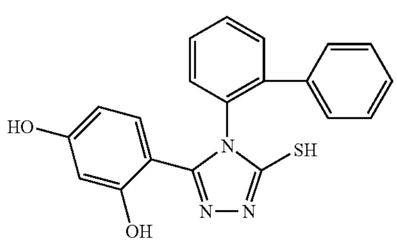 | | 3-(2,4-Dihydroxy-phenyl)-4-(biphenyl-2-yl)-5-mercapto-triazole |
| 45 | 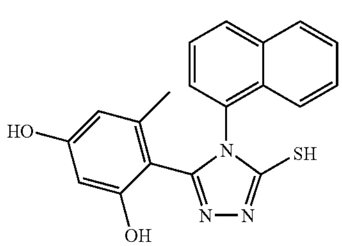 | | 3-(2,4-Dihydroxy-6-methyl-phenyl)-4-(naphthalene-1-yl)-5-mercapto-triazole |

| No. | Structure | Tautomeric Structure | Name |
|---|---|---|---|
| 46 | 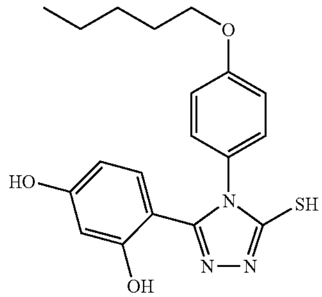 | | 3-(2,4-Dihydroxy-phenyl)-4-(4-pentyloxy-phenyl)-5-mercapto-triazole |
| 47 | 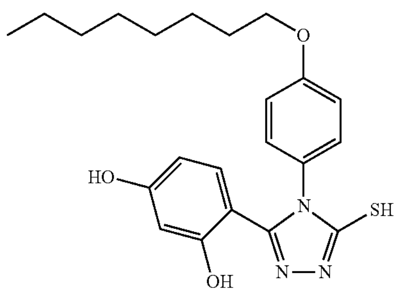 | | 3-(2,4-Dihydroxy-phenyl)-4-(4-octyloxy-phenyl)-5-mercapto-triazole |
| 48 | 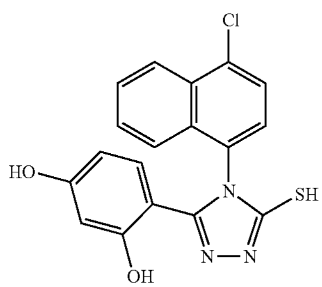 | | 3-(2,4-Dihydroxy-phenyl)-4-(4-chloro-naphthalen-1-yl)-5-mercapto-triazole |
| 49 | 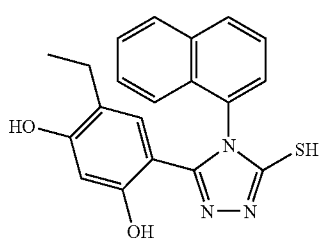 | | 3-(2,4-Dihydroxy-5-ethyl-phenyl)-4-(naphthalen-1-yl)-5-mercapto-triazole |
| 50 | 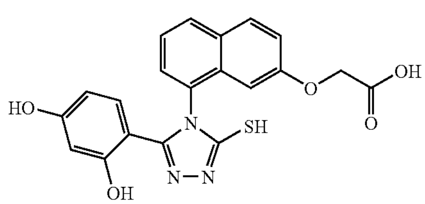 | | 3-(2,4-Dihydroxy-5-ethyl-phenyl)-4-(7-carboxymethoxy-naphthalen-1-yl)-5-mercapto-triazole |
| 51 | 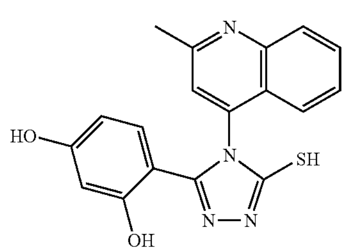 | | 3-(2,4-Dihydroxy-phenyl)-4-(2-methyl-quinolin-4-yl)-5-mercapto-triazole |

TABLE 5-continued

| No. | Structure | Tautomeric Structure | Name |
|---|---|---|---|
| 52 | 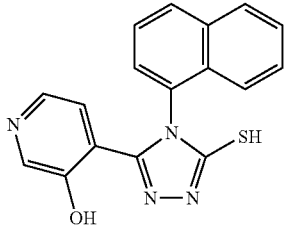 | 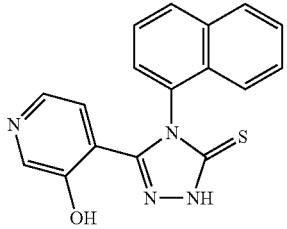 | 3-(3-Hydroxy-pyridin-4-yl)-4-(naphthalen-1-yl)-5-mercapto-triazole |
| 53 | 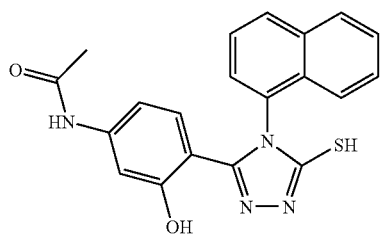 | 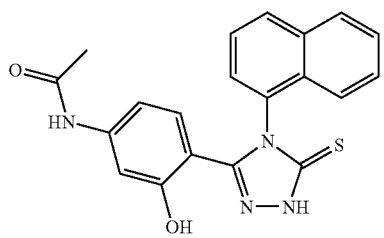 | 3-(2-Hydroxy-4-acetylamino-phenyl)-4-(naphthalen-1-yl)-5-mercapto-triazole |
| 54 | 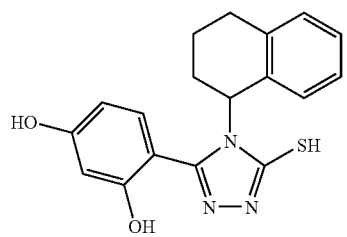 | 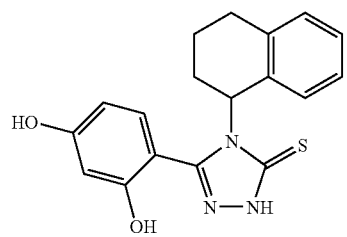 | 3-(2,4-Dihydroxy-phenyl)-4-(1,2,3,4-tetrahydronaphthalen-1-yl)-5-mercapto-triazole |
| 55 | 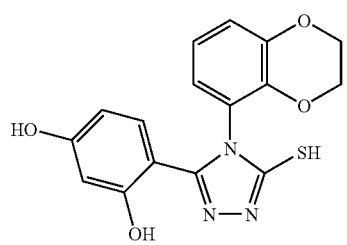 | 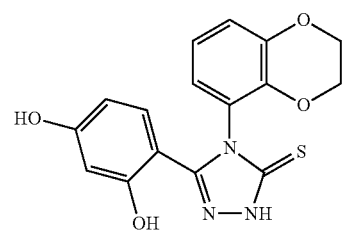 | 3-(2,4-Dihydroxy-phenyl)-4-(2,3-dihydro-benzo[1,4]dioxin-5-yl)-5-mercapto-triazole |
| 56 | 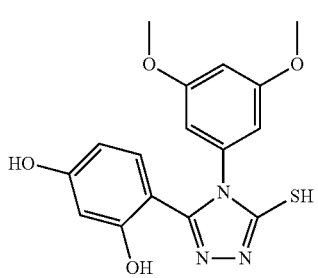 | 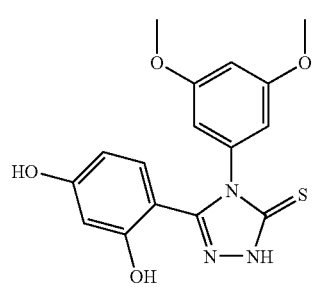 | 3-(2,4-Dihydroxy-phenyl)-4-(3,5-dimethoxyphenyl)-5-mercapto-triazole |
| 57 | 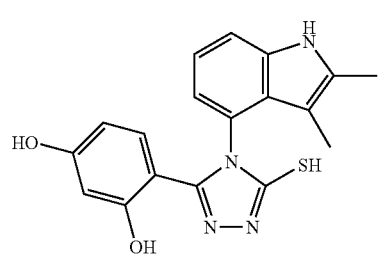 | 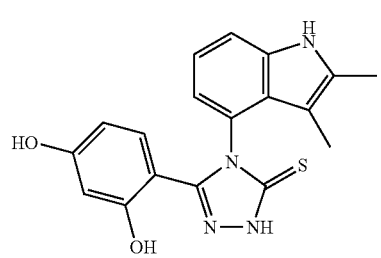 | 3-(2,4-Dihydroxy-phenyl)-4-(2,3-dimethyl-1H-indol-4-yl)-5-mercapto-triazole |

TABLE 5-continued

| No. | Structure | Tautomeric Structure | Name |
|---|---|---|---|
| 58 | 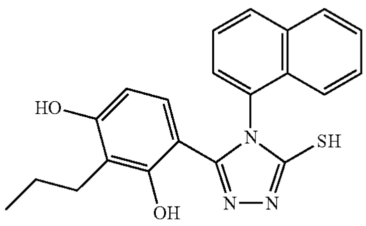 | | 3-(2,4-Dihydroxy-3-propyl-phenyl)-4-(naphthalen-1-yl)-5-mercapto-triazole |
| 59 | 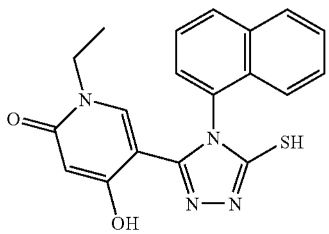 | | 3-(1-ethyl-4-hydroxy-6-oxo-1,6-dihydro-pyridin-3-yl)-4-(naphthalen-1-yl)-5-mercapto-triazole |
| 60 | 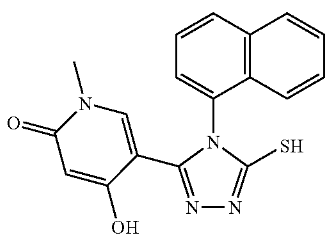 | | 3-(4-hydroxy-6-oxo-pyridin-3-yl)-4-(naphthalen-1-yl)-5-mercapto-triazole |
| 61 | 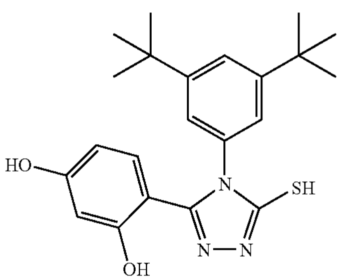 | | 3-(2,4-Dihydroxy-phenyl)-4-(3,5-di-tert-butylphenyl)-5-mercapto-triazole |
| 62 | 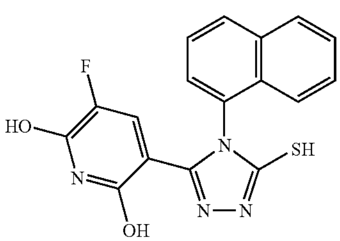 | | 3-(2,6-Dihydroxy5-fluoro-pyridin-3-yl) 4-(naphthalen-1-yl)-5-mercapto-triazole |
| 63 | 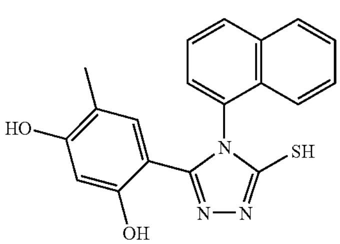 | | 3-(2,4-Dihydroxy-5-methyl-phenyl)-4-(naphthalene-1-yl)-5-mercapto-triazole |

TABLE 5-continued

| No. | Structure | Tautomeric Structure | Name |
|---|---|---|---|
| 64 | 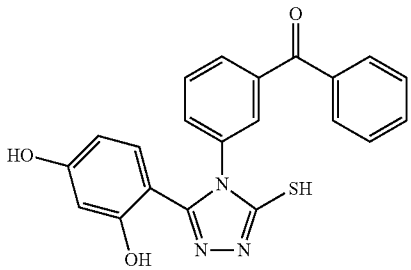 | | 3-[2,4-Dihydroxy-phenyl]-4-(3-benzoylphenyl)-5-mercapto-triazole |
| 65 | 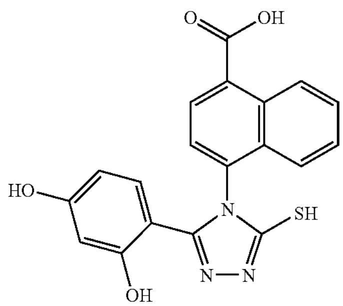 | | 3-(2,4-Dihydroxy-phenyl)-4-(4-carboxy-naphthalen-1-yl)-5-mercapto-triazole |
| 66 | 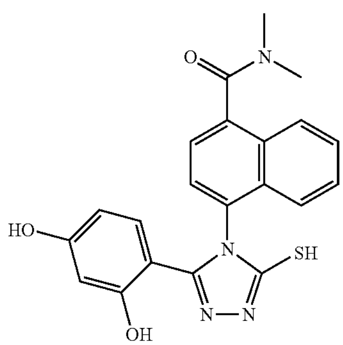 | | 3-(2,4-Dihydroxy-phenyl)-4-[4-(N,N-dimethylcarbamoyl)-naphthalen-1-yl]-5-mercapto-triazole |
| 67 | 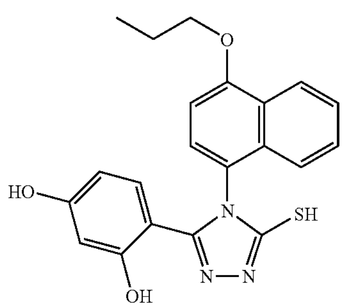 | | 3-(2,4-Dihydroxy-phenyl)-4-(4-propoxy-naphthalen-1-yl)-5-mercapto-triazole |
| 68 | 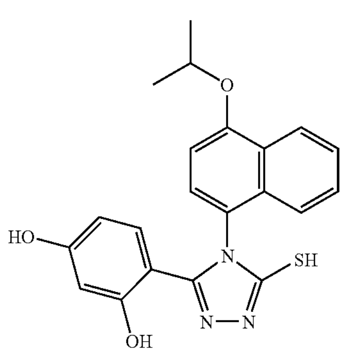 | | 3-(2,4-Dihydroxy-phenyl)-4-(4-isopropoxy-naphthalen-1-yl)-5-mercapto-triazole |

TABLE 5-continued

| No. | Structure | Tautomeric Structure | Name |
|---|---|---|---|
| 69 | 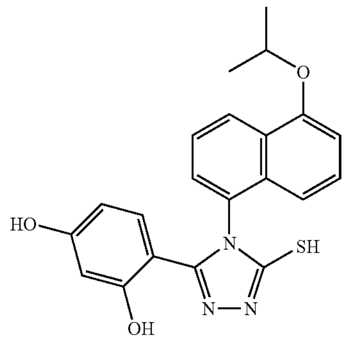 | | 3-(2,4-Dihydroxy-phenyl)-4-(5-isopropoxy-naphthalen-1-yl)-5-mercapto-triazole |
| 70 | 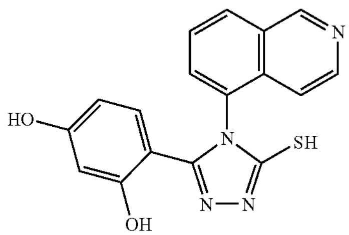 | | 3-(2,4-Dihydroxy-phenyl)-4-(isoquinolin-5-yl)-5-mercapto-triazole |
| 71 | 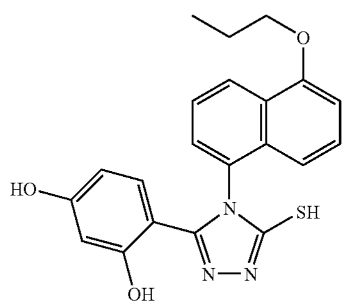 | | 3-(2,4-Dihydroxy-phenyl)-4-(5-propoxy-naphthalen-1-yl)-5-mercapto-triazole |
| 72 | 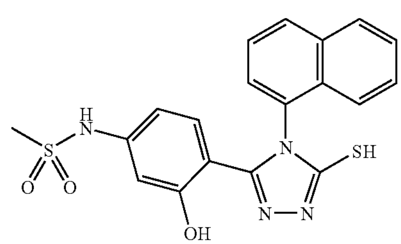 | | 3-(2-Hydroxy-4-methanesulfonamino-phenyl)-4-(naphthalen-1-yl)-5-mercapto-triazole |
| 73 | 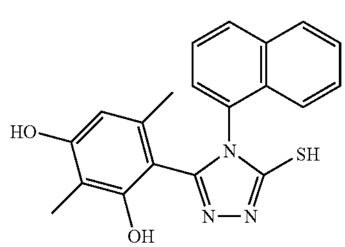 | | 3-(2,4-Dihydroxy-3,6-dimethyl-phenyl)-4-(naphthalen-1-yl)-5-mercapto-triazole |
| 74 | 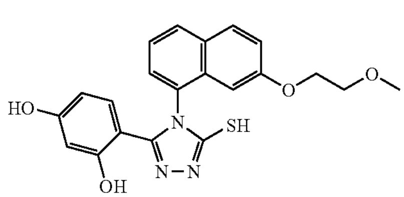 | | 3-(2,4-Dihydroxy-phenyl)-4-[7-(2-methoxyethoxy)-naphthalen-1-yl]-5-mercapto-triazole |

TABLE 5-continued

| No. | Structure | Tautomeric Structure | Name |
|---|---|---|---|
| 75 | 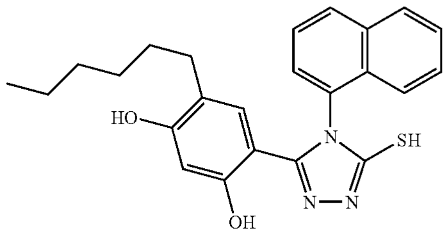 | | 3-(2,4-Dihydroxy-5-hexyl-phenyl)-4-(naphthalen-1-yl)-5-mercapto-triazole |
| 76 | 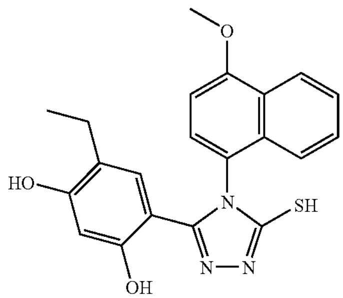 | | 3-(2,4-Dihydroxy-5-ethyl-phenyl)-4-(4-methoxy-naphthalen-1-yl)-5-mercapto-triazole |
| 77 | 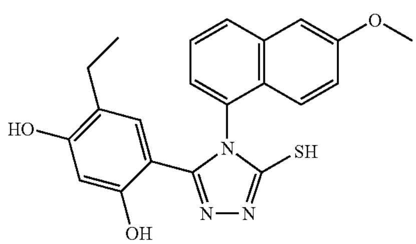 | | 3-(2,4-Dihydroxy-5-ethyl-phenyl)-4-(6-methoxy-naphthalin-1-yl)-5-mercapto-triazole |
| 78 | 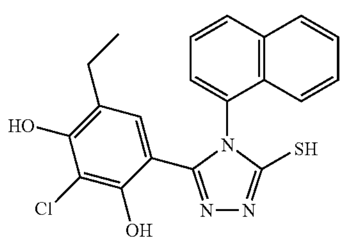 | | 3-(2,4-Dihydroxy-3-chloro-5-ethyl-phenyl)-4-(naphthalen-1-yl)-5-mercapto-triazole |
| 79 | 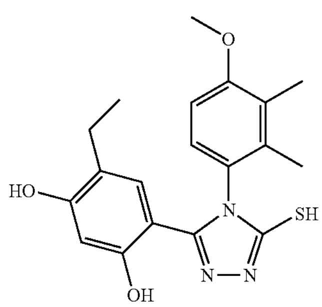 | | 3-(2,4-Dihydroxy-5-ethyl-phenyl)-4-(2,3-dimethy-4-methoxy-phenyl)-5-mercapto-triazole |
| 80 | 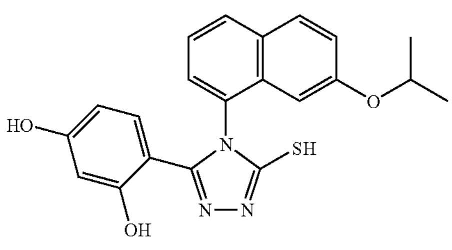 | | 3-(2,4-Dihydroxy-phenyl)-4-(7-isopropoxy-naphthalen-1-yl)-5-mercapto-triazole |

TABLE 5-continued

| No. | Structure | Tautomeric Structure | Name |
|---|---|---|---|
| 81 | 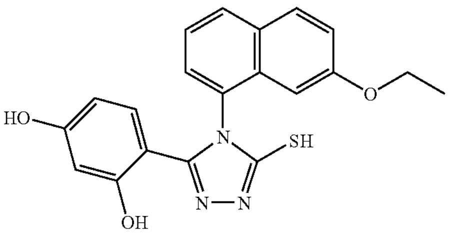 | | 3-(2,4-Dihydroxy-phenyl)-4-(7-ethoxy-naphthalen-1-yl)-5-mercapto-triazole |
| 82 | 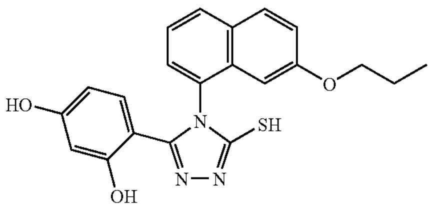 | | 3-(2,4-Dihydroxy-phenyl)-4-(7-propoxy-naphthalen-1-yl)-5-mercapto-triazole |
| 83 | 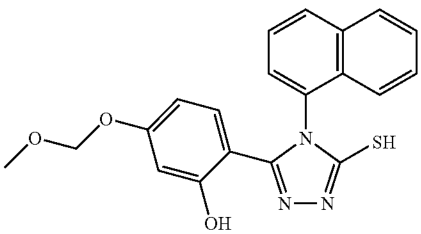 | | 3-(2-Hydroxy-4-methoxymethyoxy-phenyl)-4-(naphthalen-1-yl)-5-mercapto-triazole |
| 84 | 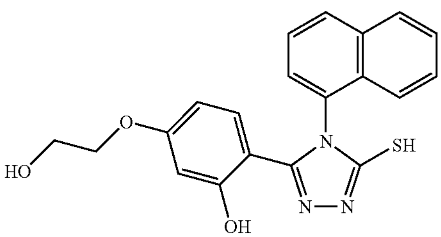 | | 3-[2-Hydroxy-4-(2-hydroxy-ethoxy)-phenyl]-4-(naphthalen-1-yl)-5-mercapto-triazole |
| 85 | 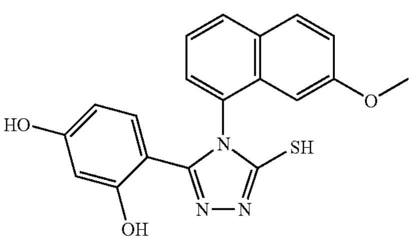 | | 3-(2,4-Dihydroxy-phenyl)-4-(7-methoxy-naphthalen-1-yl)-5-mercapto-triazole |
| 86 | 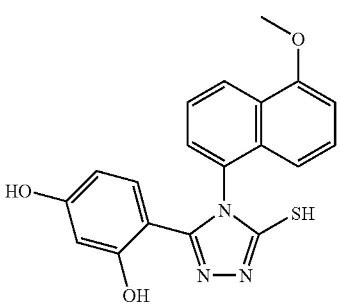 | | 3-(2,4-Dihydroxy-phenyl)-4-(5-methoxy-naphthalen-1-yl)-5-mercapto-triazole |

TABLE 5-continued

| No. | Structure | Tautomeric Structure | Name |
|---|---|---|---|
| 87 | 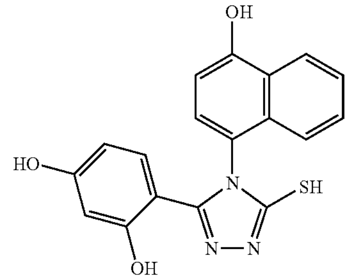 | | 3-(2,4-Dihydroxy-phenyl)-4-(4-hydroxy-naphthalen-1-yl)-5-mercapto-triazole |
| 88 | 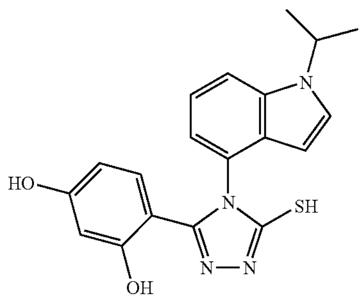 | | 3-(2,4-Dihydroxy-phenyl)-4-(1-isopropyl-indol-4-yl)-5-mercapto-triazole |
| 89 | 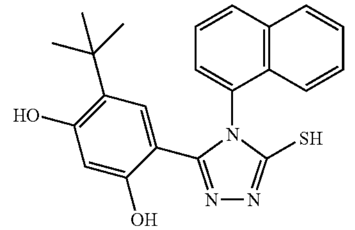 | | 3-(2,4-Dihydroxy-5-tert-butyl-phenyl)-4-(naphthalen-1-yl)-5-mercapto-triazole |
| 90 | 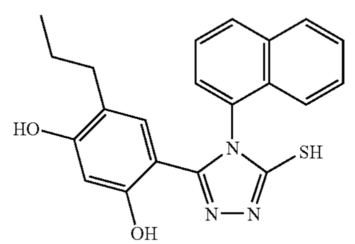 | | 3-(2,4-Dihydroxy-5-propyl-phenyl)-4-(naphthalen-1-yl)-5-mercapto-triazole |
| 91 | 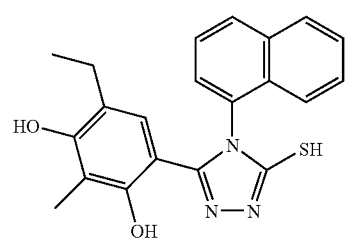 | | 3-(2,4-Dihydroxy-3-methyl-5-ethyl-phenyl)-4-(naphthalen-1-yl)-5-mercapto-triazole |
| 92 | 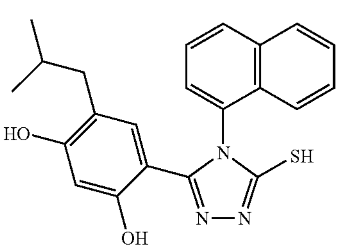 | | 3-(2,4-Dihydroxy-5-isobutyl-phenyl)-4-(naphthalen-1-yl)-5-mercapto-triazole |

TABLE 5-continued

| No. | Structure | Tautomeric Structure | Name |
|---|---|---|---|
| 93 | 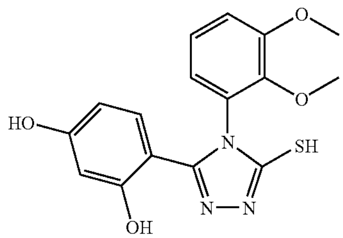 | | 3-(2,4-Dihydroxy-phenyl)-4-(2,3-dimethoxy-phenyl)-5-mercapto-triazole |
| 94 | 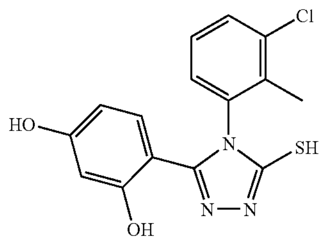 | | 3-(2,4-Dihydroxy-phenyl)-4-(2-methoxy-3-chloro-phenyl)-5-mercapto-triazole |
| 95 | 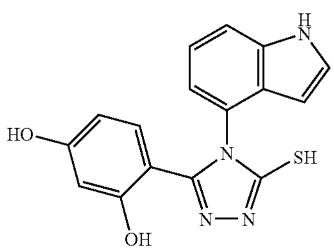 | | 3-(2,4-Dihydroxy-phenyl)-4-(indol-4-yl)-5-mercapto-triazole |
| 96 | 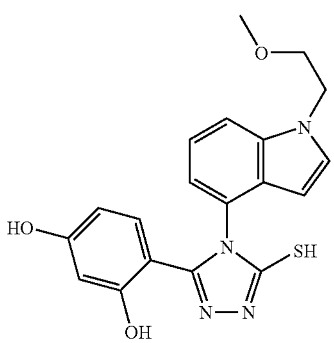 | | 3-(2,4-Dihydroxy-phenyl)-4-[1-(2-methoxyethoxy)-indol-4-yl]-5-mercapto-triazole |
| 97 | 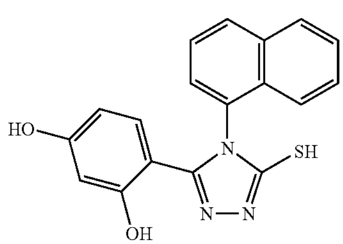 | | 3-(2,4-Dihydroxy-phenyl)-4-(naphthalen-1-yl)-5-hydroxy-triazole |
| 98 | 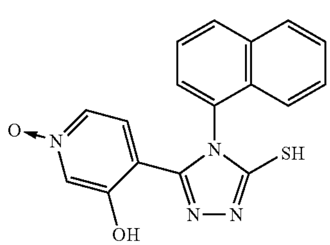 | | 3-(1-Oxo-3-hydroxy-pyridin-4-yl)-4-(naphthalen-1-yl)-5-mercapto-triazole |

TABLE 5-continued

| No. | Structure | Tautomeric Structure | Name |
|---|---|---|---|
| 99 | 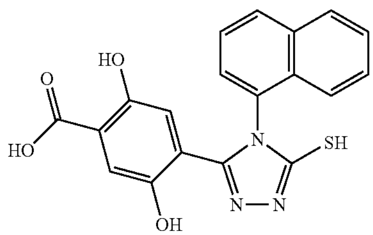 | | 3-(2,5-Dihydroxy-4-carboxy)-4-(naphthalen-1-yl)-5-mercapto-triazole |
| 100 | 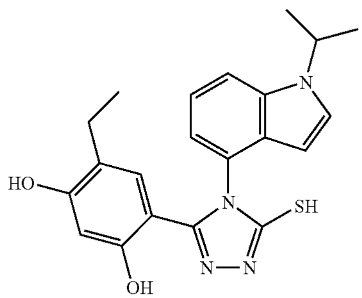 | | 3-(2,4-Dihydroxy-5-ethyl-phenyl)-4-(1-isopropyl-indol-4-yl)-5-mercapto-triazole |
| 101 | 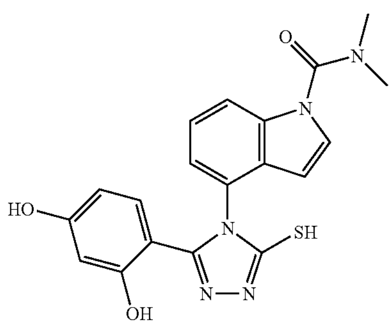 | | 3-(2,4-Dihydroxy-5-ethyl-phenyl)-4-[1-(dimethyl-carbamoyl)-indol-4-yl]-5-mercapto-triazole |
| 102 | 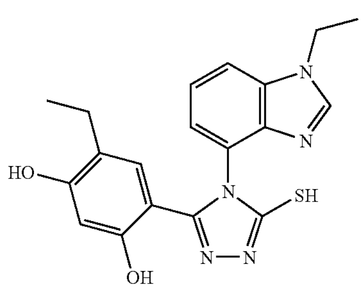 | | 3-(2,4-Dihydroxy-5-ethyl-phenyl)-4-(1-ethyl-benzoimidazol-4-yl)-5-mercapto-triazole |
| 103 | 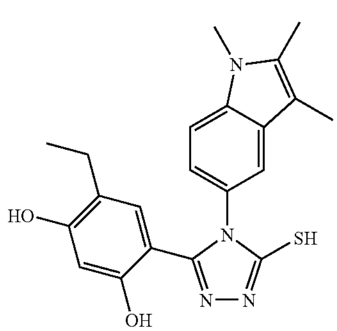 | | 3-(2,4-Dihydroxy-5-ethyl-phenyl)-4-(1,2,3-trimethyl-indol-5-yl)-5-mercapto-triazole |

TABLE 5-continued

| No. | Structure | Tautomeric Structure | Name |
|---|---|---|---|
| 104 | 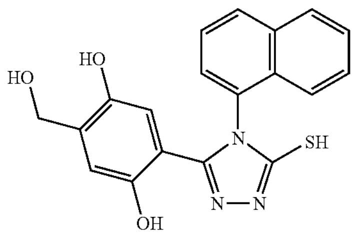 | | 3-(2,5-Dihydroxy-4-hydroxymethyl-phenyl)-4-(naphthalen-1-yl)-5-mercapto-triazole |
| 105 | 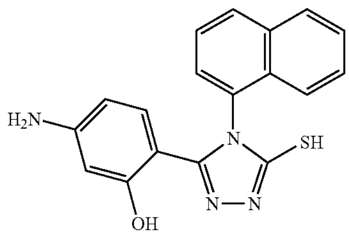 | | 3-(2-Hydroxy-4-amino-phenyl)-4-(naphthalen-1-yl)-5-mercapto-triazole |
| 106 | 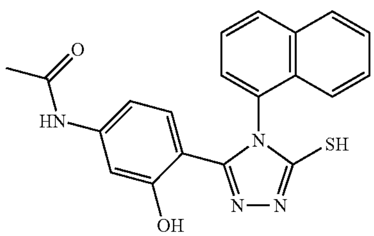 | | 3-(2-Hydroxy-4-acetylamino-phenyl)-4-(naphthalen-1-yl)-5-mercapto-triazole |
| 107 | 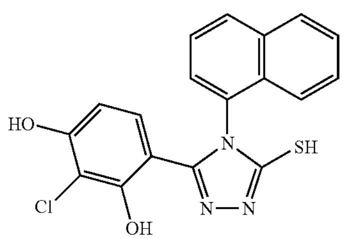 | | 3-(2,4-Dihydroxy-3-chloro-phenyl)-4-(naphthalen-1-yl)-5-mercapto-triazole |
| 108 | 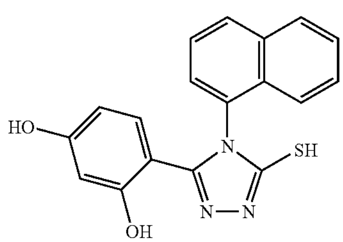 | | 3-(2,4-Dihydroxy-phenyl)-4-(naphthalen-1-yl)-5-mercapto-triazole |
| 109 | 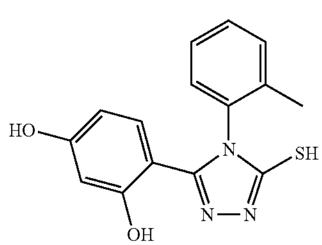 | | 3-(2,4-Dihydroxy-phenyl)-4-(2-methyl-phenyl)-5-mercapto-triazole |

TABLE 5-continued

| No. | Structure | Tautomeric Structure | Name |
|---|---|---|---|
| 110 | 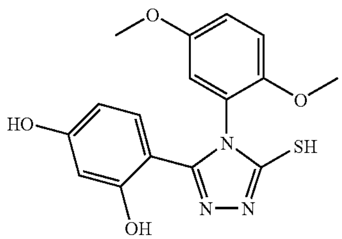 | | 3-(2,4-Dihydroxy-phenyl)-4-(2,5-dimethoxy-phenyl)-5-mercapto-triazole |
| 111 | 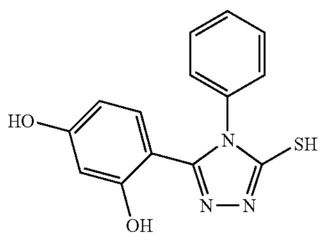 | | 3-(2,4-Dihydroxy-phenyl)-4-phenyl-5-mercapto-triazole |
| 112 | 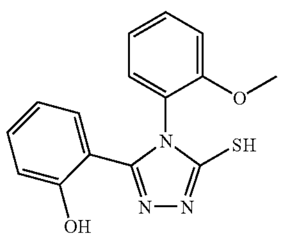 | | 3-(2-Hydroxy-phenyl)-4-(2-methoxy-phenyl)-5-mercapto-triazole |
| 113 | 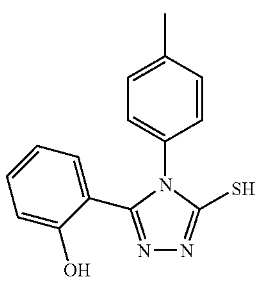 | | 3-(2-Hydroxy-phenyl)-4-(4-methyl-phenyl)-5-mercapto-triazole |
| 114 | 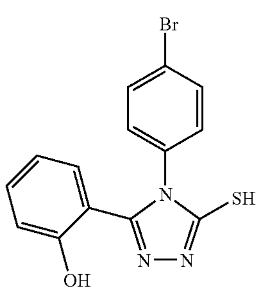 | | 3-(2-Hydroxy-phenyl)-4-(4-bromo-phenyl)-5-mercapto-triazole |
| 115 | 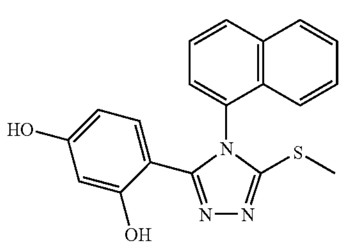 | | 3-(2,4-Dihydroxy-phenyl)-4-(naphthalen-1-yl)-5-(methyl sulfanyl)-triazole |

TABLE 5-continued

| No. | Name |
|---|---|
| 116 | 3-(2,4-Dimethoxy-phenyl)-4-(naphthalen-1-yl)-5-mercapto-triazole |
| 117 | 3-[2,4-Di-(dimethyl-carbamoyloxy)-phenyl]-4-(naphthalen-1-yl)-5-(dimethyl-carbamoylsulfanyl)-triazole |
| 118 | 3-(2,4-Dihydroxy-phenyl)-4-(naphthalen-1-yl)-5-(dimethylcarbamoyl sulfanyl)-triazole |
| 119 | 3-(2,4-Diethoxy-carbonyloxy-phenyl)-4-(naphthalen-1-yl)-5-(ethoxycarbonyl-sulfanyl)-triazole |
| 120 | 3-(2,4-Di-isobutyryl-oxy-phenyl)-4-(naphthalen-1-yl)-5-(isobutyrylsulfanyl)-triazole |

TABLE 5-continued

| No. | Structure | Tautomeric Structure | Name |
| --- | --- | --- | --- |
| 121 | 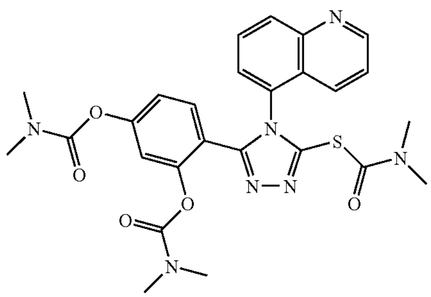 | | 3-[2,4-Di-(dimethyl-carbamoyloxy)-phenyl]-4-(quinolin-5-yl)-5-(dimethyl-carbamoylsulfanyl)-triazole |
| 122 | 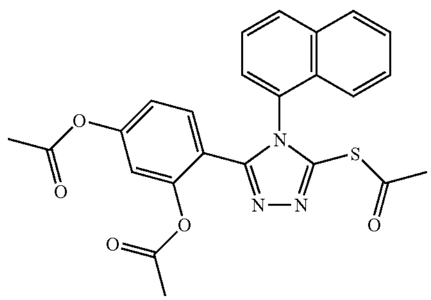 | | 3-(2,4-Diacetoxy-phenyl)-4-(naphthalen-1-yl)-5-(acetylsulfanyl)-triazole |
| 123 | 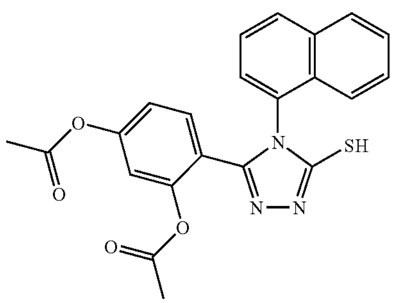 | | 3-(2,4-Diacetoxy-phenyl)-4-(naphthalen-1-yl)-5-mercapto-triazole |
| 124 | 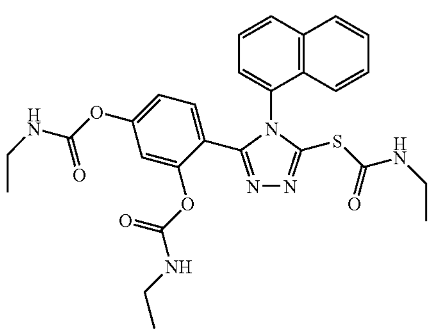 | | 3-(2,4-Diethyl-carbamoyloxy-phenyl)-4-(naphthalen-1-yl)-5-(ethylcarbamoyl-sulfanyl)-triazole |
| 125 | 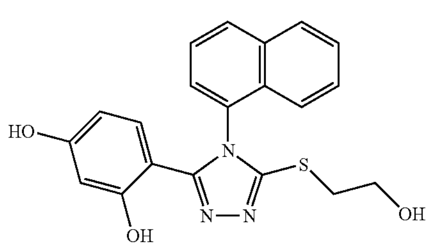 | | 3-(2,4-Dihydroxy-phenyl)-4-(naphthalen-1-yl)-5-(2-hydroxyethyl-sulfanyl)-triazole |

TABLE 5-continued

| No. | Structure | Tautomeric Structure | Name |
|---|---|---|---|
| 126 | 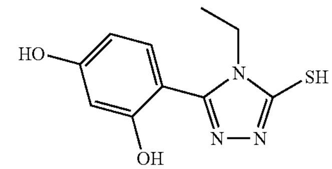 | | 3-(2,4-Dihydroxy-phenyl)-4-ethyl-5-mercapto-triazole |
| 127 | 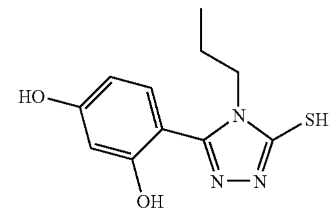 | | 3-(2,4-Dihydroxy-phenyl)-4-propyl-5-mercapto-triazole |
| 128 | 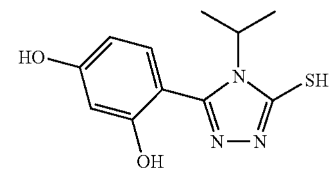 | | 3-(2,4-Dihydroxy-phenyl)-4-isopropyl-5-mercapto-triazole |
| 129 | 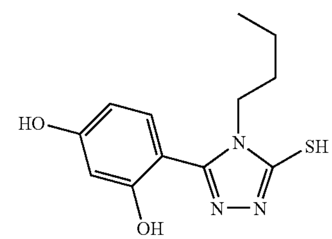 | | 3-(2,4-Dihydroxy-phenyl)-4-butyl-5-mercapto-triazole |
| 130 | 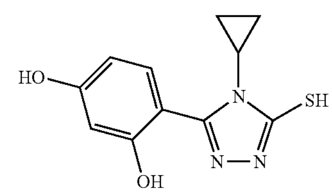 | | 3-(2,4-Dihydroxy-phenyl)-4-cyclopropyl-5-mercapto-triazole |
| 131 | 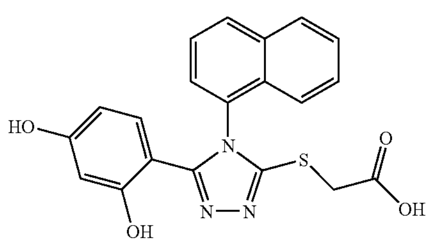 | | 3-(2,4-Dihydroxy-phenyl)-4-(naphthalen-1-yl)-5-(carboxy-ethylsulfanyl)-triazole |
| 132 | 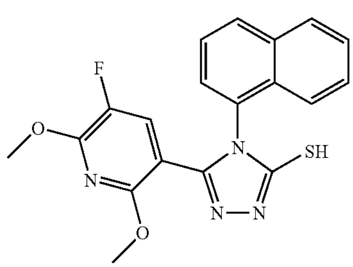 | | 3-(2,6-Dimethoxy-5-fluoro-pyridin-3-yl)-4-(naphthalen-1-yl)-5-mercapto-triazole |

TABLE 5-continued

| No. | Structure | Tautomeric Structure | Name |
|---|---|---|---|
| 133 | 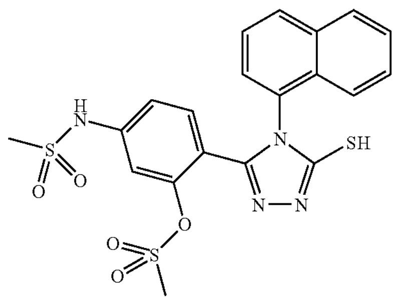 | | 3-(2-Methanesulfonyloxy-4-methanesulfonyl-amino-phenyl)-4-(naphthalen-1-yl)-5-mercapto-triazole |
| 134 | 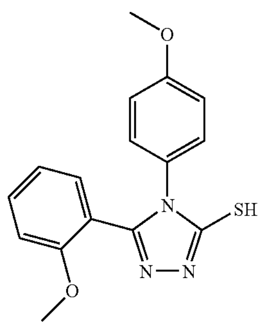 | | 3-(2-Methoxy-phenyl)-4-(4-methoxy-phenyl)-5-mercapto-triazole |
| 135 | 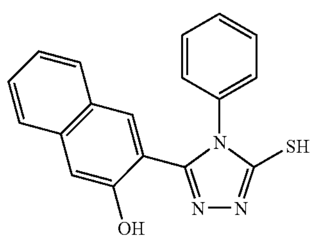 | | 3-(3-Hydroxy-naphthalen-2-yl)-4-phenyl-5-mercapto-triazole |
| 136 | 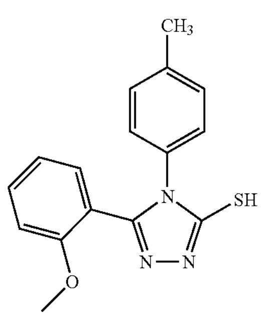 | | 3-(2-Methoxy-phenyl)-4-(4-methyl-phenyl)-5-mercapto-triazole |
| 137 | 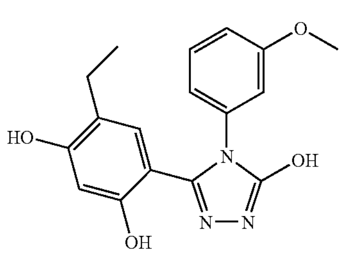 | | 3-(2,4-Dihydroxy-5-ethyl-phenyl)-4-(3-methox-phenyl)-5-hydroxy-triazole |

TABLE 5-continued

| No. | Structure | Tautomeric Structure | Name |
|---|---|---|---|
| 138 | 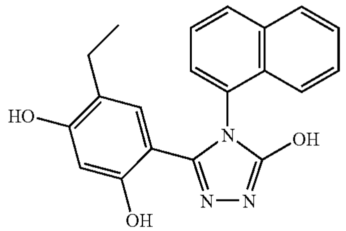 | | 3-(2,4-Dihydroxy-5-ethyl-phenyl)-4-(naphthalen-1-yl)-5-hydroxy-triazole |
| 139 | 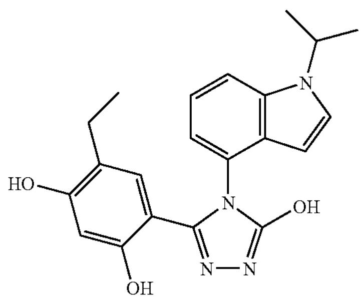 | | 3-(2,4-Dihydroxy-5-ethyl-phenyl)-4-(1-isopropyl-indol-3-yl)-5-hydroxy-triazole |
| 140 | 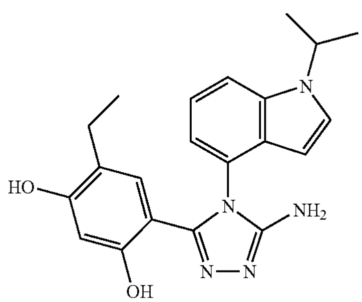 | | 3-(2,4-Dihydroxy-5-ethyl-phenyl)-4-(1-isopropyl-indol-4-yl)-5-amino-triazole |
| 141 | 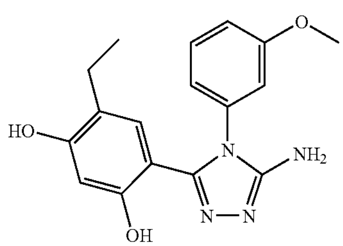 | | 3-(2,4-Dihydroxy-5-ethyl-phenyl)-4-(3-methoxy-phenyl)-5-amino-triazole |
| 142 | 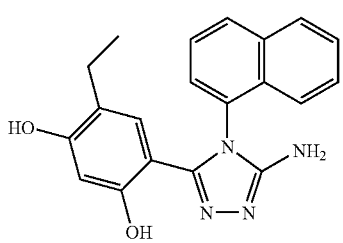 | | 3-(2,4-Dihydroxy-5-ethyl-phenyl)-4-(naphthalen-1-yl)-5-amino-triazole |
| 143 | 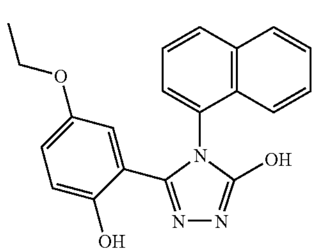 | | 3-(2-Hydroxy-5-ethyloxy-phenyl)-4-(naphthalen-1-yl)-5-hydroxy-triazole |

TABLE 5-continued

| No. | Structure | Tautomeric Structure | Name |
|---|---|---|---|
| 144 | 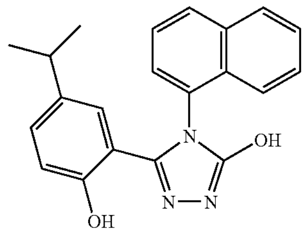 | | 3-(2-Hydroxy-5-isopropyl-phenyl)-4-(naphthalen-1-yl)-5-hydroxy-triazole |
| 145 | 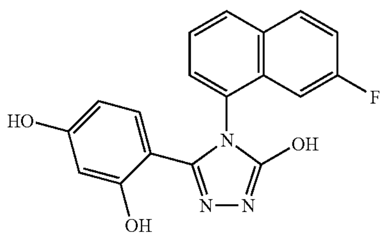 | | 3-(2-Dihydroxy-phenyl)-4-(7-fluoro-naphthalen-1-yl)-5-hydroxy-triazole |
| 146 | 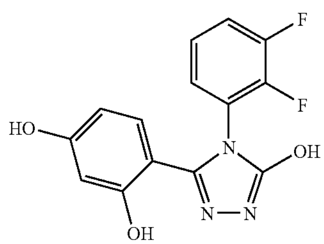 | | 3-(2,4-Dihydroxy-phenyl)-4-(2,3-difluorophenyl)-5-hydroxy-triazole |
| 147 | 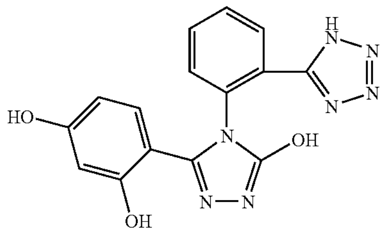 | | 3-(2,4-Dihydroxy-phenyl)-4-[2-(1H-tetrazol-5-yl)-phenyl]-5-hydroxy-triazole |
| 148 | 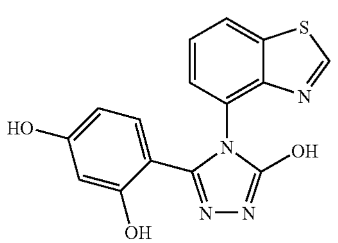 | | 3-(2,4-Dihydroxy-phenyl)-4-(benzothiazol-4-yl)-5-hydroxy-triazole |
| 149 | 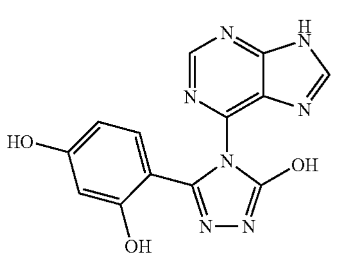 | | 3-(2,4-Dihydroxy-phenyl)-4-(9H-purin-6-yl)-5-hydroxy-triazole |

TABLE 5-continued

| No. | Structure | Tautomeric Structure | Name |
|---|---|---|---|
| 150 | 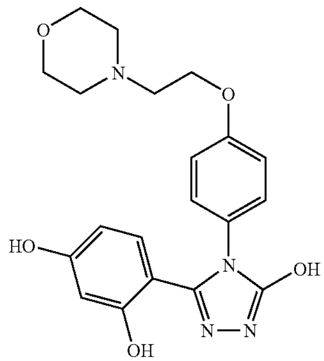 | | 3-(2,4-Dihydroxy-phenyl)-4-{4-[2-(moropholin-1-yl)-ethoxy]-phenyl}-5-hydroxy-triazole |
| 151 | 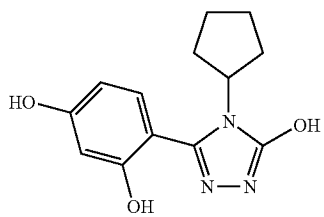 | | 3-(2,4-Dihydroxy-phenyl)-4-cyclopentyl-5-hydroxy-triazole |
| 152 | 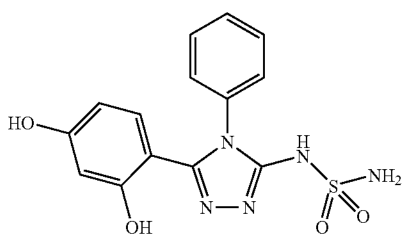 | | 3-(2,4-Dihydroxy-phenyl)-4-phenyl-5-(sulfamoylamino)-triazole |
| 153 | 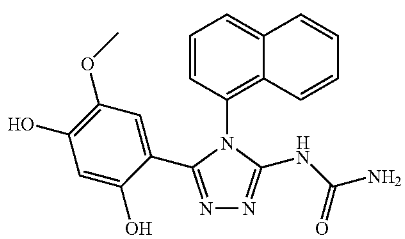 | | 3-(2,4-Dihydroxy-5-methoxy-phenyl)-4-(naphthalene-1-yl)-5-ureido-triazole |
| 154 | 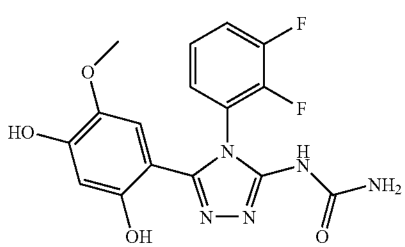 | | 3-(2,4-Dihydroxy-5-methoxy-phenyl)-4-(2,3-difluorophenyl)-5-ureido-triazole |
| 155 | 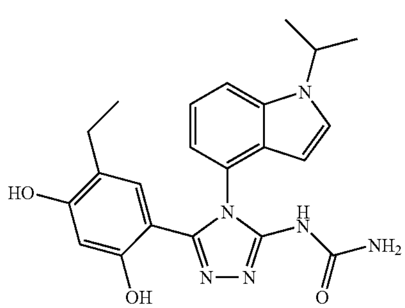 | | 3-(2,4-Dihydroxy-5-ethyl-phenyl)-4-(1-isopropyl-indol-4-yl)-5-ureido-triazole |

TABLE 5-continued

| No. | Structure | Tautomeric Structure | Name |
|---|---|---|---|
| 156 | 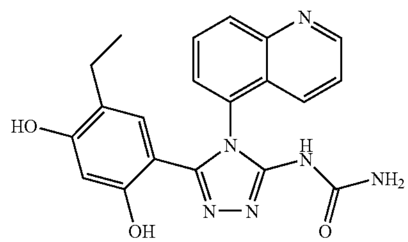 | | 3-(2,4-Dihydroxy-5-ethyl-phenyl)-4-(quinolin-5-yl)-5-ureido-triazole |
| 157 | 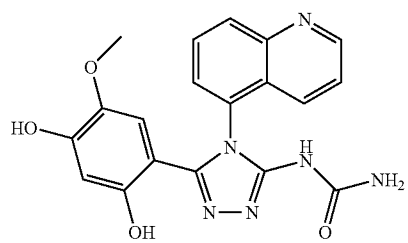 | | 3-(2,4-Dihydroxy-5-methoxy-phenyl)-4-(naphthalene-1-yl)-5-carbamoyloxy-triazole |
| 158 | 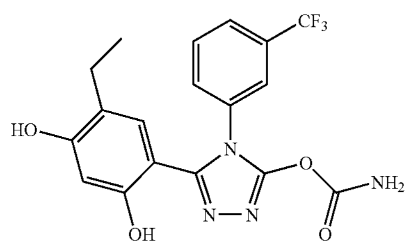 | | 3-(2,4-Dihydroxy-5-ethyl-phenyl)-4-(3-trifluoromethyl-phenyl)-5-carbamoyloxy-triazole |
| 159 | 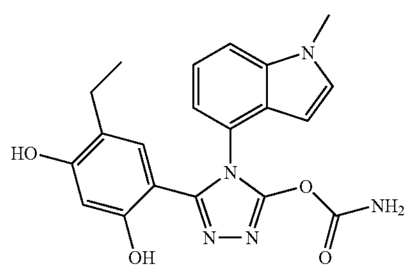 | | 3-(2,4-Dihydroxy-5-ethyl-phenyl)-4-(1-methyl-indol-4-yl)-5-carbamoyloxy-triazole |
| 160 | 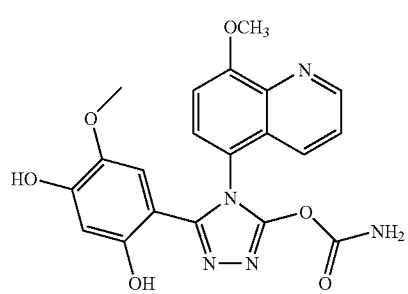 | | 3-(2,4-Dihydroxy-5-methoxy-phenyl)-4-(8-methoxy-quinolin-5-yl)-5-carbamoyloxy-triazole |
| 161 | 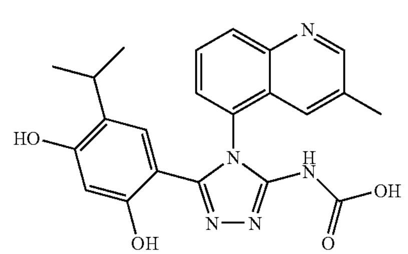 | | 3-(2,4-Dihydroxy-5-isopropyl-phenyl)-4-(3-methyl-quinolin-5-yl)-5-carboxy-amino-triazole |

TABLE 5-continued

| No. | Structure | Tautomeric Structure | Name |
|---|---|---|---|
| 162 | 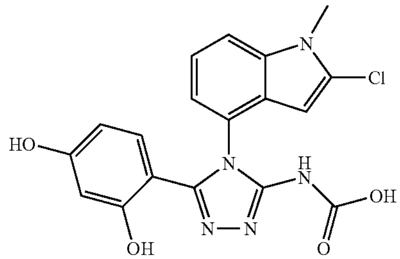 | | 3-(2,4-Dihydroxy-phenyl)-4-(1-methyl-2-chloro-indol-4-yl)-5-carbamoyloxy-triazole |
| 163 | 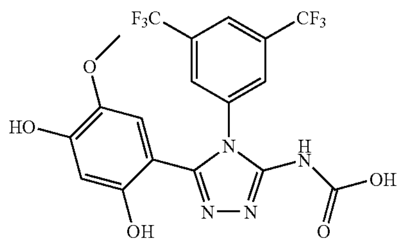 | | 3-(2,4-Dihydroxy-5-methoxy-phenyl)-4-[3,5-di-(trifluoro-methyl)-phenyl]-5-carbamoyloxy-triazole |
| 164 | 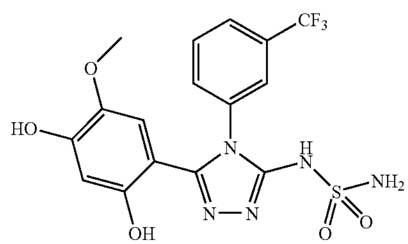 | | 3-(2,4-Dihydroxy-5-methoxy-phenyl)-4-(3-trifluoro-methyl-phenyl)-5-(sulfamoylamino)-triazole |
| 165 | 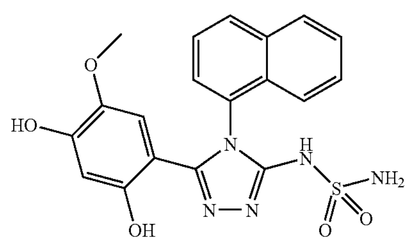 | | 3-(2,4-Dihydroxy-5-methoxy-phenyl)-4-(naphthalene-1-yl)-5-(sulfamoylamino)-triazole |
| 166 | 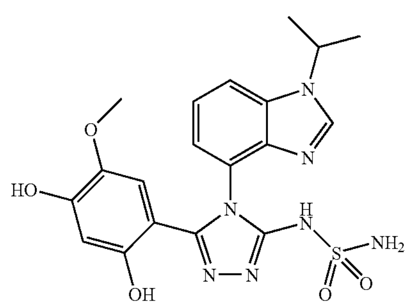 | | 3-(2,4-Dihydroxy-5-methoxy-phenyl)-4-(1-isopropyl-benzoimidazol-4-yl)-5-(sulfamoylamino)-triazole |
| 167 | 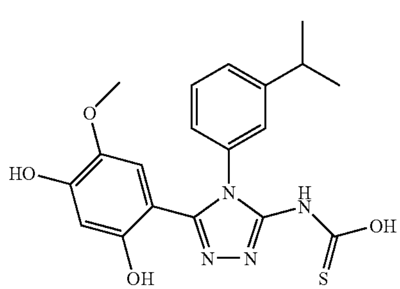 | | 3-(2,4-Dihydroxy-5-methoxy-phenyl)-4-(3-isopropylphenyl)-5-(thiocarboxy-amino)-triazole |

TABLE 5-continued

| No. | Structure | Tautomeric Structure | Name |
|---|---|---|---|
| 168 | 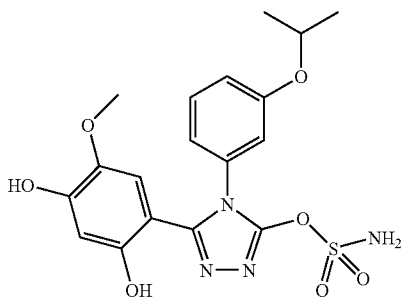 | | 3-(2,4-Dihydroxy-5-methoxy-phenyl)-4-(3-isopropyloxy-phenyl)-5-(sulfamoyloxy)-triazole |
| 169 | 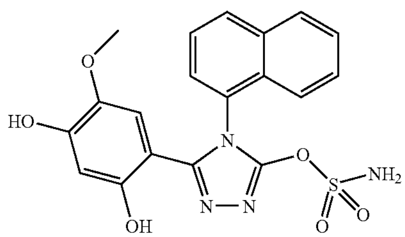 | | 3-(2,4-Dihydroxy-5-methoxy-phenyl)-4-(naphthalene-1-yl)-5-(sulfamoyloxy)-triazole |
| 170 | 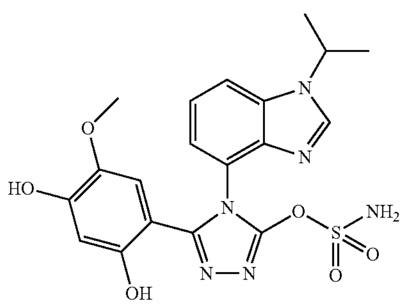 | | 3-(2,4-Dihydroxy-5-methoxy-phenyl)-4-(1-isopropyl-benzoimidazol-4-yl)-5-(sulfamoyloxy)-triazole |
| 171 | 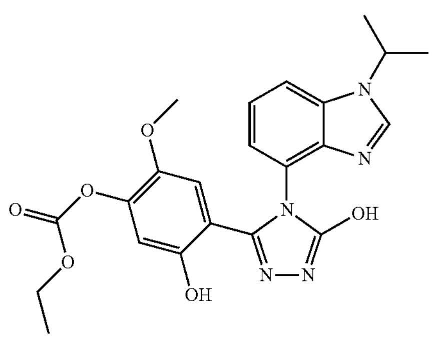 | | 3-(2-Hydroxy-4-ethoxycarbonyoxy-5-methoxy-phenyl)-4-(1-isopropyl-benzoimidazol-4-yl)-5-hydroxy-triazole |
| 172 | 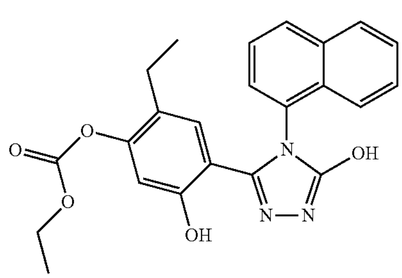 | | 3-(2-Hydroxy-4-ethoxycarbonyoxy-5-ethyl-phenyl)-4-(naphthalin-2-yl)-5-hydroxy-triazole |

TABLE 5-continued

| No. | Structure | Tautomeric Structure | Name |
|---|---|---|---|
| 173 | 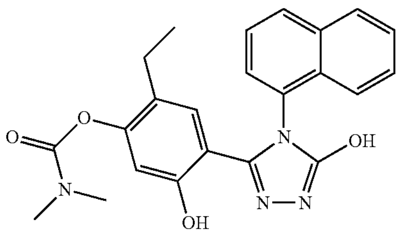 | | 3-[2-Hydroxy-4-(dimethyl-carbamoyoxy)-5-ethyl-phenyl]-4-(naphthalin-2-yl)-5-hydroxy-triazole |
| 174 | 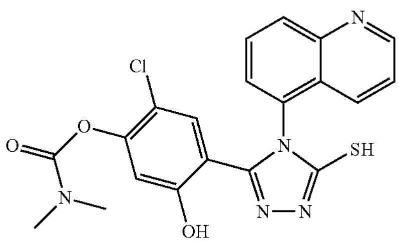 | | 3-[2-Hydroxy-4-(dimethyl-carbamoyoxy)-5-chloro-phenyl]-4-(quinolin-5-yl)-5-mercapto-triazole |
| 175 | 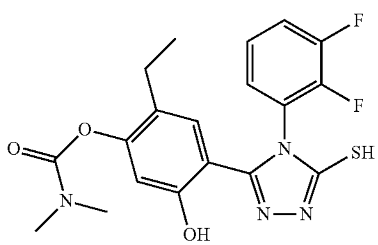 | | 3-[2-Hydroxy-4-(dimethyl-carbamoyoxy)-5-ethyl-phenyl]-4-(2,3-difluoro-phenyl)-5-mercapto-triazole |
| 176 | 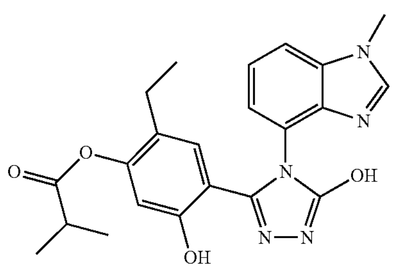 | | 3-[2-Hydroxy-4-isobutyryloxy-5-ethyl-phenyl]-4-(1-methyl-benzo-imidazol-4-yl)-5-hydroxy-triazole |
| 177 | 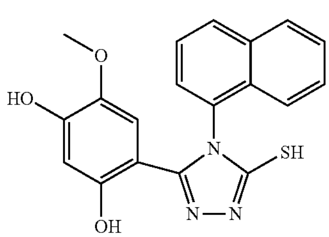 | | 3-(2,4-Dihydroxy-5-methoxy-phenyl)-4-(naphthalen-1-yl)-5-mercapto-triazole |
| 178 | 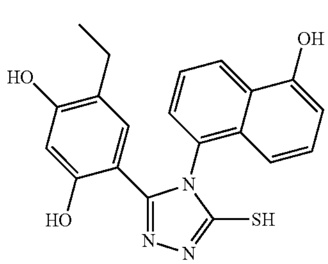 | | 3-(2,4-Dihydroxy-5-ethyl-phenyl)-4-(5-hydroxy-naphthalen-1-yl)-5-mercapto-triazole |

TABLE 5-continued

| No. | Structure | Tautomeric Structure | Name |
|---|---|---|---|
| 179 | 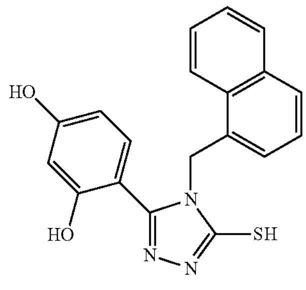 | | 3-(2,4-Dihydroxy-phenyl)-4-(naphthalen-1-ylmethyl)-5-mercapto-triazole |
| 180 | 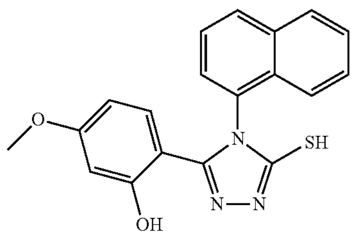 | | 3-(2-Hydroxy-4-methoxyphenyl)-4-(naphthalen-1-yl)-5-mercapto-triazole |
| 181 | 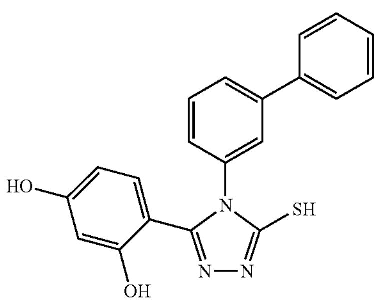 | | 3-(2,4-Dihydroxy-phenyl)-4-(biphenyl-3-yl)-5-mercapto-triazole |
| 182 | 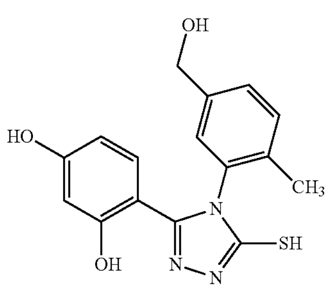 | | 3-(2,4-Dihydroxy-phenyl)-4-(2-methyl-5-hydroxymethyl-phenyl)-5-mercapto-triazole |
| 183 | 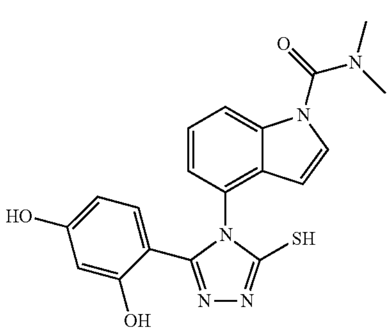 | | 3-(2,4-Dihydroxy-phenyl)-4-(1-dimethylcarbamoyl-indol-4-yl)-5-mercapto-triazole |

TABLE 5-continued

| No. | Structure | Tautomeric Structure | Name |
|---|---|---|---|
| 184 | 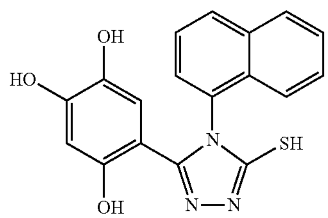 | | 3-(2,4,5-Trihydroxy-phenyl)-4-(naphthalene-1-yl)-5-mercapto-triazole |
| 185 | 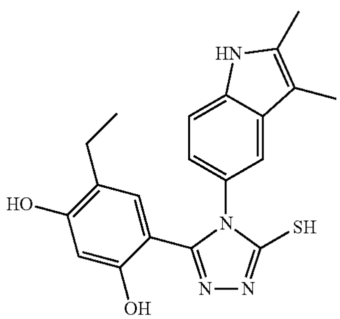 | | 3-(2,4-Dihydroxy-5-ethyl-phenyl)-4-(2,3-dimethyl-indol-5-yl)-5-mercapto-triazole |
| 186 | 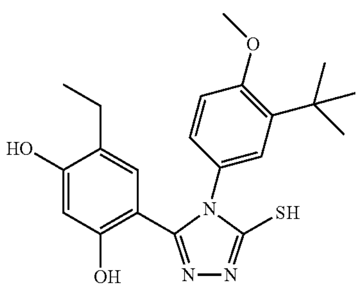 | | 3-(2,4-Dihydroxy-5-ethyl-phenyl)-4-(3-t-butyl-4-methoxy-phenyl)-5-mercapto-triazole |
| 187 | 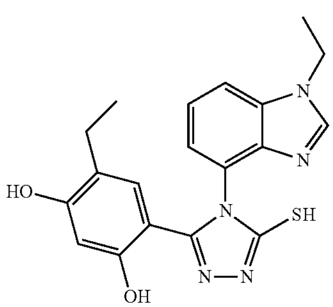 | | 3-(2,4-Dihydroxy-5-ethyl-phenyl)-4-(1-ethyl-1H-benzoimidazol-4-yl)-5-mercapto-triazole, HCl salt |
| 188 | 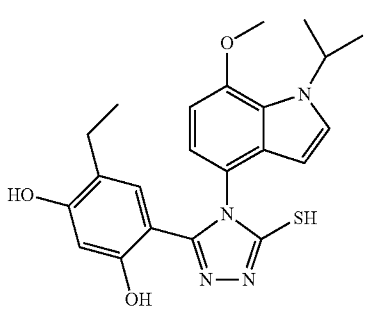 | | 3-(2,4-Dihydroxy-5-ethyl-phenyl)-4-(1-isopropyl-7-methoxy-indol-4-yl)-5-mercapto-triazole |

TABLE 5-continued

| No. | Structure | Tautomeric Structure | Name |
|---|---|---|---|
| 189 | 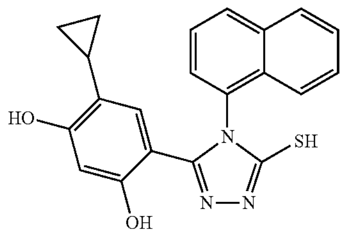 | | 3-(2,4-Dihydroxy-5-cyclopropyl-phenyl)-4-(naphthalene-1-yl)-5-mercapto-triazole |
| 190 | 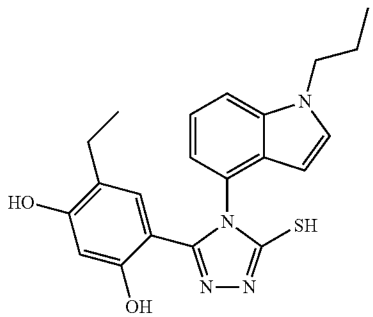 | | 3-(2,4-dihydroxy-5-ethyl-phenyl)-4-(1-propyl-indol-4-yl)-5-mercapto-[1,2,4]triazole |
| 191 | 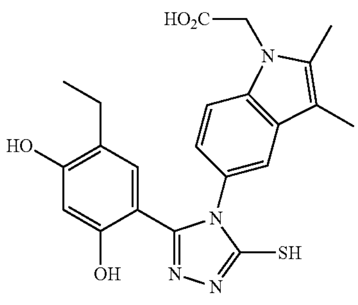 | | 3-(2,4-dihydroxy-5-ethyl-phenyl)-4-(1-acetyl-2,3-dimethyl-indol-5-yl)-5-mercapto-[1,2,4]triazole |
| 192 | 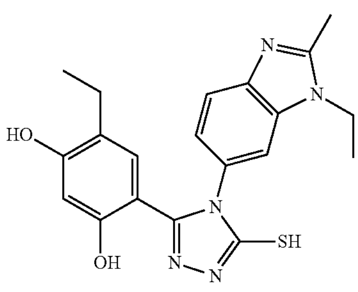 | | 3-(2,4-dihydroxy-5-ethyl-phenyl)-4-(2-methyl-3-ethyl-benzimidazol-5-yl)-5-mercapto-[1,2,4]triazole |
| 193 | 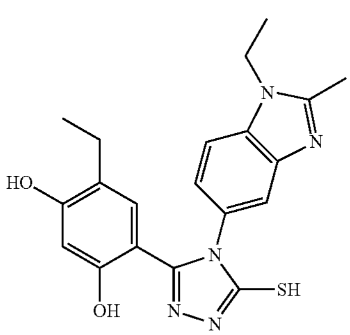 | | 3-(2,4-dihydroxy-5-ethyl-phenyl)-4-(1-ethyl-2-methyl-benzimidazol-5-yl)-5-mercapto-[1,2,4]triazole |

TABLE 5-continued
| No. | Structure | Tautomeric Structure | Name |
|---|---|---|---|
| 194 | 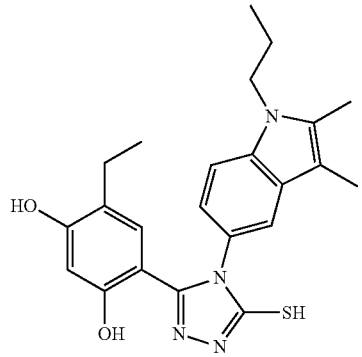 | 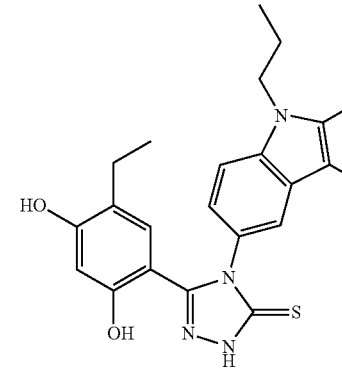 | 3-(2,4-dihydroxy-5-ethyl-phenyl)-4-(1-propyl-2,3-dimethyl-indol-5-yl)-5-mercapto-[1,2,4] triazole |
| 195 | 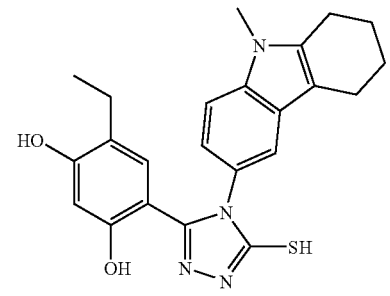 | 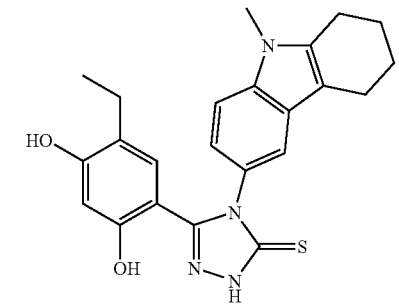 | 3-(2,4-dihydroxy-5-ethyl-phenyl)-4-(N-methyl-tetrahydrocarbozol-7-yl)-5-mercapto-[1,2,4] triazole |
| 196 | 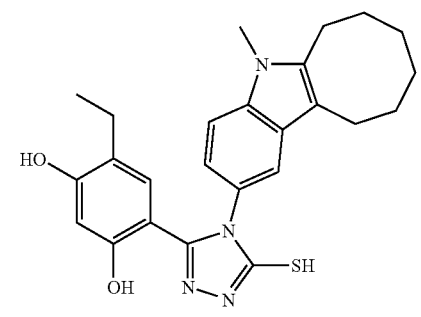 | 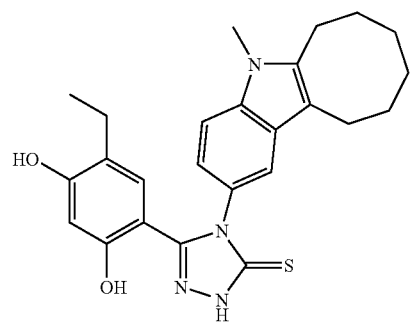 | 3-(2,4-dihydroxy-5-ethyl-phenyl)-4-(N-methyl-cyclononan[a]indol-5-yl)-5-mercapto-[1,2,4] triazole |
| 197 | 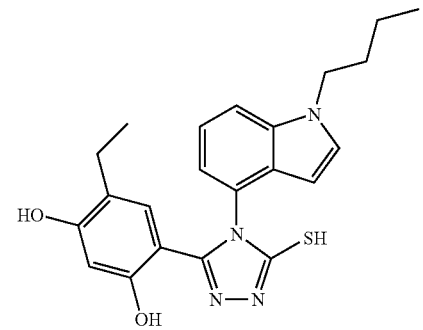 | 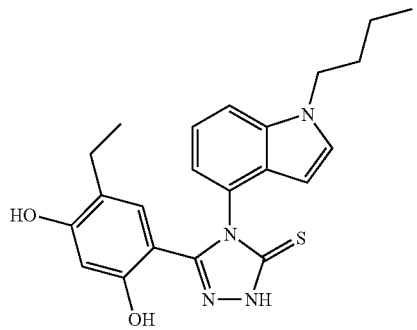 | 3-(2,4-dihydroxy-5-ethyl-phenyl)-4-(1-n-butyl-indol-4-yl)-5-mercapto-[1,2,4] triazole |

TABLE 5-continued
| No. | Structure | Tautomeric Structure | Name |
|---|---|---|---|
| 198 | 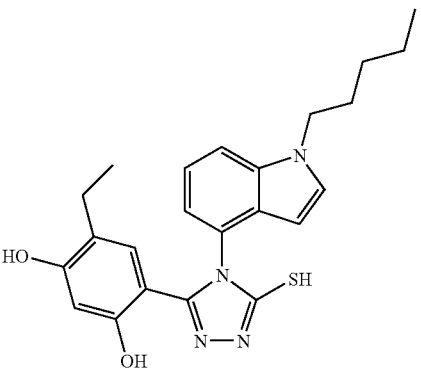 | 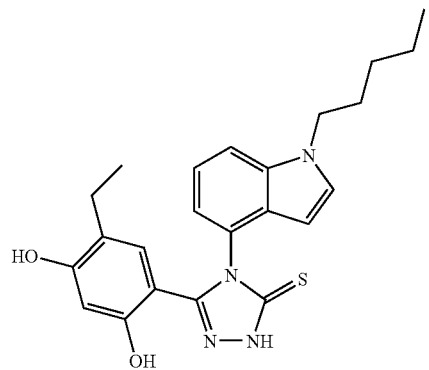 | 3-(2,4-dihydroxy-5-ethyl-phenyl)-4-(1-n-pentyl-indol-4-yl)-5-mercapto-[1,2,4]triazole |
| 199 | 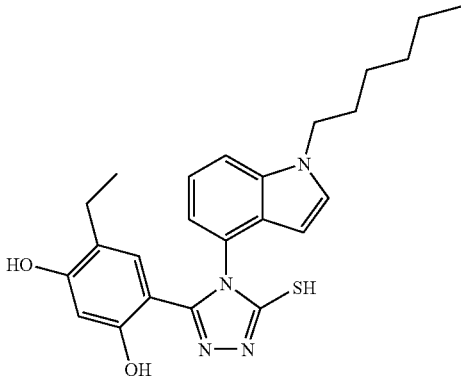 | 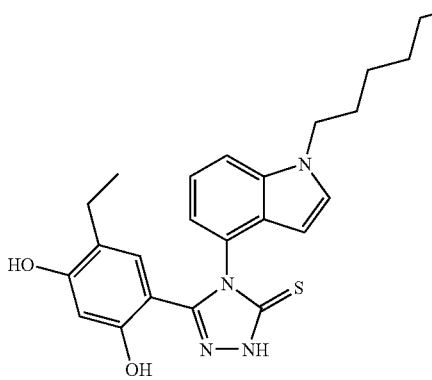 | 3-(2,4-dihydroxy-5-ethyl-phenyl)-4-(1-n-hexyl-indol-4-yl)-5-mercapto-[1,2,4]triazole |
| 200 | 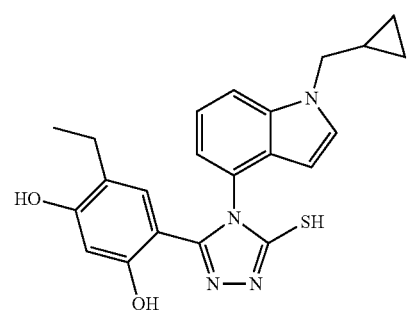 | 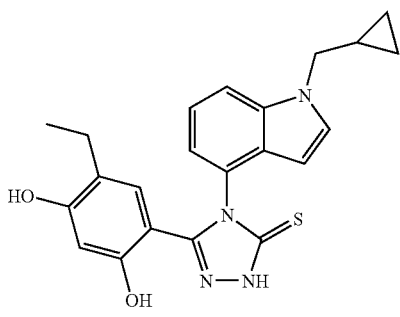 | 3-(2,4-dihydroxy-5-cyclopropyl-phenyl)-4-(1-(1-methylcyclopropyl)-indol-4-yl)-5-mercapto-[1,2,4]triazole |
| 201 | 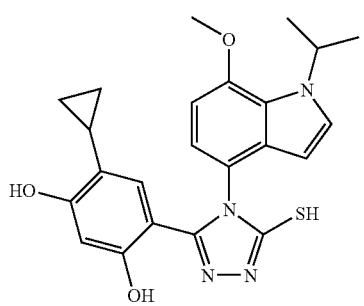 | 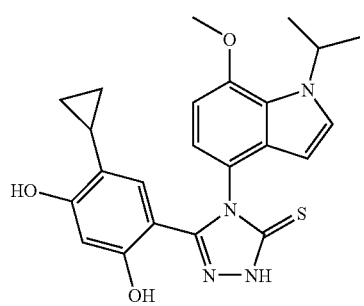 | 3-(2,4-dihydroxy-5-cyclopropyl-phenyl)-4-(1-isopropyl-7-methoxy-indol-4-yl)-5-mercapto-[1,2,4]triazole |

TABLE 5-continued

| No. | Structure | Tautomeric Structure | Name |
|---|---|---|---|
| 202 | 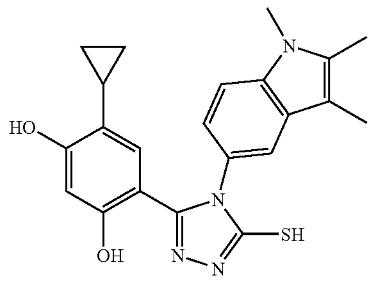 | | 3-(2,4-dihydroxy-5-cyclopropyl-phenyl)-4-(1,2,3-trimethyl-indol-5-yl)-5-mercapto-[1,2,4] triazole |
| 203 | 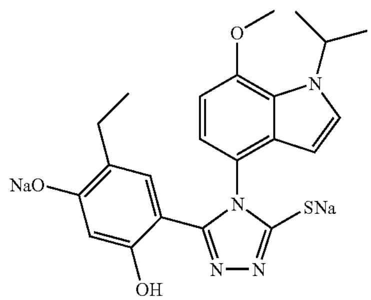 | | 3-(2,4-dihydroxy-5-ethyl-phenyl)-4-(1-isopropyl-7-methoxy-indol-4-yl)-5-mercapto-[1,2,4] triazole disodium salt |
| 204 | 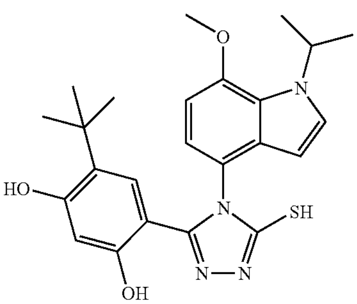 | | 3-(2,4-dihydroxy-5-tert-butyl-phenyl)-4-(1-isopropyl-7-methoxy-indol-4-yl)-5-mercapto-[1,2,4] triazole |
| 205 | 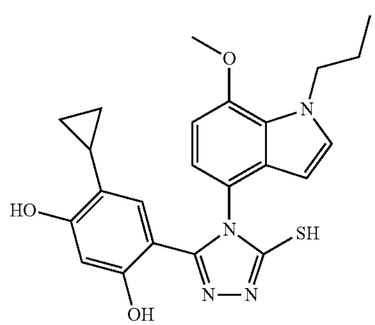 | | 3-(2,4-dihydroxy-5-cyclopropyl-phenyl)-4-(1-propyl-7-methoxy-indol-4-yl)-5-mercapto-[1,2,4] triazole |
| 206 | 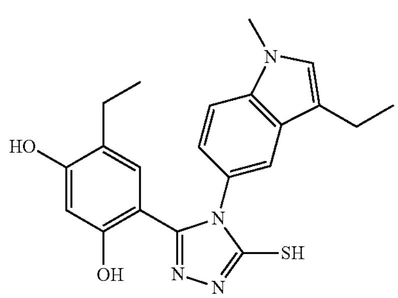 | | 3-(2,4-dihydroxy-5-ethyl-phenyl)-4-(1-methyl-3-ethyl-indol-5-yl)-5-mercapto-[1,2,4] triazole |

TABLE 5-continued

| No. | Structure | Tautomeric Structure | Name |
|---|---|---|---|
| 207 | 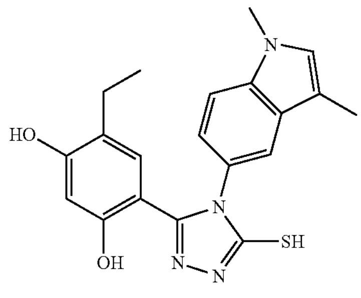 | | 3-(2,4-dihydroxy-5-ethyl-phenyl)-4-(1,3-dimethyl-indol-5-yl)-5-mercapto-[1,2,4] triazole |
| 208 | 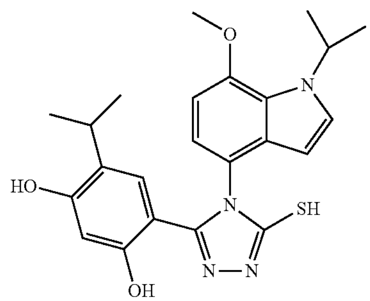 | | 3-(2,4-dihydroxy-5-isopropyl-phenyl)-4-(1-isopropyl-7-methoxy-indol-4-yl)-5-mercapto-[1,2,4] triazole |
| 209 | 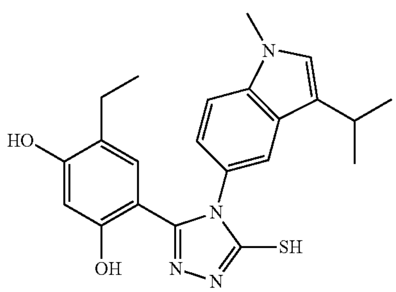 | | 3-(2,4-dihydroxy-5-ethyl-phenyl)-4-(1-methyl-3-isopropyl-indol-5-yl)-5-mercapto-[1,2,4] triazole |
| 210 | 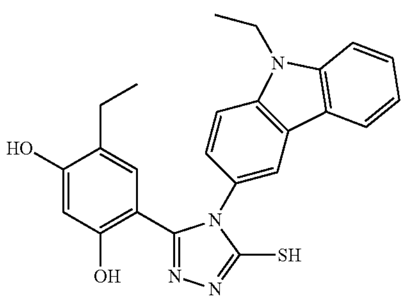 | | 3-(2,4-dihydroxy-5-ethyl-phenyl)-4-(N-ethyl-carbozol-7-yl)-5-mercapto-[1,2,4] triazole |
| 211 | 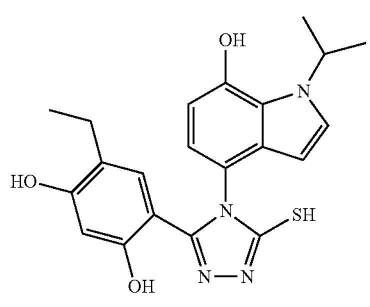 | | 3-(2,4-dihydroxy-5-ethyl-phenyl)-4-(1-isopropyl-7-hydroxy-indol-4-yl)-5-mercapto-[1,2,4] triazole |

TABLE 5-continued

| No. | Structure | Tautomeric Structure | Name |
|---|---|---|---|
| 212 | 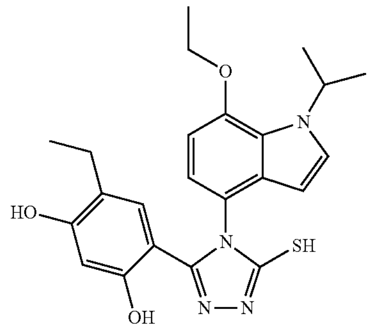 | | 3-(2,4-dihydroxy-5-ethyl-phenyl)-4-(1-isopropyl-7-ethoxy-indol-4-yl)-5-mercapto-[1,2,4] triazole |
| 213 | 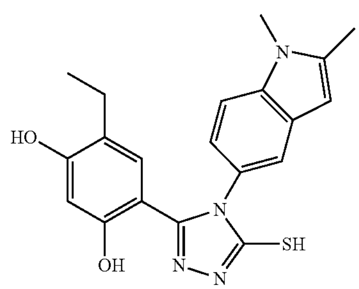 | | 3-(2,4-dihydroxy-5-ethyl-phenyl)-4-(1,2-dimethyl-indol-5-yl)-5-mercapto-[1,2,4] triazole |
| 214 | 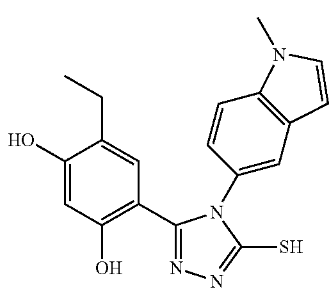 | | 3-(2,4-dihydroxy-5-ethyl-phenyl)-4-(N-methyl-indol-5-yl)-5-mercapto-[1,2,4] triazole |
| 215 | 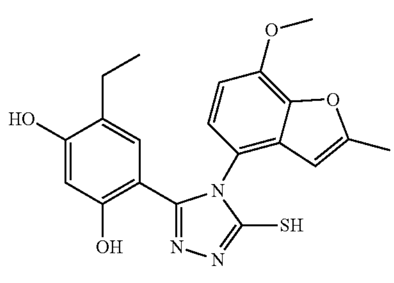 | | 3-(2,4-dihydroxy-5-ethyl-phenyl)-4-(2-methyl-7-methoxy-benzofuran-4-yl)-5-mercapto-[1,2,4] triazole |
| 216 | 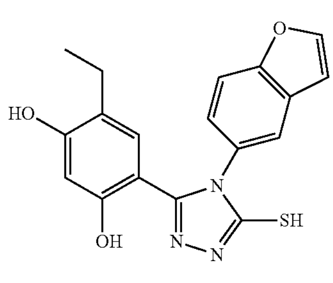 | | 3-(2,4-dihydroxy-5-ethyl-phenyl)-4-(benzofuran-5-yl)-5-mercapto-[1,2,4] triazole |

TABLE 5-continued

| No. | Structure | Tautomeric Structure | Name |
|---|---|---|---|
| 217 | 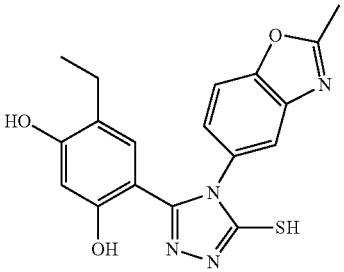 | 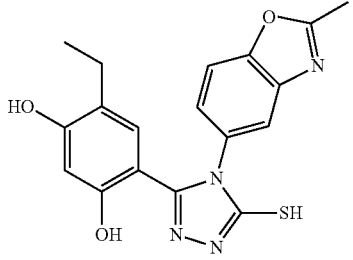 | 3-(2,4-dihydroxy-5-ethyl-phenyl)-4-(2-methyl-1,3-benzoxaz-5-yl)-5-mercapto-[1,2,4]triazole |
| 218 | 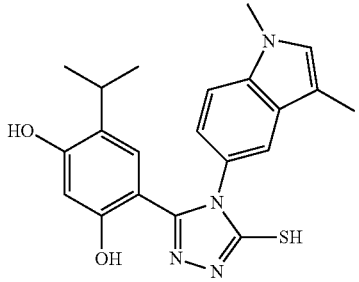 | 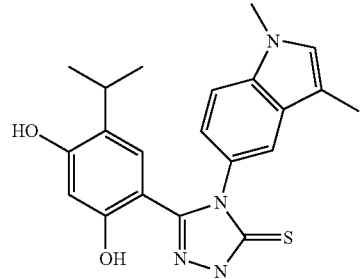 | 3-(2,4-dihydroxy-5-isopropyl-phenyl)-4-(1,3-dimethyl-indol-5-yl)-5-mercapto-[1,2,4]triazole |
| 219 | 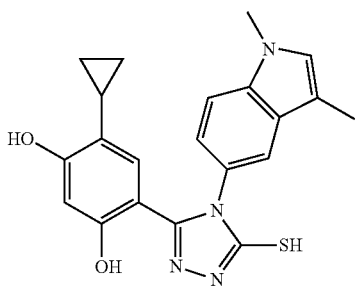 | 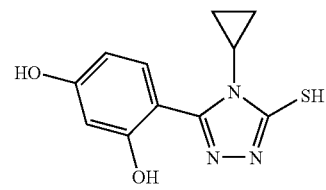 | 3-(2,4-dihydroxy-5-cyclopropyl-phenyl)-4-(1,3-dimethyl-indol-5-yl)-5-mercapto-[1,2,4]triazole |
| 220 | 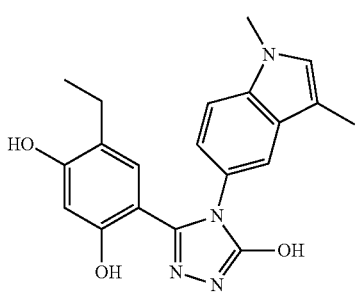 | 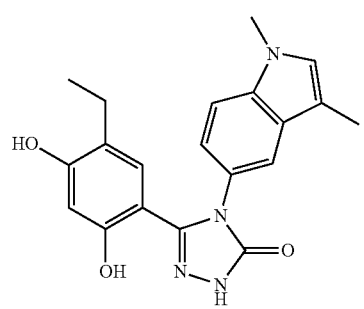 | 3-(2,4-dihydroxy-5-ethyl-phenyl)-4-(1,3-dimethyl-indol-5-yl)-5-hydroxy-[1,2,4]triazole |
| 221 | 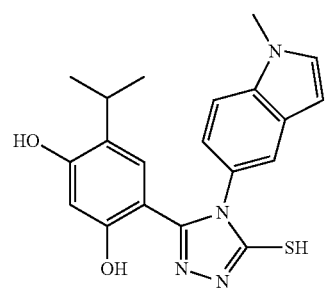 | 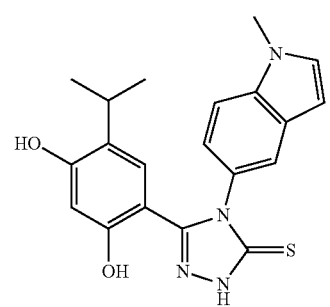 | 3-(2,4-dihydroxy-5-isopropyl-phenyl)-4-(N-methyl-indol-5-yl)-5-mercapto-[1,2,4]triazole |

TABLE 5-continued

| No. | Structure | Tautomeric Structure | Name |
|---|---|---|---|
| 222 | 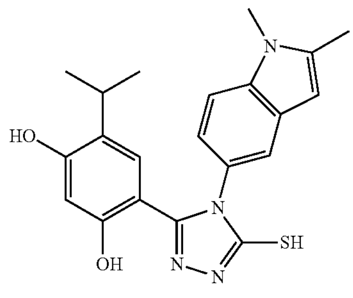 | | 3-(2,4-dihydroxy-5-isopropyl-phenyl)-4-(1,2-dimethyl-indol-5-yl)-5-mercapto-[1,2,4] triazole |
| 223 | 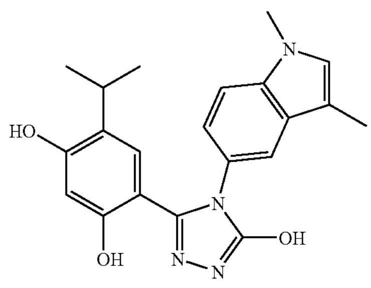 | | 3-(2,4-dihydroxy-5-isopropyl-phenyl)-4-(1,3-dimethyl-indol-5-yl)-5-hydroxy-[1,2,4] triazole |
| 224 | 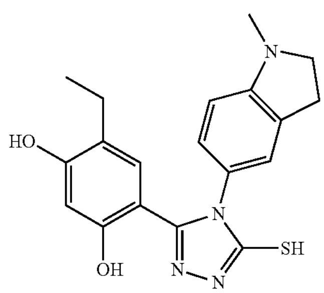 | | 3-(2,4-dihydroxy-5-cyclopropyl-phenyl)-4-(1-methyl-indol-5-yl)-5-mercapto-[1,2,4] triazole |
| 225 | 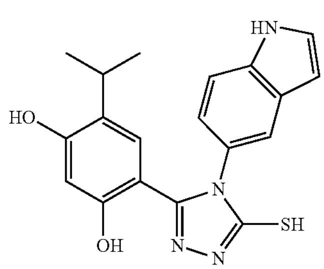 | | 3-(2,4-dihydroxy-5-isopropyl-phenyl)-4-(1H-indol-5-yl)-5-mercapto-[1,2,4] triazole |
| 226 | 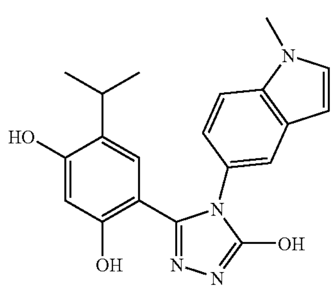 | | 3-(2,4-dihydroxy-5-isopropyl-phenyl)-4-(1-methyl-indol-5-yl)-5-hydroxy-[1,2,4] triazole |

TABLE 5-continued

| No. | Structure | Tautomeric Structure | Name |
|---|---|---|---|
| 227 | 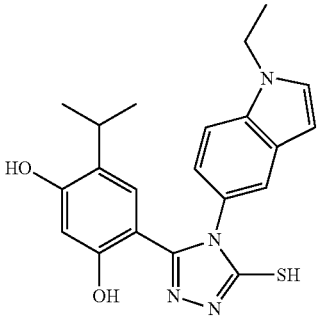 | 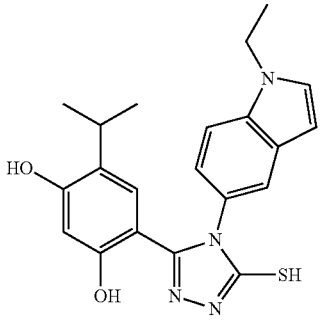 | 3-(2,4-dihydroxy-5-isopropyl-phenyl)-4-(1-ethyl-indol-5-yl)-5-mercapto-[1,2,4]triazole |
| 228 | 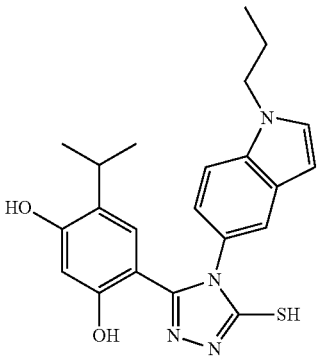 | 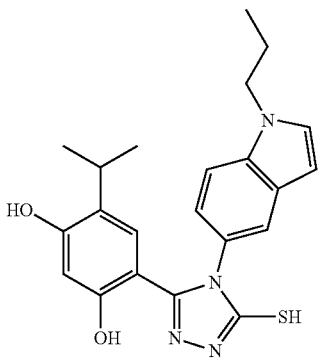 | 3-(2,4-dihydroxy-5-isopropyl-phenyl)-4-(1-propyl-indol-5-yl)-5-mercapto-[1,2,4]triazole |
| 229 | 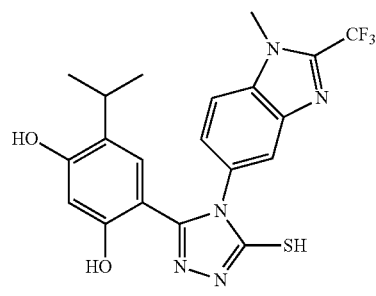 | 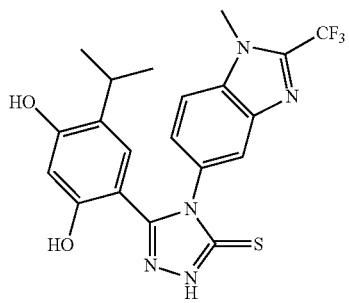 | 3-(2,4-dihydroxy-5-isopropyl-phenyl)-4-(1-methyl-2-trifluoromethyl-benzimidazol-5-yl)-5-mercapto-[1,2,4]triazole |
| 230 | 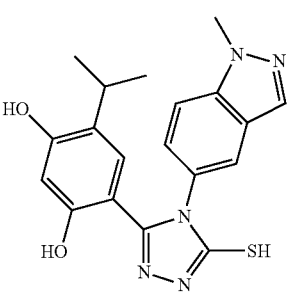 | 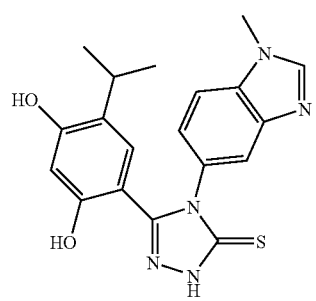 | 3-(2,4-dihydroxy-5-isopropyl-phenyl)-4-(1-methyl-indazol-5-yl)-5-mercapto-[1,2,4]triazole |
| 231 | 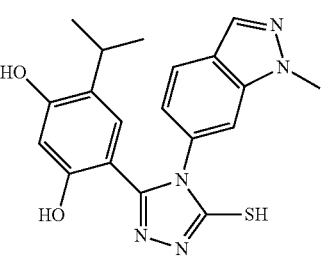 | 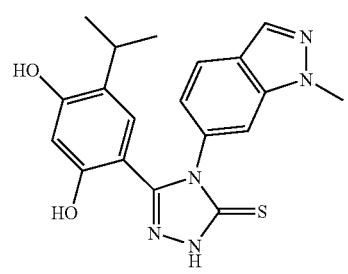 | 3-(2,4-dihydroxy-5-isopropyl-phenyl)-4-(1-methyl-indazol-6-yl)-5-mercapto-[1,2,4]triazole |

TABLE 5-continued

| No. | Structure | Tautomeric Structure | Name |
|---|---|---|---|
| 232 | 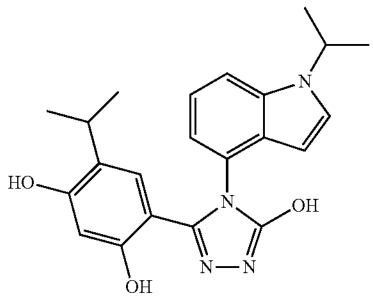 | | 3-(2,4-dihydroxy-5-isopropyl-phenyl)-4-(1-isopropyl-indol-4-yl)-5-hydroxy-[1,2,4] triazole |
| 233 | 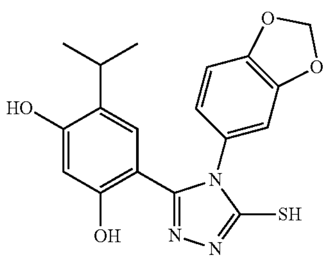 | | 3-(2,4-dihydroxy-5-isopropyl-phenyl)-4-(1,3-benzodiaxol-5-yl)-5-mercapto-[1,2,4] triazole |
| 234 | 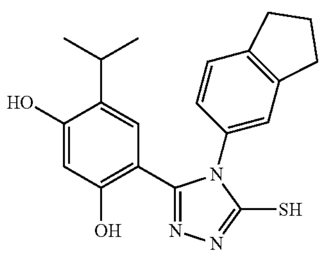 | | 3-(2,4-dihydroxy-5-isopropyl-phenyl)-4-(indan-5-yl)-5-mercapto-[1,2,4] triazole |
| 235 | 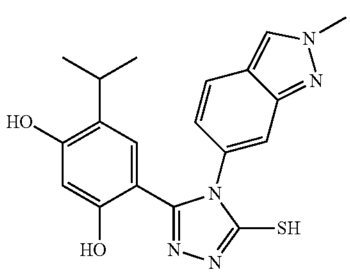 | | 3-(2,4-dihydroxy-5-isopropyl-phenyl)-4-(2-methyl-indazol-6-yl)-5-mercapto-[1,2,4] triazole |
| 236 | 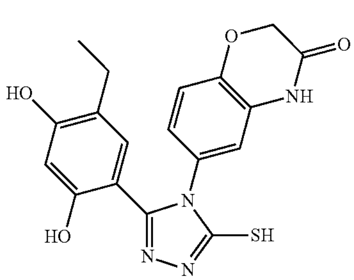 | | 3-(2,4-dihydroxy-5-ethyl-phenyl)-4-(3-oxo-benzo[1,4]oxazin-6-yl)-5-mercapto-[1,2,4] triazole |

TABLE 5-continued

| No. | Structure | Tautomeric Structure | Name |
|---|---|---|---|
| 237 | 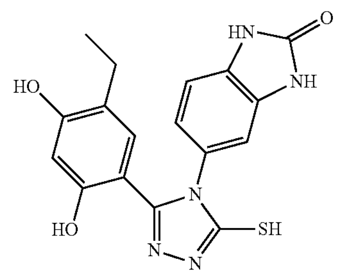 | | 3-(2,4-dihydroxy-5-ethyl-phenyl)-4-(2-oxo-1,3-dihydro-benzoimidazol-5-yl)-5-mercapto-[1,2,4] triazole |
| 238 | 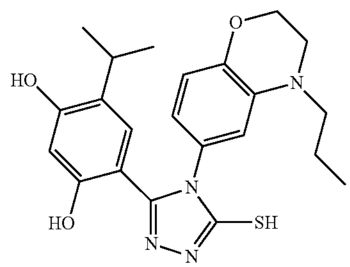 | | 3-(2,4-dihydroxy-5-isopropyl-phenyl)-4-(2H-benzo[1,4]oxazin-6-yl)-5-mercapto-[1,2,4] triazole |
| 239 | 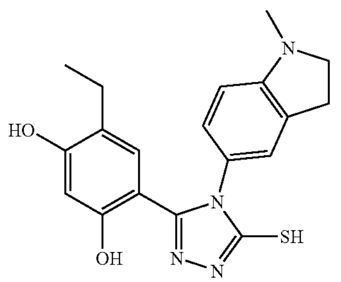 | | 4-Ethyl-6-[5-mercapto-4-(1-methyl-2,3-dihydro-1H-indol-5-yl)-4H-[1,2,4] triazol-3-yl]-benzene-1,3-diol |
| 240 | 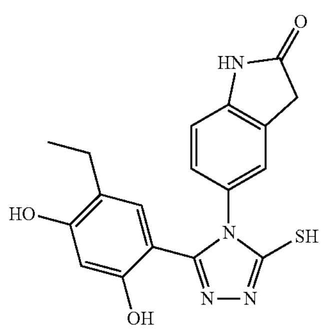 | | 5-(3-(5-ethyl-2,4-dihydroxyphenyl)-5-mercapto-4H-1,2,4-triazol-4-yl)indolin-2-one |
| 241 | 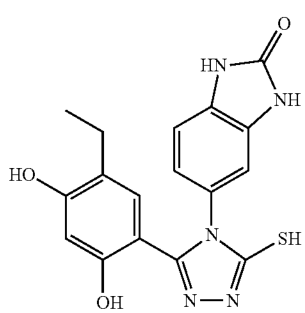 | | 5-(3-(5-ethyl-2,4-dihydroxyphenyl)-5-mercapto-4H-1,2,4-triazol-4-yl)-1H-benzo[d]imidazol-2(3H)-one |

TABLE 5-continued

| No. | Structure | Tautomeric Structure | Name |
|---|---|---|---|
| 242 | 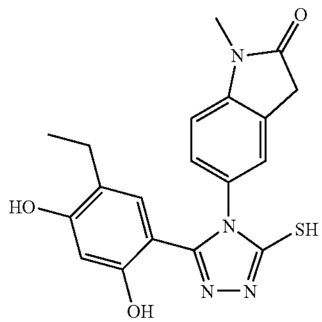 | | 5-(3-(5-ethyl-2,4-dihydroxyphenyl)-5-mercapto-4H-1,2,4-triazol-4-yl)-1-methylindolin-2-one |
| 243 | 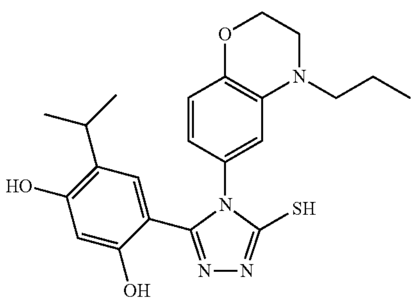 | | 4-isopropyl-6-(5-mercapto-4-(4-propyl-3,4-dihydro-2H-benzo[b][1,4]oxazin-6-yl)-4H-1,2,4-triazol-3-yl)benzene-1,3-diol |
| 244 | 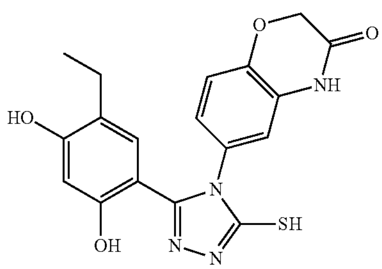 | | 6-(3-(5-ethyl-2,4-dihydroxyphenyl)-5-mercapto-4H-1,2,4-triazol-4-yl)-2H-benzo[b][1,4]oxazin-3(4H)-one |
| 245 | 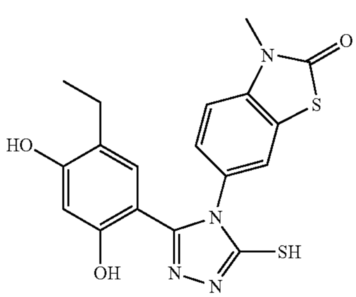 | | 6-(3-(5-ethyl-2,4-dihydroxyphenyl)-5-mercapto-4H-1,2,4-triazol-4-yl)-3-methylbenzo[d]thiazol-2(3H)-one |
| 246 | 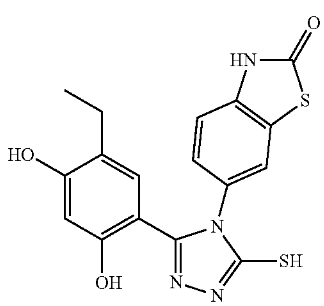 | | 6-(3-(5-ethyl-2,4-dihydroxyphenyl)-5-mercapto-4H-1,2,4-triazol-4-yl)benzo[d]thiazol-2(3H)-one |

TABLE 5-continued

| No. | Structure | Tautomeric Structure | Name |
|---|---|---|---|
| 247 | 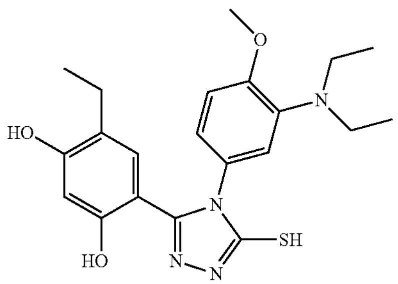 | | 4-(4-(3-(diethylamino)-4-methoxyphenyl)-5-mercapto-4H-1,2,4-triazol-3-yl)-6-ethylbenzene-1,3-diol |
| 248 | 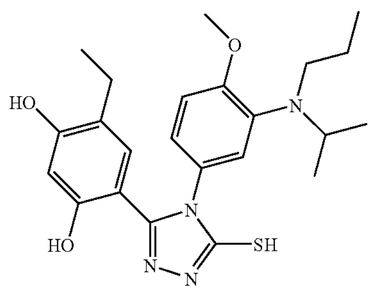 | | 4-(4-(3-(N-isopropyl-N-propylamino)-4-methoxyphenyl)-5-mercapto-4H-1,2,4-triazol-3-yl)-6-ethylbenzene-1,3-diol |
| 249 | 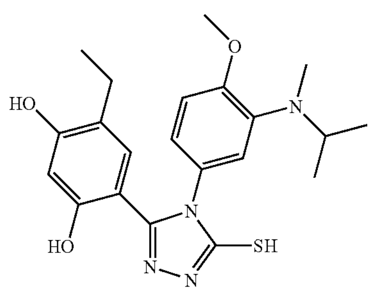 | | 4-(4-(3-(N-isopropyl-N-methylamino)-4-methoxyphenyl)-5-mercapto-4H-1,2,4-triazol-3-yl)-6-ethylbenzene-1,3-diol |
| 250 | 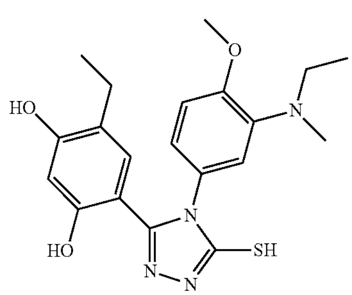 | | 4-(4-(3-(N-ethyl-N-methylamino)-4-methoxyphenyl)-5-mercapto-4H-1,2,4-triazol-3-yl)-6-ethylbenzene-1,3-diol |
| 251 | 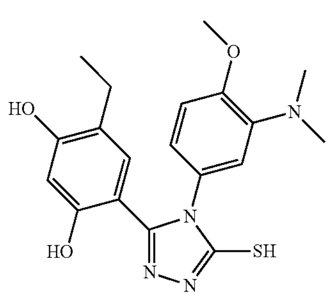 | | 4-(4-(3-(dimethylamino)-4-methoxyphenyl)-5-mercapto-4H-1,2,4-triazol-3-yl)-6-ethylbenzene-1,3-diol |

TABLE 5-continued

| No. | Structure | Tautomeric Structure | Name |
|---|---|---|---|
| 252 | 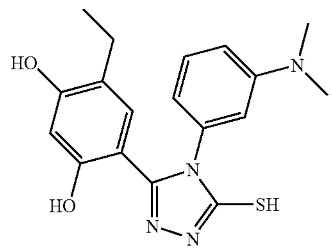 | | 4-(4-(3-(dimethylamino)phenyl)-5-mercapto-4H-1,2,4-triazol-3-yl)-6-ethylbenzene-1,3-diol |
| 253 | 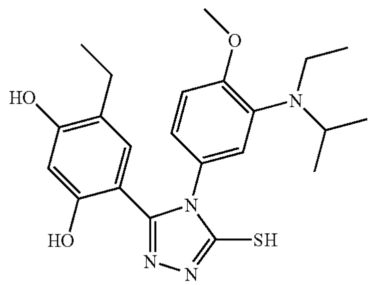 | | 4-(4-(3-(N-ethyl-N-isopropylamino)-4-methoxyphenyl)-5-mercapto-4H-1,2,4-triazol-3-yl)-6-ethylbenzene-1,3-diol |
| 254 | 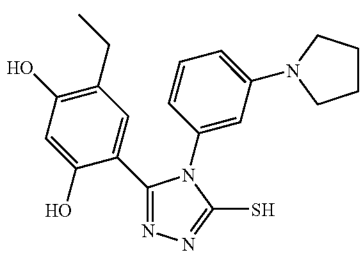 | | 4-ethyl-6-(5-mercapto-4-(3-(pyrrolidin-1-yl)phenyl)-4H-1,2,4-triazol-3-yl)benzene-1,3-diol |
| 255 | 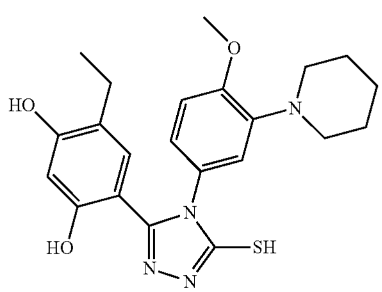 | | 4-ethyl-6-(5-mercapto-4-(4-methoxy-3-morpholinophenyl)-4H-1,2,4-triazol-3-yl)benzene-1,3-diol |
| 256 | 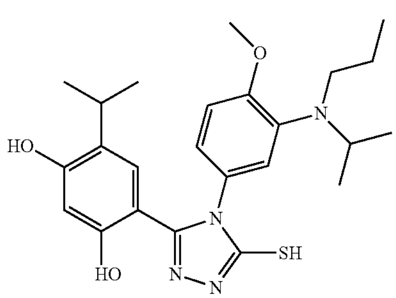 | | 4-(4-(3-(N-isopropyl-N-propylamino)-4-methoxyphenyl)-5-mercapto-4H-1,2,4-triazol-3-yl)-6-isopropylbenzene-1,3-diol |

TABLE 5-continued

| No. | Structure | Tautomeric Structure | Name |
| --- | --- | --- | --- |
| 257 | 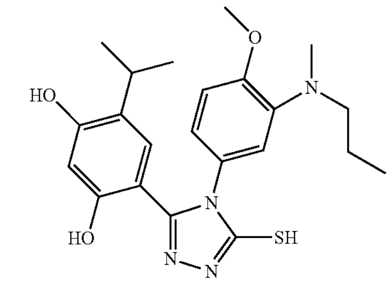 | | 4-(4-(3-(N-methyl-N-propylamino)-4-methoxyphenyl)-5-mercapto-4H-1,2,4-triazol-3-yl)-6-isopropylbenzene-1,3-diol |
| 258 | 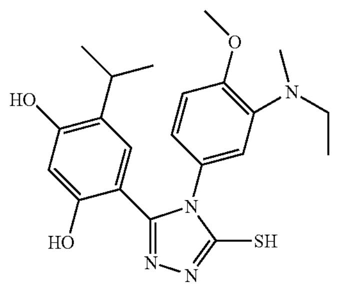 | | 4-(4-(3-(N-methyl-N-ethylamino)-4-methoxy-phenyl)-5-mercapto-4H-1,2,4-triazol-3-yl)-6-isopropylbenzene-1,3-diol |
| 259 | 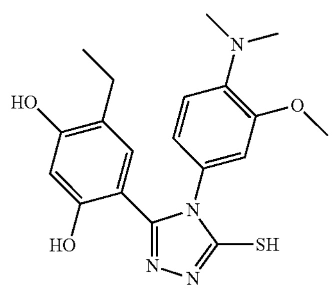 | | 4-(4-(4-(dimethylamino)-3-methoxyphenyl)-5-mercapto-4H-1,2,4-triazol-3-yl)-6-ethylbenzene-1,3-diol |
| 260 | 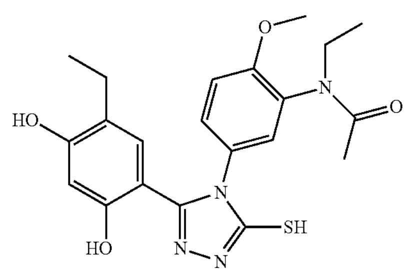 | | |
| 261 | 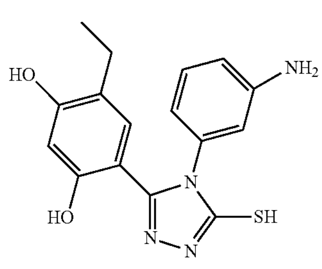 | | 4-(4-(3-aminophenyl)-5-mercapto-4H-1,2,4-triazol-3-yl)-6-ethylbenzene-1,3-diol |

TABLE 5-continued
| No. | Structure | Tautomeric Structure | Name |
|---|---|---|---|
| 262 | 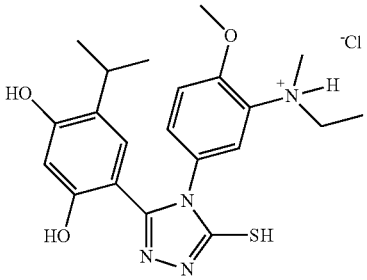 | 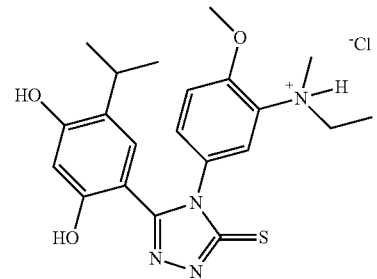 | |
| 263 | 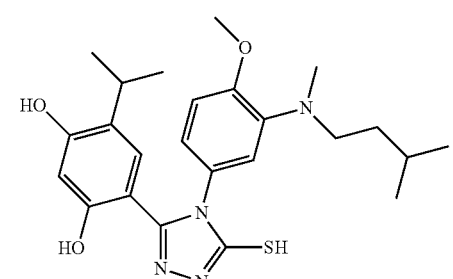 | 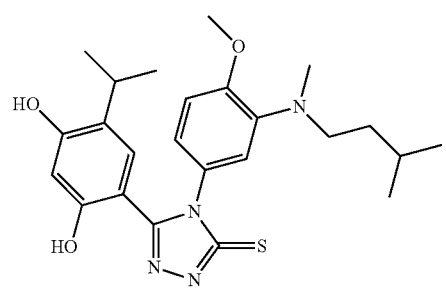 | 4-(4-(3-(N-isopentyl-N-methylamino)-4-methoxyphenyl)-5-mercapto-4H-1,2,4-triazol-3-yl)-6-isopropylbenzene-1,3-diol |
| 264 | 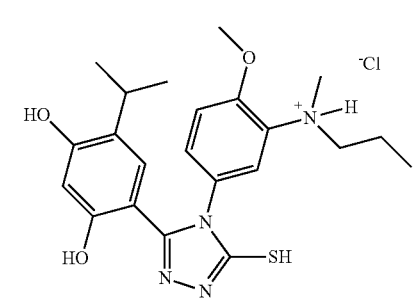 | 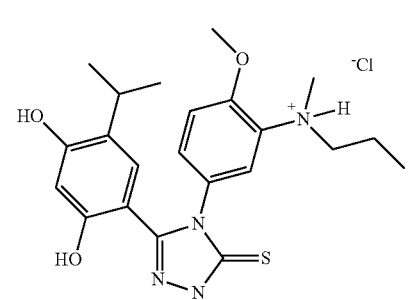 | |
| 265 | 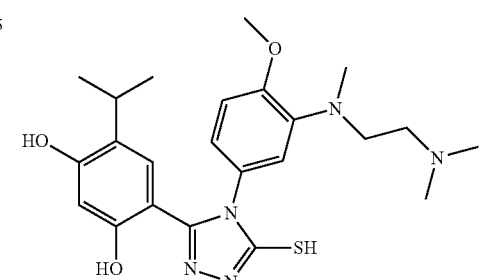 | 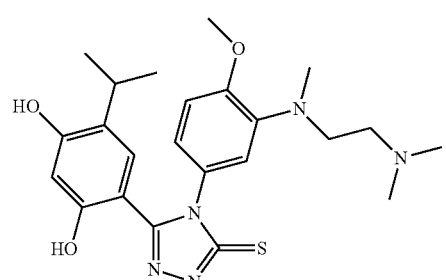 | 4-(4-(3-(N-(2-(dimethylamino)ethyl)-N-methylamino)-4-methoxyphenyl)-5-mercapto-4H-1,2,4-triazol-3-yl)-6-isopropylbenzene-1,3-diol |
| 266 | 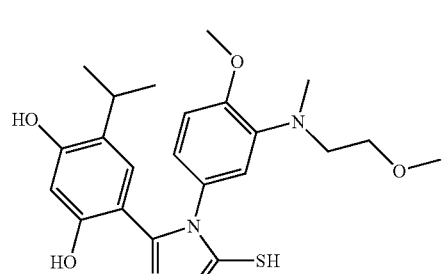 | 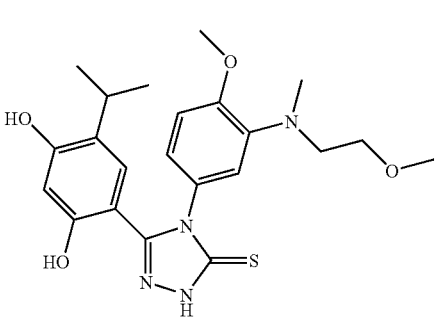 | 4-(4-(3-(N-(2-methoxyethyl)-N-methylamino)-4-methoxyphenyl)-5-mercapto-4H-1,2,4-triazol-3-yl)-6-isopropylbenzene-1,3-diol |

TABLE 5-continued

| No. | Structure | Tautomeric Structure | Name |
|---|---|---|---|
| 267 | 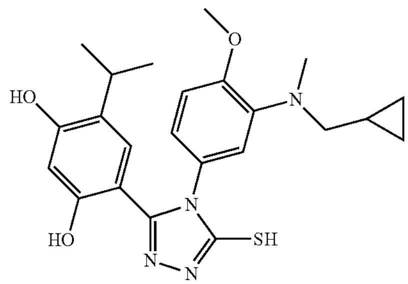 | | 4-(4-(3-(N-(cyclopropylmethyl)-N-methylamino)-4-methoxyphenyl)-5-mercapto-4H-1,2,4-triazol-3-yl)-6-isopropylbenzene-1,3-diol |
| 268 | 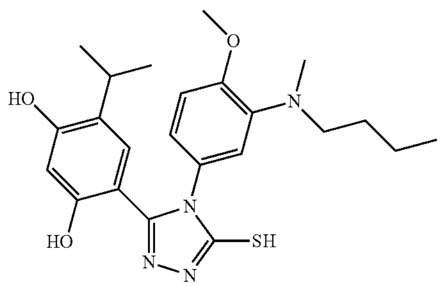 | | 4-(4-(3-(N-butyl-N-methylamino)-4-methoxyphenyl)-5-mercapto-4H-1,2,4-triazol-3-yl)-6-isopropylbenzene-1,3-diol |
| 269 | 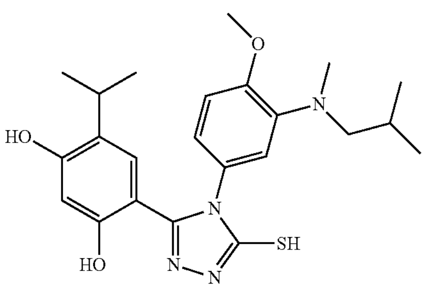 | | 4-(4-(3-(N-isobutyl-N-methylamino)-4-methoxyphenyl)-5-mercapto-4H-1,2,4-triazol-3-yl)-6-isopropylbenzene-1,3-diol |
| 270 | 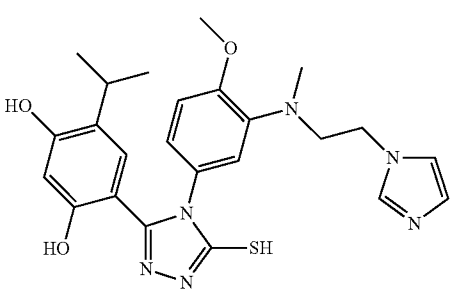 | | 4-(4-(3-(N-(2-(1H-imidazol-1-yl)ethyl)-N-methylamino)-4-methoxyphenyl)-5-mercapto-4H-1,2,4-triazol-3-yl)-6-isopropylbenzene-1,3-diol |
| 271 | 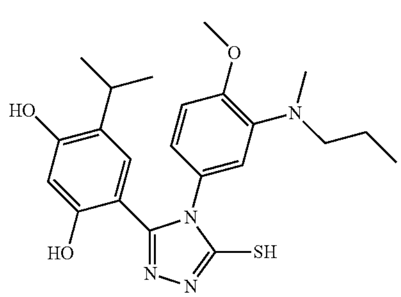 | | 4-(4-(3-(N-methyl-N-propylamino)-4-methoxyphenyl)-5-mercapto-4H-1,2,4-triazol-3-yl)-6-isopropylbenzene-1,3-diol |

TABLE 5-continued

| No. | Structure | Tautomeric Structure | Name |
|---|---|---|---|
| 272 | 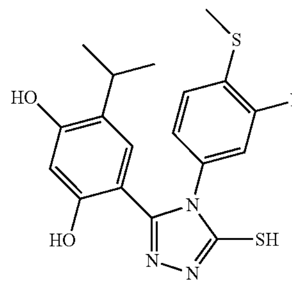 | | 4-(4-(3-(dimethylamino)-4-(methylthio)phenyl)-5-mercapto-4H-1,2,4-triazol-3-yl)-6-isopropylbenzene-1,3-diol |
| 273 | 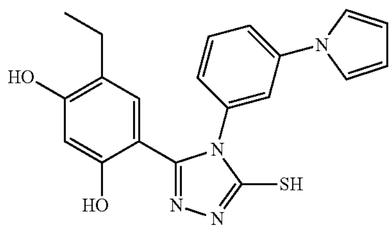 | | 4-(4-(3-(1H-pyrrol-1-yl)phenyl)-5-hydroxy-4H-1,2,4-triazol-3-yl)-6-ethylbenzene-1,3-diol |
| 274 | 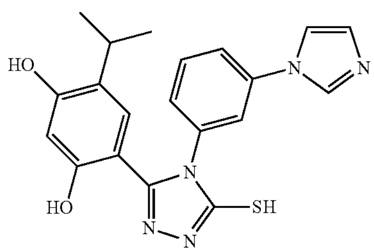 | | 4-(4-(3-(1H-imidazol-1-yl)phenyl)-5-mercapto-4H-1,2,4-triazol-3-yl)-6-isopropylbenzene-1,3-diol |
| 275 | 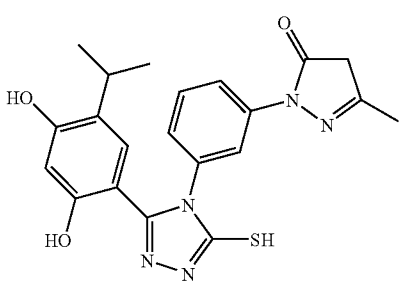 | | |
| 276 | 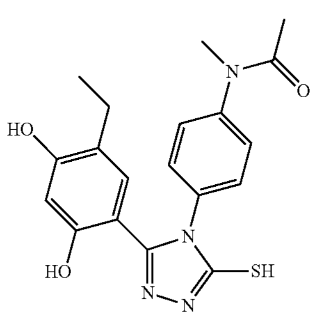 | | |

TABLE 5-continued

| No. | Structure | Tautomeric Structure | Name |
|---|---|---|---|
| 277 | 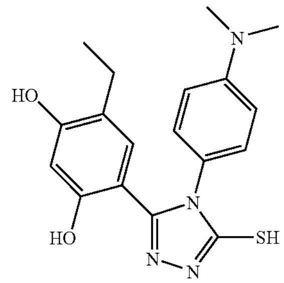 | | 4-(4-(4-(dimethylamino)phenyl)-5-mercapto-4H-1,2,4-triazol-3-yl)-6-ethylbenzene-1,3-diol |
| 278 | 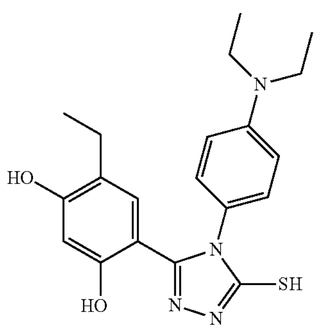 | | 4-(4-(4-(diethylamino)phenyl)-5-mercapto-4H-1,2,4-triazol-3-yl)-6-ethylbenzene-1,3-diol |
| 279 | 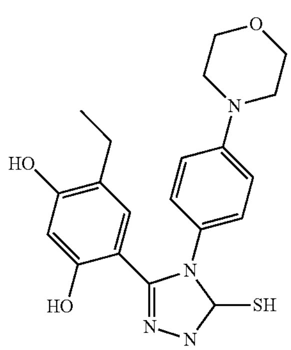 | | 4-ethyl-6-(5-mercapto-4-(4-morpholinophenyl)-4H-1,2,4-triazol-3-yl)benzene-1,3-diol |
| 280 | 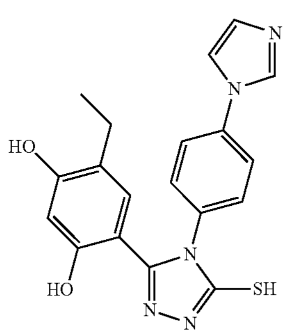 | | 4-(4-(4-(1H-imidazol-1-yl)phenyl)-5-mercapto-4H-1,2,4-triazol-3-yl)-6-ethylbenzene-1,3-diol |

TABLE 5-continued

| No. | Structure | Tautomeric Structure | Name |
|---|---|---|---|
| 281 | 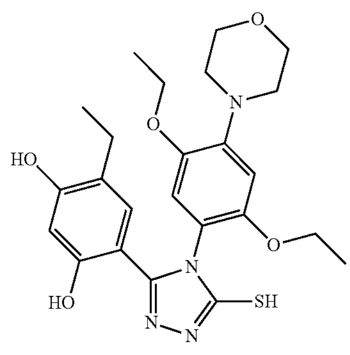 | | 4-(4-(2,5-diethoxy-4-morpholinophenyl)-5-mercapto-4H-1,2,4-triazol-3-yl)-6-ethylbenzene-1,3-diol |
| 282 | 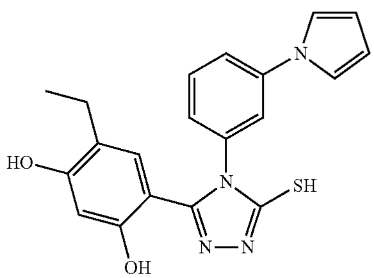 | | 4-(4-(3-(1H-pyrrol-1-yl)phenyl)-5-mercapto-4H-1,2,4-triazol-3-yl)-6-ethylbenzene-1,3-diol |
| 283 | 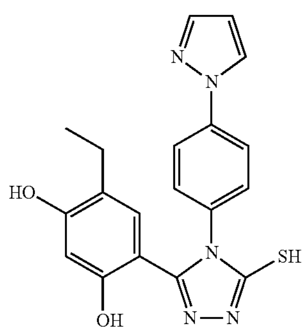 | | 4-(4-(4-(1H-pyrazol-1-yl)phenyl)-5-mercapto-4H-1,2,4-triazol-3-yl)-6-ethylbenzene-1,3-diol |
| 284 | 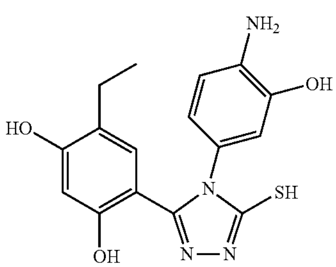 | | 4-(4-(4-(amino)-3-hydroxyphenyl)-5-mercapto-4H-1,2,4-triazol-3-yl)-6-ethylbenzene-1,3-diol |
| 285 | 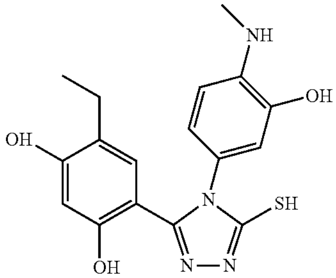 | | 4-(4-(4-(methylamino)-3-hydroxyphenyl)-5-mercapto-4H-1,2,4-triazol-3-yl)-6-ethylbenzene-1,3-diol |

TABLE 5-continued

| No. | Structure | Tautomeric Structure | Name |
|---|---|---|---|
| 286 | 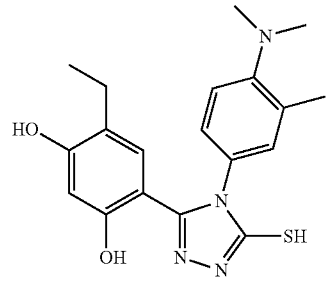 | | 4-(4-(4-(dimethylamino)-3-methylphenyl)-5-mercapto-4H-1,2,4-triazol-3-yl)-6-ethylbenzene-1,3-diol |

Exemplary pyrazole compounds of the invention are depicted in Table 6 below, including tautomers, pharmaceutically acceptable salts, solvates, clathrates, hydrates, polymorphs or prodrugs thereof.

TABLE 6

| No. | Structure | Name |
|---|---|---|
| 287 | 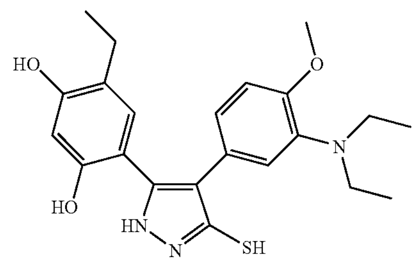 | 4-[3-(N,N-diethylamino)-4-methoxyphenyl]-3-(5-ethyl-2,4-dihydroxyphenyl)-5-mercapto-2H-pyrazole |
| 288 | 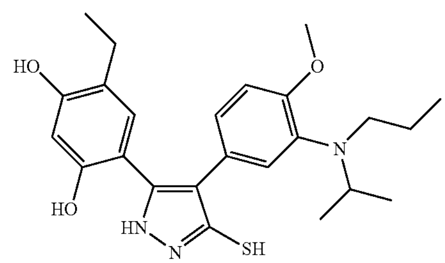 | 4-[3-(isopropyl-propyl-amino)-4-methoxy-phenyl]-3-(5-ethyl-2,4-dihydroxy-phenyl)-5-mercapto-2H-pyrazole |
| 289 | 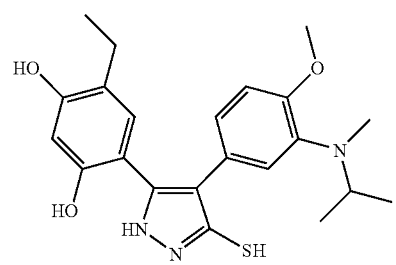 | 4-[3-(isopropyl-methyl-amino)-4-methoxy-phenyl]-3-(5-ethyl-2,4-dihydroxy-phenyl)-5-mercapto-2H-pyrazole |
| 290 | 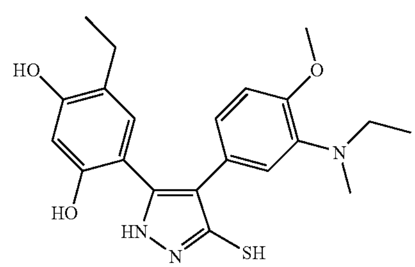 | 4-[3-(ethyl-methyl-amino)-4-methoxy-phenyl]-3-(5-ethyl-2,4-dihydroxy-phenyl)-5-mercapto-2H-pyrazole |

TABLE 6-continued

| No. | Structure | Name |
|---|---|---|
| 291 | 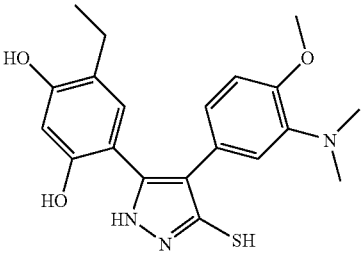 | 4-[3-(N,N-methylamino)-4-methoxy-phenyl]-3-(5-ethyl-2,4-dihydroxy-phenyl)-5-mercapto-2H-pyrazole |
| 292 | 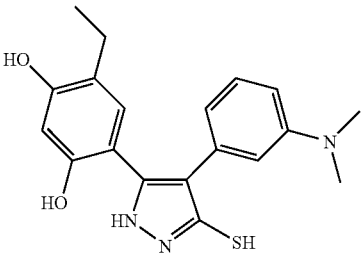 | 4-[3-(N,N-methylamino)-phenyl]-3-(5-ethyl-2,4-dihydroxy-phenyl)-5-mercapto-2H-pyrazole |
| 293 | 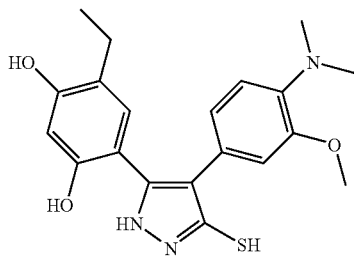 | 4-[4-(N,N-methylamino)-3-methoxy-phenyl]-3-(5-ethyl-2,4-dihydroxy-phenyl)-5-mercapto-2H-pyrazole |
| 294 | 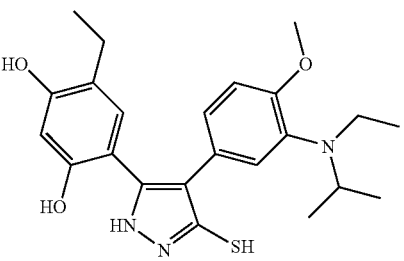 | 4-[3-(isopropyl-ethyl-amino)-4-methoxy-phenyl]-3-(5-ethyl-2,4-dihydroxy-phenyl)-5-mercapto-2H-pyrazole |
| 295 | 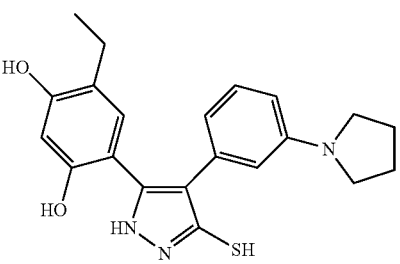 | 4-[3-(pyrrolidin-1-yl)-phenyl]-3-(5-ethyl-2,4-dihydroxy-phenyl)-5-mercapto-2H-pyrazole |
| 296 | 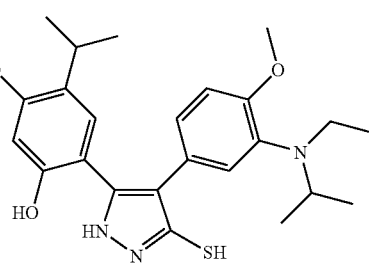 | 4-[3-(isopropyl-propyl-amino)-4-methoxy-phenyl]-3-(5-isopropyl-2,4-dihydroxy-phenyl)-5-mercapto-2H-pyrazole |

TABLE 6-continued

| No. | Structure | Name |
| --- | --- | --- |
| 297 | 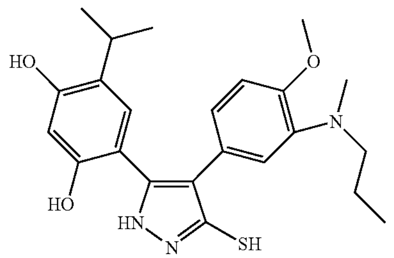 | 4-[3-(methyl-propyl-amino)-4-methoxy-phenyl]-3-(5-isopropyl-2,4-dihydroxy-phenyl)-5-mercapto-2H-pyrazole |
| 298 | 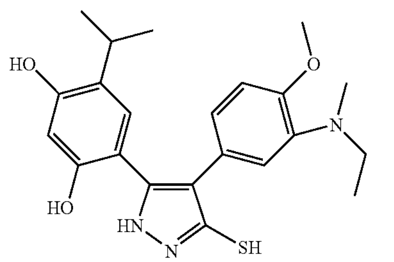 | 4-[3-(ethyl-methyl-amino)-4-methoxy-phenyl]-3-(5-isopropyl-2,4-dihydroxy-phenyl)-5-mercapto-2H-pyrazole |
| 299 | 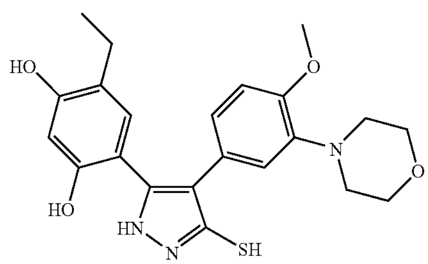 | 4-[3-(morpholino-1-yl)-4-methoxy-phenyl]-3-(5-ethyl-2,4-dihydroxy-phenyl)-5-mercapto-2H-pyrazole |
| 300 | 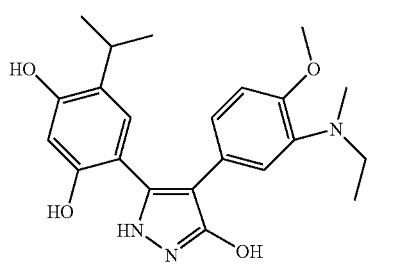 | 4-[3-(ethyl-methyl-amino)-4-methoxy-phenyl]-3-(5-isopropyl-2,4-dihydroxy-phenyl)-5-hydroxy-2H-pyrazole |
| 301 | 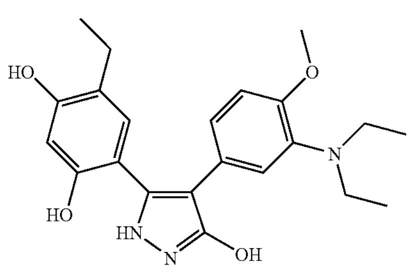 | 4-[3-(N,N-diethyl-amino)-4-methoxy-phenyl]-3-(5-ethyl-2,4-dihydroxy-phenyl)-5-hydroxy-2H-pyrazole |
| 302 | 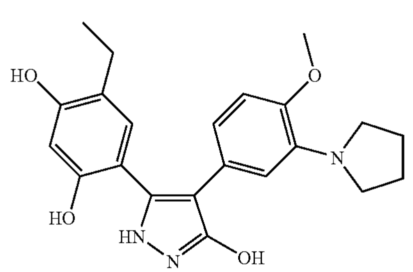 | 4-[3-(pyrrolidin-1-yl)-4-methoxy-phenyl]-3-(5-ethyl-2,4-dihydroxy-phenyl)-5-hydroxy-2H-pyrazole |

TABLE 6-continued

| No. | Structure | Name |
|---|---|---|
| 303 | 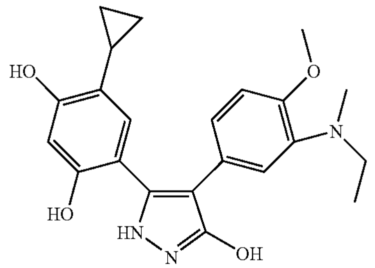 | 4-[3-(ethyl-methyl-amino)-4-methoxy-phenyl]-3-(5-cyclopropyl-2,4-dihydroxy-phenyl)-5-hydroxy-2H-pyrazole |
| 304 | 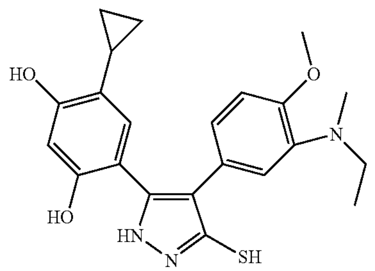 | 4-[3-(ethyl-methyl-amino)-4-methoxy-phenyl]-3-(5-cyclopropyl-2,4-dihydroxy-phenyl)-5-mercapto-2H-pyrazole |
| 305 | 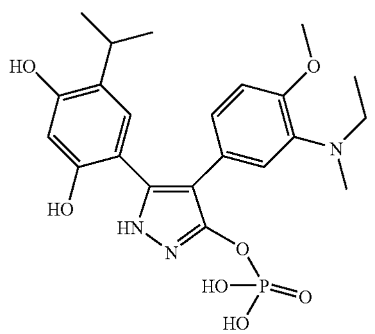 | Phosphoric acid mono {4-[3-(ethyl-methyl-amino)-4-methoxy-phenyl]-3-(5-isopropyl-2,4-dihydroxy-phenyl)-2H-pyrazol-5-yl} ester |
| 306 | 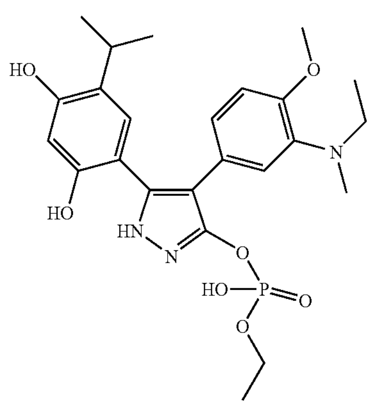 | Phosphoric acid {4-[3-(ethyl-methyl-amino)-4-methoxy-phenyl]-3-(5-isopropyl-2,4-dihydroxy-phenyl)-2H-pyrazol-5-yl} ester ethyl ester |
| 307 | 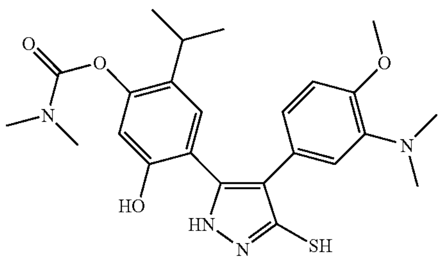 | 4-[3-(N,N-methylamino)-4-methoxy-phenyl]-3-(5-isopropyl-2-hydroxy-4-dimethylaminocarbamoyloxy-phenyl)-5-mercapto-2H-pyrazole |

TABLE 6-continued

| No. | Structure | Name |
|---|---|---|
| 308 | 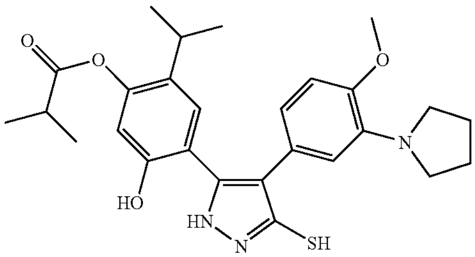 | 4-[3-(pyrrolidin-1-yl)-4-methoxy-phenyl]-3-(5-isopropyl-2-hydroxy-4-dimethylaminocarbamoyloxy-phenyl)-5-mercapto-2H-pyrazole |
| 309 | 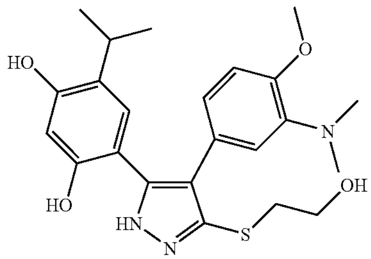 | 4-[3-(N,N-methylamino)-4-methoxy-phenyl]-3-(5-isopropyl-2,4-dihydroxy-phenyl)-5-(2-hydroxy-ethylsulfanyl)-2H-pyrazole |
| 310 | 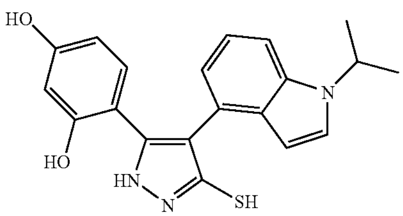 | 4-(1-isopropyl-1H-indol-4-yl)-3-(2,4-dihydroxy-phenyl)-5-mercapto-2H-pyrazole |
| 311 | 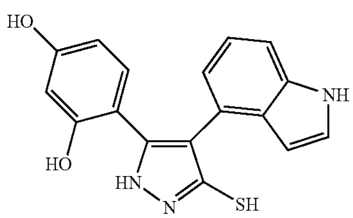 | 4-(1H-indol-4-yl)-3-(2,4-dihydroxy-phenyl)-5-mercapto-2H-pyrazole |
| 312 | 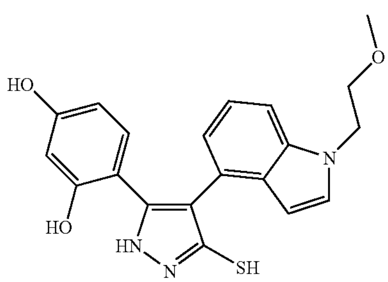 | 4-[1-(2-methoxy-ethyl)-1H-indol-4-yl]-3-(2,4-dihydroxy-phenyl)-5-mercapto-2H-pyrazole |
| 313 | 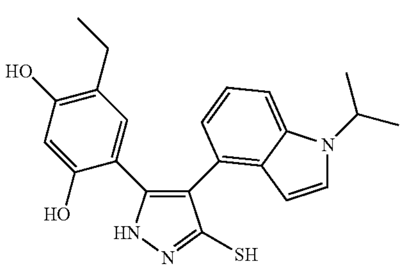 | 4-(1-isopropyl-1H-indol-4-yl)-3-(5-ethyl-2,4-dihydroxy-phenyl)-5-mercapto-2H-pyrazole |

TABLE 6-continued

| No. | Structure | Name |
|---|---|---|
| 314 | 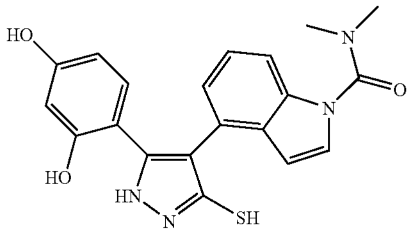 | 4-(1-dimethylcarbamoyl-1H-indol-4-yl)-3-(2,4-dihydroxy-phenyl)-5-mercapto-2H-pyrazole |
| 315 | 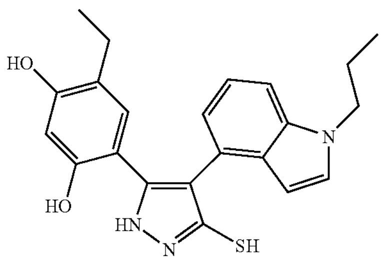 | 4-(1-propyl-1H-indol-4-yl)-3-(5-ethyl-2,4-dihydroxy-phenyl)-5-mercapto-2H-pyrazole |
| 316 | 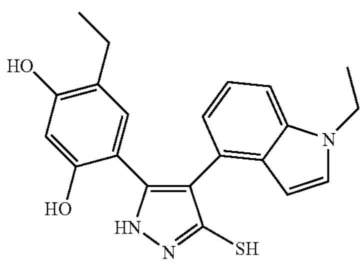 | 4-(1-ethyl-1H-indol-4-yl)-3-(5-ethyl-2,4-dihydroxy-phenyl)-5-mercapto-2H-pyrazole |
| 317 | 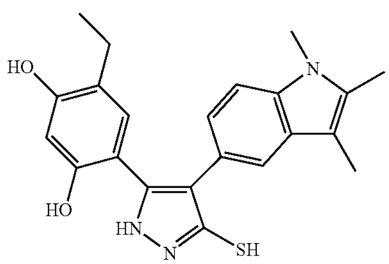 | 4-(1,2,3-trimethyl-1H-indol-4-yl)-3-(5-ethyl-2,4-dihydroxy-phenyl)-5-mercapto-2H-pyrazole |
| 318 | 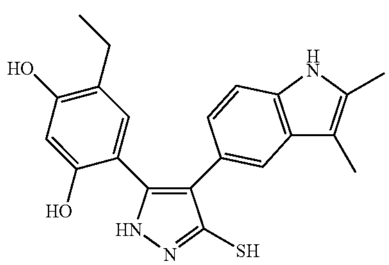 | 4-(2,3-dimethyl-1H-indol-4-yl)-3-(5-ethyl-2,4-dihydroxy-phenyl)-5-mercapto-2H-pyrazole |
| 319 | 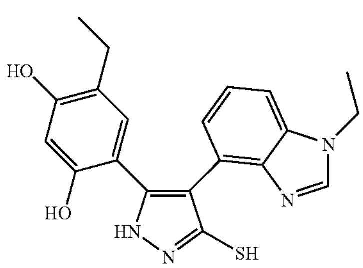 | 4-(1-ethyl-1H-benzoimidazol-4-yl)-3-(5-ethyl-2,4-dihydroxy-phenyl)-5-mercapto-2H-pyrazole |

TABLE 6-continued

| No. | Structure | Name |
| --- | --- | --- |
| 320 | 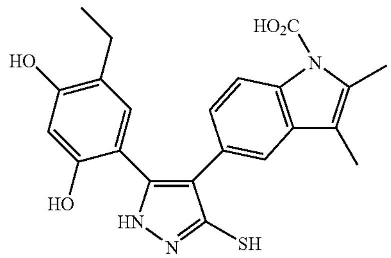 | 4-(1-carboxy-2,3-dimethyl-1H-indol-5-yl)-3-(5-ethyl-2,4-dihydroxy-phenyl)-5-mercapto-2H-pyrazole |
| 321 | 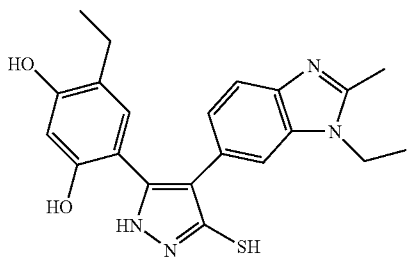 | 4-(1-ethyl-2-methyl-1H-benzoimidazol-6-yl)-3-(5-ethyl-2,4-dihydroxy-phenyl)-5-mercapto-2H-pyrazole |
| 322 | 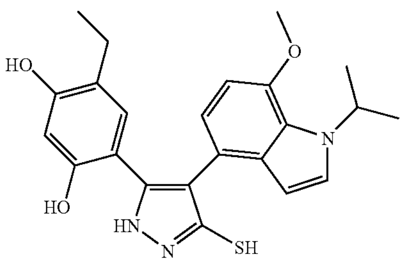 | 4-(1-isopropy-7-methoxy-1H-indol-4-yl)-3-(5-ethyl-2,4-dihydroxy-phenyl)-5-mercapto-2H-pyrazole |
| 323 | 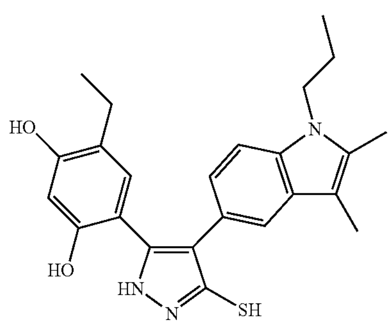 | 4-(1-propy-2,3-dimethyl-1H-indol-5-yl)-3-(5-ethyl-2,4-dihydroxy-phenyl)-5-mercapto-2H-pyrazole |
| 324 | 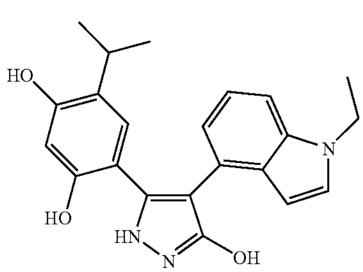 | 4-(1-ethyl-1H-indol-4-yl)-3-(5-isopropyl-2,4-dihydroxy-phenyl)-5-hydroxy-2H-pyrazole |

TABLE 6-continued

| No. | Structure | Name |
|---|---|---|
| 325 | 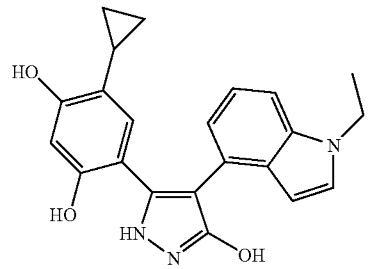 | 4-(1-ethyl-1H-indol-4-yl)-3-(5-cyclopropyl-2,4-dihydroxy-phenyl)-5-hydroxy-2H-pyrazole |
| 326 | 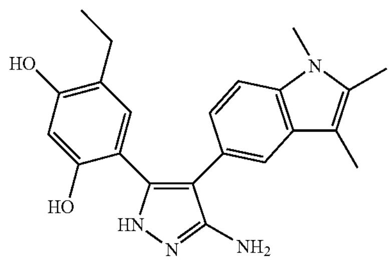 | 4-(1,2,3-trimethyl-1H-indol-5-yl)-3-(5-ethyl-2,4-dihydroxy-phenyl)-5-amino-2H-pyrazole |
| 327 | 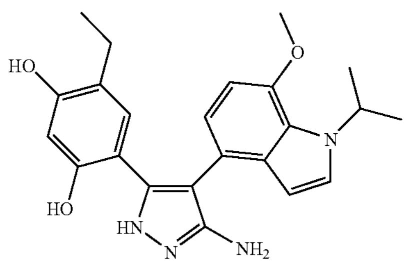 | 4-(1-isopropyl-7-methoxy-1H-indol-4-yl)-3-(5-ethyl-2,4-dihydroxy-phenyl)-5-amino-2H-pyrazole |
| 328 | 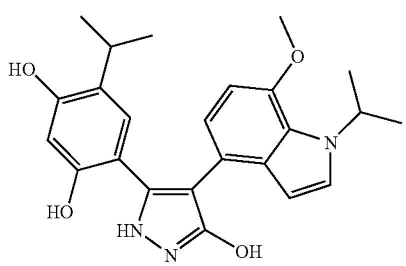 | 4-(1-isopropyl-7-methoxy-1H-indol-4-yl)-3-(5-isopropyl-2,4-dihydroxy-phenyl)-5-hydroxy-2H-pyrazole |
| 329 | 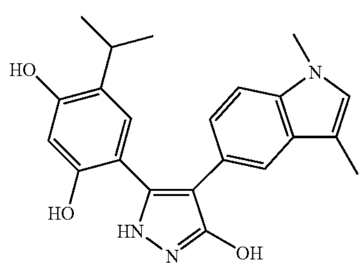 | 4-(1,3-dimethyl-1H-indol-5-yl)-3-(5-isopropyl-2,4-dihydroxy-phenyl)-5-hydroxy-2H-pyrazole |
| 330 | 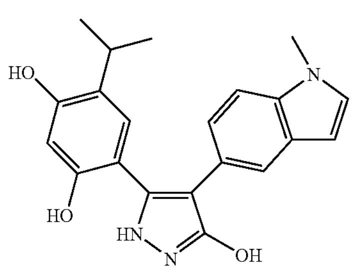 | 4-(1-methyl-1H-indol-5-yl)-3-(5-isopropyl-2,4-dihydroxy-phenyl)-5-hydroxy-2H-pyrazole |

TABLE 6-continued

| No. | Structure | Name |
|---|---|---|
| 331 | 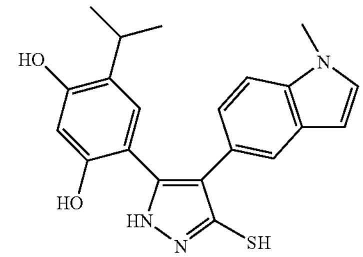 | 4-(1-methyl-1H-indol-5-yl)-3-(5-isopropyl-2,4-dihydroxy-phenyl)-5-mercapto-2H-pyrazole |
| 332 | 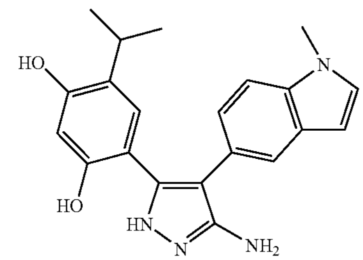 | 4-(1-methyl-1H-indol-5-yl)-3-(5-isopropyl-2,4-dihydroxy-phenyl)-5-amino-2H-pyrazole |
| 333 | 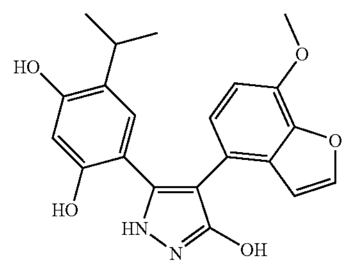 | 4-(7-methoxy-benzofuran-4-yl)-3-(5-isopropyl-2,4-dihydroxy-phenyl)-5-hydroxy-2H-pyrazole |
| 334 | 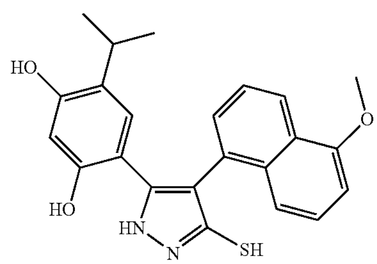 | 4-(5-methoxy-naphthalene-1-yl)-3-(5-isopropyl-2,4-dihydroxy-phenyl)-5-mercapto-2H-pyrazole |
| 335 | 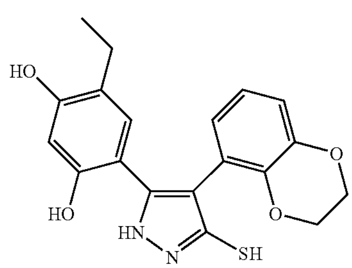 | 4-(benzo[1,4]dioxin-5-yl)-3-(5-ethyl-2,4-dihydroxy-phenyl)-5-mercapto-2H-pyrazole |
| 336 | 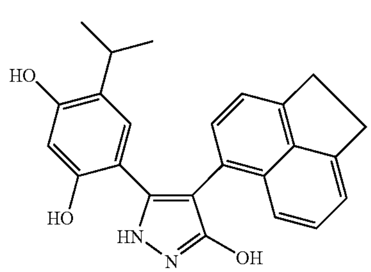 | 4-(acenaphthen-5-yl)-3-(5-isopropyl-2,4-dihydroxy-phenyl)-5-hydroxy-2H-pyrazole |

TABLE 6-continued

| No. | Structure | Name |
|-----|-----------|------|
| 337 | 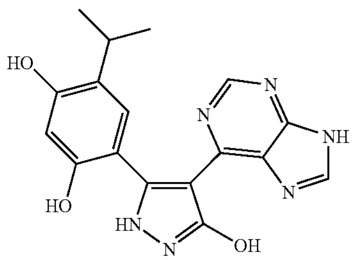 | 4-(9H-purin-6-yl)-3-(5-isopropyl-2,4-dihydroxy-phenyl)-5-hydroxy-2H-pyrazole |
| 338 | 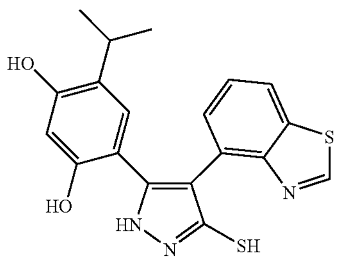 | 4-(benzothiazol-4-yl)-3-(5-isopropyl-2,4-dihydroxy-phenyl)-5-mercapto-2H-pyrazole |
| 339 | 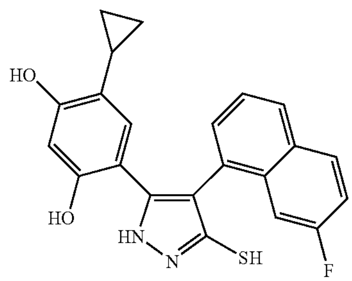 | 4-(7-fluoro-naphthylen-1-yl)-3-(5-cyclopropyl-2,4-dihydroxy-phenyl)-5-mercapto-2H-pyrazole |
| 340 | 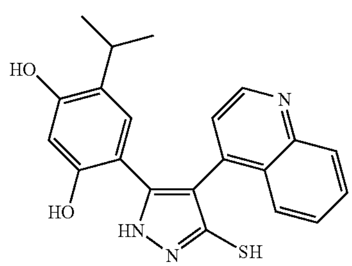 | 4-(quinolin-4-yl)-3-(5-isopropyl-2,4-dihydroxy-phenyl)-5-mercapto-2H-pyrazole |
| 341 | 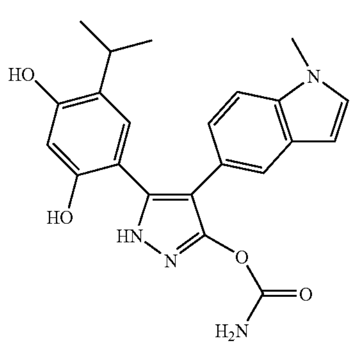 | 4-(1-methyl-1H-indol-5-yl)-3-(5-isopropyl-2,4-dihydroxy-phenyl)-5-carbamoyloxy-2H-pyrazole |

TABLE 6-continued

| No. | Structure | Name |
|---|---|---|
| 342 | 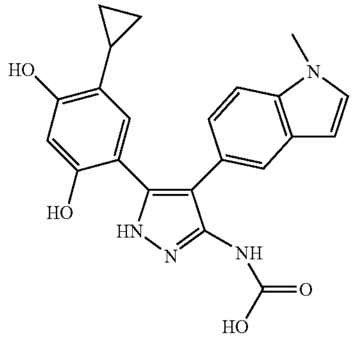 | 4-(1-methyl-1H-indol-5-yl)-3-(5-cyclopropyl-2,4-dihydroxy-phenyl)-5-carboxyamino-2H-pyrazole |
| 343 | 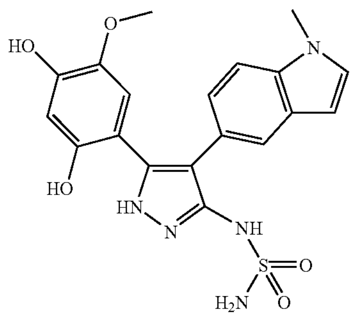 | 4-(1-methyl-1H-indol-5-yl)-3-(5-methoxy-2,4-dihydroxy-phenyl)-5-aminosulfamido-2H-pyrazole |
| 344 | 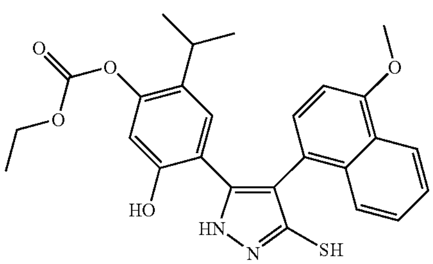 | 4-(4-methoxy-naphthalene-1-yl)-3-(5-isopropyl-2-hydroxy-4-ethoxycarbonyloxy-phenyl)-5-mercapto-2H-pyrazole |
| 345 | 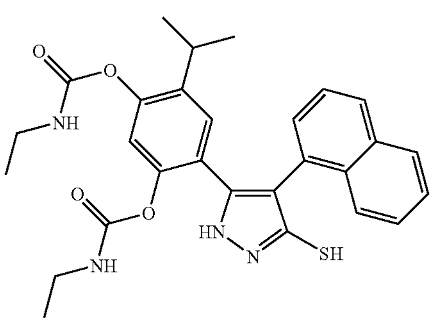 | 4-(naphthalene-1-yl)-3-(5-isopropyl-2,4-ethylcarbamoyloxy-phenyl)-5-mercapto-2H-pyrazole |
| 346 | 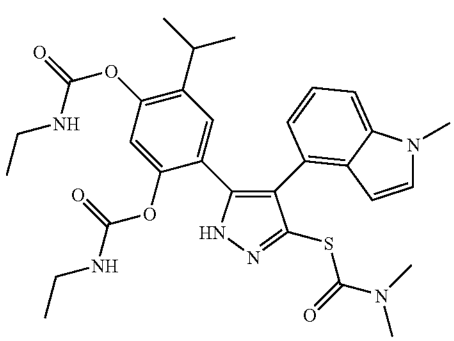 | 4-(1-methyl-1H-indol-4-yl)-3-(5-isopropyl-2,4-ethylcarbamoyloxy-phenyl)-5-dimethylcarbamoylsulfanyl-2H-pyrazole |

TABLE 6-continued

| No. | Structure | Name |
|---|---|---|
| 347 | 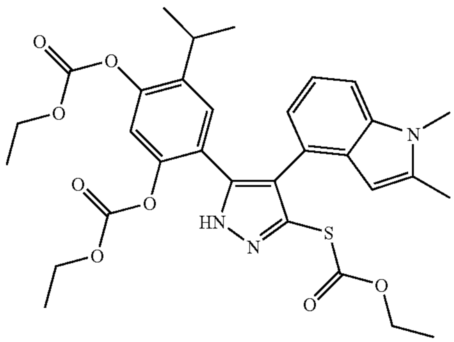 | 4-(1,2-dimethyl-1H-indol-4-yl)-3-(5-isopropyl-2,4-ethyloxycarbonyloxy-phenyl)-5-ethoxycarbamoylsulfanyl-2H-pyrazole |
| 348 | 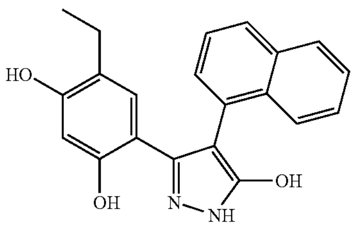 | 4-(naphthalen-1-yl)-3-(5-ethyl-2,4-dihydroxy-phenyl)-5-hydroxy-2H-pyrazole |
| 349 | 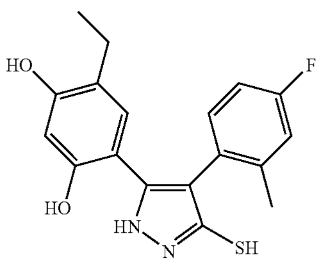 | 4-(2-methyl-4-fluorophenyl)-3-(5-ethyl-2,4-dihydroxy-phenyl)-5-mercapto-2H-pyrazole |
| 350 | 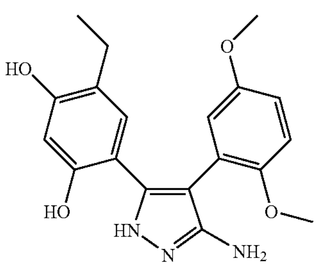 | 4-(3,5-dimethoxyphenyl)-3-(5-ethyl-2,4-dihydroxy-phenyl)-5-amino-2H-pyrazole |
| 351 | 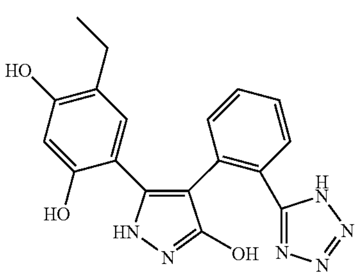 | 4-[2-(1H-tetrazol-5-yl)-phenyl]-3-(5-ethyl-2,4-dihydroxy-phenyl)-5-hydroxy-2H-pyrazole |

Exemplary imidazolyl compounds of the invention are depicted in Table 7 below, including tautomers, pharmaceutically acceptable salts, solvates, clathrates, hydrates, polymorphs or prodrugs thereof.

TABLE 7

| No. | Structure | Name |
|---|---|---|
| 352 | 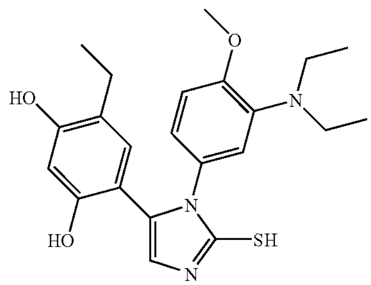 | 1-(3-diethylamino-4-methoxy-phenyl)-2-mercapto-5-(2,4-dihydroxy-5-ethyl-phenyl)-1H-imidazole |
| 353 | 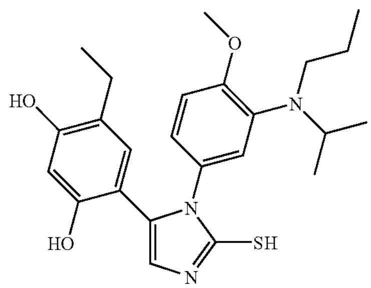 | 1-[3-(propyl-isopropylamino)-4-methoxy-phenyl]-2-mercapto-5-(2,4-dihydroxy-5-ethyl-phenyl)-1H-imidazole |
| 354 | 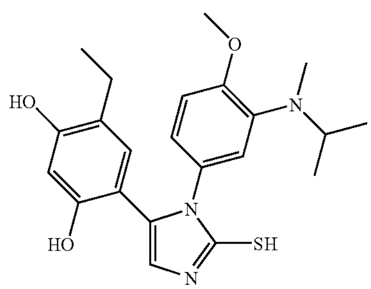 | 1-[3-(methyl-isopropylamino)-4-methoxy-phenyl]-2-mercapto-5-(2,4-dihydroxy-5-ethyl-phenyl)-1H-imidazole |
| 355 | 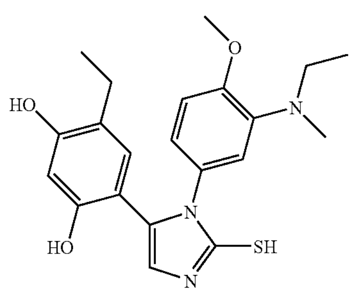 | 1-[3-(methyl-ethylamino)-4-methoxy-phenyl]-2-mercapto-5-(2,4-dihydroxy-5-ethyl-phenyl)-1H-imidazole |
| 356 | 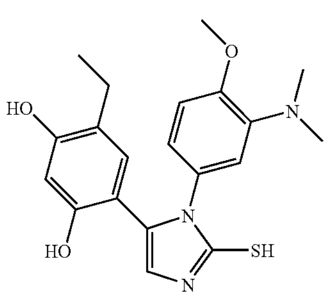 | 1-(3-dimethylamino-4-methoxy-phenyl)-2-mercapto-5-(2,4-dihydroxy-5-ethyl-phenyl)-1H-imidazole |

TABLE 7-continued

| No. | Structure | Name |
|---|---|---|
| 357 | 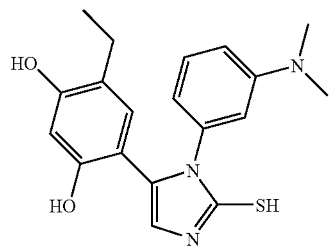 | 1-(3-dimethylamino-phenyl)-2-mercapto-5-(2,4-dihydroxy-5-ethyl-phenyl)-1H-imidazole |
| 358 | 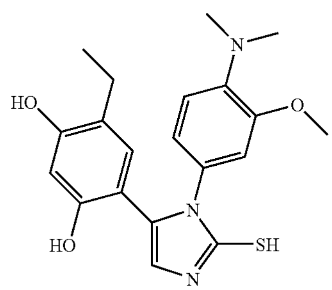 | 1-(3-methoxy-4-dimethylamino-phenyl)-2-mercapto-5-(2,4-dihydroxy-5-ethyl-phenyl)-1H-imidazole |
| 360 | 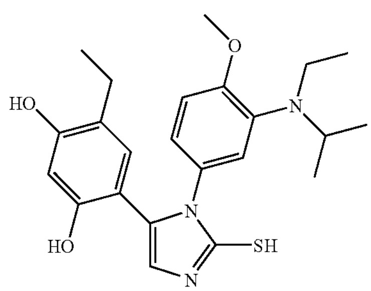 | 1-[3-(ethyl-isopropylamino)-4-methoxy-phenyl]-2-mercapto-5-(2,4-dihydroxy-5-ethyl-phenyl)-1H-imidazole |
| 361 | 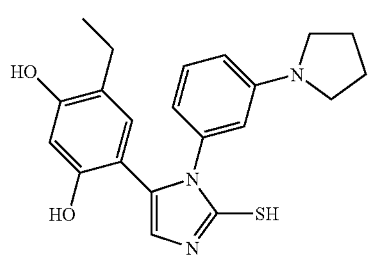 | 1-(3-pyrrolidin-1-yl-phenyl)-2-mercapto-5-(2,4-dihydroxy-5-ethyl-phenyl)-1H-imidazole |
| 362 | 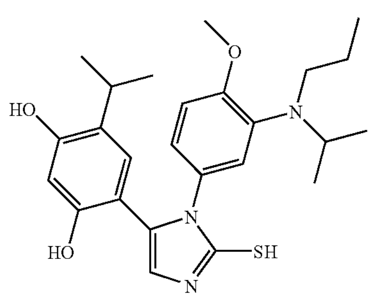 | 1-[3-(propyl-isopropylamino)-4-methoxy-phenyl]-2-mercapto-5-(2,4-dihydroxy-5-isopropyl-phenyl)-1H-imidazole |

TABLE 7-continued

| No. | Structure | Name |
|---|---|---|
| 363 | 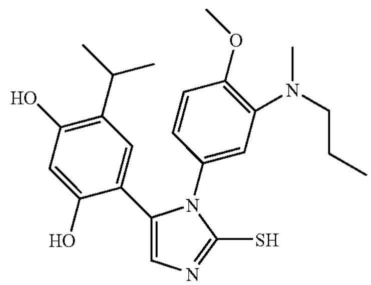 | 1-[3-(methyl-propylamino)-4-methoxy-phenyl]-2-mercapto-5-(2,4-dihydroxy-5-isopropyl-phenyl)-1H-imidazole |
| 364 | 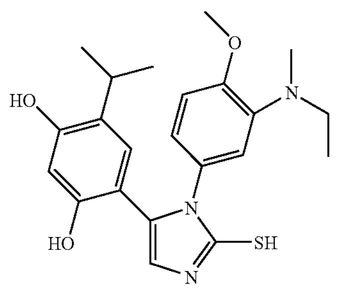 | 1-[3-(methyl-ethylamino)-4-methoxy-phenyl]-2-mercapto-5-(2,4-dihydroxy-5-isopropyl-phenyl)-1H-imidazole |
| 365 | 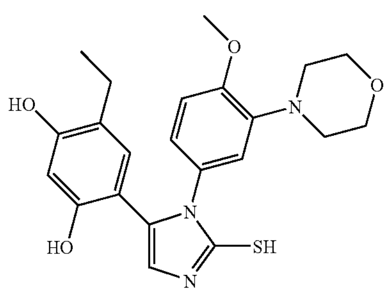 | 1-[3-(morpholino-1-yl)-4-methoxy-phenyl]-2-mercapto-5-(2,4-dihydroxy-5-ethyl-phenyl)-1H-imidazole |
| 366 | 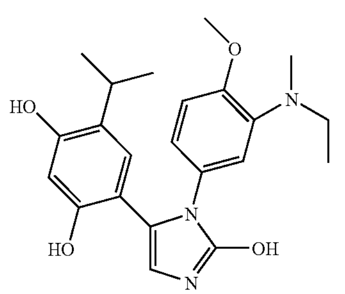 | 1-[3-(methyl-ethylamino)-4-methoxy-phenyl]-2-hydroxy-5-(2,4-dihydroxy-5-isopropyl-phenyl)-1H-imidazole |
| 367 | 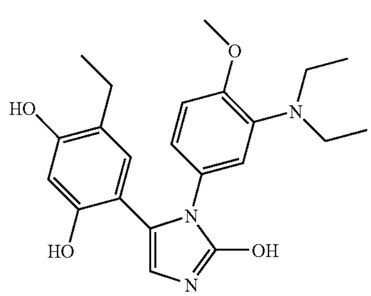 | 1-(3-diethylamino-4-methoxy-phenyl)-2-hydroxy-5-(2,4-dihydroxy-5-ethyl-phenyl)-1H-imidazole |

TABLE 7-continued

| No. | Structure | Name |
|---|---|---|
| 368 | 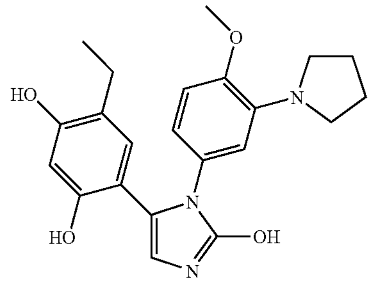 | 1-[3-(pyrrolidin-1-yl)-4-methoxy-phenyl]-2-hydroxy-5-(2,4-dihydroxy-5-ethyl-phenyl)-1H-imidazole |
| 369 | 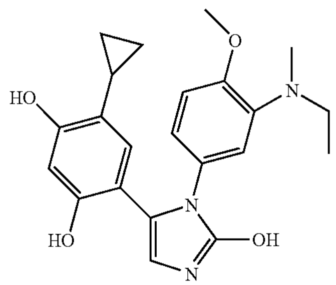 | 1-[3-(methyl-ethylamino)-4-methoxy-phenyl]-2-hydroxy-5-(2,4-dihydroxy-5-cyclopropyl-phenyl)-1H-imidazole |
| 370 | 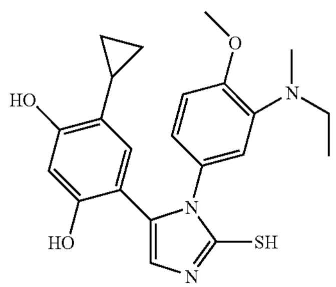 | 1-[3-(methyl-ethylamino)-4-methoxy-phenyl]-2-mercapto-5-(2,4-dihydroxy-5-cyclopropyl-phenyl)-1H-imidazole |
| 371 | 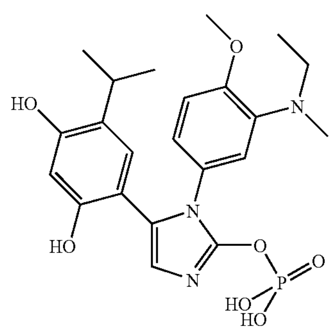 | 1-[3-(methyl-ethylamino)-4-methoxy-phenyl]-2-phosphonooxy-5-(2,4-dihydroxy-5-isopropyl-phenyl)-1H-imidazole |
| 372 | 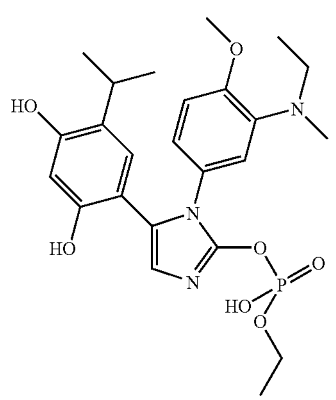 | 1-[3-(methyl-ethylamino)-4-methoxy-phenyl]-2-(ethoxy-hydroxy-phosphoryloxy)-5-(2,4-dihydroxy-5-isopropyl-phenyl)-1H-imidazole |

TABLE 7-continued

| No. | Structure | Name |
|---|---|---|
| 373 | 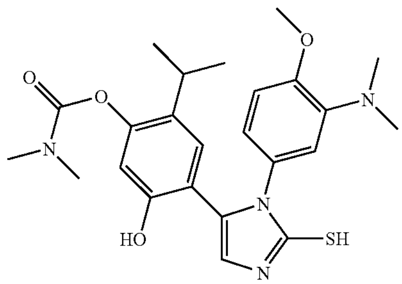 | 1-(3-dimethylamino-4-methoxy-phenyl)-2-mercapto-5-(2-hydroxy-4-dimethylcarbamoyloxy-5-isopropyl-phenyl)-1H-imidazole |
| 374 | 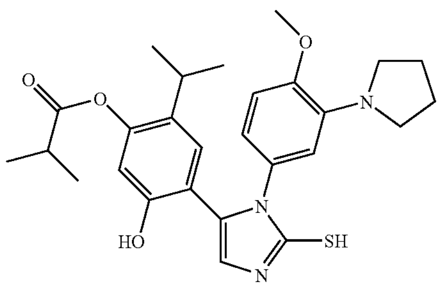 | 1-[3-(pyrrolidin-1-yl)-4-methoxy-phenyl]-2-mercapto-5-(2-hydroxy-4-isobutyryloxy-5-isopropyl-phenyl)-1H-imidazole |
| 375 | 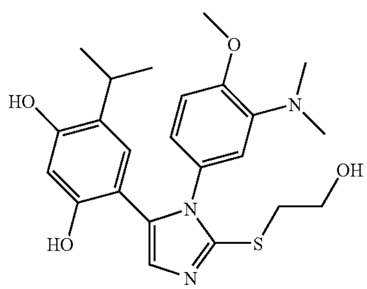 | 1-(3-dimethylamino-4-methoxy-phenyl)-2-(2-hydroxy-ethylsulfanyl)-5-(2,4-dihydroxy-5-isopropyl-phenyl)-1H-imidazole |
| 376 | 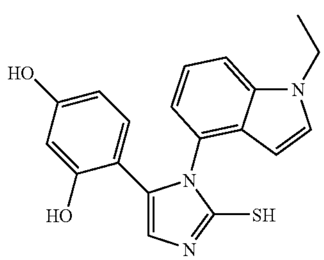 | 1-(1-ethyl-1H-indol-4-yl)-2-mercapto-5-(2,4-dihydroxy-phenyl)-1H-imidazole |
| 377 | 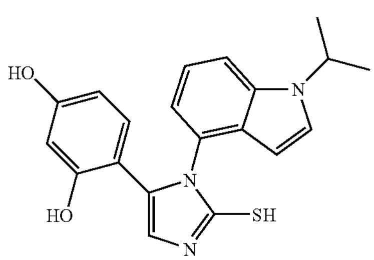 | 1-(1-isopropyl-1H-indol-4-yl)-2-mercapto-5-(2,4-dihydroxy-phenyl)-1H-imidazole |
| 378 | 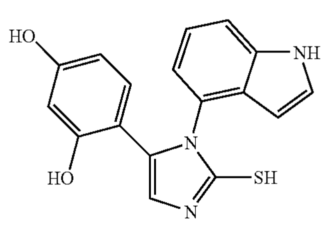 | 1-(1H-indol-4-yl)-2-mercapto-5-(2,4-dihydroxy-phenyl)-1H-imidazole |

TABLE 7-continued
| No. | Structure | Name |
|---|---|---|
| 379 | 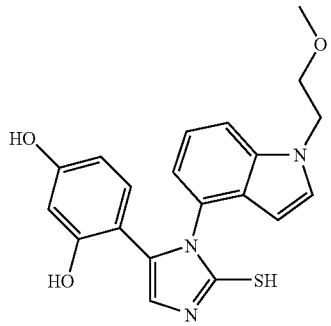 | 1-[1-(2-methoxy-ethyl)-1H-indol-4-yl]-2-mercapto-5-(2,4-dihydroxy-phenyl)-1H-imidazole |
| 380 | 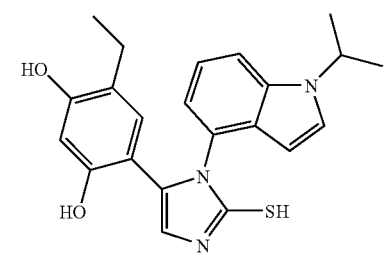 | 1-(1-isopropyl-1H-indol-4-yl)-2-mercapto-5-(2,4-dihydroxy-5-ethyl-phenyl)-1H-imidazole |
| 381 | 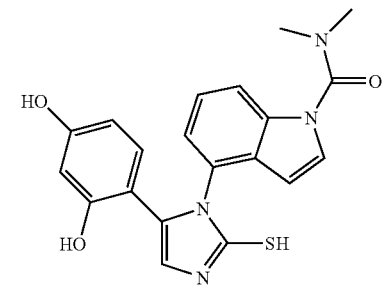 | 1-(1-dimethylcarbamoyl-1H-indol-4-yl)-2-mercapto-5-(2,4-dihydroxy-phenyl)-1H-imidazole |
| 382 | 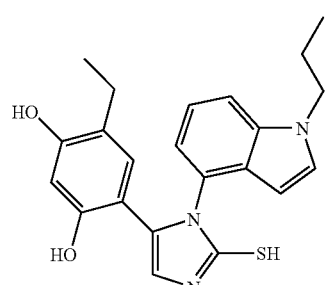 | 1-(1-propyl-1H-indol-4-yl)-2-mercapto-5-(2,4-dihydroxy-5-ethyl-phenyl)-1H-imidazole |
| 383 | 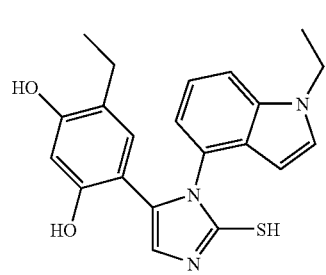 | 1-(1-ethyl-1H-indol-4-yl)-2-mercapto-5-(2,4-dihydroxy-5-ethyl-phenyl)-1H-imidazole |

TABLE 7-continued

| No. | Structure | Name |
|-----|-----------|------|
| 384 | 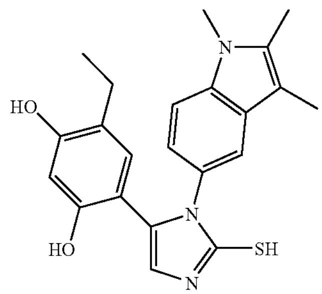 | 1-(1,2,3-trimethyl-1H-indol-5-yl)-2-mercapto-5-(2,4-dihydroxy-5-ethyl-phenyl)-1H-imidazole |
| 385 | 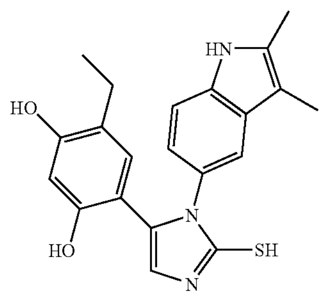 | 1-(2,3-dimethyl-1H-indol-5-yl)-2-mercapto-5-(2,4-dihydroxy-5-ethyl-phenyl)-1H-imidazole |
| 386 | 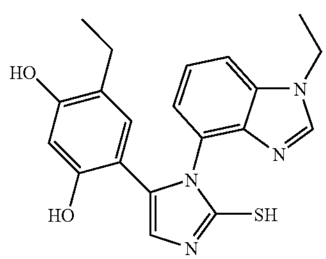 | 1-(1-ethyl-1H-benzoimidazol-4-yl)-2-mercapto-5-(2,4-dihydroxy-5-ethyl-phenyl)-1H-imidazole |
| 387 | 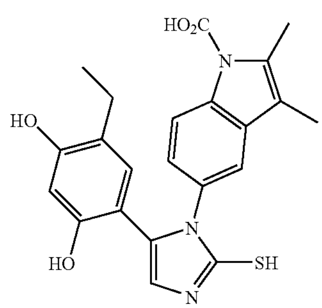 | 1-(1-carboxy-2,3-dimethyl-1H-indol-5-yl)-2-mercapto-5-(2,4-dihydroxy-5-ethyl-phenyl)-1H-imidazole |
| 388 | 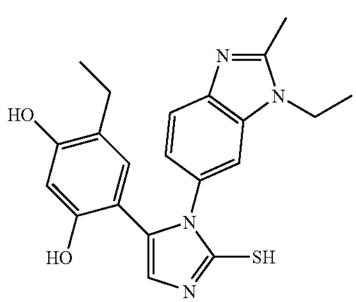 | 1-(1-ethyl-2-methyl-1H-benzoimidazol-6-yl)-2-mercapto-5-(2,4-dihydroxy-5-ethyl-phenyl)-1H-imidazole |

TABLE 7-continued

| No. | Structure | Name |
| --- | --- | --- |
| 389 | 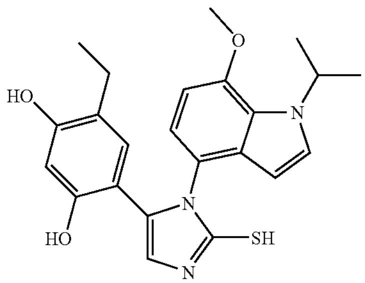 | 1-(1-isopropyl-7-methoxy-1H-indol-4-yl)-2-mercapto-5-(2,4-dihydroxy-5-ethyl-phenyl)-1H-imidazole |
| 390 | 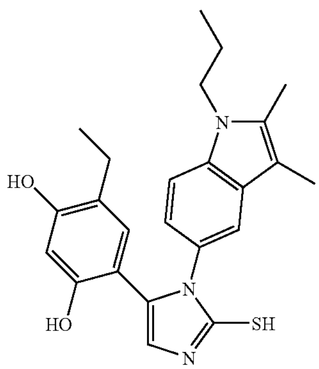 | 1-(1-propyl-2,3-dimethyl-1H-indol-5-yl)-2-mercapto-5-(2,4-dihydroxy-5-ethyl-phenyl)-1H-imidazole |
| 391 | 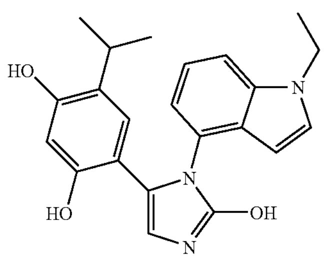 | 1-(1-ethyl-1H-indol-4-yl)-2-hydroxy-5-(2,4-dihydroxy-5-isopropyl-phenyl)-1H-imidazole |
| 392 | 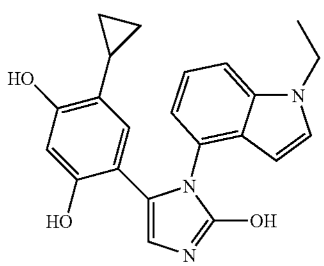 | 1-(1-ethyl-1H-indol-4-yl)-2-hydroxy-5-(2,4-dihydroxy-5-cyclopropyl-phenyl)-1H-imidazole |
| 393 | 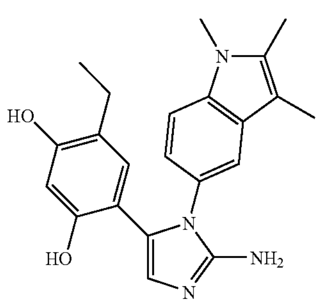 | 1-(1,2,3-trimethyl-1H-indol-5-yl)-2-amino-5-(2,4-dihydroxy-5-ethyl-phenyl)-1H-imidazole |

TABLE 7-continued

| No. | Structure | Name |
|-----|-----------|------|
| 394 | 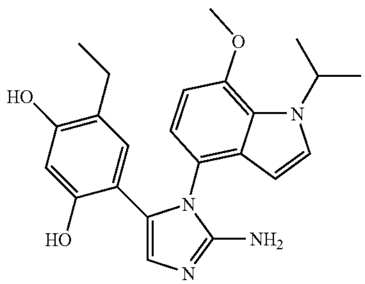 | 1-(1-isopropyl-7-methoxy-1H-indol-4-yl)-2-amino-5-(2,4-dihydroxy-5-ethyl-phenyl)-1H-imidazole |
| 395 | 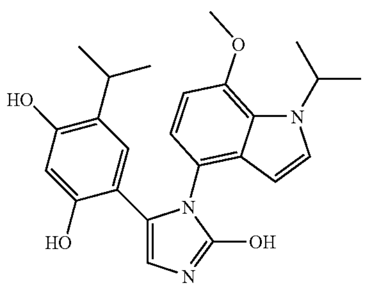 | 1-(1-isopropyl-7-methoxy-1H-indol-4-yl)-2-hydroxy-5-(2,4-dihydroxy-5-isopropyl-phenyl)-1H-imidazole |
| 396 | 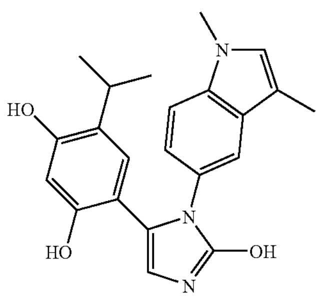 | 1-(1,3-dimethyl-1H-indol-5-yl)-2-hydroxy-5-(2,4-dihydroxy-5-isopropyl-phenyl)-1H-imidazole |
| 397 | 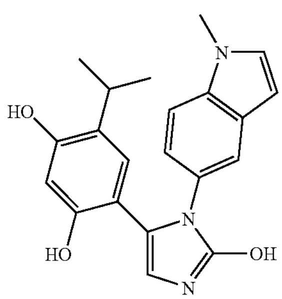 | 1-(1-methyl-1H-indol-5-yl)-2-hydroxy-5-(2,4-dihydroxy-5-isopropyl-phenyl)-1H-imidazole |
| 398 | 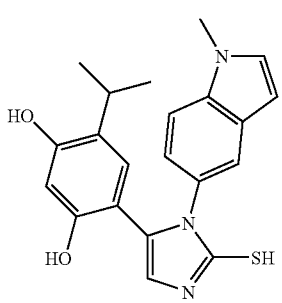 | 1-(1-methyl-1H-indol-5-yl)-2-mercapto-5-(2,4-dihydroxy-5-isopropyl-phenyl)-1H-imidazole |

TABLE 7-continued

| No. | Structure | Name |
|---|---|---|
| 399 | 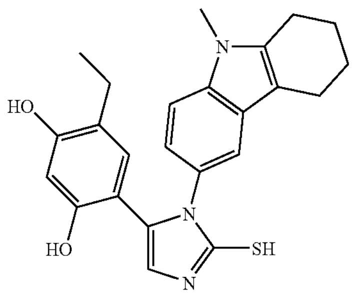 | 1-(9-methyl-6,7,8,9-tetrahydro-5H-carbazol-3-yl)-2-mercapto-5-(2,4-dihydroxy-5-ethyl-phenyl)-1H-imidazole |
| 400 | 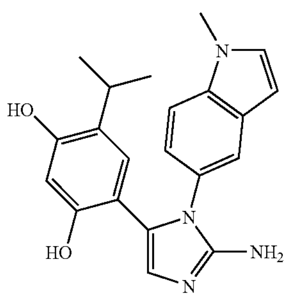 | 1-(1-methyl-1H-indol-5-yl)-2-amino-5-(2,4-dihydroxy-5-isopropyl-phenyl)-1H-imidazole |
| 401 | 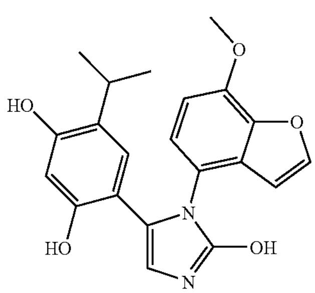 | 1-(7-methoxy-benzofuran-4-yl)-2-hydroxy-5-(2,4-dihydroxy-5-isopropyl-phenyl)-1H-imidazole |
| 402 | 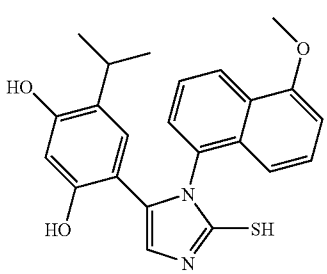 | 1-(5-methoxy-naphthylen-1-yl)-2-mercapto-5-(2,4-dihydroxy-5-isopropyl-phenyl)-1H-imidazole |
| 403 | 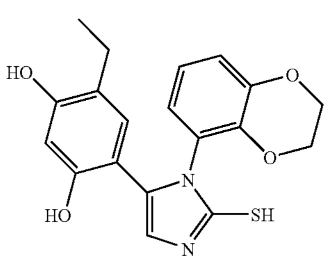 | 1-(2,3-dihydro-benzo[1,4]dioxin-5-yl)-2-mercapto-5-(2,4-dihydroxy-5-ethyl-phenyl)-1H-imidazole |

TABLE 7-continued

| No. | Structure | Name |
| --- | --- | --- |
| 404 | 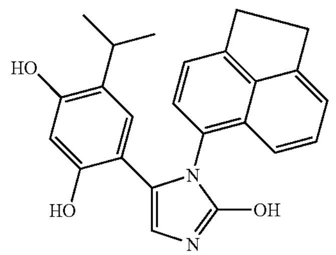 | 1-(3-acenaphthylen-5-yl)-2-hydroxy-5-(2,4-dihydroxy-5-isopropyl-phenyl)-1H-imidazole |
| 405 | 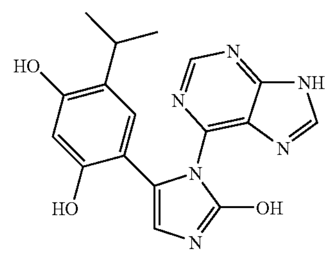 | 1-(9H-purin-6-yl)-2-hydroxy-5-(2,4-dihydroxy-5-isopropyl-phenyl)-1H-imidazole |
| 406 | 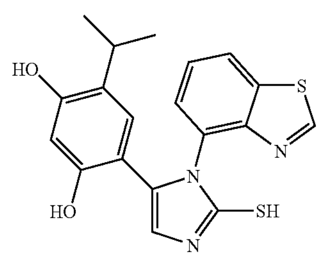 | 1-(benzothiazol-4-yl)-2-mercapto-5-(2,4-dihydroxy-5-isopropyl-phenyl)-1H-imidazole |
| 407 | 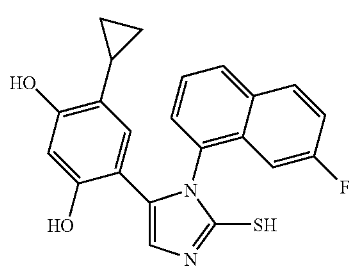 | 1-(7-fluoro-naphthylen-1-yl)-2-mercapto-5-(2,4-dihydroxy-5-cyclopropyl-phenyl)-1H-imidazole |
| 408 | 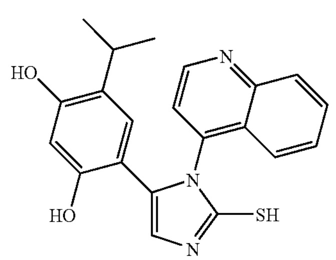 | 1-(quinolin-4-yl)-2-mercapto-5-(2,4-dihydroxy-5-isopropyl-phenyl)-1H-imidazole |

TABLE 7-continued

| No. | Structure | Name |
| --- | --- | --- |
| 409 | 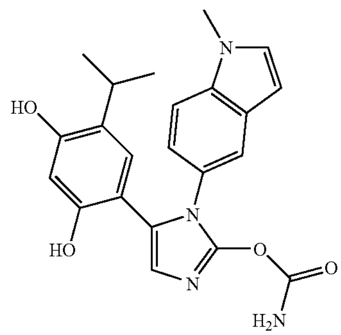 | 1-(1-methyl-indol-5-yl)-2-carbamoyloxy-5-(2,4-dihydroxy-5-isopropyl-phenyl)-1H-imidazole |
| 410 | 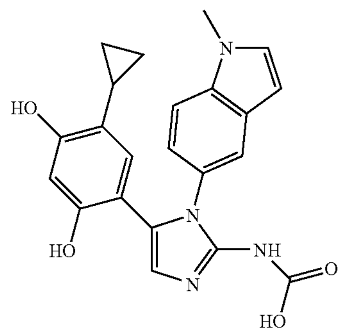 | 1-(1-methyl-indol-5-yl)-2-carboxyamino-5-(2,4-dihydroxy-5-cycolpropyl-phenyl)-1H-imidazole |
| 411 | 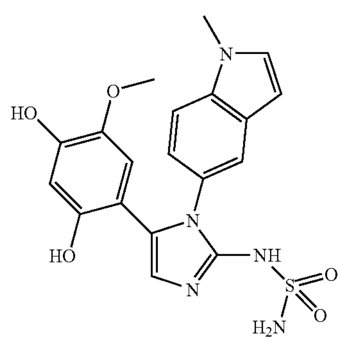 | 1-(1-methyl-1H-indol-5-yl)-2-aminosulfamido-5-(5-methoxy-2,4-dihydroxy-phenyl)-1H-imidazole |
| 412 | 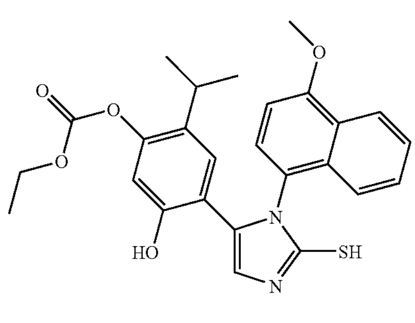 | 1-(4-methoxy-naphthylen-1-yl)-2-mercapto-5-(2-hydroxy-4-ethoxycarbonyloxy-5-isopropyl-phenyl)-1H-imidazole |

TABLE 7-continued

| No. | Structure | Name |
|---|---|---|
| 413 | 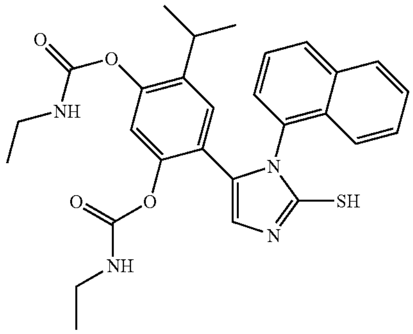 | 1-(naphthylen-1-yl)-2-mercapto-5-[2,4-di-(ethoxycarbamoyloxy)-5-isopropyl-phenyl]-1H-imidazole |
| 414 | 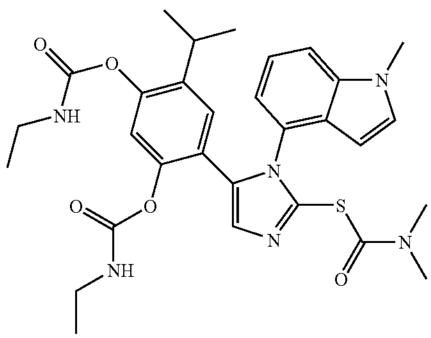 | 1-(1-methyl-1H-indol-4-yl)-2-dimethylcarbamoylsulfanyl-5-[2,4-di-(ethoxycarbamoyloxy)-5-isopropyl-phenyl]-1H-imidazole |
| 415 | 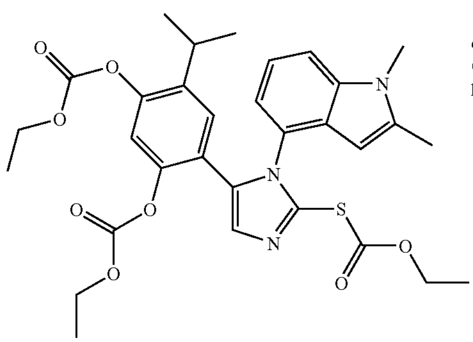 | 1-(1,2-dimethyl-1H-indol-4-yl)-2-ethoxycarbonylsulfanyl-5-[2,4-di-(ethoxycarbonyloxy)-5-isopropyl-phenyl]-1H-imidazole |
| 416 | 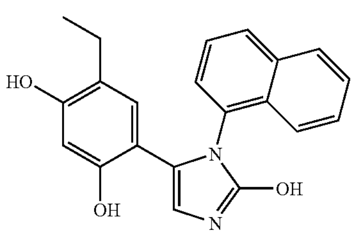 | 1-(naphthylen-1-yl)-2-hydroxy-5-(2,4-dihydroxy-5-ethyl-phenyl)-1H-imidazole |
| 417 | 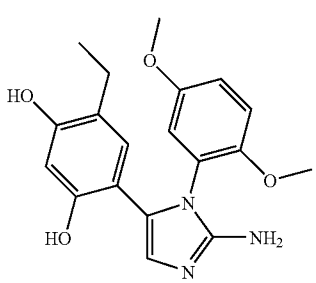 | 1-(2,5-dimethoxyphenyl)-2-amino-5-(2,4-dihydroxy-5-ethyl-phenyl)-1H-imidazole |

TABLE 7-continued

| No. | Structure | Name |
|---|---|---|
| 418 | 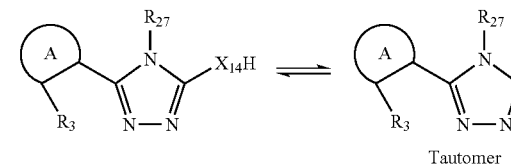 | 1-(2-methyl-4-fluoro-phenyl)-2-mercapto-5-(2,4-dihydroxy-5-ethyl-phenyl)-1H-imidazole |
| 419 | 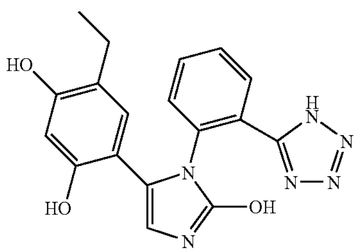 | 1-[2-(1H-tetrazol-5-yl)-phenyl]-2-hydroxy-5-(2,4-dihydroxy-5-ethyl-phenyl)-1H-imidazole |

Preferred triazole compounds of the invention are those compounds that can form a tautomeric structure as shown below and as exemplified by the tautomeric structures shown in Table 5:

$R_{27} = R_2, R_5, \text{ or } R_{18}$
$X_{14} = O, S, \text{ or } NR_7$

Also preferred are compounds which can be metabolized or hydrolyzed in vivo to a compound which can form the tautomeric structure shown above. For example, the following embodiments of a compound of formula (I) can be produced in vivo in the following reaction:

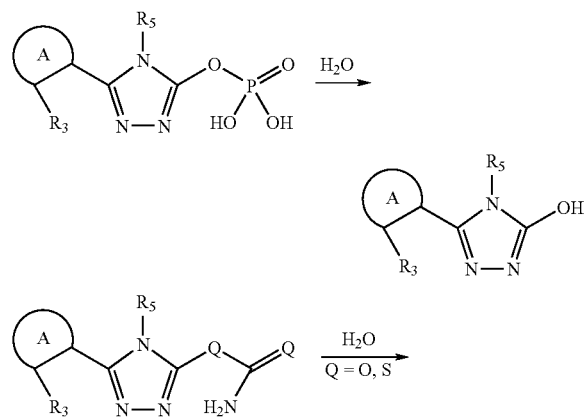

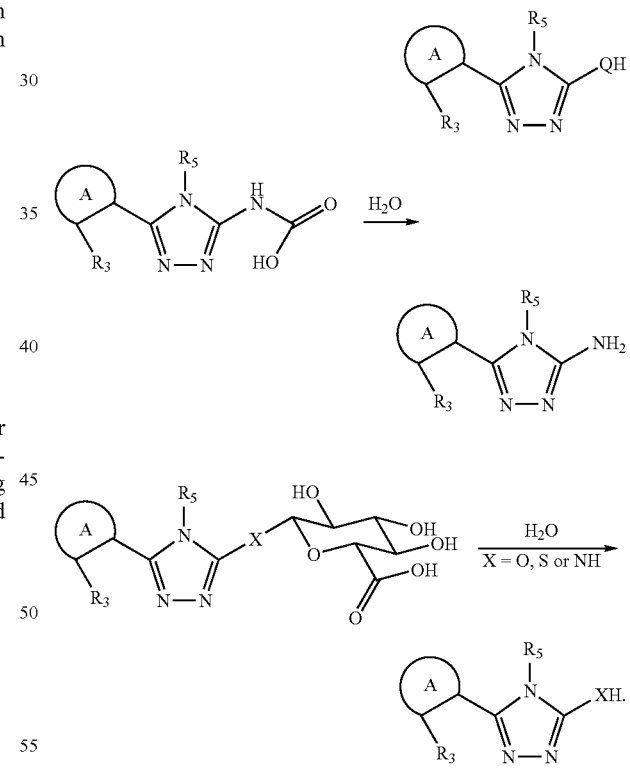

Without wishing to be bound by any theory, it is believed that the compounds of the invention preferentially bind to Hsp90 in the tautomeric form shown above, and thereby inhibit the activity of Hsp90.

It is understood that the pyrazole compounds of the present invention, including compounds of formulas (VI) through (VIII) and Table 6 can be purified, isolated, obtained and used in a form of a pharmaceutically acceptable salt, a solvate, a clathrate, a tautomer or a prodrug.

For example, a compound of formula (VI) can undergo the following tautomerization:

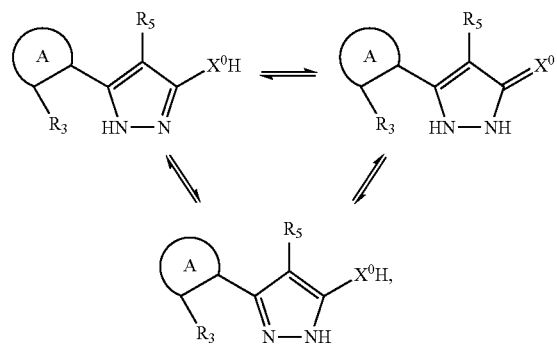

where $X^0$ is O, S, or $NR_7$. It is understood that where a structural formula is depicted, all possible tautomeric forms of the compound are encompassed within that formula.

Similarly, prodrugs, i.e. compounds which can be metabolized or hydrolyzed in vivo to a compound of the present invention are encompassed by the present description. For example, the following embodiments of a compound of formula (VI) can be produced in vivo in the following reaction:

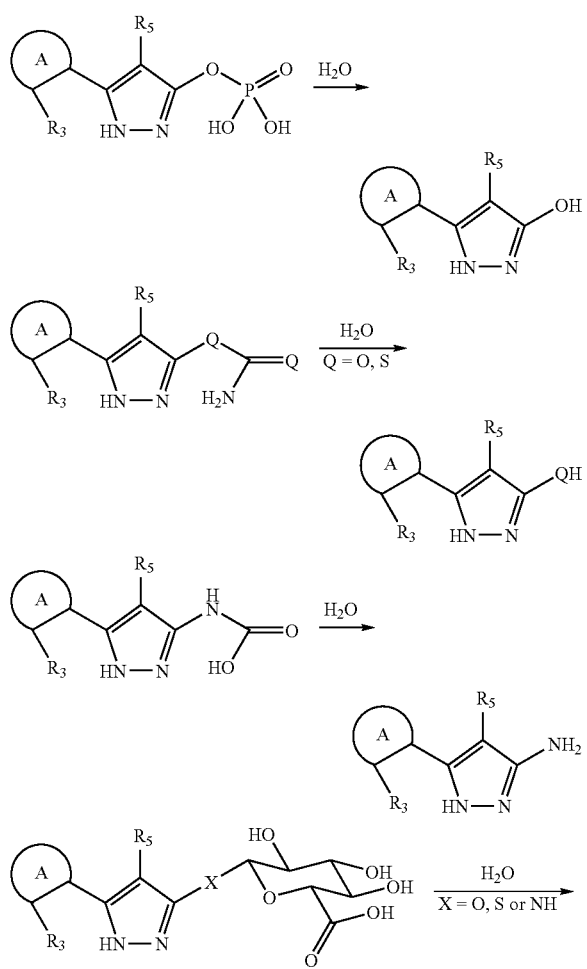

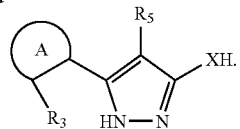

One skilled in the art will understand that other hydrolyzable protecting groups can be employed with the compounds of the present invention to obtain prodrugs encompassed by the present description.

It is understood that the compounds of the present invention, including compounds of formulas (IX) through (XI) and Tables 7 can be purified, isolated, obtained and used in a form of a pharmaceutically acceptable salt, a solvate, a clathrate, a tautomer or a prodrug.

For example, a compound of formula (IX) can undergo the following tautomerization:

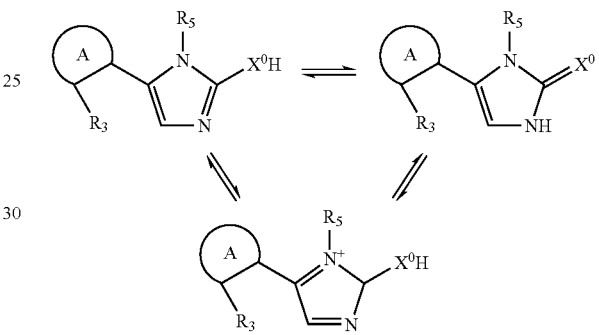

where $X^0$ is O, S, or $NR_7$. It is understood that where a structural formula is depicted, all possible tautomeric forms of the compound are encompassed within that formula.

Similarly, prodrugs, i.e. compounds which can be metabolized or hydrolyzed in vivo to a compound of the present invention are encompassed by the present description. For example, the following embodiments of a compound of formula (IX) can be produced in vivo in the following reaction:

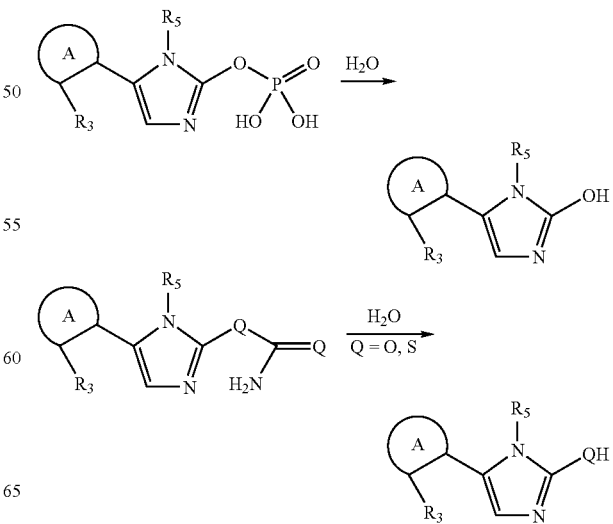

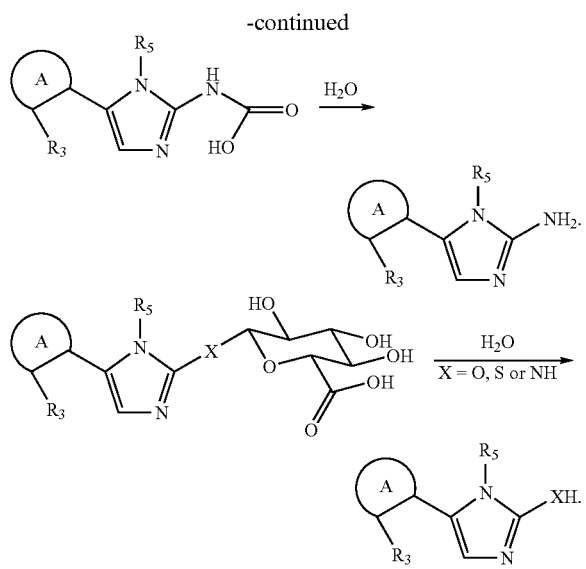

One skilled in the art will understand that other hydrolyzable protecting groups can be employed with the compounds of the present invention to obtain prodrugs encompassed by the present description.

C. METHODS FOR MAKING COMPOUNDS OF THE INVENTION

Methods of making the compounds of the invention are disclosed in U.S. patent application Ser. No. 11/282,119, filed on Nov. 17, 2005; and in U.S. Provisional Patent Application Ser. No. 60/709,310, filed Aug. 18, 2005; U.S. Provisional Patent Application Ser. No. 60/724,105, filed Oct. 6, 2005; U.S. Provisional Patent Application Ser. No. 60/709,358, filed Aug. 18, 2005; U.S. Provisional Patent Application Ser. No. 60/725,044, filed Oct. 6, 2005; U.S. Provisional Patent Application Ser. No. 60/707,836, filed Aug. 12, 2005; U.S. Provisional Patent Application Ser. No. 60/709,228, file Aug. 18, 2005; the entire teachings of each of these patent applications is incorporated herein by reference.

Additional methods of preparing the compounds of the invention can be found in the following U.S. provisional applications: entitled "Synthesis of HSP90 Inhibitors," filed on May 25, 2006; entitled "Synthesis of HSP90 Inhibitors," filed on May 25, 2006; and entitled "Synthesis of HSP90 Inhibitors," filed on May 25, 2006, the entire teachings of each of these applications are incorporated herein by reference.

D. Uses of Compounds of the Invention

The present invention is directed to therapies which involve administering one or more compounds of the invention, or compositions comprising said compounds to a subject, preferably a human subject, to inhibit the activity of Hsp90 or to prevent, treat, manage, or ameliorate a proliferative disorder, such as cancer (including non-Hodgkin's lymphoma), or one or more symptoms thereof.

In one aspect, the invention provides a method of inhibiting the activity of Hsp90 in a cell, comprising administering to the cell an effective amount of a compound represented by formula (I) through (LXXII), or any embodiment thereof, or a compound shown in Table 5, 6, or 7. In one embodiment, the compound is administered to a cell in a subject, preferably a mammal, and more preferably a human.

In another aspect, the invention provides a method of treating or preventing a proliferation disorder in a mammal, comprising administering to the mammal an effective amount of a compound represented by formula (I) through (LXXII), or any embodiment thereof, or a compound shown in Table 5, 6, or 7. In one embodiment, the compound is administered to a human to treat or prevent a proliferative disorder. In another embodiment, the proliferation disorder is cancer. In another embodiment, the cancer is non-Hodgkin's lymphoma. In another embodiment, the compound is administered with one or more additional therapeutic agents. In a preferred embodiment, the additional therapeutic agent is an anticancer agent.

In another aspect, the invention provides a method for treating cancer in a mammal, comprising administering to the mammal an effective amount of a compound represented by formula (I) through (LXXII), or any embodiment thereof, or a compound shown in Table 5, 6, or 7. In one embodiment, the compound is administered to a human to treat or prevent cancer. In another embodiment, the compound is administered to a human to treat or prevent non-Hodgkin's lymphoma. In another embodiment, the compound is administered with one or more additional therapeutic agents. In a preferred embodiment, the one or more additional therapeutic agents are anticancer agents.

In another aspect, the invention provides a method of treating a non-Hodgkin's lymphoma, comprising administering to the mammal an effective amount of a compound represented by formula (I) through (LXXII), or any embodiment thereof, or a compound shown in Table 5, 6, or 7. In one embodiment, the non-Hodgkin's lymphoma is a B-cell non-Hodgkin's lymphoma. Examples of B-cell non-Hodgkin's lymphoma include Burkitt's lymphoma, follicular lymphoma, diffuse large B-cell lymphoma, nodal marginal zone B-cell lymphoma, plasma cell neoplasms, small lymphocytic lymphoma/chronic lymphocytic leukemia, mantle cell lymphoma, and lymphoplamacytic lymphoma/Waldenstrom macroglobulinemia. In another embodiment, the non-Hodgkin's lymphoma is T-cell non-Hodgkin's lymphoma. Examples of T-cell non-Hodgkin's lymphoma include anaplastic large-cell lymphoma, precursor-T-cell lymphoblastic leukemia/lymphoma, unspecified peripheral T-cell lymphoma, and angioimmunoblastic T-cell lymphoma.

1) Agents Useful in Combination with the Compounds of the Invention

Without wishing to be bound by theory, it is believed that the compounds of the invention can be particularly effective at treating subjects whose cancer has become multi-drug resistant. Although chemotherapeutic agents initially cause tumor regression, most agents that are currently used to treat cancer target only one pathway to tumor progression. Therefore, in many instances, after treatment with one or more chemotherapeutic agents, a tumor develops multidrug resistance and no longer response positively to treatment. One of the advantages of inhibiting Hsp90 activity is that several of its client proteins, which are mostly protein kinases or transcription factors involved in signal transduction, have been shown to be involved in the progression of cancer. Thus, inhibition of Hsp90 provides a method of short circuiting several pathways for tumor progression simultaneously. Therefore, it is believed that treatment of cancer with an Hsp90 inhibitor of the invention either alone, or in combination with other chemotherapeutic agents, is more likely to result in regression or elimination of the tumor, and less likely to result in the development of more aggressive multidrug resistant tumors than other currently available therapies.

Anticancer agents that can be co-administered with the compounds of the invention include Taxol™, also referred to as "paclitaxel", is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules.

Other anti-cancer agents that can be employed in combination with the compounds of the invention include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs that can be employed in combination with the compounds of the invention include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefuir; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred anticancer drugs are 5-fluorouracil and leucovorin.

Other chemotherapeutic agents that can be employed in combination with the compounds of the invention include but are not limited to alkylating agents, antimetabolites, natural products, or hormones. Examples of alkylating agents useful for the treatment or prevention of T-cell malignancies in the methods and compositions of the invention include but are not limited to, nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites useful for the treatment or prevention of T-cell malignancies in the methods and compositions of the invention include but are not limited to folic acid analog (e.g., methotrexate), or pyrimidine analogs (e.g., Cytarabine), purine analogs (e.g., mercaptopurine, thioguanine, pentostatin). Examples of natural products useful for the treatment or prevention of T-cell malignancies in the methods and compositions of the invention include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination with the compounds of the invention include but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful for the treatment or prevention of cancer in the methods and compositions of the invention include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of natural products useful for the treatment or prevention of cancer in the methods and compositions of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin), enzymes (e.g., L-asparaginase), or biological response modifiers (e.g., interferon alpha). Examples of hormones and antagonists useful for the treatment or prevention of cancer in the methods and compositions of the invention include but are not limited to adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions of the invention for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Other examples of anti-cancer agents which act by arresting cells in the G2-M phases due to stabilized microtubules include without limitation the following marketed drugs and drugs in development:

Examples of anti-cancer agents which act by arresting cells in the G2-M phases due to stabilized microtubules and which can be used in combination with the compounds of the invention include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-0Y-007 (National Health Research Institutes), and SSR-250411 (Sanofi).

2) Compositions and Methods for Administering Therapies

The present invention provides compositions for the treatment, prophylaxis, and amelioration of proliferative disorders, such as cancer. In a specific embodiment, a composition comprises one or more compounds of the invention, or a pharmaceutically acceptable salt, solvate, clathrate, hydrate or prodrug thereof. In another embodiment, a composition of the invention comprises one or more prophylactic or therapeutic agents other than a compound of the invention, or a pharmaceutically acceptable salt, solvate, clathrate, hydrate, prodrug thereof. In another embodiment, a composition of the invention comprises one or more compounds of the invention, or a pharmaceutically acceptable salt, solvate, clathrate, hydrate or prodrug thereof, and one or more other prophylactic or therapeutic agents. In another embodiment, the composition comprises a compound of the invention, or a pharmaceutically acceptable salt, solvate, clathrate, hydrate, or prodrug thereof, and a pharmaceutically acceptable carrier, diluent or excipient.

In a preferred embodiment, a composition of the invention is a pharmaceutical composition or a single unit dosage form. Pharmaceutical compositions and dosage forms of the invention comprise one or more active ingredients in relative amounts and formulated in such a way that a given pharmaceutical composition or dosage form can be used to treat or prevent proliferative disorders, such as cancer, including non-Hodgkin's lymphoma. Preferred pharmaceutical compositions and dosage forms comprise a compound of formula (I) through (LXXII), or any embodiment thereof, or a compound shown in Table 5, 6, or 7, or a pharmaceutically acceptable prodrug, salt, solvate, clathrate, hydrate, or prodrug thereof, optionally in combination with one or more additional active agents.

A pharmaceutical composition of the invention is formulated to be compatible with its intended route of administration. Examples of routes of administration include, but are not limited to, parenteral, e.g., intravenous, intradermal, subcutaneous, oral (e.g., inhalation), intranasal, transdermal (topical), transmucosal, and rectal administration. In a specific embodiment, the composition is formulated in accordance with routine procedures as a pharmaceutical composition adapted for intravenous, subcutaneous, intramuscular, oral, intranasal or topical administration to human beings. In a preferred embodiment, a pharmaceutical composition is formulated in accordance with routine procedures for subcutaneous administration to human beings.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art. See, e.g., Remington's Pharmaceutical Sciences (1990) 18th ed., Mack Publishing, Easton Pa.

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms.

The suitability of a particular excipient may also depend on the specific active ingredients in the dosage form. For example, the decomposition of some active ingredients can be accelerated by some excipients such as lactose, or when exposed to water. Active ingredients that comprise primary or secondary amines (e.g., N-desmethylvenlafaxine and N,N-didesmethylvenlafaxine) are particularly susceptible to such accelerated decomposition. Consequently, this invention encompasses pharmaceutical compositions and dosage forms that contain little, if any, lactose. As used herein, the term "lactose-free" means that the amount of lactose present, if any, is insufficient to substantially increase the degradation rate of an active ingredient. Lactose-free compositions of the invention can comprise excipients that are well known in the art and are listed, for example, in the U.S. Pharmocopia (USP)SP(XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen (1995) Drug Stability: Principles & Practice, 2d. Ed., Marcel Dekker, NY, N.Y., 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizer" include, but are not limited to, antioxidants such as ascorbic acid, pH buffers, or salt buffers.

i) Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences (1990) 18th ed., Mack Publishing, Easton Pa.

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

ii) Controlled Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

A particular extended release formulation of this invention comprises a therapeutically or prophylactically effective amount of a compound of formula (I) through (LXXII), or any embodiment thereof, or a compound shown in Table 5, 6, or 7, or a pharmaceutically acceptable salt, solvate, hydrate, clathrate, or prodrug thereof, in spheroids which further comprise microcrystalline cellulose and, optionally, hydroxypropylmethyl-cellulose coated with a mixture of ethyl cellulose and hydroxypropylmethylcellulose. Such extended release formulations can be prepared according to U.S. Pat. No. 6,274,171, the entirely of which is incorporated herein by reference.

A specific controlled-release formulation of this invention comprises from about 6% to about 40% a compound of formula (I) through (LXXII), or any embodiment thereof, or a compound shown in Table 5, 6, or 7, or a pharmaceutically acceptable salt, solvate, hydrate, clathrate, or prodrug thereof, by weight, about 50% to about 94% microcrystalline cellulose, NF, by weight, and optionally from about 0.25% to about 1% by weight of hydroxypropyl-methylcellulose, USP, wherein the spheroids are coated with a film coating composition comprised of ethyl cellulose and hydroxypropylmethylcellulose.

iii) Parenteral Dosage Forms

Parenteral dosage forms can be administered to patients by various routes including, but not limited to, subcutaneous, intravenous (including bolus injection), intramuscular, and intraarterial. Because their administration typically by passes patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

iv) Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences (1980 & 1990) 16th and 18th eds., Mack Publishing, Easton Pa. and Introduction to Pharmaceutical Dosage Forms (1985) 4th ed., Lea & Febiger, Philadelphia. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences (1980 & 1990) 16th and 18th eds., Mack Publishing, Easton Pa.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

v) Dosage & Frequency of Administration

The amount of the compound or composition of the invention which will be effective in the prevention, treatment, management, or amelioration of a proliferative disorders, such as cancer, or one or more symptoms thereof, will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems. Suitable regiments can be selected by one skilled in the art by considering such factors and by following, for example, dosages reported in the literature and recommended in the *Physician's Desk Reference* (57th ed., 2003).

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

In general, the recommended daily dose range of a compound of the invention for the conditions described herein lie within the range of from about 0.01 mg to about 1000 mg per day, given as a single once-a-day dose preferably as divided doses throughout a day. In one embodiment, the daily dose is administered twice daily in equally divided doses. In another embodiment, the compounds of the invention are administered one to three times a week. Specifically, a dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different proliferative disorders, as will be readily known by those of ordinary skill in the art. Similarly, amounts sufficient to prevent, manage, treat or ameliorate such proliferative disorders, but insufficient to cause, or sufficient to reduce, adverse effects associated with the compounds of the invention are also encompassed by the above described dosage amounts and dose frequency schedules. Further, when a patient is administered multiple dosages of a compound of the invention, not all of the dosages need be the same. For example, the dosage administered to the patient may be increased to improve the prophylactic or therapeutic effect of the compound or it may be decreased to reduce one or more side effects that a particular patient is experiencing.

In a specific embodiment, the dosage of the composition of the invention or a compound of the invention administered to prevent, treat, manage, or ameliorate a proliferative disorders, such as cancer, or one or more symptoms thereof in a patient is 150 µg/kg, preferably 250 µg/kg, 500 µg/kg, 1 mg/kg, 5 mg/kg, 10 mg/kg, 25 mg/kg, 50 mg/kg, 75 mg/kg, 100 mg/kg, 125 mg/kg, 150 mg/kg, or 200 mg/kg or more of a patient's body weight. In another embodiment, the dosage of the composition of the invention or a compound of the invention administered to prevent, treat, manage, or ameliorate a proliferative disorders, such as cancer, or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosages of prophylactic or therapeutic agents other than compounds of the invention, which have been or are currently being used to prevent, treat, manage, or proliferative disorders, such as cancer, or one or more symptoms thereof can be used in the combination therapies of the invention. Preferably, dosages lower than those which have been or are currently being used to prevent, treat, manage, or ameliorate a proliferative disorders, or one or more symptoms thereof, are used in the combination therapies of the invention. The recommended dosages of agents currently used for the prevention, treatment, management, or amelioration of a proliferative disorders, such as cancer, or one or more symptoms thereof, can obtained from any reference in the art including, but not limited to, Hardman et al., eds., 1996, Goodman & Gilman's The Pharmacological Basis Of Basis Of Therapeutics 9$^{th}$ Ed, Mc-Graw-Hill, N.Y.; Physician's Desk Reference (PDR) 57$^{th}$ Ed., 2003, Medical Economics Co., Inc., Montvale, N.J., which are incorporated herein by reference in its entirety.

In certain embodiments, when the compounds of the invention are administered in combination with another therapy, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one embodiment, two or more therapies (e.g., prophylactic or therapeutic agents) are administered within the same patent visit.

In certain embodiments, one or more compounds of the invention and one or more other the therapies (e.g., prophylactic or therapeutic agents) are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same compound of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In a specific embodiment, the invention provides a method of preventing, treating, managing, or ameliorating a proliferative disorders, such as cancer, or one or more symptoms thereof, said methods comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention once every day, preferably, once every 2 days, once every 3 days, once every 4 days, once every 5 days, once every 6 days, once every 7 days, once every 8 days, once every 10 days, once every two weeks, once every three weeks, or once a month.

D. OTHER EMBODIMENTS

The compounds of the invention may be used as research tools (for example, to evaluate the mechanism of action of new drug agents, to isolate new drug discovery targets using affinity chromatography, as antigens in an ELISA or ELISA-like assay, or as standards in vitro or in vivo assays). These and other uses and embodiments of the compounds and compositions of this invention will be apparent to those of ordinary skill in the art.

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

1. EXAMPLES

Reagents and solvents used below can be obtained from commercial sources such as Aldrich Chemical Co. (Milwaukee, Wis., USA). $^1$H-NMR and $^{13}$C-NMR spectra were recorded on a Varian 300 MHz NMR spectrometer. Significant peaks are tabulated in the order: δ (ppm): chemical shift, multiplicity (s, singlet; d, doublet; t, triplet; q, quartet; m, multiplet; br s, broad singlet), coupling constant(s) in Hertz (Hz) and number of protons.

Example 1

Synthesis of Compound 76

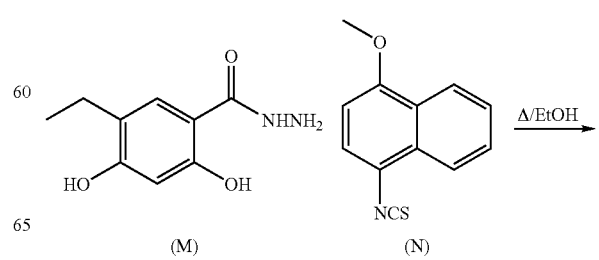

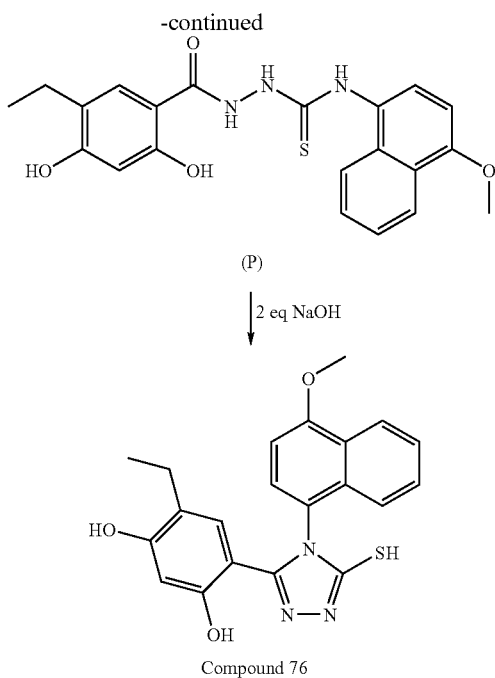

(P)

↓ 2 eq NaOH

Compound 76

The hydrazide (M) (1.45 g, 7.39 mmol) and the isothiocyanate (N) (1.59 g, 7.39 mmol) were dissolved in ethanol (20 ml) with heating. When the starting materials were dissolved the solution was allowed to cool to room temperature and a precipitate formed. This precipitate was filtered then washed with ether to provide the intermediate (P) as a white solid (2.85 g, 97%). The intermediate (VII) (1.89 g, 4.77 mmol) was heated in a solution of sodium hydroxide (0.38 g, 9.54 mmol) in water (20 mL) at 110° C. for 2 hours. The solution was allowed to cool to room temperature then acidified with conc. HCl. The resulting precipitate was filtered then washed with water (100 mL) and dried. The crude product was recrystallized from ethanol to produce compound 76 as a white solid (1.4 g, 75%).

$^1$H NMR (DMSO-$d_6$) δ 9.43-9.53 (bs, 2H), 8.11-8.16 (m, 1H), 7.47-7.55 (m, 2H), 7.38 (d, J=8.1 Hz, 1H), 7.31-7.36 (m, 1H), 6.98 (d, J=8.1 Hz, 1H), 6.71 (s, 1H), 6.17 (s, 1H), 3.98 (s, 3H), 2.17 (q, J=7.5 Hz, 2H), 0.73 (t, J=7.5 Hz, 3H);

ESMS calculated for ($C_{21}H_{19}N_3O_3S$) 393.11. Found 394.1 $(M+1)^+$.

Example 2

Synthesis of Compound 124

3-(2,4-Dihydroxy-phenyl)-4-(naphthalen-1-yl)-5-mercapto-triazole (505 mg, 1.5 mmol), which is commercially available from Scientific Exchange, Inc., Center Ossipee, N.H. 03814, and $Et_3N$ (0.84 ml, 6.0 mmol) in 15 ml $CH_2Cl_2$ were treated dropwise with ethyl isocyanate (360 mg, 5.0 mmol) at 0° C. The mixture was then warmed to room temperature and stirred for 3 h. The reaction mixture was diluted with $CH_2Cl_2$, washed with $H_2O$ and saturated brine, dried with $Na_2SO_4$, and concentrated in vacuo. The residue was chromatographed (Hexane/EtOAc 3:1) to give Compound. 124 as a white solid (480 mg, 58%).

$^1$H-NMR (CDCl$_3$) δ 10.13 (s, 1H), 7.96 (d, J=9.0 Hz, 2H), 7.61-7.57 (m, 3H), 7.49-7.36 (m, 2H), 7.01 (s, 1H), 6.88 (d, J=8.4 Hz, 1H), 6.70 (d, J=8.4 Hz, 1H), 4.98-4.96 (m, 2H), 3.56 (q, J=7.2 Hz, J=12.6 Hz, 2H), 3.28-3.10 (m, 4H), 1.33 (t, J=7.2 Hz, 3H), 1.13 (q, J=15.0 Hz, 6H);

ESMS calculated for $C_{27}H_{28}N_6O_5S$: 548.18. Found: 549.1 $(M+1)^+$.

Example 3

Synthesis of Compound 188

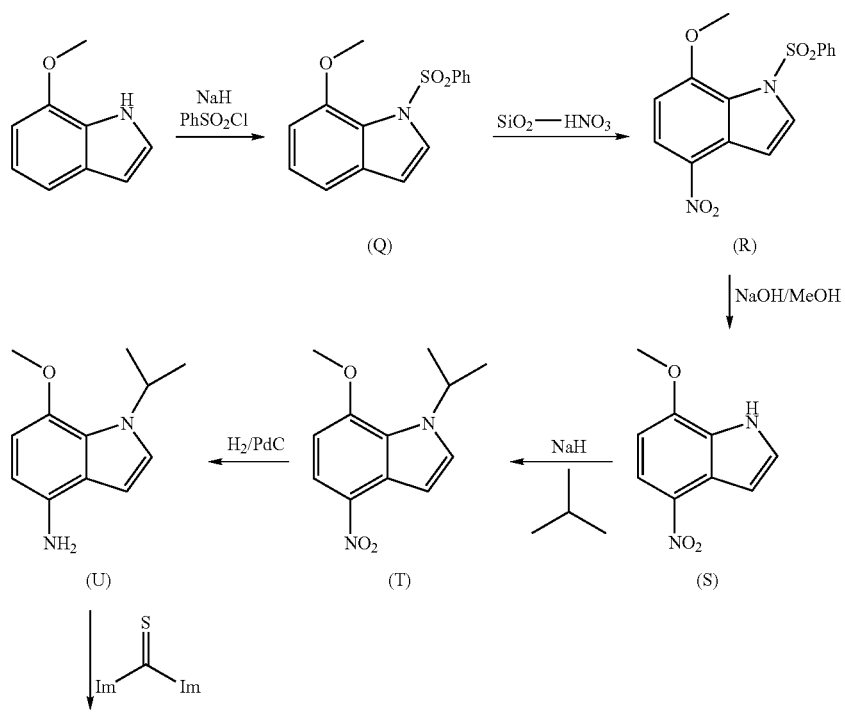

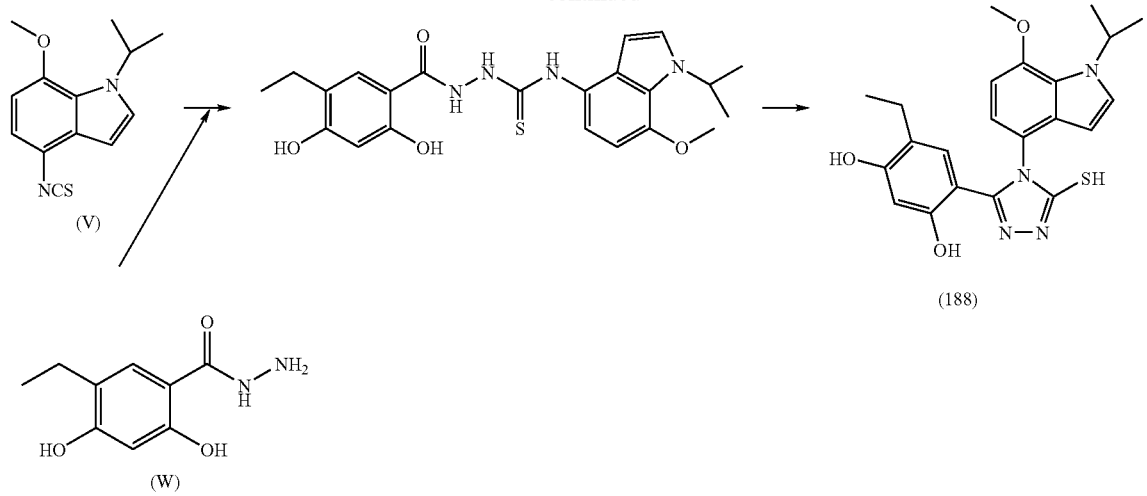

(188)

1-Benzenesulfonyl-7-methoxy-1H-indole (Q)

To a solution of 7-methoxyindole (1 eq) in DMF cooled in an ice bath was added NaH (60% dispersion in oil, 1.2 eq). The reaction was stirred for 1 hr at room temperature then recooled in an ice bath. Benzenesulfonyl chloride (1.1 eq) was added then the reaction was stirred for 2 hrs at room temperature. Water/ethyl acetate were added and the ethyl acetate layer was washed repeatedly (3×) with water. The ethyl acetate layer was concentrated and evaporated to dryness.

1-Benzenesulfonyl-7-methoxy-4-nitro-1H-indole (R)

To a solution of 1-benzenesulfonyl-7-methoxy-1H-indole (Q) (1 eq) in dichloromethane cooled in an ice bath was added $SiO_2$—$HNO_3$ (2 wt eq) in small portions. The reaction was stirred for 1 hr at room temperature. Activated carbon (2 wt eq) was added then the entire mixture was stirred for 1 hr. The mixture was then filtered and evaporated to dryness. Separation of the isomers was achieved by column chromatography.

7-Methoxy-4-nitro-1H-indole (S)

To a solution of 1-benzenesulfonyl-7-methoxy-4-nitro-1H-indole (R) (1 eq) in methanol was added a solution of sodium hydroxide (5 eq) in water. The solution was heated to reflux for 3 hrs. Methanol was removed under reduced pressure then water and ethyl acetate were added. The ethyl acetate layer separated and washed repeatedly (3×) with water. The ethyl acetate layer was concentrated and evaporated to dryness to produce the desired product.

1-Isopropyl-7-methoxy-4-nitro-1H-indole (T)

To a solution of 7-methoxy-4-nitro-1H-indole (S) (1 eq) in DMF cooled in an ice bath was added NaH (60% dispersion in oil, 1.2 eq). The reaction was stirred for 1 hr at room temperature then recooled in an ice bath. 2-Iodopropane (1.1 eq) was added then the reaction was stirred for 2 hrs at room temperature. Water and ethyl acetate were added. The ethyl acetate layer was separated and washed repeatedly (3×) with water. The ethyl acetate layer was concentrated then evaporated to dryness. Further purification by column chromatography produced the pure desired product.

1-Isopropyl-7-methoxy-1H-indol-4-ylamine (U)

A solution of 1-isopropyl-7-methoxy-4-nitro-1H-indole (T) (1 eq) and palladium 10% on activated carbon (0.1 wt eq) in methanol/ethyl acetate (1:1) was shaken on a Parr hydrogenation apparatus under hydrogen for 1 hr. The reaction was then filtered through Celite and evaporated to dryness to produce the desired product.

1-Isopropyl-4-isothiocyanato-7-methoxy-1H-indole (V)

To a solution of 1-isopropyl-7-methoxy-1H-indol-4-ylamine (U) (1 eq) in dichloromethane was added 1,1'-thiocarbonyldiimidazole (1.2 eq). The reaction was stirred for 2 hrs at room temperature then evaporated to dryness. Further purification by column chromatography produced the pure desired product.

3-(2,4-Dihydroxy-5-ethyl-phenyl)-4-(1-isopropyl-7-methoxy-indol-4-yl)-5-mercapto-[1,2,4]triazole (Compound 188)

5-Ethyl-2,4-dihydroxy-benzoic acid hydrazide (W) (1 eq) and 1-isopropyl-4-isothiocyanato-7-methoxy-1H-indole (V) (1.01 eq) were heated in ethanol (0.02 M based on isothiocyante) at 80° C. for 1 hr. The solution was allowed to cool to room temperature overnight. The resulting precipitate was filtered, washed with ether, dried and used without further purification (yield 80%). The precipitate was suspended in aqueous NaOH solution (2 eq NaOH) and nitrogen was bubbled through this suspension for 10 min. The reaction was then heated to 110° C. for 1 hr under a nitrogen atmosphere then allowed to cool to room temperature. Neutralisation with conc. HCl produced a white precipitate which was filtered and washed with water. Repeated recrystallisation from EtOH/water produced the desired product (purity >95%, yield 50-70%)

$^1$H-NMR (DMSO-$d_6$) δ (ppm), 9.52 (s, 1H), 9.42 (s, 1H), 7.40 (d, J=3.3 Hz, 1H), 6.82 (d, J=8.4 Hz, 1H), 6.61 (s, 1H), 6.20 (s, 1H), 6.05 (d, J=3.3 Hz, 1H), 5.30 (qn, J=6.6 Hz, 1H), 3.89 (s, 3H), 2.14 (q, J=7.5 Hz, 2H), 1.41-1.47 (m, 6H), 0.68 (t, J=7.5 Hz, 3H);

2. ESMS calculated. for $C_{22}H_{24}N_4O_3S$: 424.16. Found: 425.1 (M+1)$^+$.

Example 4

Synthesis of Compound 223

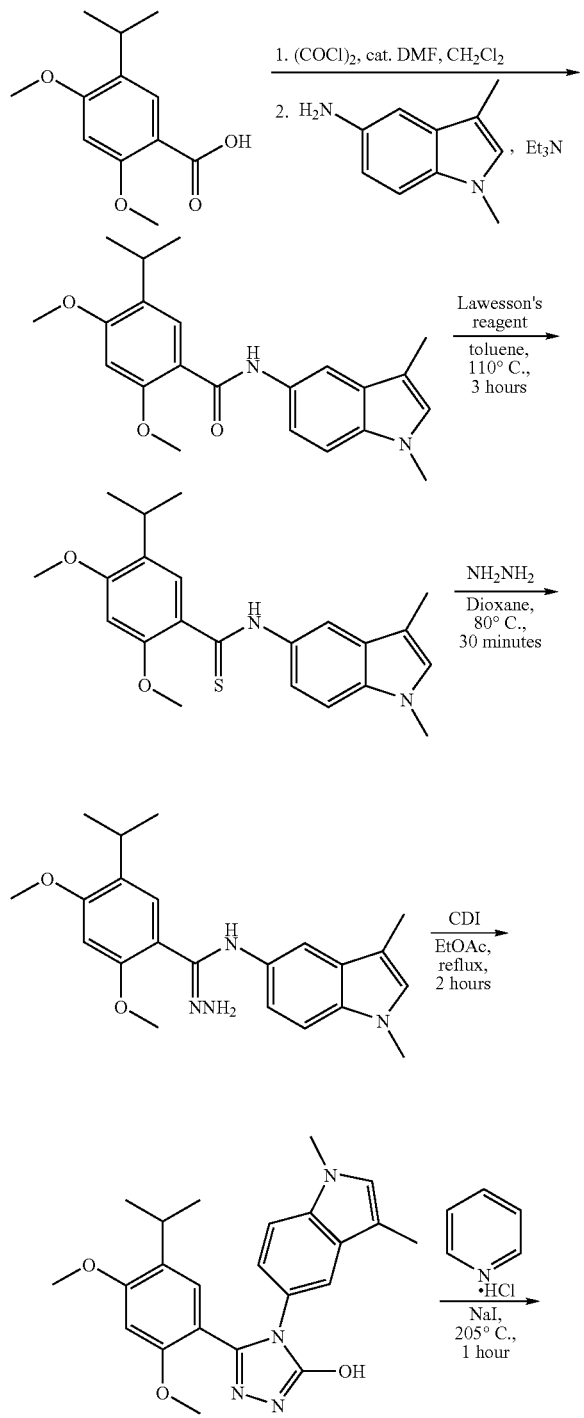

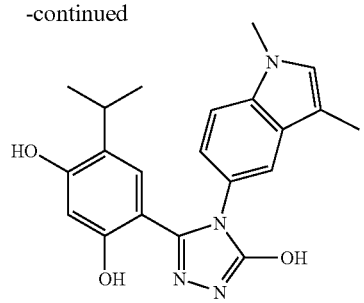

Compound 223

2,4-Dimethoxy-5-isopropylbenzoic acid (2.24 g, 10.0 mmol, 1.00 equiv.) in 50 mL $CH_2Cl_2$ at room temperature was treated with $(COCl)_2$ (1.40 g, 11.0 mmol, 1.10 equiv.) and catalytic amount of DMF (0.1 mL) for 1 hour. Solvent and excess $(COCl)_2$ were removed in vacuo. The residue was dissolved in 100 mL $CH_2Cl_2$, and treated with 1,3-dimethyl-5-aminoindole (1.60 g, 10.0 mmol, 1.00 equiv.) and triethylamine (1.55 g, 15.0 mmol, 1.50 equiv.) at 0° C. for one hour. Aqueous workup and removal of solvent gave a light brown solid which was washed with ether to yield off-white solid (2.28 g, 6.22 mmol, 62%).

$^1$H NMR (CDCl$_3$) α (ppm) 9.78 (br s, 1H), 8.21 (s, 1H), 8.09 (d, J=2.1 Hz, 1H), 7.31 (dd, J=8.7 Hz, 2.1 Hz, 1H), 7.22 (d, J=8.7 Hz, 1H), 6.82 (s, 1H), 6.50 (s, 1H), 4.09 (s, 3H), 3.92 (s, 3H), 3.73 (s, 3H), 3.26 (hept, J=6.9 Hz, 1H), 2.32 (s, 3H), 1.24 (d, J=6.9 Hz, 6H).

The off-white solid obtained above was treated with Lawesson's reagent (1.51 g, 3.74 mmol, 0.6 equiv.) in 50 mL toluene at 110° C. for three hours. Toluene was removed on rotary evaporator and vacuum pump, and the residue was treated with hydrazine (anhydrous, 3.0 g, 94 mmol, 15.0 equiv.) in 20 mL dioxane at 80° C. for 30 minutes. The reaction mixture was extracted with ethyl acetate and water to remove excess hydrazine. The organic layer was dried over MgSO$_4$, and filtered to remove drying agent. Carbodiimidazole (CDI)(3.02 g, 18.7 mmol, 3.00 equiv.) was added to the solution, and the solution was refluxed (65° C.) for 2 hours. Solvent was removed, and the residue was treated with 20 mL THF and 10 mL NaOH (2M) to destroy excess CDI. Extraction with ethyl acetate (EtOAc) and water, followed by chromatography purification gave the desired product 3-(2,4-methoxy-5-isopropyl-phenyl)-4-(1,3-dimethyl-indol-5-yl)-5-hydroxy-[1,2,4]triazole as light brown solid (2.20 g, 5.42 mmol, 87%).

$^1$H NMR (CDCl$_3$), δ (ppm) 9.63 (br s, 1H), 7.34 (d, J=2.1 Hz, 1H), 7.20 (s, 1H), 7.18 (d, J=8.4 Hz, 1H), 7.00 (dd, J=8.4 Hz, 2.1 Hz, 1H), 6.80 (s, 1H), 6.19 (s, 1H), 3.76 (s, 3H), 3.69 (s, 3H), 3.40 (s, 3H), 3.15 (hept, J=6.9 Hz, 1H), 2.20 (s, 3H), 1.10 (d, J=6.9 Hz, 6H).

3-(2,4-methoxy-5-isopropyl-phenyl)-4-(1,3-dimethyl-indol-5-yl)-5-hydroxy-[1,2,4]triazole obtained above was treated with pyridine hydrochloride (12.53 g, 108.3 mmol, 20.0 equiv.), NaI (0.812 g, 5.42 mmol, 1.0 equiv.) and 0.5 mL water at 205° C. under nitrogen protection for 1 hour. The reaction mixture was treated with 200 mL water. The solid was collected by filtration, washed with 3×20 mL water, and dissolved in 50 mL 2M NaOH solution. The aqueous solution was extracted with 100 mL EtOAc, and the EtOAc layer was extracted with 2×20 mL 0.5M NaOH. EtOAc layer was discarded. The aqueous layer were combined, neutralized with HCl to PH around 5, and extracted with 3×100 mL EtOAc. The combined EtOAc layer was diluted with 50 mL THF, dried over MgSO₄, and filtered through silica gel plug. Most of solvents were removed to form a slurry with around 2 mL of solvent left. Solid was collected by filtration, washed with 2 mL EtOAc, and dried. The desired product 3-(2,4-dihydroxy-5-isopropyl-phenyl)-4-(1,3-dimethyl-indol-5-yl)-5-hydroxy-[1,2,4]triazole (Compound 223) was obtained as an off-white solid (1.75 g, 4.63 mmol, 85%).

$^1$H NMR (CD$_3$OD), δ (ppm) 7.46 (d, J=1.8 Hz, 1H), 7.41 (d, J=8.4 Hz, 1H), 7.04 (dd, J=8.4 Hz, 1.8 Hz, 1H), 7.02 (s, 1H), 6.53 (s, 1H), 6.26 (s, 1H), 3.74 (s, 3H), 2.88 (sept, J=6.9 Hz, 1H), 2.24 (s, 3H), 0.62 (d, J=6.9 Hz, 6H);

ESMS calculated. for $C_{21}H_{23}N_4O_3$: 378.1. Found: 379.1 (M+1)$^+$.

The following compounds were prepared as described above in the section entitled "Methods of Making the Compounds of the Invention" and as exemplified in Examples 1 through 4.

Example 5

Compound 1

ESMS calcd for $C_{18}H_{13}N_3OS$: 319.1. Found: 320.0 (M+1)$^+$.

Example 6

Compound 2

ESMS calcd for $C_{21}H_{19}N_3O_4S$: 409.11. Found: 410.0 (M+H)$^+$.

Example 7

Compound 5

ESMS calcd for $C_{19}H_{15}N_3O_2S$: 365.08. Found: 266.0 (M+H)$^+$.

Example 8

Compound 6

ESMS calcd for $C_{20}H_{17}N_3O_2S$: 379.10. Found: 380.0 (M+H)$^+$.

Example 9

Compound 7

ESMS calcd for $C_{21}H_{19}N_3O_2S$: 393.11. Found: 394.0 (M+H)$^+$.

Example 10

Compound 8

ESMS calcd for $C_{21}H_{19}N_3O_3S$: 393.11. Found: 394.0 (M+H)$^+$.

Example 11

Compound 9

ESMS calcd for $C_{21}H_{19}N_3O_2S$: 393.11. Found: 394.0 (M+H)$^+$.

Example 12

Compound 13

$^1$H-NMR (DMSO-d$_6$) δ 9.65 (s, 1H), 9.57 (s, 1H), 7.50 (d, J=8.1 Hz, 1H), 7.35 (d, J=3.3 Hz, 1H), 7.14 (t, J=7.8 Hz, 1H), 6.96 (d, J=7.5 Hz, 1H), 6.88 (d, J=8.1 Hz, 1H), 6.09-6.11 (m, 2H), 6.01 (dd, J$_1$=2.1 Hz, J$_2$=8.1 Hz, 1H), 4.13-4.22 (m, 2H), 1.36 (t, J=7.2 Hz, 3H);

ESMS calcd for $C_{18}H_{16}N_4O_2S$: 352.10. Found: 353.1 (M+1)$^+$.

Example 13

Compound 14

$^1$H NMR (DMSO-d$_6$) δ 9.72 (s, 1H), 9.67 (s, 1H), 7.04-7.01 (m, 1H), 6.83-6.78 (m, 2H), 6.66-6.63 (m, 1H), 6.20-6.19 (m, 2H), 4.22 (s, 4H);

ESMS calcd for $C_{16}H_{13}N_3O_4S$: 343.06. Found: 344.0 (M+1)$^+$.

Example 14

Compound 15

ESMS calcd for $C_{15}H_{13}N_3O_2S$: 299.07. Found: 300.0 (M+H)$^+$.

Example 15

Compound 16

ESMS calcd for $C_{15}H_{13}N_3O_2S$: 299.07. Found: 300.0 (M+H)$^+$.

Example 16

Compound 17

ESMS calcd for $C_{14}H_{10}ClN_3O_2S$: 319.02. Found: 320.0 (M+H)$^+$.

Example 17

Compound 18

ESMS calcd for $C_{14}H_{10}ClN_3O_2S$: 319.02. Found: 320.0 (M+H)$^+$.

Example 18

Compound 19

ESMS calcd for $C_{14}H_{10}ClN_3O_2S$: 319.02. Found: 320.1 (M+H)$^+$.

Example 19

Compound 20

ESMS calcd for $C_{15}H_{13}N_3O_3S$: 315.07. Found: 316.0 (M+H)$^+$.

Example 20

Compound 21

ESMS calcd for $C_{15}H_{13}N_3O_3S$: 315.07. Found: 316.0 $(M+H)^+$.

Example 21

Compound 22

ESMS calcd for $C_{15}H_{13}N_3O_3S$: 315.07. Found: 316.0 $(M+H)^+$.

Example 22

Compound 23

ESMS calcd for $C_{14}H_{10}FN_3O_2S$: 303.05. Found: 304.0 $(M+H)^+$.

Example 23

Compound 23

$^1$H NMR (DMSO-$d_6$) δ 9.69 (s, 1H), 9.65 (s, 1H), 7.16 (d, J=7.2 Hz, 1H), 7.05 (t, J=7.2 Hz, 1H), 6.93 (d, J=8.1 Hz, 2H), 6.11-6.16 (m, 2H), 2.21 (s, 3H), 1.89 (s, 3H);
ESMS Calcd $C_{16}H_{15}N_3O_2S$: 313.09. Found 314.1 $(M+1)^+$.

Example 24

Compound 24

ESMS calcd for $C_{16}H_{15}N_3O_2S$: 313.09. Found: 314.0 $(M+H)^+$.

Example 25

Compound 25

$^1$H NMR (DMSO-$d_6$) δ 10.44 (m, 1H), 8.00-7.95 (m, 2H), 7.55-7.37 (m, 5H), 6.61 (d, J=7.8 and 1.8 Hz, 1H), 6.51 (t, J=8.6 Hz, 1H), 6.41 (d, J=10.8 Hz, 1H);
ESMS calcd for $C_{18}H_{12}FN_3OS$: 337.07. Found: 338.0 $(M+1)^+$.

Example 26

Compound 26

$^1$H NMR (DMSO-$d_6$) δ 9.57 (s, 1H), 7.99 (d, J=8.4 Hz, 1H), 7.96 (d, J=6.9 Hz, 1H), 7.55-7.37 (m, 5H), 6.61 (d, J=8.1 Hz, 1H), 5.83 (d, J=2.1 Hz, 1H), 5.73 (dd, J=8.1 and 1.8 Hz, 1H), 5.24 (s, 2H);
ESMS calcd for $C_{18}H_{14}N_4OS$: 334.09. Found: 335.0 $(M+1)^+$.

Example 27

Compound 27

ESMS calcd for $C_{18}H_{19}N_3O_2S$: 341.12. Found: 342.0 $(M+H)^+$.

Example 28

Compound 28

ESMS calcd for $C_{16}H_{15}N_3O_2S$: 313.09. Found: 314.0 $(M+H)^+$.

Example 29

Compound 29

ESMS calcd for $C_{16}H_{15}N_3O_2S$: 313.09. Found: 314.0 $(M+H)^+$.

Example 30

Compound 30

ESMS calcd for $C_{16}H_{15}N_3O_2S$: 313.09. Found: 314.0 $(M+H)^+$.

Example 31

Compound 31

ESMS calcd for $C_{14}H_{10}FN_3O_2S$: 303.05. Found: 304.0 $(M+H)^+$.

Example 32

Compound 32

ESMS calcd for $C_{15}H_{13}N_3O_2S$: 331.04. Found: 332.0 $(M+H)^+$.

Example 33

Compound 33

ESMS calcd for $C_{18}H_{13}N_3O_2S$: 335.07. Found: 336.0 $(M+H)^+$.

Example 34

Compound 34

ESMS calcd for $C_{16}H_{15}N_3O_2S$: 313.09. Found: 314.0 $(M+H)^+$.

Example 35

Compound 35

ESMS calcd for $C_{15}H_{12}FN_3O_2S$: 317.06. Found: 317.0 $(M+H)^+$.

Example 36

Compound 36

ESMS calcd for C20H15N3O2S: 361.1. Found: 362.0 $(M+1)^+$.

Example 37

Compound 37

$^1$H NMR (DMSO-$d_6$) δ 10.03 (s, 1H), 8.00-7.96 (m, 2H), 7.55-7.37 (m, 5H), 7.00 (d, J=8.1 Hz, 1H), 6.20 (m, 2H), 3.57 (s, 3H);
ESMS calcd for $C_{19}H_{15}N_3O_2S$: 349.09. Found: 350.0 $(M+1)^+$.

Example 38

Compound 38

ESMS calcd for $C_{14}H_9Cl_2N_3O_2S$: 352.98. Found: 353.9 (M+H)$^+$.

Example 39

Compound 39

$^1$H NMR (DMSO-d$_6$) δ 9.74 (s, 1H), 9.63 (s, 1H), 8.14 (m, 1H), 7.52-7.48 (m, 2H), 7.37 (d, J=8.4 Hz, 1H), 7.32 (m, 1H), 6.96 (d, =8.1 Hz, 1H), 6.90 (d, =8.4 Hz, 1H), 6.08 (d, =1.9 Hz, 1H), 6.01 (d, =8.4 Hz, 1H), 3.98 (s, 3H);
ESMS calcd for $C_{19}H_{15}N_3O_3S$: 365.08. Found: 366.0 (M+1)$^+$.

Example 40

Compound 40

ESMS calcd for $C_{25}H_{16}N_3O_2S$: 409.09. Found: 410.0 (M+1)$^+$.

Example 41

Compound 42

$^1$H NMR (DMSO-d$_6$) δ 9.75 (s, 1H), 9.67 (s, 1H), 7.08 (s, 2H), 6.96-6.94 (m, 2H), 6.18-6.13 (m, 2H), 2.72-2.50 (m, 3H), 2.35-2.28 (m, 1H), 1.64-1.60 (m, 4H);
ESMS calcd for $C_{18}H_{17}N_3O_2S$: 339.10. Found: 340.0 (M+1)$^+$.

Example 42

Compound 43

ESMS calcd for $C_{22}H_{15}N_3O_2S$: 385.09. Found: 386.0 (M+1)$^+$.

Example 43

Compound 44

ESMS calcd for $C_{20}H_{15}N_3O_2S$: 361.09. Found: 362.0 (M+1)$^+$.

Example 44

Compound 45

ESMS calcd for $C_{19}H_{15}N_3O_2S$: 349.09. Found: 350.0 (M+1)$^+$.

Example 45

Compound 46

ESMS calcd for $C_{19}H_{21}N_3O_3S$: 371.13. Found: 372.0 (M+1)$^+$.

Example 46

Compound 47

ESMS calcd for $C_{22}H_{27}N_3O_3S$: 413.18. Found: 414.1 (M+1)$^+$.

Example 47

Compound 48

ESMS calcd for $C_{18}H_{12}ClN_3O_2S$: 369.03. Found: 370.0 (M+H)$^+$.

Example 48

Compound 49

$^1$H NMR (DMSO-d$_6$) δ 9.49 (s, 1H), 9.40 (s, 1H), 7.94-7.99 (m, 2H), 7.38-7.56 (m, 5H), 6.70 (s, 1H), 6.13 (s, 1H), 2.12 (q, J=7.2 Hz, 2H), 0.71 (t, J=7.2 Hz, 3H);
ESMS Calcd for $C_{20}H_{17}N_3O_2S$: 363.10. Found 364.1 (M+1)$^+$.

Example 49

Compound 50

ESMS calcd for $C_{20}H_{15}N_3O_5S$: 409.07. Found: 410.0 (M+H)$^+$.

Example 50

Compound 51

ESMS calcd for $C_{18}H_{14}N_4O_2S$: 350.08. Found: 351.0 (M+H)$^+$.

Example 51

Compound 52

ESMS calcd for $C_{17}H_{12}N_4OS$: 320.07. Found: 320.9 (M+H)$^+$.

Example 52

Compound 53

$^1$H NMR (CDCl$_3$) δ 12.0 (br s, 1H), 9.87 (br s, 1H), 9.83 (br s, 1H), 7.97 (d, J=8.1 Hz, 2H), 7.41-7.56 (m, 5H), 7.13 (d, J=1.5 Hz, 1H), 7.07 (d, J=8.7 Hz, 1H), 6.71 (dd, J=1.8 Hz, 8.1 Hz, 1H), 1.93 (s, 3H);
ESMS calcd for $C_{20}H_{17}N_4O_2S$: 376.1. Found: 377.0 (M+1)$^+$.

Example 53

Compound 56

ESMS calcd for $C_{16}H_{15}N_3O_4S$: 345.08. Found: 346.0 (M+1)$^+$.

Example 54

Compound 57

ESMS calcd for $C_{18}H_{16}N_4O_2S$: 352.10. Found: 353.0 (M+1)$^+$.

Example 55

Compound 61

$^1$H NMR (DMSO-d$_6$) δ 9.66 (s, 1H), 9.60 (s, 1H), 7.29-7.27 (m, 1H), 7.12-7-10 (m, 2H), 7.03-7.00 (m, 1H), 6.19-6.17 (m, 2H), 1.18 (s, 18H);
ESMS calcd for C$_{22}$H$_{27}$N$_3$O$_2$S: 397.18. Found: 398.1 (M+1)$^+$.

Example 56

Compound 64

ESMS calcd for C$_{21}$H$_{15}$N$_3$O$_3$S: 389.08. Found: 390.0 (M+H)$^+$.

Example 57

Compound 65

ESMS calcd for C$_{19}$H$_{13}$N$_3$O$_4$S: 379.06. Found: 380.0 (M+1)$^+$.

Example 58

Compound 66

ESMS calcd for C$_{21}$H$_{18}$N$_4$O$_3$S: 406.11. Found: 407.0 (M+1)$^+$.

Example 59

Compound 67

ESMS calcd for C$_{21}$H$_{19}$N$_3$O$_3$S: 393.11. Found: 394.0 (M+1)$^+$.

Example 60

Compound 68

ESMS calcd for C$_{21}$H$_{19}$N$_3$O$_3$S: 393.11. Found: 394.0 (M+1)$^+$.

Example 61

Compound 69

ESMS calcd for C$_{21}$H$_{19}$N$_3$O$_3$S: 393.11. Found: 394.0 (M+1)$^+$.

Example 62

Compound 70

ESMS calcd for C$_{17}$H$_{12}$N$_4$O$_2$S: 336.07. Found: 337.0 (M+H)$^+$.

Example 63

Compound 71

ESMS calcd for C$_{21}$H$_{19}$N$_3$O$_3$S: 393.11. Found: 394.0 (M+1)$^+$.

Example 64

Compound 72

$^1$H NMR (DMSO-d$_6$) δ 10.3 (br s, 1H), 7.95-8.19 (m, 2H), 7.48-7.72 (m, 5H), 7.17 (d, J=8.4 Hz, 1H), 6.44 (d, J=8.4 Hz, 1H), 5.95 (d, J=2.1 Hz, 1H), 5.73 (dd, J=2.1 Hz, 8.4 Hz, 1H), 5.47 (br s, 1H), 3.62 (s, 3H);
ESMS calcd for C$_{19}$H$_{17}$N$_4$O$_2$S$_2$: 412.1. Found: 413.0 (M+1)$^+$.

Example 65

Compound 73

$^1$H NMR (DMSO-d$_6$) δ 9.37 (s, 1H), 8.94 (s, 1H), 7.94-7.98 (m, 2H), 7.43-7.60 (m, 5H), 5.97 (s, 1H), 1.85 (s, 3H), 1.81 (s, 3H);
ESMS calcd for C$_{20}$H$_{18}$N$_3$O$_2$S: 363.1. Found: 364.0 (M+1)$^+$.

Example 66

Compound 74

ESMS calcd for C$_{21}$H$_{19}$N$_3$O$_4$S: 409.11. Found: 410.0 (M+H)$^+$.

Example 67

Compound 75

$^1$H NMR (DMSO-d$_6$) δ 9.46 (s, 1H), 9.45 (s, 1H), 7.95-8.00 (m, 2H), 7.38-7.56 (m, 5H), 6.65 (s, 1H), 6.15 (s, 1H), 2.07-2.14 (m, 2H), 081-1.18 (m, 11H);
ESMS calcd for C$_{24}$H$_{26}$N$_3$O$_2$S: 419.1. Found: 420.1 (M+1)$^+$.

Example 68

Compound 76

ESMS calcd for C$_{21}$H$_{19}$N$_3$O$_3$S: 393.11. Found: 394.0 (M+H)$^+$.

Example 69

Compound 77

ESMS calcd for C$_{21}$H$_{19}$N$_3$O$_3$S: 393.11. Found: 394.0 (M+H)$^+$.

Example 70

Compound 78

$^1$H NMR (DMSO-d$_6$) δ 9.71 (s, 1H), 9.35 (s, 1H), 7.98-8.04 (m, 2H), 7.50-7.62 (m, 5H), 6.58 (s, 1H), 2.15 (q, J=7.5 Hz, 2H), 0.58 (t, J=7.5 Hz, 3H);
ESMS calcd for C$_{20}$H$_{17}$ClN$_3$O$_2$S: 397.0. Found: 398.0 (M+1)$^+$.

Example 71

Compound 79

ESMS calcd for $C_{19}H_{21}N_3O_3S$: 371.13. Found: 372.0 $(M+H)^+$.

Example 72

Compound 80

ESMS calcd for $C_{21}H_{19}N_3O_2S$: 393.11. Found: 394.0 $(M+H)^+$.

Example 73

Compound 81

ESMS calcd for $C_{20}H_{17}N_3O_2S$: 379.10. Found: 380.0 $(M+H)^+$.

Example 74

Compound 82

ESMS calcd for $C_{21}H_{19}N_3O_2S$: 393.11. Found: 394.0 $(M+H)^+$.

Example 75

Compound 83

ESMS calcd for $C_{20}H_{17}N_3O_3S$: 379.10. Found: 380.0 $(M+H)^+$.

Example 76

Compound 84

ESMS calcd for $C_{20}H_{17}N_3O_3S$: 379.10. Found: 380.0 $(M+H)^+$.

Example 77

Compound 85

ESMS calcd for $C_{19}H_{15}N_3O_2S$: 365.08. Found: 266.0 $(M+H)^+$.

Example 78

Compound 86

$^1$H NMR (DMSO-$d_6$) δ 9.68 (s, 1H), 9.58 (s, 1H), 8.2 (dd, J=7.0 and 2.4 Hz, 1H), 7.50 (m, 2H), 7.40 (tr, J=8.1 Hz, 1H), 7.32 (m, 1H), 6.97 (d, J=7.5 Hz, 1H), 6.95 (m, 1H), 6.89 (d, =8.4 Hz, 1H), 6.08 (d, =2.1 Hz, 1H), 6.0 (dd, =7.4 and 2.1 Hz, 1H), 3.96 (s, 3H);
ESMS calcd for $C_{19}H_{15}N_3O_3S$: 365.08. Found: 366.0 $(M+1)^+$.

Example 79

Compound 87

$^1$H NMR (MeOH-$d_4$) δ 8.25 (m, 1H), 7.96 (s, 1H), 7.46-7.44 (m, 2H), 7.26 (d, J=8.4 Hz, 1H), 6.83 (d, J=8.1 Hz, 1H), 6.70 (d, J=8.7 Hz, 1H), 6.17 (d, J=2.1 Hz, 1H), 5.98 (dd, J=8.4 and 2.4 Hz, 1H);
ESMS calcd for $C_{18}H_{13}N_3O_3S$: 351.07. Found: 352.0 $(M+1)^+$.

Example 80

Compound 88

$^1$H-NMR (DMSO-$d_6$) δ 9.69 (s, 1H), 9.59 (s, 1H), 7.54 (d, J=8.1 Hz, 1H), 7.46 (d, J=3 Hz, 1H), 7.14 (t, J=7.8 Hz, 1H), 6.97 (d, J=7.2 Hz, 1H), 6.89 (d, J=8.7 Hz, 1H), 6.12-6.13 (m, 2H), 6.02 (dd, $J_1$=2.4 Hz, $J_2$=8.4 Hz, 1H), 4.74 (qn, J=6.6 Hz, 1H), 1.40-1.46 (m, 6H);
ESMS calcd for $C_{19}H_{18}N_4O_2S$: 366.12. Found: 367.1 $(M+1)^+$.

Example 81

Compound 89

ESMS calcd for $C_{22}H_{21}N_3O_2S$: 391.14. Found: 392.0 $(M+H)^+$.

Example 82

Compound 90

$^1$H NMR (DMSO-$d_6$) δ 9.47 (s, 1H), 9.43 (s, 1H), 7.94-8.00 (m, 2H), 7.39-7.57 (m, 5H), 6.68 (s, 1H), 6.15 (s, 1H), 2.05-2.15 (m, 2H), 1.05-1.17 (m, 2H), 0.50 (t, J=7.5 Hz, 3H);
ESMS calcd for $C_{21}H_{20}N_3O_2S$: 377.1. Found: 378.0 $(M+1)^+$.

Example 83

Compound 91

$^1$H NMR (DMSO-$d_6$) δ 9.15 (s, 1H), 8.50 (s, 1H), 8.00-8.07 (m, 2H), 7.47-7.63 (m, 5H), 6.27 (s, 1H), 2.06 (q, J=7.5 Hz, 2H), 1.93 (s, 3H), 0.45 (t, J=7.5 Hz, 3H);
ESMS calcd for $C_{21}H_{20}N_3O_2S$: 377.1. Found: 378.0 $(M+1)^+$.

Example 84

Compound 93

ESMS calcd for $C_{16}H_{15}N_3O_4S$: 345.08. Found: 346.0 $(M+H)^+$.

Example 85

Compound 95

ESMS calcd for $C_{16}H_{12}N_4O_2S$: 324.07. Found: 325.0 $(M+H)^+$.

Example 86

Compound 96

ESMS calcd for $C_{19}H_{18}N_4O_3S$: 382.11. Found: 383.0 $(M+H)^+$.

Example 87

Compound 98

ESMS calcd for $C_{17}H_{12}N_4O_2S$: 336.07. Found: 337.0 $(M+H)^+$.

Example 88

Compound 99

ESMS calcd for $C_{19}H_{13}N_3O_4S$: 379.06. Found: 379.9 $(M+H)^+$.

Example 89

Compound 100

$^1$H-NMR (DMSO-d$_6$) δ 9.52 (s, 1H), 9.42 (s, 1H), 7.56 (d, J=8.7 Hz, 1H), 7.49 (d, J=3.3 Hz, 1H), 7.14 (t, J=7.5 Hz, 1H), 6.95 (d, J=8.4 Hz, 1H), 6.61 (s, 1H), 6.21 (s, 1H), 6.14 (dd, J=3.3 Hz, 1H), 4.76 (qn, J=6.6 Hz, 1H), 2.14 (q, J=7.5 Hz, 2H), 1.41-1.47 (m, 6H), 0.66 (t, J=7.5 Hz, 3H);

ESMS calcd for $C_{21}H_{22}N_4O_2S$: 394.15. Found: 395.1 $(M+1)^+$.

Example 90

Compound 101

ESMS calcd for $C_{19}H_{17}N_5O_3S$: 395.11. Found: 396.0 $(M+H)^+$.

Example 91

Compound 102

ESMS calcd. for $C_{19}H_{20}N_5O_2S$: 381.1. Found: 382.0 $(M+1)^+$.

Example 92

Compound 103

$^1$H NMR (DMSO-d$_6$) δ 9.48 (s, 1H), 9.38 (s, 1H), 7.29 (d, J=8.4 Hz, 1H), 7.25 (d, J=1.8 Hz, 1H), 6.85-6.89 (m, 2H), 6.18 (s, 1H), 3.61 (s, 3H), 2.30 (s, 3H), 2.29 (q, J=7.5 Hz, 2H), 2.09 (s, 3H), 0.94 (t, J=7.5 Hz, 3H);

ESMS calcd for $C_{21}H_{23}N_4O_2S$: 394.1. Found: 395.0 $(M+1)^+$.

Example 93

Compound 104

ESMS calcd for $C_{19}H_{15}N_3O_3S$: 365.08. Found: 366.0 $(M+H)^+$.

Example 94

Compound 106

ESMS calcd for $C_{20}H_{17}N_4O_2S$: 377.1. Found: 378.0 $(M+H)^+$.

Example 95

Compound 107

ESMS calcd for $C_{18}H_{13}ClN_3O_2S$: 369.0. Found: 370.0 $(M+H)^+$.

Example 96

Compound 116

$^1$H NMR (DMSO-d$_6$) δ 7.98-7.56 (m, 2H), 7.55-7.30 (m, 6H), 6.43 (dd, J=8.1 and 1.8 Hz, 1H), 6.29 (m, 1H), 3.65 (s, 3H), 3.16 (s, 3H);

ESMS calcd for $C_{20}H_{17}N_3O_2S$: 363.10. Found: 364.0 $(M+1)^+$.

Example 97

Compound 117

$^1$H-NMR (CDCl$_3$) δ 7.83 (d, J=8.1 Hz, 2H), 7.48-7.34 (m, 4H), 7.28-7.20 (m, 1H), 6.99 (d, J=1.8 Hz, 1H), 6.80 (d, J=8.7 Hz, 1H), 6.62-6.58 (m, 1H), 2.94 (s, 3H), 2.89 (s, 3H), 2.84 (s, 3H), 2.81 (s, 3H), 2.75-2.69 (m, 6H);

ESMS calcd for $C_{27}H_{28}N_6O_5S$: 548.18. Found: 549.2 $(M+1)^+$.

Example 98

Compound 122

$^1$H-NMR (CDCl$_3$) δ 7.98 (m, 2H), 7.60-7.55 (m, 3H), 7.51-7.45 (m, 1H), 7.36-7.33 (m, 1H), 6.98-6.97 (m, 1H), 6.86 (d, J=9.9 Hz, 1H), 6.70-6.67 (m, 1H), 2.86 (s, 3H), 2.26 (s, 3H), 2.21 (s, 3H);

ESMS calcd for $C_{24}H_{19}N_3O_5S$: 461.10. Found: 462.0 $(M+1)^+$.

Example 99

Compound 125

ESMS calcd for $C_{20}H_{17}N_3O_3S$: 379.10. Found: 380.0 $(M+H)^+$.

Example 100

Compound 126

ESMS calcd for $C_{10}H_{11}N_3O_2S$: 237.06. Found: 238.0 $(M+H)^+$.

Example 101

Compound 127

ESMS calcd for $C_{11}H_{13}N_3O_2S$: 251.07. Found: 252.0 $(M+H)^+$.

Example 102

Compound 128

ESMS calcd for $C_{11}H_{13}N_3O_2S$: 251.07. Found: 252.0 $(M+H)^+$.

Example 103

Compound 129

ESMS calcd for $C_{11}H_{11}N_3O_2S$: 249.06. Found: 250.0 $(M+H)^+$.

Example 104

Compound 130

ESMS calcd for $C_{12}H_{15}N_3O_2S$: 265.09. Found: 266.0 $(M+H)^+$.

Example 105

Compound 131

ESMS calcd for $C_{20}H_{15}N_3O_4S$: 393.08. Found: 394.1 $(M+H)^+$.

Example 106

Compound 177

$^1$H NMR (DMSO-$d_6$) δ 9.34 (s, 1H), 9.22 (s, 1H), 8.01-7.96 (m, 2H), 7.58-7.44 (m, 5H), 6.56 (s, 1H), 6.14 (s, 1H), 3.29 (s, 3H);
ESMS calcd for $C_{19}H_{15}N_3O_3S$: 365.08. Found: 366.0 $(M+1)^+$.

Example 107

Compound 178

$^1$H NMR (DMSO-$d_6$) δ 10.29 (s, 1H), 9.49 (s, 1H), 9.42 (s, 1H), 8.16 (t, J=5.1 Hz, 1H), 7.45-7.43 (m, 2H), 7.26 (t, J=8.0 Hz, 1H), 6.84 (d, J=7.8 Hz, 1H), 6.75 (d, J=8.7 Hz, 1H), 6.66 (s, 1H), 6.14 (s, 1H), 2.12 (q, J=7.5 Hz, 2H), 0.70 (t, J=7.2 Hz, 3H);
ESMS calcd for $C_{20}H_{17}N_3O_3S$: 379.10. Found: 379.9 $(M+1)^+$.

Example 108

Compound 179

ESMS calcd for $C_{19}H_{15}N_3O_2S$: 349.09. Found: 350.0 $(M+1)^+$.

Example 109

Compound 180

ESMS calcd for $C_{19}H_{15}N_3O_2S$: 349.09. Found: 350.0 $(M+H)^+$.

Example 110

Compound 181

ESMS calcd for $C_{20}H_{15}N_3O_2S$: 361.09. Found: 362.0 $(M+H)^+$.

Example 111

Compound 182

ESMS calcd for $C_{16}H_{15}N_3O_3S$: 329.08. Found: 330.0 $(M+H)^+$.

Example 112

Compound 183

ESMS calcd for $C_{20}H_{17}N_3O_2S$: 363.10. Found: 364.0 $(M+H)^+$.

Example 113

Compound 184

ESMS calcd for $C_{18}H_{13}N_3O_3S$: 350.38. Found: 351.9 $(M+H)^+$.

Example 114

Compound 185

ESMS calcd. for $C_{20}H_{21}N_4O_2S$: 380.1. Found: 381.0 $(M+1)^+$.
3.

Example 115

Compound 187

ESMS calcd. for $C_{19}H_{20}N_5O_2S$: 381.1. Found: 382.0 $(M+1)^+$.

Example 116

Compound 190

4. ESMS calcd. for $C_{21}H_{22}N_4O_2S$: 394.15. Found: 395.0 $(M+1)^+$.

Example 117

Compound 191

ESMS calcd. for $C_{22}H_{23}N_4O_4S$: 438.1. Found: 439.0 $(M+1)^+$.

Example 118

Compound 192

ESMS calcd. for $C_{20}H_{22}N_5O_2S$: 395.1. Found: 396.0 $(M+1)^+$.

Example 119

Compound 193

ESMS calcd. for $C_{20}H_{22}N_5O_2S$: 395.1. Found: 396.0 $(M+1)^+$.

Example 120

Compound 194

ESMS calcd. for $C_{23}H_{27}N_4O_2S$: 422.1. Found: 423.0 $(M+1)^+$.

Example 121

Compound 195

ESMS calcd. for $C_{23}H_{25}N_4O_2S$: 420.1. Found: 421.0 $(M+1)^+$.

Example 122

Compound 196

ESMS calcd. for $C_{25}H_{29}N_4O_2S$: 448.1. Found: 449.3 $(M+1)^+$.

Example 123

Compound 197

ESMS calcd. for $C_{22}H_{24}N_4O_2S$: 408.16. Found: 409.2 $(M+1)^+$.

Example 124

Compound 198

ESMS calcd. for $C_{23}H_{26}N_4O_2S$: 422.18. Found: 423.3 $(M+1)^+$.

Example 125

Compound 199

ESMS calcd. for $C_{24}H_{28}N_4O_2S$: 436.19. Found: 437.3 $(M+1)^+$.

Example 126

Compound 200

ESMS calcd. for $C_{22}H_{22}N_4O_2S$: 0.406.15. Found: 407.2 $(M+1)^+$.

Example 127

Compound 201

ESMS calcd. for $C_{23}H_{24}N_4O_3S$: 436.16. Found: 437.3 $(M+1)^+$.

Example 128

Compound 202

ESMS calcd. for $C_{22}H_{23}N_4O_2S$: 406.1. Found: 407.0 $(M+H)^+$.

Example 129

Compound 204

ESMS calcd. for $C_{24}H_{28}N_4O_3S$: 0.452.19. Found: 453.2 $(M+1)^+$.

Example 130

Compound 205

ESMS calcd. for $C_{23}H_{24}N_4O_3S$: 436.16. Found: 437.1 $(M+1)^+$.

Example 131

Compound 206

ESMS calcd. for $C_{21}H_{23}N_4O_2S$: 394.1. Found: 395.1 $(M+1)^+$.

Example 132

Compound 207

ESMS calcd. for $C_{20}H_{21}N_4O_2S$: 380.1. Found: 381.1 $(M+1)^+$.

Example 133

Compound 208

ESMS calcd. for $C_{23}H_{26}N_4O_3S$: 438.17. Found: 439.1 $(M+1)^+$.

Example 134

Compound 209

ESMS calcd. for $C_{22}H_{24}N_4O_2S$: 408.1. Found: 409.1 $(M+1)^+$.

Example 135

Compound 210

ESMS calcd. for $C_{24}H_{23}N_4O_2S$: 430.1. Found: 431.1 $(M+1)^+$.

Example 136

Compound 211

ESMS calcd. for $C_{21}H_{22}N_4O_3S$: 410.14. Found: 411.1 $(M+1)^+$.

Example 137

Compound 212

ESMS calcd. for $C_{23}H_{26}N_4O_3S$: 438.17. Found: 439.1 $(M+1)^+$.

Example 138

Compound 213

ESMS calcd. for $C_{20}H_{21}N_4O_2S$: 380.1. Found: 381.1 $(M+1)^+$.

Example 139

Compound 214

ESMS calcd. for $C_{19}H_{19}N_4O_2S$: 366.1. Found: 367.1 $(M+1)^+$.

Example 140

Compound 215

ESMS calcd. for $C_{20}H_{19}N_3O_4S$: 397.1. Found: 398.1 $(M+1)^+$.

Example 141

Compound 216

$^1$H NMR (DMSO-$d_6$): δ (ppm) 9.56 (s, 1H), 9.40 (s, 1H), 8.03 (d, J=2.4 Hz, 1H), 7.58 (d, J=8.4 Hz, 1H), 7.54 (d, J=2.1 Hz, 1H), 7.11 (dd, J=8.4, 2.1 Hz, 1H), 6.97 (d, J=2.4 Hz, 1H), 6.89 (s, 1H), 6.17 (s, 1H), 2.23 (q, J=7.2 Hz, 2H), 0.93 (t, J=7.2 Hz, 3H);
ESMS calcd. for $C_{18}H_{15}N_3O_3S$: 353.08. Found: 354.0 $(M+1)^+$.

Example 142

Compound 217

$^1$H NMR (DMSO-$d_6$): δ (ppm) 9.59 (s, 1H), 9.43 (s, 1H), 7.67 (d, J=8.7 Hz, 1H), 7.54 (d, J=2.1 Hz, 1H), 7.20 (dd, J=8.4, 2.1 Hz, 1H), 6.96 (s, 1H), 6.18 (s, 1H), 2.60 (s, 3H), 2.34 (q, J=7.2 Hz, 2H), 0.98 (t, J=7.2 Hz, 3H);
ESMS calcd. for $C_{18}H_{16}N_4O_3S$: 368.09. Found: 369.0 $(M+1)^+$.

Example 143

Compound 218

ESMS calcd. for $C_{21}H_{23}N_4O_2S$: 394.1. Found: 395.1 $(M+1)^+$.

Example 144

Compound 219

ESMS calcd. for $C_{21}H_{21}N_4O_2S$: 392.1. Found: 393.1 $(M+1)^+$.

Example 145

Compound 220

ESMS calcd. for $C_{20}H_{21}N_4O_3$: 364.1. Found: 365.1 $(M+1)^+$.

Example 146

Compound 221

ESMS calcd. for $C_{20}H_{21}N_4O_2S$: 379.1. Found: 381.1 $(M+1)^+$.

Example 147

Compound 222

ESMS calcd. for $C_{21}H_{23}N_4O_2S$: 394.1. Found: 395.1 $(M+1)^+$.

Example 148

Compound 224

ESMS calcd. for $C_{19}H_{21}N_4O_2S$: 368.1. Found: 369.1 $(M+1)^+$.

Example 149

Compound 225

ESMS calcd. for $C_{19}H_{19}N_4O_2S$: 366.1. Found: 367.1 $(M+1)^+$.

Example 150

Compound 226

ESMS calcd. for $C_{20}H_{21}N_4O_3$: 364.1. Found: 365.1 $(M+1)^+$.

Example 151

Compound 227

ESMS calcd. for $C_{21}H_{22}N_4O_2S$: 394.15. Found: 395.1 $(M+1)^+$.

Example 152

Compound 228

ESMS calcd. for $C_{22}H_{24}N_4O_2S$: 408.16. Found: 409.1 $(M+1)^+$.

Example 153

Compound 229

ESMS calcd. for $C_{20}H_{18}F_3N_5O_2S$: 449.11. Found: 450.1 $(M+1)^+$.

Example 154

Compound 230

ESMS calcd. for $C_{19}H_{19}N_5O_2S$: 381.13. Found: 382.1 $(M+1)^+$.

Example 155

Compound 231

ESMS calcd. for $C_{19}H_{19}N_5O_2S$: 381.13. Found: 382.1 $(M+1)^+$.

Example 156

Compound 232

ESMS calcd. for $C_{22}H_{24}N_4O_3S$: 392.18. Found: 393.1 $(M+1)^+$.

Example 157

Compound 233

ESMS calcd. for C18H17N3O4S: 371.09. Found: 372.1 $(M+1)^+$.

Example 158

Compound 234

ESMS calcd. for C20H21N3O2S: 367.14. Found: 368.1 $(M+1)^+$.

Example 159

Compound 235

ESMS calcd. for $C_{19}H_{19}N_5O_2S$: 381.13. Found: 382.1 $(M+1)^+$.

Example 160

Compound 239

ESMS clcd for $C_{19}H_{21}N_4O_2S$: 368.1. Found: 369.1 $(M+H)^+$.

Example 161

Compound 240

ESMS clcd for $C_{18}H_{16}N_4O_3S$: 368.09.10. Found: 369.1 $(M+H)^+$.

Example 162

Compound 241

ESMS clcd for $C_{17}H_{15}N_5O_3S$: 369.09. Found: 370.1 $(M+H)^+$.

Example 163

Compound 242

ESMS clcd for $C_{19}H_{18}N_4O_3S$: 382.11. Found: 383.1 $(M+H)^+$.

Example 164

Compound 243

ESMS clcd for $C_{22}H_{26}N_4O_3S$: 426.17. Found: 427.1 $(M+H)^+$.

Example 165

Compound 244

ESMS clcd for $C_{18}H_{16}N_4O_4S$: 384.09. Found: 385.1 (M+H)+

Example 166

Compound 245

ESMS clcd for $C_{18}H_{16}N_4O_3S_2$: 400.07. Found: 401.1 (M+H)+

Example 167

Compound 245

ESMS clcd for $C_{17}H_{14}N_4O_3S_2$: 386.05. Found: 387.0 $(M+H)^+$.

Example 168

4-{5-Hydroxy-4-[4-methoxy-3-(methylpropylamino)phenyl]-4H-[1,2,4]triazol-3-yl}-6-isopropyl-benzene-1,3-diol

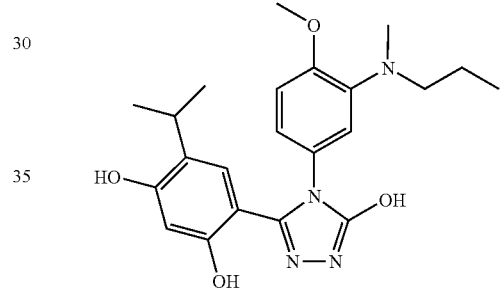

Scheme 1

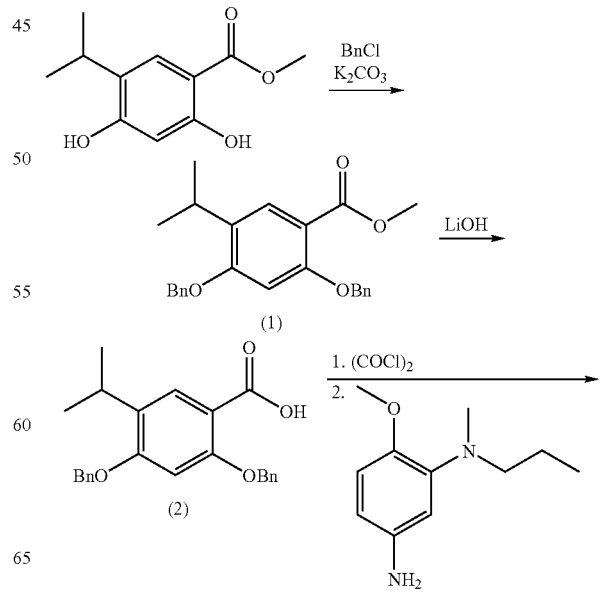

-continued

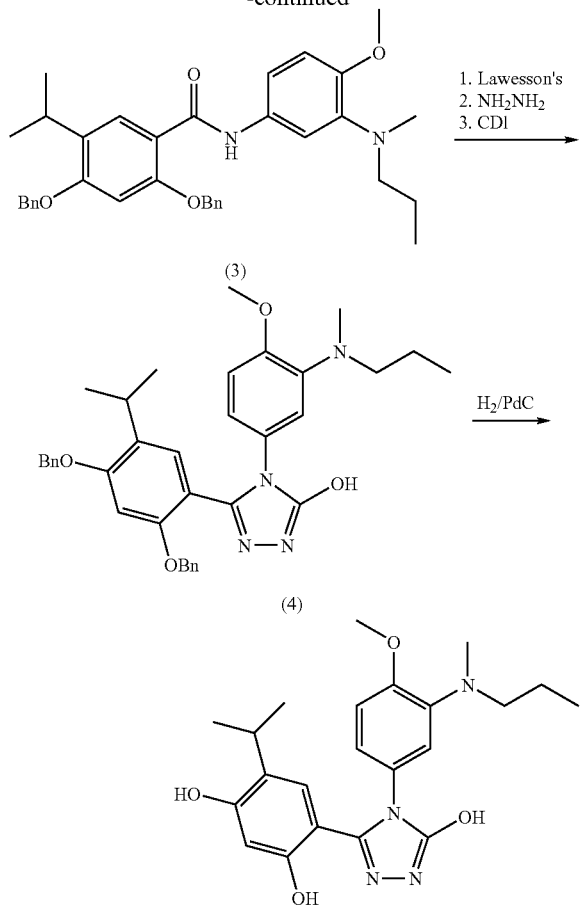

To a solution of 2,4-dihydroxy-5-isopropylbenzoic acid methyl ester (1.63 g, 7.75 mmol) in dimethylformamide (DMF) (100 mL) was added potassium carbonate (3.21 g, 23 mmol) then benzyl chloride (1.95 ml, 17 mmol). The suspension was heated to 80° C. for 16 hrs under a nitrogen atmosphere. Ethyl acetate (100 ml) and water (100 ml) were added, and then the ethyl acetate layer was washed with water (3×50 mL), and then dried over magnesium sulfate, filtered and evaporated to dryness to produce the desired compound as brown oil (2.9 g, 97%).

2,4-Bis-benzyloxy-5-isopropylbenzoic acid methyl ester (3.23 g, 8.27 mmol) and LiOH (1.0 g, 24.8 mmol) were heated in a mixture of tetrahydrofuranyl (THF)/methanol/water (100 mL, 3:1:1) for 16 hrs. Ethyl acetate (100 mL) and water (100 ml) were added, then the ethyl acetate layer was washed with water (3×50 mL), dried over magnesium sulfate, filtered and evaporated to dryness to produce the desired compound as a yellow solid (2.6 g, 83%).

2,4-Bis-benzyloxy-5-isopropylbenzoic acid (1.25 g, 3.32 mmol) was dissolved in dichloromethane (50 mL) and cooled in an ice bath. Oxalyl chloride (0.32 mL, 3.65 mmol) was added followed by the dropwise addition of DMF (0.1 mL). The reaction was stirred at room temperature for 1 hr then evaporated to dryness under reduced pressure to produce a brown solid. This solid was dissolved in THF (50 mL) and cooled in an ice bath. A solution of 4-Methoxy-$N^3$-methyl-$N^3$-propyl-benzene-1,3-diamine (0.71 g, 3.65 mmol) in THF (20 mL) was added dropwisely followed by the triethylamine (1.6 mL) and the reaction was stirred at room temperature for 16 hrs. Ethyl acetate (50 mL) and water (100 mL) were added. The ethyl acetate layer was washed with water (3×50 mL), dried over magnesium sulfate, filtered and evaporated to dryness to produce the crude product as a brown solid. Purification by silicagel chromatography (elution with 25% ethyl acetate/hexane) provided the desired compound as a white solid (1.8 g, 93%).

2,4-Bis-benzyloxy-5-isopropyl-N-[4-methoxy-3-(methylpropylamino)phenyl]benzamide (700 mg, 1.27 mmol) and Lawesson's reagent (0.31 g, 0.76 mmol) were dissolved in toluene (20 mL) and heated to 110° C. for 3 hrs then evaporated to dryness under reduced pressure to produce a yellow oil. This crude product was dissolved in dioxane (10 mL), anhydrous hydrazine (0.6 mL) was added and the reaction was heated to 80° C. for 30 min. After cooling, ethyl acetate (50 mL) and water (50 mL) were added. The ethyl acetate layer was washed with water (3×50 mL), dried over magnesium sulfate, filtered and evaporated to dryness to produce the crude product as a brown solid. This solid was dissolved in ethyl acetate (50 mL), CDI (0.66 g, 4.08 mmol) was added then the reaction was heated to reflux for 3 hrs. Removal of the solvent under reduced pressure followed by purification by silicagel chromatography (elution with 50% ethyl acetate/hexane) provided the desired compound as a white solid (250 mg, 33% over 3 steps).

5-(2,4-Bis-benzyloxy-5-isopropyl-phenyl)-4-[4-methoxy-3-(methylpropylamino)phenyl]-4H-[1,2,4]triazol-3-ol (240 mg, 0.4 mmol) was dissolved in methanol (10 mL) then 10% palladium on charcoal (200 mg) was added and the reaction was stirred under an atmosphere of hydrogen for 16 hrs. Filtration was carried out through a silca gel plug and removal of the solvent under reduced pressure produced the desired compound as a white solid (150 mg, 94%).

$^1$H NMR (300 MHz, DMSO-$d_6$), δ (ppm): 11.8 (s, 1H), 9.55 (s, 1H), 9.39 (s, 1H), 6.88 (d, J=8.7 Hz, 1H), 6.77-6.79 (m, 2H), 6.5 (s, 1H), 6.24 (s, 1H), 3.73 (s, 3H), 2.97 (qn, J=6.9 Hz, 1H), 2.79 (t, J=7.5 Hz, 2H), 2.48 (s, 3H), 1.30 (m, 2H), 0.97 (d, J=6.9 Hz, 6H), 0.73 (t, J=7.5 Hz, 3H).

ESMS clcd for $C_{22}H_{28}N_4O_4$: 412.21. Found: 413.2 (M+H)$^+$.

Example 169

4-Isopropyl-6-{5-mercapto-4-[4-methoxy-3-(methylpropyl-amino)-phenyl]-4H-[1,2,4]triazol-3-yl}-benzene-1,3-diol

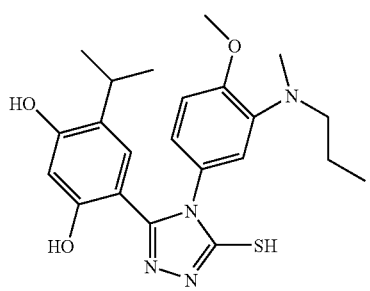

Scheme 2

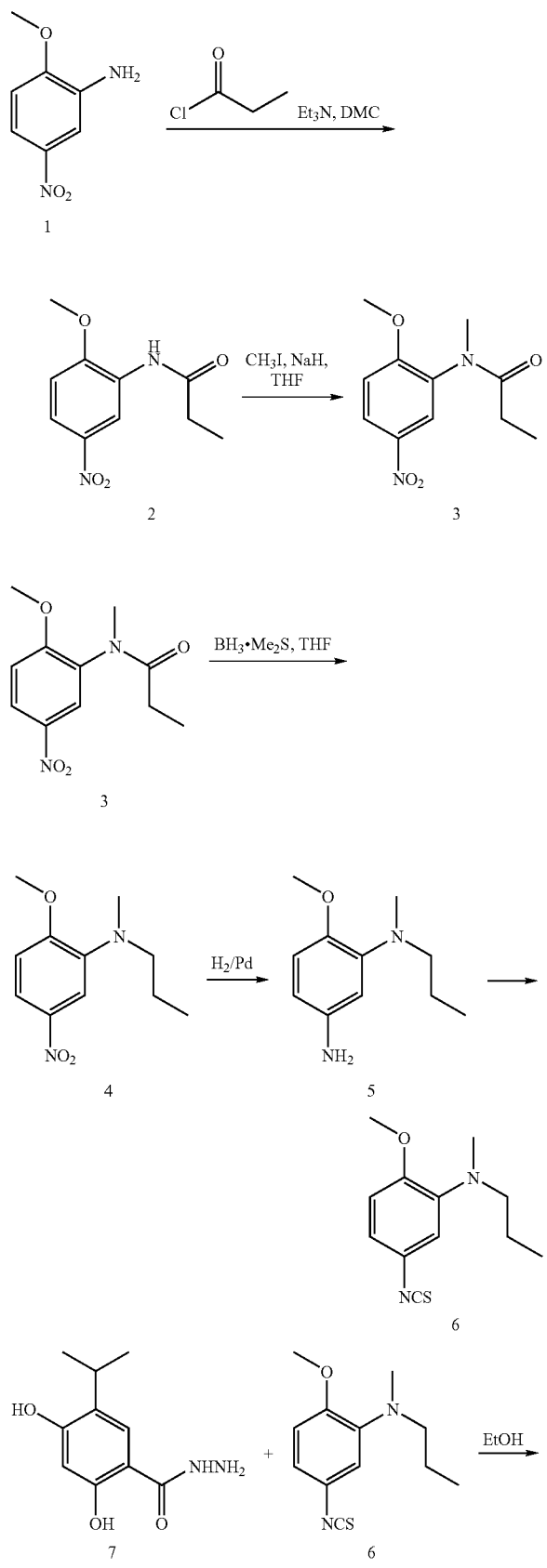

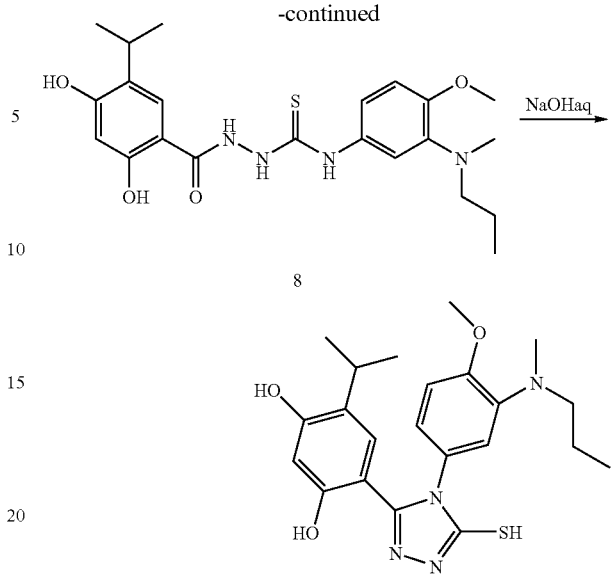

2-methoxy-5-nitroaniline (1) (10.1 g, 60.0 mmol) in 250 mL dichloromethane at 0°-5° C. was treated with triethylamine (10.0 g, 100.0 mmol) and propionyl chloride (6.7 g, 6.3 mL, 72.0 mmol) for 1 hour and 0.5 h at room temperature (RT). Normal aqueous workup and removal of solvent gave a light yellow solid which was washed with hexane/EtOAc (9:1) to yield solid N-(2-Methoxy-5-nitro-phenyl)-propionamide (2) (13.2 g, 98%).

To a stirred solution of 11.2 g (50.0 mmol) of (2) in 150 mL of anhydrous THF at 0° C. under the nitrogen, was added 3.0 g (75 mmol) of NaH (60% in oil). The suspension was stirred for 0.5 h at 0° C. and 10 mL (150 mmol) of iodomethane was added at 0° C. After the mixture warmed to room temperature and stirred for 3 h, the reaction was quenched by ice brine and extracted with EtOAc (200 mL). The organic phase was washed with brine, dried ($Na_2SO_4$), filtered, evaporated in vacuo and the solid was washed with hexane/EtOAc (9:1) to give pure product N-(2-Methoxy-5-nitro-phenyl)-N-methyl-propionamide (3) as a light yellow solid (11.3 g, 95% yield).

N-(2-Methoxy-5-nitro-phenyl)-N-methyl-propionamide (3) (10.0 g 42 mmol) and borane-methyl sulfide complex (21 mL of 2.0M solution in tetrahydrofurane) in 50 mL THF were heated under reflux for 30 min, cooled and quenched by ice-water (slowly). Extraction with EtOAc and the organic layer washed with brine dried ($Na_2SO_4$), filtered and evaporated in vacuo to give (9.1 g, 96%) (2-Methoxy-5-nitro-phenyl)-methyl-propyl-amine (4) as a yellow oil.

A solution of 9.0 g (40.1 mmol) of (2-Methoxy-5-nitro-phenyl)-methyl-propyl-amine (4) in 200 mL of MeOH/EtOAc (1:1) containing 5% w/w of Pd—C (10%) was subjected to hydrogenation (1 atm, balloon) overnight. The contents of the flask were passed through a short pad of celite and washed with EtOAc. The filtrate was evaporated under reduced pressure to give 7.7 g (92%) of crude amine 4-Methoxy-N3-methyl-N3-propyl-benzene-1,3-diamine (5) of an oil.

To a stirred solution of 6.8 g (35.0 mmol) of (5) in 150 mL of $CH_2Cl_2$ at RT was added 6.4 g (35 mmol) of 1,1'-thiocarbonyldiimidazole. The mixture was stirred at room temperature for 15 minutes and then evaporated under reduced pressure and the residue was passed through a short pad of silica gel, eluting with a gradient of hexane/EtOAc, which gave (5-Isothiocyanato-2-methoxy-phenyl)-methyl-propyl-amine (6) (7.85 g, 95%) as a colorless oil.

To a stirred solution of 4.5 g (19.0 mmol) of the isothiocyanate (6) in 60 mL of ethanol was added 4.0 g (19.0 mmol) of the hydrazide (7) portion wise. The resultant mixture was then heated at 70° C. for 1 h, then cooled. Solvent was removed on rotary evaporator and the residue was treated with hexane/EtOAc (9:1). The white precipitate thus obtained was filtered, washed with ether (2×50 mL) and vacuum dried to 7.6 g (90%) of (8) as white solid.

To a solution of 1.36 g (34 mmol) of NaOH in 80 mL of water was added 7.5 g (16.8 mmol) of the intermediate (8) portion-wise. After the dissolution of the solid (1-2 min), the flask was flushed with nitrogen and heated to 110° C. for 3 h. The reaction mixture was cooled, an additional 100 mL of water was added and the whole mixture was acidified with conc. HCl to pH 7. The white precipitate thus obtained was filtered, washed with water (3×75 mL) and dried. The crude product was then re-dissolved in a mixture of 200 mL of ethyl acetate, dried over anhydrous Na$_2$SO$_4$ and passed through a short pad of silica gel with an additional 150 mL of ethyl acetate as eluent. The filtrates were concentrated and crude product was re-precipitated in 3:1 hexane/ethyl acetate to give 6.83 g (95%) of 4-isopropyl-6-{5-mercapto-4-[4-methoxy-3-(methyl-propyl-amino)-phenyl]-4H-[1,2,4]triazol-3-yl}-benzene-1,3-diol as white solid.

$^1$H NMR (300 MHz, DMSO-d$_6$), (ppm): 9.58 (s, 1H); 9.39 (s, 1H); 6.92-6.83 (m, 3H); 6.56 (d, J=1.8 Hz, 1H); 6.23 (s, 1H); 3.74 (s, 3H); 3.0-2.93 (m, 1H); 2.81 (t, J=6.9 Hz, 2H); 2.48 (s, 3H); 1.31-1.24 (m, 2H); 0.96 (d, J=6.9 Hz, 6H); 0.72 (t, J=7.2 Hz, 3H);

ESMS clcd for C$_{22}$H$_{28}$N$_4$O$_3$S: 428.19. Found: 429.2 (M+H)$^+$.

Example 170

4-(4-{3-[(2-Dimethylamino-ethyl)-methyl-amino]-4-methoxy-phenyl}-5-mercapto-4H-[1,2,4]triazol-3-yl)-6-isopropyl-benzene-1,3-diol

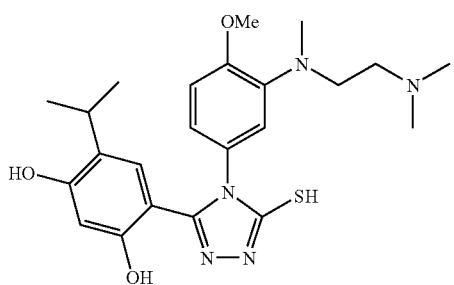

Scheme 3,

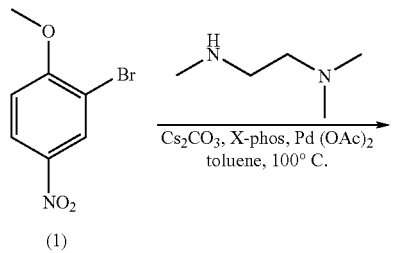

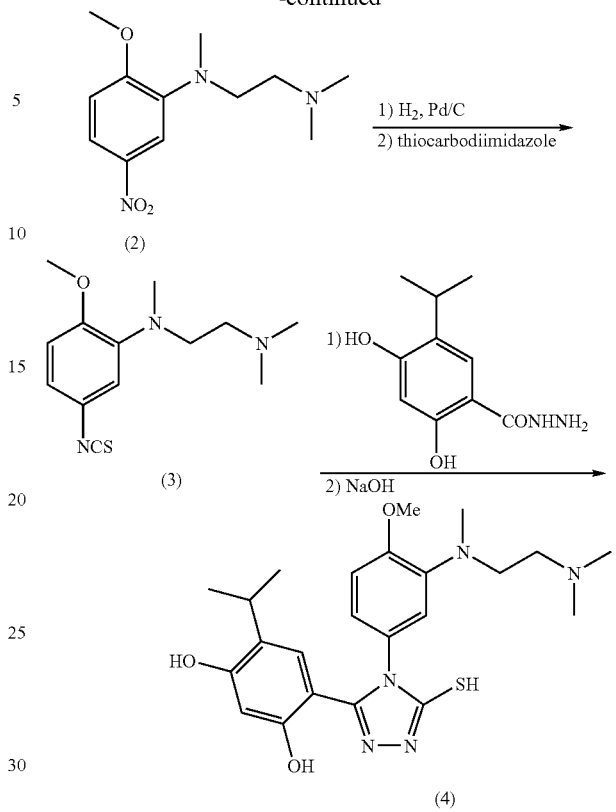

An oven-dried flask was charged with cesium carbonate (2.28 g, 7 mmol, 1.4 eq), Pd(OAc)$_2$ (79 mg, 0.35 mmol, 0.07 eq), and X-phos (238 mg, 0.5 mmol, 0.1 eq) under nitrogen. 2-bromo-1-methoxy-4-nitrobenzene (1.16 g, 5 mmol, 1 eq), N$^1$, N$^2$, N$^2$-trimethylethane-1,2-diamine (613 mg, 6 mmol, 1.2 eq) and toluene (20 mL, 0.25 M) were added, and the mixture was heated to 100° C. with stirring overnight. The reaction mixture was cooled to room temperature and concentrated. The crude product was then purified by flash chromatography on silica gel to give N$^1$-(2-methoxy-5-nitrophenyl)-N$^1$, N$^2$, N$^2$-trimethylethane-1,2-diamine(2) (340 mg, 1.34 mmol, 27%).

A solution of 340 mg of N$^1$-(2-methoxy-5-nitrophenyl)-N$^1$, N$^2$, N$^2$-trimethylethane-1,2-diamine (2) in 20 mL of ethanol containing 5% w/w of Pd—C (10%) was subjected to hydrogenation (1 atm, balloon) for 1.5 h. The contents of the flask were passed through a short pad of celite and washed with MeOH. The filtrate was evaporated under reduced pressure and crude amine obtained was carried over to the next reaction without further purification. Thiocarbodiimidazole (260 mg, 1.46 mmol) was added to the crude amine in dichloromethane (10 mL) at room temperature. The reaction mixture was stirred at room temperature for 1 h, and concentrated. The crude product was then purified by flash chromatography on silica gel to give N$^1$-(5-isothiocyanato-2-methoxyphenyl)-)-N$^1$, N$^2$, N$^2$-trimethylethane-1,2-diamine (3) (110 mg, 0.42 mmol, 31%).

To a stirred solution of 110 mg (0.54 mmol) of the isothiocyanate (3) in 5 mL of ethanol was added 105 mg (0.54 mmol) of 2,4-dihydroxy-5-isopropyl-benzoic acid hydrazide portion wise. The resultant mixture was then heated at 80° C. for 1 h, and then cooled. Solvent was removed on rotary evaporator and the residue was treated with hexane/EtOAc (9:1). The white precipitate thus obtained was filtered, washed with ether (2×20 mL) and vacuum dried to crude product as white solid. This solid was added to a solution of 44 mg (1.08 mmol) of NaOH in 5 mL of water portion-wise. After the dissolution of the solid (1-2 min), the flask was flushed with nitrogen and heated to 110° C. for 1.5 h. The reaction mixture was cooled, an additional 20 mL of water was added and the whole mixture was acidified with conc. HCl to pH 7. The white precipitate thus obtained was filtered, washed with water (3×20 mL) and dried. The crude product was then re-dissolved in a mixture of 20 mL of ethyl acetate, dried over anhydrous $Na_2SO_4$ and passed through a short pad of silica gel with an additional 15 mL of ethyl acetate as eluent. The filtrates were concentrated and crude product was re-precipitated in 3:1 hexane/ethyl acetate to give 97 mg of 4-(4-(3-((2-(dimethylamino)ethyl)(methyl)amino)-4-methoxyphenyl)-5-mercapto-4H-1,2,4-triazol-3-yl)-6-isopropylbenzene-1,3-diol (4) as white solid.

$^1$H-NMR 300 MHz, DMSO-$d_6$) δ (ppm): 9.80 (s, 1H), 9.62 (br s, 1H), 6.85 (m. 3H), 6.63 (m, 1H), 6.41 (s, 1H), 3.78 (s, 3H), 3.06 (m, 2H), 2.97 (q, J=6.9 Hz, 1H), 2.55 (s, 3H), 2.47 (m, 2H), 2.24 (s, 6H), 0.99 (s, 3H), 0.97 (s, 3H).

ESMS clcd for $C_{23}H_{31}N_5O_3S$: 457.21. Found: 458.2 (M+H)$^+$.

Example 171

4-Isopropyl-6-(5-mercapto-4-{4-methoxy-3-[(2-methoxy-ethyl)methylamino]phenyl}-4H-[1,2,4]triazol-3-yl)-benzene-1,3-diol

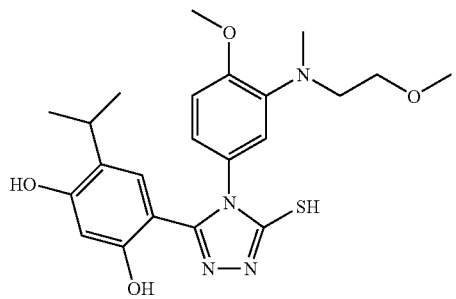

$^1$H NMR (300 MHz, DMSO-$d_6$) δ (ppm): 9.57 (s, 1H), 9.39 (s, 1H), 6.83-6.90 (m, 3H), 6.59 (d, J=2.1 Hz, 1H), 6.23 (s, 1H), 3.74 (s, 3H), 3.39 (t, J=6 Hz, 2H), 3.14 (s, 3H), 3.07 (t, J=6 Hz, 2H), 2.96 (qn, J=6.9 Hz, 1H), 2.54 (s, 3H), 0.97 (d, J=6.9 Hz, 6H). ESMS clcd for $C_{22}H_{28}N_4O_4S$: 444.18. Found: 445.2 (M+H)$^+$.

Example 172

4-{4-[3-(Cyclopropylmethylmethylamino)-4-methoxy-phenyl]-5-mercapto-4H-[1,2,4]triazol-3-yl}-6-isopropylbenzene-1,3-diol

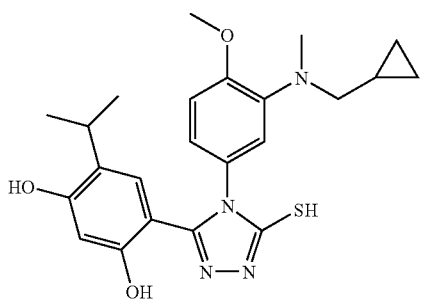

$^1$H NMR (300 MHz, DMSO-$d_6$) δ (ppm): 9.56 (s, 1H), 9.39 (s, 1H), 6.85-6.90 (m, 3H), 6.58 (d, J=2.1 Hz, 1H), 6.23 (s, 1H), 3.76 (s, 3H), 2.96 (qn, J=6.9 Hz, 1H), 2.76 (d, J=6.3 Hz, 2H), 2.57 (s, 3H), 0.99 (d, J=6.9 Hz, 6H), 0.58-0.64 (m, 1H), 0.32-0.34 (m, 2H), −0.03-0.01 (m, 2H).

ESMS clcd for $C_{23}H_{28}N_4O_3S$: 440.19. Found: 441.1 (M+H)$^+$.

Example 173

N-{4-[3-(5-Ethyl-2,4-dihydroxy-phenyl)-5-mercapto-[1,2,4]triazol-4-yl]-phenyl}-N-methyl-acetamide,

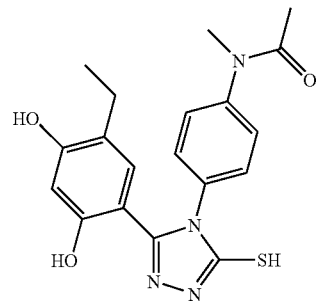

ESMS clcd for $C_{19}H_{20}N_4O_3S$: 384.13. Found: 385.1 (M+H)$^+$.

Example 174

N-Ethyl-N-{5-[3-(5-ethyl-2,4-dihydroxy-phenyl)-5-mercapto-[1,2,4]triazol-4-yl]-2-methoxy-phenyl}-acetamide,

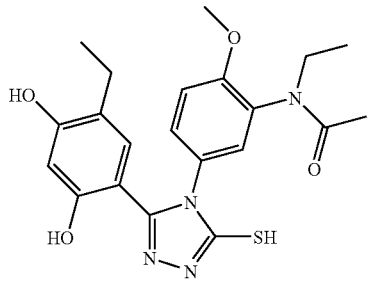

ESMS clcd for $C_{21}H_{24}N_4O_4S$: 428.15. Found: 429.2 (M+H)$^+$.

Example 175

4-[4-(3-Diethylamino-4-methoxy-phenyl)-5-mercapto-4H-[1,2,4]triazol-3-yl]-6-ethyl-benzene-1,3-diol

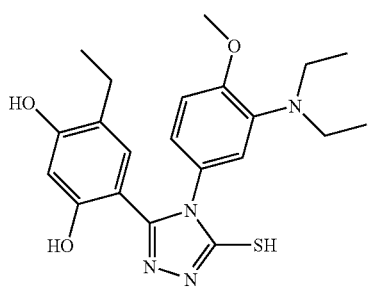

ESMS clcd for $C_{21}H_{26}N_4O_3S$: 414.17. Found: 415.2 (M+H)$^+$.

Example 176

4-[4-(4-Dimethylamino-phenyl)-5-mercapto-4H-[1,2,4]triazol-3-yl]-6-ethyl-benzene-1,3-diol

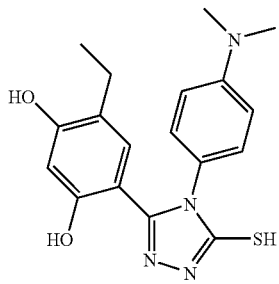

ESMS clcd for $C_{18}H_{20}N_4O_2S$: 356.13. Found: 357.2 $(M+H)^+$.

Example 177

4-[4-(4-Diethylamino-phenyl)-5-mercapto-4H-[1,2,4]triazol-3-yl]-6-ethyl-benzene-1,3-diol

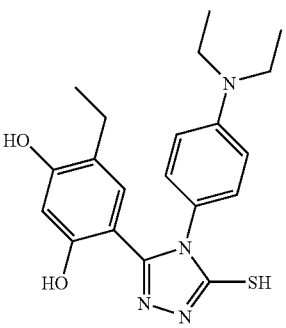

ESMS clcd for $C_{20}H_{24}N_4O_2S$: 384.16. Found: 385.2 $(M+H)^+$.

Example 178

4-Ethyl-6-[5-mercapto-4-(4-morpholin-4-yl-phenyl)-4H-[1,2,4]triazol-3-yl]-benzene-1,3-diol

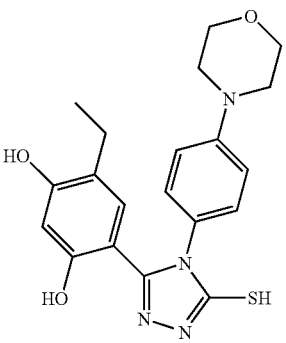

ESMS clcd for $C_{20}H_{22}N_4O_3S$: 398.14. Found: 399.2 $(M+H)^+$.

Example 179

4-Ethyl-6-[4-(4-imidazol-1-yl-phenyl)-5-mercapto-4H-[1,2,4]triazol-3-yl]-benzene-1,3-diol

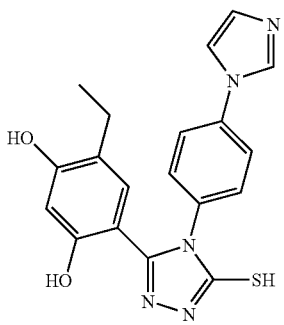

ESMS clcd for $C_{19}H_{17}N_5O_2S$: 379.11. Found: 380.2 $(M+H)^+$.

Example 180

4-[4-(2,5-Diethoxy-4-morpholin-4-yl-phenyl)-5-mercapto-4H-[1,2,4]triazol-3-yl]-6-ethyl-benzene-1,3-diol

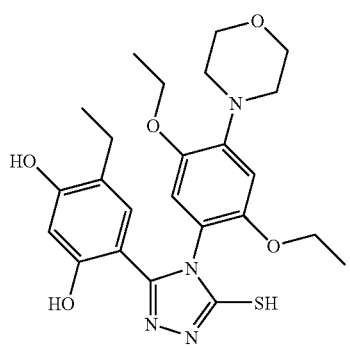

ESMS clcd for $C_{24}H_{30}N_4O_5S$: 486.19. Found: 487.3 $(M+H)^+$.

Example 181

4-Ethyl-6-{4-[3-(isopropyl-propyl-amino)-4-methoxy-phenyl]-5-mercapto-4H-[1,2,4]triazol-3-yl}-benzene-1,3-diol

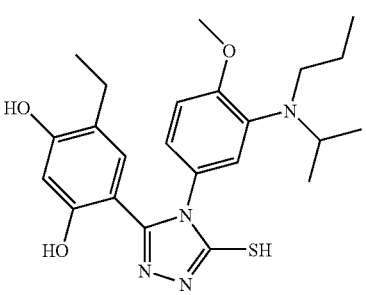

ESMS clcd for $C_{23}H_{30}N_4O_3S$: 442.20. Found: 443.3 $(M+H)^+$.

Example 182

4-[4-(4-Dimethylamino-3-methoxy-phenyl)-5-mercapto-4H-[1,2,4]triazol-3-yl]-6-ethyl-benzene-1,3-diol

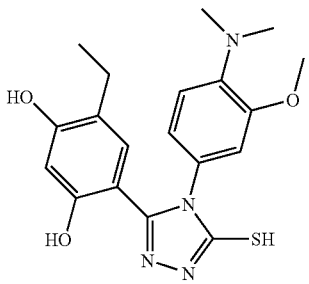

ESMS clcd for $C_{19}H_{22}N_4O_3S$: 386.14. Found: 387.2 (M+H)$^+$.

Example 183

4-Ethyl-6-[5-mercapto-4-(3-pyrrolidin-1-yl-phenyl)-4H-[1,2,4]triazol-3-yl]-benzene-1,3-diol

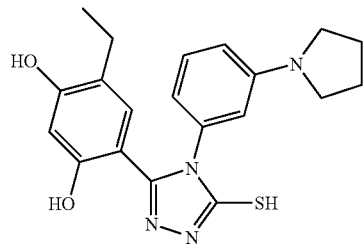

ESMS clcd for $C_{20}H_{22}N_4O_2S$: 382.15. Found: 383.2 (M+H)$^+$.

Example 184

4-[4-(3-Dimethylamino-phenyl)-5-mercapto-4H-[1,2,4]triazol-3-yl]-6-ethyl-benzene-1,3-diol

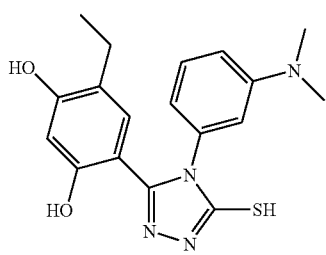

ESMS clcd for $C_{18}H_{20}N_4O_2S$: 356.13. Found: 357.2 (M+H)$^+$.

Example 185

4-Ethyl-6-{4-[3-(isopropyl-methyl-amino)-4-methoxy-phenyl]-5-mercapto-4H-[1,2,4]triazol-3-yl}-benzene-1,3-diol

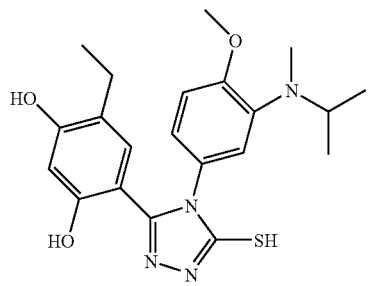

ESMS clcd for $C_{21}H_{26}N_4O_3S$: 414.17. Found: 415.2 (M+H)$^+$.

Example 186

4-[4-(3-Dimethylamino-4-methoxy-phenyl)-5-mercapto-4H-[1,2,4]triazol-3-yl]-6-ethyl-benzene-1,3-diol

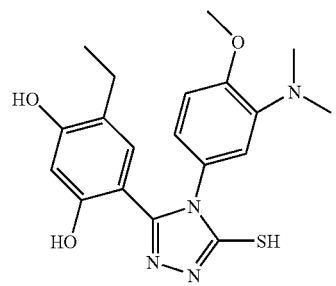

ESMS clcd for $C_{19}H_{22}N_4O_3S$: 386.14. Found: 387.2 (M+H)$^+$.

Example 187

4-Ethyl-6-{4-[3-(ethyl-methyl-amino)-4-methoxy-phenyl]-5-mercapto-4H-[1,2,4]triazol-3-yl}-benzene-1,3-diol

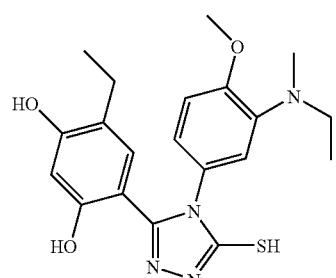

ESMS clcd for $C_{20}H_{24}N_4O_3S$: 400.16. Found: 401.2 (M+H)$^+$.

Example 188

4-Isopropyl-6-{4-[3-(isopropyl-propyl-amino)-4-methoxy-phenyl]-5-mercapto-4H-[1,2,4]triazol-3-yl}-benzene-1,3-diol

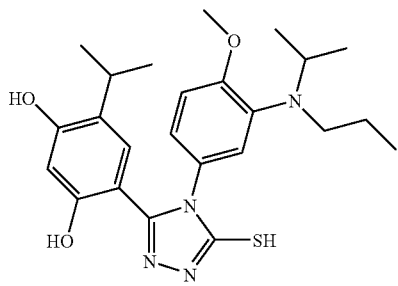

ESMS clcd for $C_{24}H_{32}N_4O_3S$: 456.22. Found: 457.3 (M+H)$^+$.

Example 189

4-Ethyl-6-{4-[3-(ethyl-isopropyl-amino)-4-methoxy-phenyl]-5-mercapto-4H-[1,2,4]triazol-3-yl}-benzene-1,3-diol

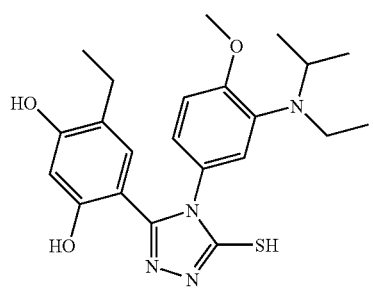

ESMS clcd for $C_{22}H_{28}N_4O_3S$: 428.19. Found: 429.3 (M+H)$^+$.

Example 190

4-Ethyl-6-[5-mercapto-4-(4-methoxy-3-morpholin-4-yl-phenyl)-4H-[1,2,4]triazol-3-yl]-benzene-1,3-diol

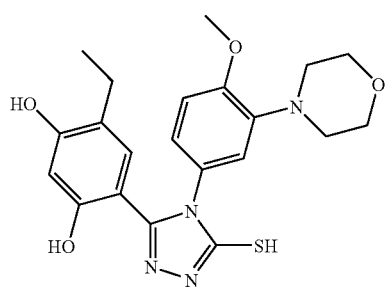

ESMS clcd for $C_{21}H_{24}N_4O_4S$: 428.15. Found: 429.2 (M+H)$^+$.

Example 191

4-Isopropyl-6-{5-mercapto-4-[4-methoxy-3-(methyl-propyl-amino)-phenyl]-4H-[1,2,4]triazol-3-yl}-benzene-1,3-diol

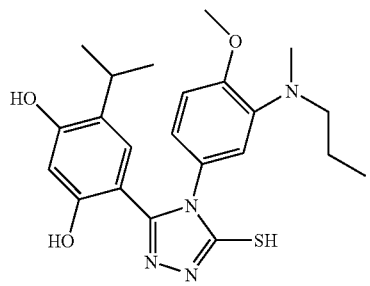

$^1$H NMR (300 MHz, DMSO-d$_6$) δ (ppm): 9.58 (s, 1H); 9.39 (s, 1H); 6.92-6.83 (m, 3H); 6.56 (d, J=1.8 Hz, 1H); 6.23 (s, 1H); 3.74 (s, 3H); 3.0-2.93 (m, 1H); 2.81 (t, J=6.9 Hz, 2H); 2.48 (s, 3H); 1.31-1.24 (m, 2H); 0.96 (d, J=6.9 Hz, 6H); 0.72 (t, J=7.2 Hz, 3H);

ESMS clcd for $C_{22}H_{28}N_4O_3S$: 428.19. Found: 429.2 (M+H)$^+$.

Example 192

4-{4-[3-(Ethyl-methyl-amino)-4-methoxy-phenyl]-5-mercapto-4H-[1,2,4]triazol-3-yl}-6-isopropyl-benzene-1,3-diol

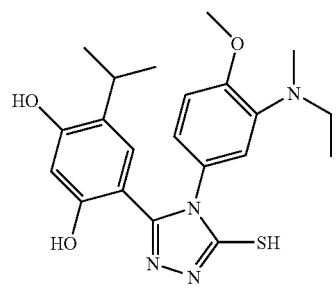

$^1$H NMR (300 MHz, DMSO-d$_6$) δ (ppm): 9.58 (s, 1H); 9.40 (s, 1H); 6.92-6.85 (m, 3H); 6.58 (d, J=1.8 Hz, 1H); 6.24 (s, 1H); 3.76 (s, 3H); 3.02-2.90 (m, 3H); 2.49 (s, 3H) 0.99 (d, J=6.9 Hz, 6H); 0.86 (t, J=7.2 Hz, 3H).

ESMS clcd for $C_{21}H_{26}N_4O_3S$: 414.17. Found: 415.1 (M+H)$^+$.

Example 193

4-Isopropyl-6-(5-mercapto-4-{4-methoxy-3-[methyl-(3-methyl-butyl)-amino]-phenyl}-4H-[1,2,4]triazol-3-yl)-benzene-1,3-diol

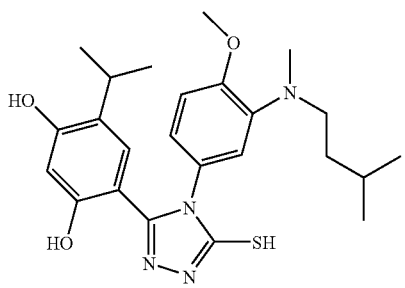

ESMS clcd for $C_{24}H_{32}N_4O_3S$: 456.22. Found: 457.2 $(M+H)^+$.

Example 194

4-Isopropyl-6-{5-mercapto-4-[4-methoxy-3-(methyl-propyl-amino)-phenyl]-4H-[1,2,4]triazol-3-yl}-benzene-1,3-diol; compound with hydrogen chloride

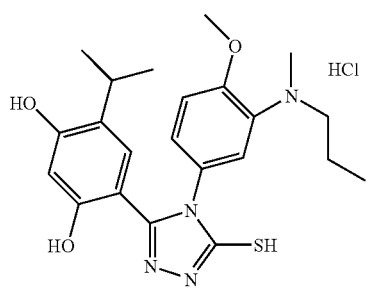

ESMS clcd for $C_{22}H_{29}ClN_4O_3S$: 464.16. Found: 429.3 $(M+H)^+$.

Example 195

4-{4-[3-(Butyl-methyl-amino)-4-methoxy-phenyl]-5-mercapto-4H-[1,2,4]triazol-3-yl}-6-isopropyl-benzene-1,3-diol

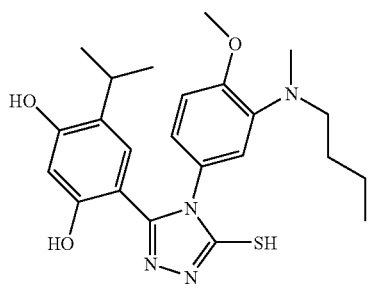

ESMS clcd for $C_{23}H_{30}N_4O_3S$: 442.20. Found: 443.3 $(M+H)^+$.

Example 196

4-{4-[3-(Isobutyl-methyl-amino)-4-methoxy-phenyl]-5-mercapto-4H-[1,2,4]triazol-3-yl}-6-isopropyl-benzene-1,3-diol

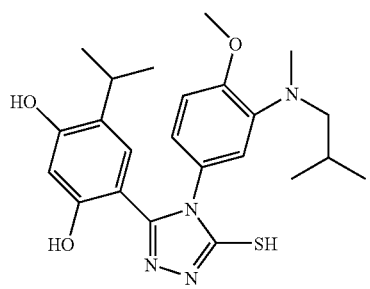

ESMS clcd for $C_{23}H_{30}N_4O_3S$: 442.20. Found: 443.1 $(M+H)^+$.

Example 197

4-(4-{3-[(2-Imidazol-1-yl-ethyl)-methyl-amino]-4-methoxy-phenyl}-5-mercapto-4H-[1,2,4]triazol-3-yl)-6-isopropyl-benzene-1,3-diol

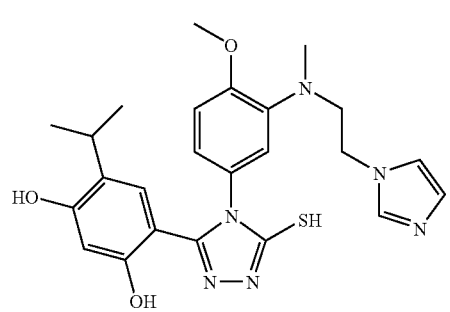

ESMS clcd for $C_{24}H_{28}N_6O_3S$: 480.19. Found: 481.1 $(M+H)^+$.

Example 198

4-(4-(3-(1H-pyrrol-1-yl)phenyl)-5-mercapto-4H-1,2,4-triazol-3-yl)-6-ethylbenzene-1,3-diol

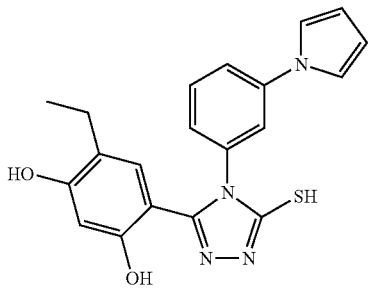

ESMS clcd for $C_{20}H_{18}N_4O_2S$: 378.12. Found: 379.1 $(M+H)^+$.

Example 199

4-(4-(4-(1H-pyrazol-1-yl)phenyl)-5-mercapto-4H-1,2,4-triazol-3-yl)-6-ethylbenzene-1,3-diol

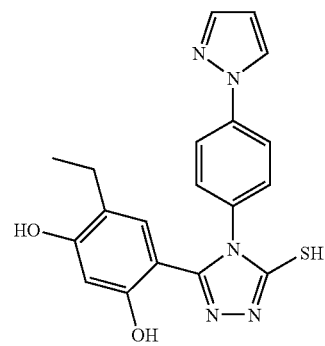

ESMS clcd for $C_{19}H_{17}N_5O_2S$: 379.11. Found: 380.1 (M+H)+.

Example 200

4-(4-(3-(dimethylamino)-4-(methylthio)phenyl)-5-mercapto-4H-1,2,4-triazol-3-yl)-6-isopropylbenzene-1,3-diol

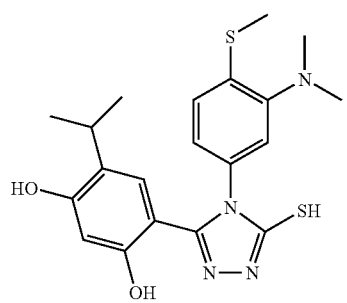

ESMS clcd for $C_{20}H_{24}N_4O_2S_2$: 416.13. Found: 417.1 (M+H)+.

Example 201

4-isopropyl-6-(5-mercapto-4-(4-methoxy-3-(propylamino)phenyl)-4H-1,2,4-triazol-3-yl)benzene-1,3-diol

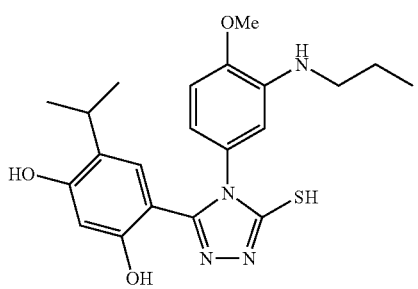

ESMS clcd for $C_{21}H_{26}N_4O_3S$: 414.17. Found: 415.1 (M+H)+.

Example 202

4-[4-(4-Amino-3-hydroxy-phenyl)-5-mercapto-4H-[1,2,4]triazol-3-yl]-6-ethyl-benzene-1,3-diol

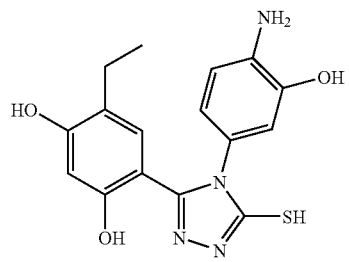

ESMS clcd for $C_{16}H_{16}N_4O_3S$: 344.09. Found: 345.1 (M+H)+.

Example 203

4-ethyl-6-(4-(3-hydroxy-4-(methylamino)phenyl)-5-mercapto-4H-1,2,4-triazol-3-yl)benzene-1,3-diol

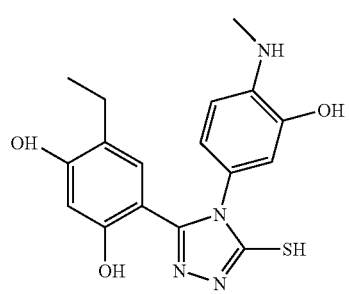

ESMS clcd for $C_{17}H_{18}N_4O_3S$: 358.11. Found: 359.1 (M+H)+

Example 204

4-(4-(3-aminophenyl)-5-mercapto-4H-1,2,4-triazol-3-yl)-6-ethylbenzene-1,3-diol

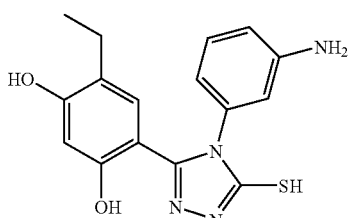

ESMS clcd for $C_{16}H_{16}N_4O_2S$: 328.10. Found: 329.1 (M+H)+.

Example 205

4-[4-(4-Dimethylamino-3-methyl-phenyl)-5-mercapto-4H-[1,2,4]triazol-3-yl]-6-ethyl-benzene-1,3-diol

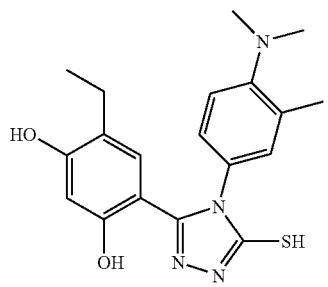

ESMS clcd for $C_{19}H_{23}N_4O_2S$: 371.1. Found: 371.1 (M+H)$^+$.

Example 206

4-[4-(3-Imidazol-1-yl-phenyl)-5-mercapto-4H-[1,2,4]triazol-3-yl]-6-isopropyl-benzene-1,3-diol

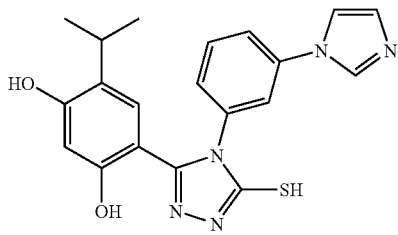

ESMS clcd. for $C_{20}H_{20}N_5O_2S$: 394.1. Found: 394.1 (M+H)$^+$.

Example 207

4-[4-(3-Imidazol-1-yl-phenyl)-5-mercapto-4H-[1,2,4]triazol-3-yl]-6-isopropyl-benzene-1,3-diol

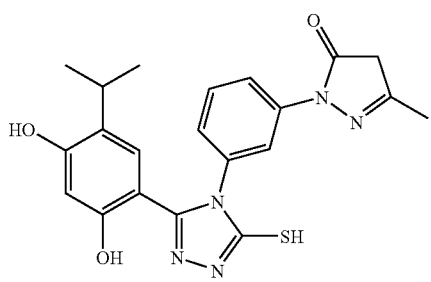

2-{3-[3-(2,4-Dihydroxy-5-isopropyl-phenyl)-5-mercapto-[1,2,4]triazol-4-yl]-phenyl}-5-methyl-2,4-dihydro-pyrazol-3-one $^1$H NMR (300 MHz, DMSO-d$_6$) δ (ppm): 9.63 (br s, 1H); 7.70-7.80 (m, 2H); 7.37-7.43 (m, 1H); 6.99-7.02 (m, 1H); 6.91 (s, 1H); 6.25 (s, 1H); 5.35 (s, 1H); 3.70 (s, 2H); 2.96 (hept, J=6.9 Hz, 1H); 2.09 (s, 3H); 0.99 (d, J=6.9 Hz, 6H);

ESMS clcd. for $C_{21}H_{22}N_5O_3S$: 424.1. Found: 424.1 (M+H)$^+$.

Example 208

Inhibition of Hsp90

Hsp90 protein was obtained from Stressgen (Cat#SPP-770). Assay buffer: 100 mM Tris-HCl, Ph 7.4, 20 mM KCl, 6 mM MgCl$_2$. Malachite green (0.0812% w/v) (M9636) and polyviny alcohol USP (2.32% w/v) (P1097) were obtained from Sigma. A Malachite Green Assay (see Methods Mol Med, 2003, 85:149 for method details) was used for examination of ATPase activity of Hsp90 protein. Briefly, Hsp90 protein in assay buffer (100 mM Tris-HCl, Ph 7.4, 20 mM KCl, 6 mM MgCl$_2$) was mixed with ATP alone (negative control) or in the presence of Geldanamycin (a positive control) or Compound 108 in a 96-well plate. Malachite green reagent was added to the reaction. The mixtures were incubated at 37° C. for 4 hours and sodium citrate buffer (34% w/v sodium citrate) was added to the reaction. The plate was read by an ELISA reader with an absorbance at 620 nm.

As can be seen in FIG. 1, 40 μM of geldanamycin, a natural product known to inhibit Hsp90 activity, the ATPase activity of Hsp90 was only slightly higher than background. 40 μM Compound 108 showed an even greater inhibition of ATPase activity of Hsp90 than geldanamycin, and even at 4 μM Compound 108 showed significant inhibition of ATPase activity of Hsp90 protein.

Example 209

Degradation of Her2 via Inhibition of Hsp90 Activity

A. Cells and Cell Culture

Human high-Her2 breast carcinoma BT474 (HTB-20), SK-BR-3 (HTB-30) and MCF-7 breast carcinoma (HTB-22) from American Type Culture Collection, VA, USA were grown in Dulbecco's modified Eagle's medium with 4 mM L-glutamine and antibiotics (100 IU/ml penicillin and 100 ug/ml streptomycine; GibcoBRL). To obtain exponential cell growth, cells were trypsinized, counted and seeded at a cell density of 0.5×10$^6$ cells/ml regularly, every 3 days. All experiments were performed on day 1 after cell passage.

B. Degradation of Her2 in Cells after Treatment with a Compound of the Invention 1. Method 1

BT-474 cells were treated with 0.5 μM, 2 μM, or 5 μM of 17AAG (a positive control) or 0.5 μM, 2 μM, or 5 μM of Compound 108 or Compound 49 overnight in DMEM medium. After treatment, each cytoplasmic sample was prepared from 1×10$^6$ cells by incubation of cell lysis buffer (#9803, cell Signaling Technology) on ice for 10 minutes. The resulting supernatant used as the cytosol fractions were dissolved with sample buffer for SDS-PAGE and run on a SDS-PAGE gel, blotted onto a nitrocellulose membrane by using semi-dry transfer. Non-specific binding to nitrocellulose was blocked with 5% skim milk in TBS with 0.5% Tween at room temperature for 1 hour, then probed with anti-Her2/ErB2 mAb (rabbit IgG, #2242, Cell Signaling) and anti-Tubulin (T9026, Sigma) as housekeeping control protein. HRP-conjugated goat anti-rabbit IgG (H+L) and HRP-conjugated horse anti-mouse IgG (H+L) were used as secondary Ab (#7074, #7076, Cell Signaling) and LumiGLO reagent, 20× Peroxide (#7003, Cell Signaling) was used for visualization.

Figure 2:
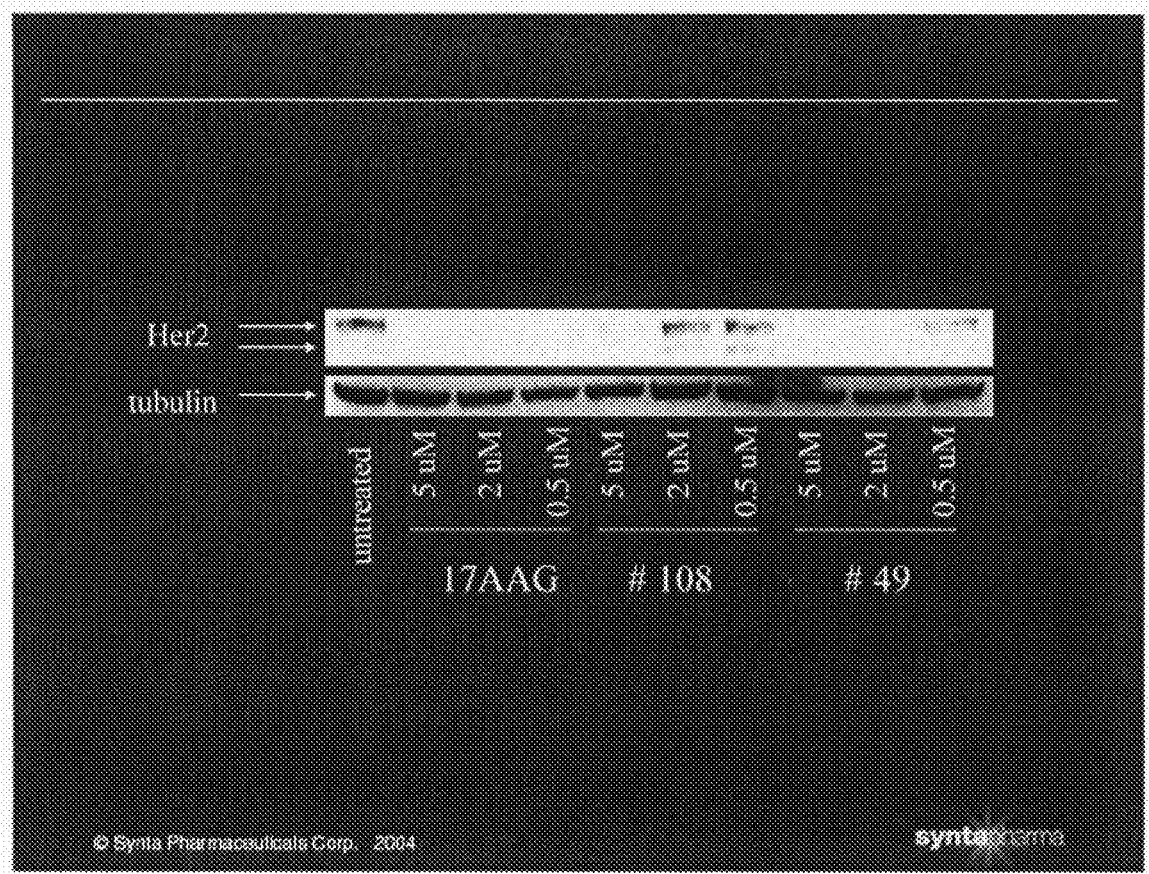
FIG. 2 is gel showing the amount of Her2, an Hsp90 client protein, in cells that are untreated, in cells that have been treated with 0.5 µM, 2 µM, or 5 µM of 17AAG, a known Hsp90 inhibitor, and in cells that have been treated with 0.5 µM, 2 µM, or 5 µM of Compound 108 or Compound 49.

As can be seen from FIG. 2, Her2, an Hsp90 client protein, is almost completely degraded when cells are treated with 5 µM of Compound 108 and partially degradated when cells are treated with 2 µM and 0.5 µM of Compound 108. Compound 49 which is even more active than Compound 108 causes complete degradation of Her2 when cells are treated with 2 µM and 5 µM and causes partial degradated when cells are treated with 0.5 µM 17AAG is a known Hsp90 inhibitor and is used as a positive control.

2. Method 2

MV-4-11 cells (20,000 cells/well) are cultured in 96-well plates and maintained at 37° C. for several hours. The cells are treated with a compound of the invention or 17AAG (a positive control) at various concentrations and incubated at 37° C. for 72 hours. Cell survival is measured with Cell Counting Kit-8 (Dojindo Laboratories, Cat. # CK04).

TABLE 8

$IC_{50}$ range of compounds of the invention for inhibition of Her2 degradation

| $IC_{50}$ Range | Compound Number |
|---|---|
| <3 µM | 8, 13, 39, 49, 63, 76, 77, 79, 87, 88, 95, 96, 100, 103, 177, 178, 185, 188, 189, 247, 248, 249, 250, 251, 252, 259 |
| 3 µM to 10 µM | 2, 5, 6, 7, 9, 14, 27, 28, 34, 36, 38, 42, 48, 64, 70, 93, 97, 108, 122, 183, 184 |
| 10 µM to 100 µM | 21, 22, 30, 51, 59, 60, 61, 62, 94, 98, 99, 102, 104, 123, 181, 182, 186, 187, 348 |

C. Fluorescent Staining of Her2 on the Surface of Cells Treated with a Compound of the Invention After treatment with a compound of the invention, cells were washed twice with 1×PBS/1% FBS, and then stained with anti-Her2-FITC (#340553, BD) for 30 min at 4° C. Cells were then washed three times in FACS buffer before the fixation in 0.5 ml 1% paraformadehydrede. Data was acquired on a FACSCalibur system. Isotype-matched controls were used to establish the non-specific staining of samples and to set the fluorescent markers. A total 10,000 events were recorded from each sample. Data were analysed by using CellQuest software (BD Biosciences). The $IC_{50}$ range for Hsp90 inhibition by compounds of the invention are listed below in Table 2.

D. Apoptosis Analysis

After treatment with the compounds of the invention, cells were washed once with 1×PBS/1% FBS, and then stained in binding buffer with FITC-conjugated Annexin V and Propidium iodide (PI) (all obtained from BD Biosciences) for 30 min at 4° C. Flow cytometric analysis was performed with FACSCalibur (BD Biosciences) and a total 10,000 events were recorded from each sample. Data were analyzed by using CellQuest software (BD Biosciences). The relative fluorescence was calculated after subtraction of the fluorescence of control.

Example 113

Compound 49 Displays Anti-tumor Activity Against the Human Tumor Cell Line MDA-MB-435S in a nude Mouse Xenograft Model The human tumor cell line, MDA-MB-435S (ATCC #HTB-129; G. Ellison, et al., *Mol. Pathol.* 55:294-299, 2002), was obtained from the American Type Culture Collection (Manassas, Va., USA). The cell line was cultured in growth media prepared from 50% Dulbecco's Modified Eagle Medium (high glucose), 50% RPMI Media 1640, 10% fetal bovine serum (FBS), 1% 100×L-glutamine, 1% 100× Penicillin-Streptomycin, 1% 100× sodium pyruvate and 1% 100× MEM non-essential amino acids. FBS was obtained from Sigma-Aldrich Corp. (St. Louis, Mo., USA), and all other reagents were obtained from Invitrogen Corp. (Carlsbad, Calif., USA). Approximately 4-5×10(6) cells that had been cryopreserved in liquid nitrogen were rapidly thawed at 37° C. and transferred to a 175 cm² tissue culture flask containing 50 ml of growth media and then incubated at 37° C. in a 5% $CO_2$ incubator. The growth media was replaced every 2-3 days until the flask became 90% confluent, typically in 5-7 days. To passage and expand the cell line, a 90% confluent flask was washed with 10 ml of room temperature phosphate buffered saline (PBS) and the cells were disassociated by adding 5 ml 1× Trypsin-EDTA (Invitrogen) and incubating at 37° C. until the cells detached from the surface of the flask. To inactivate the trypsin, 5 ml of growth media was added and then the contents of the flask were centrifuged to pellet the cells. The supernatant was aspirated and the cell pellet was resuspended in 10 ml of growth media and the cell number determined using a hemocytometer. Approximately 1-3×10 (6) cells per flask were seeded into 175 cm² flasks containing 50 ml of growth media and incubated at 37° C. in a 5% $CO_2$ incubator. When the flasks reached 90% confluence, the above passaging process was repeated until sufficient cells had been obtained for implantation into mice.

Six to eight week old, female Crl:CD-1-nuBR (nude) mice were obtained from Charles River Laboratories (Wilmington, Mass., USA). Animals were housed 4-5/cage in micro-isolators, with a 12 hr/12 hr light/dark cycle, acclimated for at least 1 week prior to use and fed normal laboratory chow ad libitum. Studies were conducted on animals between 7 and 12 weeks of age at implantation. To implant tumor cells into nude mice, the cells were trypsinized as above, washed in PBS and resuspended at a concentration of 50×10(6) cells/ml in PBS. Using a 27 gauge needle and 1 cc syringe, 0.1 ml of the cell suspension was injected into the corpus adiposum of nude mice. The corpus adiposum is a fat body located in the ventral abdominal vicera in the right quadrant of the abdomen at the juncture of the os coxae (pelvic bone) and the os femoris (femur). Tumors were then permitted to develop in vivo until they reached approximately 150 mm³ in volume, which typically required 2-3 weeks following implantation. Tumor volumes (V) were calculated by caliper measurement of the width (W), length (L) and thickness (T) of tumors using the following formula: V=0.5326×(L×W×T). Animals were randomized into treatment groups so that the average tumor volumes of each group were similar at the start of dosing.

Sock solutions of test compounds were prepared by dissolving the appropriate amounts of each compound in dimethyl sulfoxide (DMSO) by sonication in an ultrasonic water bath. Stock solutions were prepared at the start of the study, stored at −20° C. and diluted fresh each day for dosing. A solution of 20% Cremophore RH40 (polyoxyl 40 hydrogenated castor oil; BASF Corp., Aktiengesellschaft, Ludwigshafen, Germany) in 80% D5W (5% dextrose in water; Abbott Laboratories, North Chicago, Ill., USA) was also prepared by first heating 100% Cremophore RH40 at 50-60° C. until liquefied and clear, diluting 1:5 with 100% D5W, reheating again until clear and then mixing well. This solution was stored at room temperature for up to 3 months prior to use. To prepare formulations for daily dosing, DMSO stock solutions were diluted 1:10 with 20% Cremophore RH40. The final formulation for dosing contained 10% DMSO, 18%

Cremophore RH40, 3.6% dextrose and 68.4% water and the appropriate amount of test article. Animals were intraperitoneal (IP) injected with this solution at 10 ml per kg body weight on a schedule of 5 days per week (Monday thru Friday, with no dosing on Saturday and Sunday) for 3 weeks.

Figure 3:
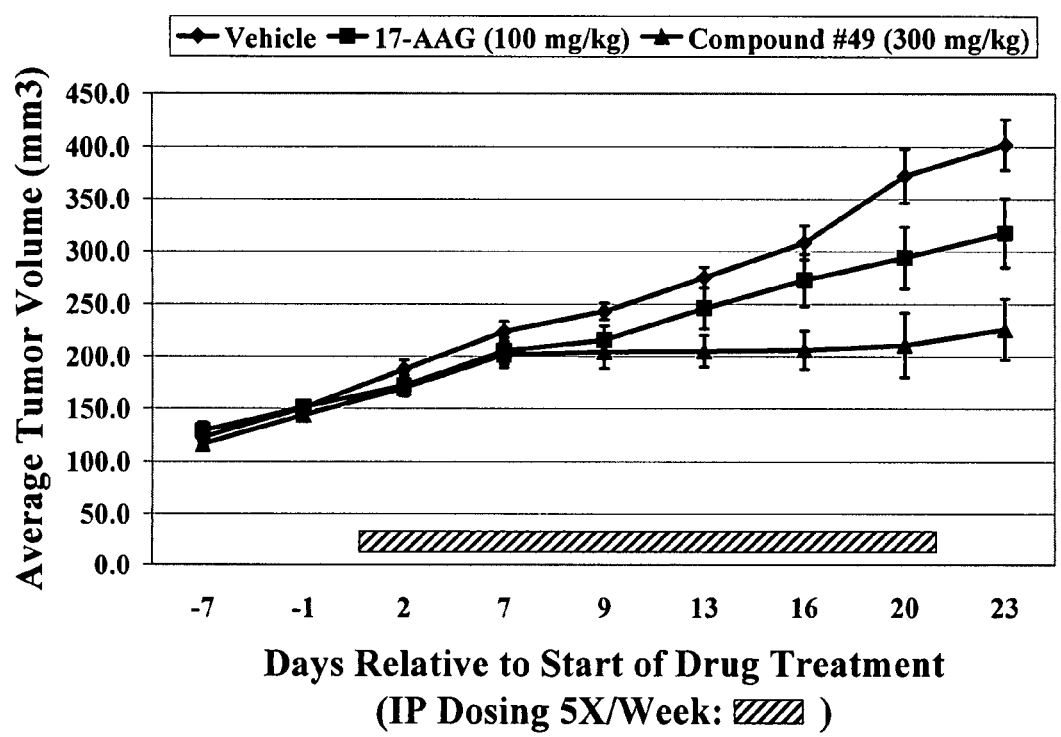
FIG. 3 displays the results of a nude mouse xenograft study to determine the effect of Compound 49 on the in vivo growth rate of the human tumor cell line MDA-MB-435S. Tumor bearing animals (8 mice/group) were intraperitoneal (IP) injected 5 times per week for 3 weeks (hatched bar) and the average tumor volumes for each group (+/−SEM) were determined every 3-5 days. Treatment with a dose of 300 mg/kg body weight of Compound 49 decreased the growth rate of MDA-MB-435S cells in nude mice to a greater extent than did a dose of 100 mg/kg body weight of the Hsp90 inhibitor 17-allylamino-17-demethoxygeldanamycin (17-AAG).
Figure 4:
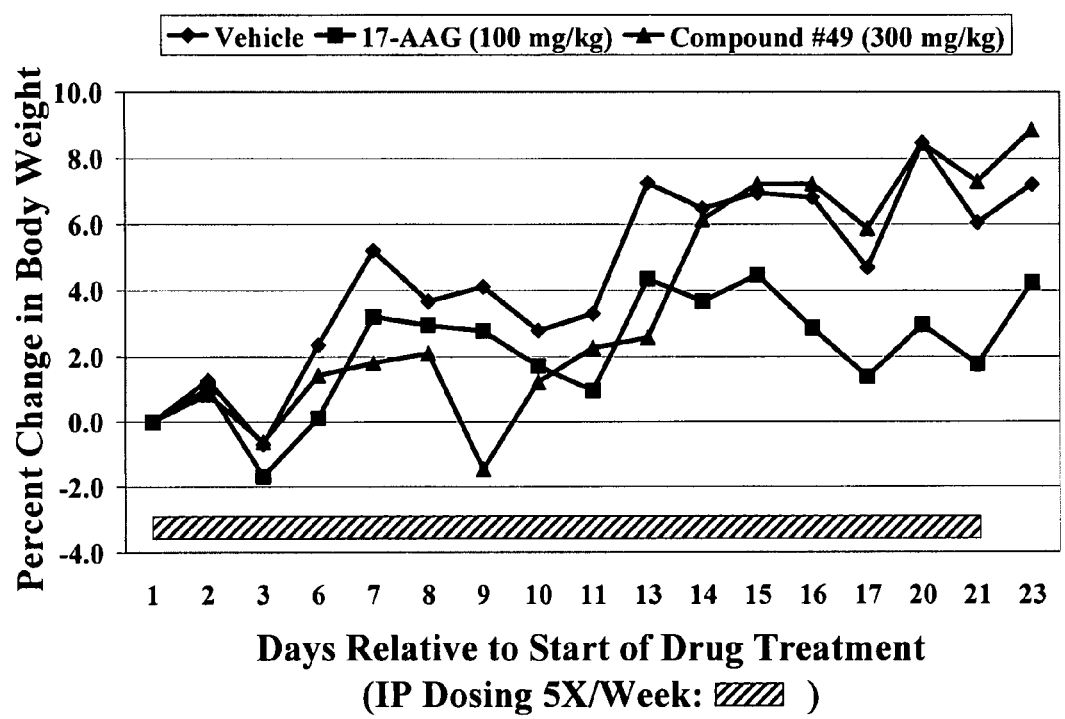
FIG. 4 demonstrates that treatment with Compound 49 did not cause toxicity in a nude mouse xenograft model using the human tumor cell line MDA-MB-435S (tumor growth data from the same study is presented in FIG. 3). Tumor bearing animals (8 mice/group) were intraperitoneal (IP) injected 5 times per week for 3 weeks (hatched bar) and the average percent changes in body weights for each group relative to the start of dosing were determined every 1-3 days (error bars not shown for clarity; mean coefficient of variation=18%). Treatment with a dose of 300 mg/kg body weight of Compound 49 was not toxic, as indicated by its lack of an effect on the body weights in animals treated with Compound 49 versus vehicle treated animals.

As shown in FIG. 3, treatment with 300 mg/kg body weight of Compound 49 decreased the growth rate of MDA-MB-435S cells in nude mice to a greater extent than did a dose of 100 mg/kg body weight of the Hsp90 inhibitor 17-AAG. This effect was not associated with significant toxicity, as shown by the lack of an effect on body weights (FIG. 4).

Example 113

Compound #226 Displays Anti-tumor Activity Against Human Non-Hodgkin's Lymphoma Tumor Cells in Mouse Xenograft Models The human non-Hodgkin's lymphoma tumor cell line, Daudi (ATCC #CCL-213; E. Klein, et al., *Cancer Res.* 28:1300-1310, 1968, the entire teachings of which are incorporated herein by reference), sub-classified as a Burkitt's lymphoma, was obtained from the American Type Culture Collection (ATCC; Manassas, Va., USA). The cells were cultured in growth media prepared with RPMI Media 1640 (high glucose), 10% fetal bovine serum (FBS), 1% 100× Penicillin-Streptomycin, 1% 100× sodium pyruvate and 1% 100×MEM non-essential amino acids. FBS was obtained from ATCC and all other reagents were obtained from Invitrogen Corp. (Carlsbad, Calif., USA). Cells that had been cryopreserved in liquid nitrogen were rapidly thawed at 37° C. and transferred to a tissue culture flask containing growth media and then incubated at 37° C. in a 5% $CO_2$ incubator. To expand the cell line, cultures were passaged 1:2 to a density of 5×10(6) cells/ml every three days by adding an equal volume of fresh growth media. When the flasks reached a density of approximately 10×10(6) cells/ml, the above passaging process was repeated until sufficient cells had been obtained for implantation into mice.

The human non-Hodgkin's lymphoma tumor cell line, SU-DHL-4 (DSMZ #ACC 495), sub-classified as a GCB-type diffuse large B-cell lymphoma, was obtained from Deutsche Sammlung von Mikroorganismen und Zellkulturen GmbH (DSMZ; Braunschweig, Germany). The cell line was cultured in growth media prepared from RPMI Media 1640 containing 10% fetal bovine serum (FBS) and 1% 100× Penicillin-Streptomycin. FBS was obtained from ATCC and all other reagents were obtained from Invitrogen Corp. (Carlsbad, Calif., USA). Approximately 3-4×10(7) cells that had been cryopreserved in liquid nitrogen were rapidly thawed at 37° C. and transferred to a 175 cm² tissue culture flask containing 50 ml of growth media and then incubated at 37° C. in a 5% $CO_2$ incubator. To passage and expand the cell line, the contents of a flask were centrifuged to pellet the cells, the supernatant was aspirated and the cell pellet was resuspended in 10 ml of growth media and the cell number determined using a hemocytometer. Approximately 3-4×10(7) cells per flask were seeded into 175 cm² flasks containing 50 ml of growth media and incubated at 37° C. in a 5% $CO_2$ incubator. The above passaging process was repeated every 2-3 days until sufficient cells had been obtained for implantation into mice.

Seven to eight week old, female CB17/Icr-Prkdc$^{scid}$/Crl (SCID) mice were obtained from Charles River Laboratories (Wilmington, Mass., USA). Animals were housed 4-5/cage in micro-isolators, with a 12 hr/12 hr light/dark cycle, acclimated for at least 1 week prior to use and fed normal laboratory chow ad libitum. Studies were conducted on animals that were between 8 and 12 weeks of age at the time of tumor cell implantation. To implant Daudi tumor cells into SCID mice, cell cultures were centrifuged to pellet the cells, the supernatant was aspirated and the cell pellet was resuspended in 10 ml of growth media and the cell number determined using a hemocytometer, washed in phosphate-buffered saline (PBS) and resuspended at a concentration of 50×10(6) cells/ml in 50% non-supplemented RPMI Media 1640 and 50% Matrigel Basement Membrane Matrix (#354234; BD Biosciences; Bedford, Mass., USA). Using a 27 gauge needle and 1 cc syringe, 0.1 ml of the cell suspension was injected subcutaneously into the shaved flanks of SCID mice. To implant SU-DHL-4 tumor cells into SCID mice, cell cultures were centrifuged to pellet the cells, the supernatant was aspirated and the cell pellet was resuspended in 10 ml of growth media and the cell number determined using a hemocytometer, washed in PBS and resuspended at a concentration of 10×10(7) cells/ml in 50% PBS and 50% Matrigel Basement Membrane Matrix (#354234; BD Biosciences; Bedford, Mass., USA). Using a 27 gauge needle and 1 cc syringe, 0.1 ml of the cell suspension was injected subcutaneously into the shaved flanks of SCID mice.

Tumors were then permitted to develop in vivo until the majority reached 100-200 mm³ in tumor volume, which typically required 2-3 weeks following implantation. Animals with oblong, very small or large tumors were discarded, and only animals carrying tumors that displayed consistent growth rates were selected for studies. Tumor volumes (V) were calculated by caliper measurement of the width (W), length (L) and thickness (T) of tumors using the following formula: V=0.5236×(L×W×T). Animals were randomized into treatment groups so that the median tumor volumes of each group were similar at the start of dosing. % T/C values, as a measure of efficacy, were determined as follows:

(i) If $\Delta T>0$: % T/C=($\Delta T/\Delta C$)×100
(ii) If $\Delta T<0$: % T/C=($\Delta T/T_0$)×100
(iii) $\Delta T$=Change in median tumor volume between start of dosing and the end of study.
(iv) $\Delta C$=Change in median tumor volume between start of dosing and the end of study.
(v) $T_0$=Median tumor volume at start of dosing.

To formulate Compound #226 in DRD, stock solutions of the test article were prepared by dissolving the appropriate amounts of the compound in dimethyl sulfoxide (DMSO) by sonication in an ultrasonic water bath. Stock solutions were prepared weekly, stored at −20° C. and diluted fresh each day for dosing. A solution of 20% Cremophore RH40 (polyoxyl 40 hydrogenated castor oil; BASF Corp., Aktiengesellschaft, Ludwigshafen, Germany) in 5% dextrose in water (Abbott Laboratories, North Chicago, Ill., USA) was also prepared by first heating 100% Cremophore RH40 at 50-60° C. until liquefied and clear, diluting 1:5 with 100% D5W, reheating again until clear and then mixing well. This solution was stored at room temperature for up to 3 months prior to use. To prepare DRD formulations for daily dosing, DMSO stock solutions were diluted 1:10 with 20% Cremophore RH40. The final DRD formulation for dosing contained 10% DMSO, 18% Cremophore RH40, 3.6% dextrose, 68.4% water and the appropriate amount of test article. Animals were intravenously (i.v.) injected with these formulations at 10 ml per kg body weight on schedules of either 2 days per week (Tuesday and Friday) for a total of 4 doses, or 5 days per week (Monday, Tuesday, Wednesday, Thursday and Friday, with no dosing on Saturday and Sunday) for a total of 15 doses.

Figure 5:
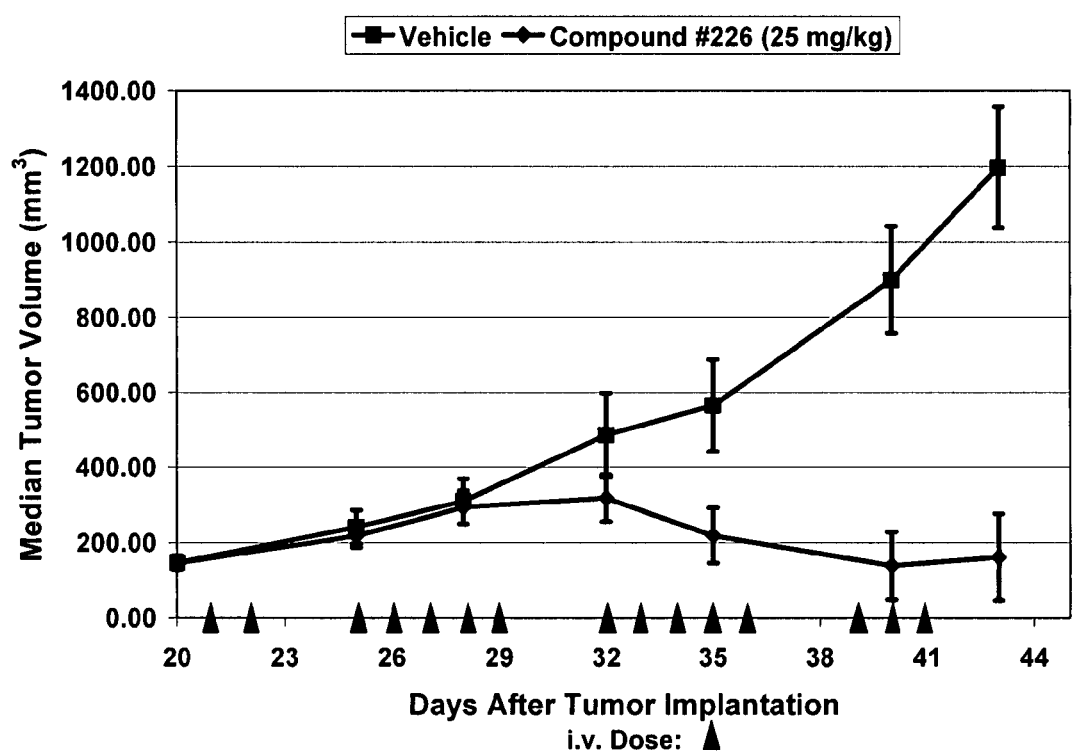
FIG. 5 shows the results of a SCID mouse xenograft study to determine the effects of Compound #226 on the in vivo growth rate of the human non-Hodgkin's lymphoma tumor cell line Daudi. Tumor bearing animals (8 mice/group) were i.v. injected 5 times per week for a total of 15 doses (arrowheads) and the median tumor volumes for each group (error bars represent SEM) were determined every 3-5 days. Treatment with a dose of 25 mg/kg body weight of Compound #226 substantially inhibited tumor growth, with a % T/C value of 1.5. Overt toxicity was not observed, with the Compound #226-treated group having an average bodyweight loss relative to the start of the study of −1.0% (+/−3.1 SEM) on day 41.

As shown in FIG. 5, treatment 5 times per week with a dose of 25 mg/kg body weight of Compound #226 substantially decreased the growth rate of Daudi cells in SCID mice, with a % T/C value of 1.5. This effect was not associated with overt toxicity, with the Compound #226-treated group having an average bodyweight loss −1.0% (+/−3.1 SEM) over the course of the study.

Figure 6:
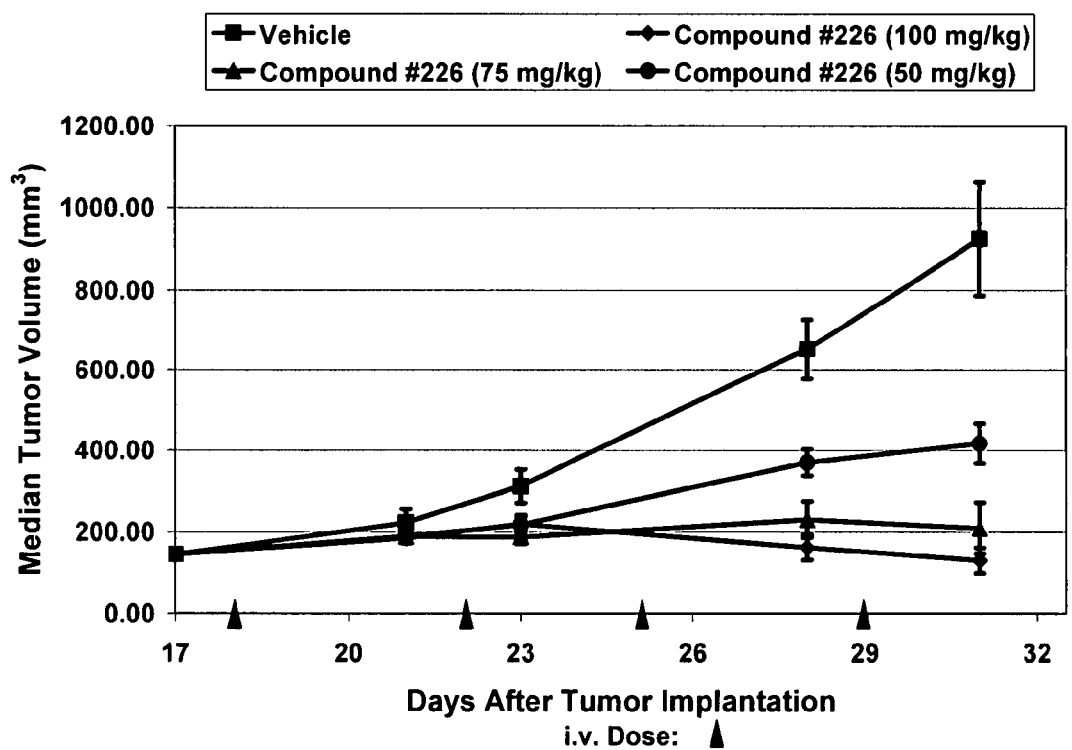
FIG. 6 shows the results of a SCID mouse xenograft study to determine the effects of Compound #226 on the in vivo growth rate of the human non-Hodgkin's lymphoma tumor cell line SU-DHL-4. Tumor bearing animals (8 mice/group) were i.v. injected 2 times per week for a total of 4 doses (arrowheads) and the median tumor volumes for each group (error bars represent SEM) were determined every 2-5 days. Treatment with doses of 50, 75 and 100 mg/kg body weight of Compound #226 substantially inhibited tumor growth, with % T/C values of 34.9, 8.1 and −10.4, respectively. Overt toxicity was not observed, with the highest dose group treated with 100 mg/kg Compound #226 having an average bodyweight loss relative to the start of the study of −4.2% (+/−0.6 SEM) on day 31.

As shown in FIG. 6, treatment 2 times per week with doses of 50, 75 and 100 mg/kg body weight of Compound #226 substantially decreased the growth rate of SU-DHL-4 cells in SCID mice, with % T/C values of 34.9, 8.1 and −10.4, respectively. This effect was not associated with overt toxicity, with the Compound #226-treated group having an average bodyweight loss −1.0% (+/−3.1 SEM) over the course of the study.

All publications, patent applications, patents, and other documents cited herein are incorporated by reference in their entirety. In case of conflict, the present specification, including definitions, will control. In addition, the materials, methods, and examples are illustrative only and not intended to be limiting.

B. Degradation of Her2 in Cells after Treatment with a Compound of the Invention 1. Method 1

BT-474 cells were treated with 0.5 μM, 2 μM, or 5 μM of 17AAG (a positive control) or 0.5 μM, 2 μM, or 5 μM of Compound 108 or Compound 49 overnight in DMEM medium. After treatment, each cytoplasmic sample was prepared from 1×10$^6$ cells by incubation of cell lysis buffer (#9803, cell Signaling Technology) on ice for 10 minutes. The resulting supernatant used as the cytosol fractions were dissolved with sample buffer for SDS-PAGE and run on a SDS-PAGE gel, blotted onto a nitrocellulose membrane by using semi-dry transfer. Non-specific binding to nitrocellulose was blocked with 5% skim milk in TBS with 0.5% Tween at room temperature for 1 hour, then probed with anti-Her2/ErB2 mAb (rabbit IgG, #2242, Cell Signaling) and anti-Tubulin (T9026, Sigma) as housekeeping control protein. HRP-conjugated goat anti-rabbit IgG (H+L) and HRP-conjugated horse anti-mouse IgG (H+L) were used as secondary Ab (#7074. #7076, Cell Signaling) and LumiGLO reagent, 20× Peroxide (#7003, Cell Signaling) was used for visualization.

As can be seen from FIG. 2, Her2, an Hsp90 client protein, is almost completely degraded when cells are treated with 5 μM of Compound 108 and partially degradated when cells are treated with 2 μM and 0.5 μM of Compound 108. Compound 49 which is even more active than Compound 108 causes complete degradation of Her2 when cells are treated with 2 μM and 5 μM and causes partial degradated when cells are treated with 0.5 μM 17AAG is a known Hsp90 inhibitor and is used as a positive control.

2. Method 2

MV-4-11 cells (20,000 cells/well) are cultured in 96-well plates and maintained at 37° C. for several hours. The cells are treated with a compound of the invention or 17AAG (a positive control) at various concentrations and incubated at 37° C. for 72 hours. Cell survival is measured with Cell Counting Kit-8 (Dojindo Laboratories, Cat. # CK04).

TABLE 8

IC$_{50}$ range of compounds of the invention for inhibition of Her2 degradation

| IC$_{50}$ Range | Compound Number |
|---|---|
| <3 μM | 8, 13, 39, 49, 63, 76, 77, 79, 87, 88, 95, 96, 100, 103, 177, 178, 185, 188, 189, 247, 248, 249, 250, 251, 252, 259 |
| 3 μM to 10 μM | 2, 5, 6, 7, 9, 14, 27, 28, 34, 36, 38, 42, 48, 64, 70, 93, 97, 108, 122, 183, 184 |

TABLE 8-continued

IC$_{50}$ range of compounds of the invention for inhibition of Her2 degradation

| IC$_{50}$ Range | Compound Number |
|---|---|
| 10 μM to 100 μM | 21, 22, 30, 51, 59, 60, 61, 62, 94, 98, 99, 102, 104, 123, 181, 182, 186, 187, 348 |

C. Fluorescent Staining of Her2 on the Surface of Cells Treated with a Compound of the Invention After treatment with a compound of the invention, cells were washed twice with 1×PBS/1% FBS, and then stained with anti-Her2-FITC (#340553, BD) for 30 min at 4° C. Cells were then washed three times in FACS buffer before the fixation in 0.5 ml 1% paraformadehyrede. Data was acquired on a FACSCalibur system. Isotype-matched controls were used to establish the non-specific staining of samples and to set the fluorescent markers. A total 10,000 events were recorded from each sample. Data were analysed by using CellQuest software (BD Biosciences). The IC$_{50}$ range for Hsp90 inhibition by compounds of the invention are listed below in Table 2.

D. Apoptosis Analysis

After treatment with the compounds of the invention, cells were washed once with 1×PBS/1% FBS, and then stained in binding buffer with FITC-conjugated Annexin V and Propidium iodide (PI) (all obtained from BD Biosciences) for 30 min at 4° C. Flow cytometric analysis was performed with FACSCalibur (BD Biosciences) and a total 10,000 events were recorded from each sample. Data were analyzed by using CellQuest software (BD Biosciences). The relative fluorescence was calculated after subtraction of the fluorescence of control.

Example 113

Compound 49 Displays Anti-tumor Activity Against the Human Tumor Cell Line MDA-MB-435S in a nude Mouse Xenograft Model The human tumor cell line, MDA-MB-435S (ATCC #HTB-129; G. Ellison, et al., *Mol. Pathol.* 55:294-299, 2002), was obtained from the American Type Culture Collection (Manassas, Va., USA). The cell line was cultured in growth media prepared from 50% Dulbecco's Modified Eagle Medium (high glucose), 50% RPMI Media 1640, 10% fetal bovine serum (FBS), 1% 100×L-glutamine, 1% 100× Penicillin-Streptomycin, 1% 100× sodium pyruvate and 1% 100× MEM non-essential amino acids. FBS was obtained from Sigma-Aldrich Corp. (St. Louis, Mo., USA), and all other reagents were obtained from Invitrogen Corp. (Carlsbad, Calif., USA). Approximately 4-5×10(6) cells that had been cryopreserved in liquid nitrogen were rapidly thawed at 37° C. and transferred to a 175 cm$^2$ tissue culture flask containing 50 ml of growth media and then incubated at 37° C. in a 5% CO$_2$ incubator. The growth media was replaced every 2-3 days until the flask became 90% confluent, typically in 5-7 days. To passage and expand the cell line, a 90% confluent flask was washed with 10 ml of room temperature phosphate buffered saline (PBS) and the cells were disassociated by adding 5 ml 1× Trypsin-EDTA (Invitrogen) and incubating at 37° C. until the cells detached from the surface of the flask. To inactivate the trypsin, 5 ml of growth media was added and then the contents of the flask were centrifuged to pellet the cells. The supernatant was aspirated and the cell pellet was resuspended in 10 ml of growth media and the cell number determined using a hemocytometer. Approximately 1-3×10(6) cells per flask were seeded into 175 cm² flasks containing 50 ml of growth media and incubated at 37° C. in a 5% $CO_2$ incubator. When the flasks reached 90% confluence, the above passaging process was repeated until sufficient cells had been obtained for implantation into mice.

Six to eight week old, female Crl:CD-1-nuBR (nude) mice were obtained from Charles River Laboratories (Wilmington, Mass., USA). Animals were housed 4-5/cage in micro-isolators, with a 12 hr/12 hr light/dark cycle, acclimated for at least 1 week prior to use and fed normal laboratory chow ad libitum. Studies were conducted on animals between 7 and 12 weeks of age at implantation. To implant tumor cells into nude mice, the cells were trypsinized as above, washed in PBS and resuspended at a concentration of 50×10(6) cells/ml in PBS. Using a 27 gauge needle and 1 cc syringe, 0.1 ml of the cell suspension was injected into the corpus adiposum of nude mice. The corpus adiposum is a fat body located in the ventral abdominal vicera in the right quadrant of the abdomen at the juncture of the os coxae (pelvic bone) and the os femoris (femur). Tumors were then permitted to develop in vivo until they reached approximately 150 mm³ in volume, which typically required 2-3 weeks following implantation. Tumor volumes (V) were calculated by caliper measurement of the width (W), length (L) and thickness (T) of tumors using the following formula: $V=0.5326 \times (L \times W \times T)$. Animals were randomized into treatment groups so that the average tumor volumes of each group were similar at the start of dosing.

Sock solutions of test compounds were prepared by dissolving the appropriate amounts of each compound in dimethyl sulfoxide (DMSO) by sonication in an ultrasonic water bath. Stock solutions were prepared at the start of the study, stored at −20° C. and diluted fresh each day for dosing. A solution of 20% Cremophore RH40 (polyoxyl 40 hydrogenated castor oil; BASF Corp., Aktiengesellschaft, Ludwigshafen, Germany) in 80% D5W (5% dextrose in water; Abbott Laboratories, North Chicago, Ill., USA) was also prepared by first heating 100% Cremophore RH40 at 50-60° C. until liquefied and clear, diluting 1:5 with 100% D5W, reheating again until clear and then mixing well. This solution was stored at room temperature for up to 3 months prior to use. To prepare formulations for daily dosing, DMSO stock solutions were diluted 1:10 with 20% Cremophore RH40. The final formulation for dosing contained 10% DMSO, 18% Cremophore RH40, 3.6% dextrose and 68.4% water and the appropriate amount of test article. Animals were intraperitoneal (IP) injected with this solution at 10 ml per kg body weight on a schedule of 5 days per week (Monday thru Friday, with no dosing on Saturday and Sunday) for 3 weeks.

As shown in FIG. 3, treatment with 300 mg/kg body weight of Compound 49 decreased the growth rate of MDA-MB-435S cells in nude mice to a greater extent than did a dose of 100 mg/kg body weight of the Hsp90 inhibitor 17-AAG. This effect was not associated with significant toxicity, as shown by the lack of an effect on body weights (FIG. 4).

Example 113

Compound #226 Displays Anti-tumor Activity Against Human Non-Hodgkin's Lymphoma Tumor Cells in Mouse Xenograft Models The human non-Hodgkin's lymphoma tumor cell line, Daudi (ATCC #CCL-213; E. Klein, et al., *Cancer Res.* 28:1300-1310, 1968, the entire teachings of which are incorporated herein by reference), sub-classified as a Burkitt's lymphoma, was obtained from the American Type Culture Collection (ATCC; Manassas, Va., USA). The cells were cultured in growth media prepared with RPMI Media 1640 (high glucose), 10% fetal bovine serum (FBS), 1% 100× Penicillin-Streptomycin, 1% 100× sodium pyruvate and 1% 100×MEM non-essential amino acids. FBS was obtained from ATCC and all other reagents were obtained from Invitrogen Corp. (Carlsbad, Calif., USA). Cells that had been cryopreserved in liquid nitrogen were rapidly thawed at 37° C. and transferred to a tissue culture flask containing growth media and then incubated at 37° C. in a 5% $CO_2$ incubator. To expand the cell line, cultures were passaged 1:2 to a density of 5×10(6) cells/ml every three days by adding an equal volume of fresh growth media. When the flasks reached a density of approximately 10×10(6) cells/ml, the above passaging process was repeated until sufficient cells had been obtained for implantation into mice.

The human non-Hodgkin's lymphoma tumor cell line, SU-DHL-4 (DSMZ #ACC 495), sub-classified as a GCB-type diffuse large B-cell lymphoma, was obtained from Deutsche Sammlung von Mikroorganismen und Zellkulturen GmbH (DSMZ; Braunschweig, Germany). The cell line was cultured in growth media prepared from RPMI Media 1640 containing 10% fetal bovine serum (FBS) and 1% 100× Penicillin-Streptomycin. FBS was obtained from ATCC and all other reagents were obtained from Invitrogen Corp. (Carlsbad, Calif., USA). Approximately 3-4×10(7) cells that had been cryopreserved in liquid nitrogen were rapidly thawed at 37° C. and transferred to a 175 cm² tissue culture flask containing 50 ml of growth media and then incubated at 37° C. in a 5% $CO_2$ incubator. To passage and expand the cell line, the contents of a flask were centrifuged to pellet the cells, the supernatant was aspirated and the cell pellet was resuspended in 10 ml of growth media and the cell number determined using a hemocytometer. Approximately 3-4×10(7) cells per flask were seeded into 175 cm² flasks containing 50 ml of growth media and incubated at 37° C. in a 5% $CO_2$ incubator. The above passaging process was repeated every 2-3 days until sufficient cells had been obtained for implantation into mice.

Seven to eight week old, female CB17/Icr-Prkdc$^{scid}$/Crl (SCID) mice were obtained from Charles River Laboratories (Wilmington, Mass., USA). Animals were housed 4-5/cage in micro-isolators, with a 12 hr/12 hr light/dark cycle, acclimated for at least 1 week prior to use and fed normal laboratory chow ad libitum. Studies were conducted on animals that were between 8 and 12 weeks of age at the time of tumor cell implantation. To implant Daudi tumor cells into SCID mice, cell cultures were centrifuged to pellet the cells, the supernatant was aspirated and the cell pellet was resuspended in 10 ml of growth media and the cell number determined using a hemocytometer, washed in phosphate-buffered saline (PBS) and resuspended at a concentration of 50×10(6) cells/ml in 50% non-supplemented RPMI Media 1640 and 50% Matrigel Basement Membrane Matrix (#354234; BD Biosciences; Bedford, Mass., USA). Using a 27 gauge needle and 1 cc syringe, 0.1 ml of the cell suspension was injected subcutaneously into the shaved flanks of SCID mice. To implant SU-DHL-4 tumor cells into SCID mice, cell cultures were centrifuged to pellet the cells, the supernatant was aspirated and the cell pellet was resuspended in 10 ml of growth media and the cell number determined using a hemocytometer, washed in PBS and resuspended at a concentration of 10×10(7) cells/ml in 50% PBS and 50% Matrigel Basement Membrane Matrix (#354234; BD Biosciences; Bedford, Mass., USA). Using a 27 gauge needle and 1 cc syringe, 0.1 ml of the cell suspension was injected subcutaneously into the shaved flanks of SCID mice.

Tumors were then permitted to develop in vivo until the majority reached 100-200 mm³ in tumor volume, which typically required 2-3 weeks following implantation. Animals with oblong, very small or large tumors were discarded, and only animals carrying tumors that displayed consistent growth rates were selected for studies. Tumor volumes (V) were calculated by caliper measurement of the width (W), length (L) and thickness (T) of tumors using the following formula: V=0.5236×(L×W×T). Animals were randomized into treatment groups so that the median tumor volumes of each group were similar at the start of dosing. % T/C values, as a measure of efficacy, were determined as follows:

(i) If ΔT>0: % T/C=(ΔT/ΔC)×100

(ii) If ΔT<0: % T/C=(ΔT/T$_0$)×100

(iii) ΔT=Change in median tumor volume between start of dosing and the end of study.

(iv) ΔC=Change in median tumor volume between start of dosing and the end of study.

(v) T$_0$=Median tumor volume at start of dosing.

To formulate Compound #226 in DRD, stock solutions of the test article were prepared by dissolving the appropriate amounts of the compound in dimethyl sulfoxide (DMSO) by sonication in an ultrasonic water bath. Stock solutions were prepared weekly, stored at −20° C. and diluted fresh each day for dosing. A solution of 20% Cremophore RH40 (polyoxyl 40 hydrogenated castor oil; BASF Corp., Aktiengesellschaft, Ludwigshafen, Germany) in 5% dextrose in water (Abbott Laboratories, North Chicago, Ill., USA) was also prepared by first heating 100% Cremophore RH40 at 50-60° C. until liquefied and clear, diluting 1:5 with 100% D5W, reheating again until clear and then mixing well. This solution was stored at room temperature for up to 3 months prior to use. To prepare DRD formulations for daily dosing, DMSO stock solutions were diluted 1:10 with 20% Cremophore RH40. The final DRD formulation for dosing contained 10% DMSO, 18% Cremophore RH40, 3.6% dextrose, 68.4% water and the appropriate amount of test article. Animals were intravenously (i.v.) injected with these formulations at 10 ml per kg body weight on schedules of either 2 days per week (Tuesday and Friday) for a total of 4 doses, or 5 days per week (Monday, Tuesday, Wednesday, Thursday and Friday, with no dosing on Saturday and Sunday) for a total of 15 doses.

As shown in FIG. 5, treatment 5 times per week with a dose of 25 mg/kg body weight of Compound #226 substantially decreased the growth rate of Daudi cells in SCID mice, with a % T/C value of 1.5. This effect was not associated with overt toxicity, with the Compound #226-treated group having an average bodyweight loss −1.0% (+/−3.1 SEM) over the course of the study.

As shown in FIG. 6, treatment 2 times per week with doses of 50, 75 and 100 mg/kg body weight of Compound #226 substantially decreased the growth rate of SU-DHL-4 cells in SCID mice, with % T/C values of 34.9, 8.1 and −10.4, respectively. This effect was not associated with overt toxicity, with the Compound #226-treated group having an average body-weight loss −1.0% (+/−3.1 SEM) over the course of the study.

All publications, patent applications, patents, and other documents cited herein are incorporated by reference in their entirety. In case of conflict, the present specification, including definitions, will control. In addition, the materials, methods, and examples are illustrative only and not intended to be limiting.

What is claimed is:

1. A method of treating a B-cell non-Hodgkin's lymphoma in a subject, comprising administering to the subject an effective amount of a compound represented by the following formula:

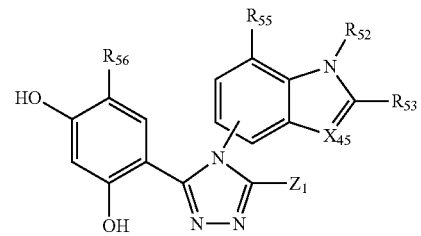

(XXXII)

or a tautomer or a pharmaceutically acceptable salt thereof, wherein:

$X_{45}$ is $CR_{54}$;

$Z_1$ is —OH or —SH;

$R_{52}$ is selected from the group consisting of —H, methyl, ethyl, n-propyl, isopropyl, n-butyl, n-pentyl, n-hexyl, —(CH$_2$)$_2$OCH$_3$, —CH$_2$C(O)OH, and —C(O)N(CH$_3$)$_2$;

$R_{53}$ and $R_{54}$ are each, independently, —H, methyl, ethyl, or isopropyl;

$R_{55}$ is selected from the group consisting of —H, —OH, —OCH$_3$, and —OCH$_2$CH$_3$; and $R_{56}$ is selected from the group consisting of —H, methyl, ethyl, isopropyl, and cyclopropyl.

2. The method of claim 1, wherein $Z_1$ is —OH.

3. The method of claim 1, wherein $Z_1$ is —SH.

4. The method of claim 1, wherein $R_{53}$ is H or a lower alkyl.

5. The method of claim 1, wherein $R_{54}$ is H or a lower alkyl.

6. The method of claim 1, wherein the compound is selected from the group consisting of:

3-(2,4-dihydroxyphenyl)-4-(1-ethyl-indol-4-yl)-5-mercapto-[1,2,4]triazole, 3-(2,4-dihydroxyphenyl)-4-(1-isopropyl-indol-4-yl)-5-mercapto-[1,2,4]triazole, 3-(2,4-dihydroxyphenyl)-4-(indol-4-yl)-5-mercapto-[1,2,4]triazole, 3-(2,4-dihydroxyphenyl)-4-(1-methoxyethyl-indol-4-yl)-5-mercapto-[1,2,4]triazole, 3-(2,4-dihydroxy-5-ethyl-phenyl)-4-(1-isopropyl-indol-4-yl)-5-mercapto-[1,2,4]triazole, 3-(2,4-dihydroxyphenyl)-4-(1-dimethylcarbamoyl-indol-4-yl)-5-mercapto-[1,2,4]triazole, 3-(2,4-dihydroxy-5-ethyl-phenyl)-4-(1-propyl-indol-4-yl)-5-mercapto-[1,2,4]triazole, 3-(2,4-dihydroxy-5-ethyl-phenyl)-4-(1,2,3-trimethyl-indol-5-yl)-5-mercapto-[1,2,4]triazole, 3-(2,4-dihydroxy-5-ethyl-phenyl)-4-(2,3-dimethyl-indol-5-yl)-5-mercapto-[1,2,4]triazole, 3-(2,4-dihydroxy-5-ethyl-phenyl)-4-(1-acetyl-2,3-dimethyl-indol-5-yl)-5-mercapto-[1,2,4]triazole, 3-(2,4-dihydroxy-5-ethyl-phenyl)-4-(1-isopropyl-7-methoxy-indol-4-yl)-5-mercapto-[1,2,4]triazole, 3-(2,4-dihydroxy-5-ethyl-phenyl)-4-(1-propyl-2,3-dimethyl-indol-5-yl)-5-mercapto-[1,2,4]triazole, 3-(2,4-dihydroxy-5-ethyl-phenyl)-4-(1-n-butyl-indol-4-yl)-5-mercapto-[1,2,4]triazole, 3-(2,4-dihydroxy-5-ethyl-phenyl)-4-(1-n-pentyl-indol-4-yl)-5-mercapto-[1,2,4]triazole, 3-(2,4-dihydroxy-5-ethyl-phenyl)-4-(1-n-hexyl-indol-4-yl)-5-mercapto-[1,2,4]triazole,
3-(2,4-dihydroxy-5-cyclopropyl-phenyl)-4-(1-(1-methyl-cyclopropyl)-indol-4-yl)-5-mercapto-[1,2,4]triazole,
3-(2,4-dihydroxy-5-cyclopropyl-phenyl)-4-(1-isopropyl-7-methoxy-indol-4-yl)-5-mercapto-[1,2,4]triazole,
3-(2,4-dihydroxy-5-cyclopropyl-phenyl)-4-(1,2,3-trimethyl-indol-5-yl)-5-mercapto-[1,2,4]triazole,
3-(2,4-dihydroxy-5-ethyl-phenyl)-4-(1-isopropyl-7-methoxy-indol-4-yl)-5-mercapto-[1,2,4]triazole disodium salt,
3-(2,4-dihydroxy-5-tert-butyl-phenyl)-4-(1-isopropyl-7-methoxy-indol-4-yl)-5-mercapto-[1,2,4]triazole,
3-(2,4-dihydroxy-5-cyclopropyl-phenyl)-4-(1-propyl-7-methoxy-indol-4-yl)-5-mercapto-[1,2,4]triazole,
3-(2,4-dihydroxy-5-ethyl-phenyl)-4-(1-methyl-3-ethyl-indol-5-yl)-5-mercapto-[1,2,4]triazole,
3-(2,4-dihydroxy-5-ethyl-phenyl)-4-(1,3-dimethyl-indol-5-yl)-5-mercapto-[1,2,4]triazole,
3-(2,4-dihydroxy-5-isopropyl-phenyl)-4-(1-isopropyl-7-methoxy-indol-4-yl)-5-mercapto-[1,2,4]triazole,
3-(2,4-dihydroxy-5-ethyl-phenyl)-4-(1-methyl-3-isopropyl-indol-5-yl)-5-mercapto-[1,2,4]triazole,
3-(2,4-dihydroxy-5-ethyl-phenyl)-4-(N-ethyl-carbozol-7-yl)-5-mercapto-[1,2,4]triazole,
3-(2,4-dihydroxy-5-ethyl-phenyl)-4-(1-isopropyl-7-hydroxy-indol-4-yl)-5-mercapto-[1,2,4]triazole,
3-(2,4-dihydroxy-5-ethyl-phenyl)-4-(1-isopropyl-7-ethoxy-indol-4-yl)-5-mercapto-[1,2,4]triazole,
3-(2,4-dihydroxy-5-ethyl-phenyl)-4-(1,2-dimethyl-indol-5-yl)-5-mercapto-[1,2,4]triazole,
3-(2,4-dihydroxy-5-ethyl-phenyl)-4-(N-methyl-indol-5-yl)-5-mercapto-[1,2,4]triazole,
3-(2,4-dihydroxy-5-isopropyl-phenyl)-4-(1,3-dimethyl-indol-5-yl)-5-mercapto-[1,2,4]triazole,
3-(2,4-dihydroxy-5-cyclopropyl-phenyl)-4-(1,3-dimethyl-indol-5-yl)-5-mercapto-[1,2,4]triazole,
3-(2,4-dihydroxy-5-cyclopropyl-phenyl)-4-(1-methyl-indol-5-yl)-5-mercapto-[1,2,4]triazole,
3-(2,4-dihydroxy-5-isopropyl-phenyl)-4-(1H-indol-5-yl)-5-mercapto-[1,2,4]triazole,
3-(2,4-dihydroxy-5-ethyl-phenyl)-4-(1,2-dimethyl-indol-5-yl)-5-mercapto-[1,2,4]triazole,
3-(2,4-dihydroxy-5-isopropyl-phenyl)-4-(1-ethyl-indol-5-yl)-5-mercapto-[1,2,4]triazole,
3-(2,4-dihydroxy-5-isopropyl-phenyl)-4-(1-propyl-indol-5-yl)-5-mercapto-[1,2,4]triazole,
3-(2,4-dihydroxy-5-ethyl-phenyl)-4-(1,3-dimethyl-indol-5-yl)-5-hydroxy-[1,2,4]triazole,
3-(2,4-dihydroxy-5-isopropyl-phenyl)-4-(1,3-dimethyl-indol-5-yl)-5-hydroxy-[1,2,4]triazole,
3-(2,4-dihydroxy-5-isopropyl-phenyl)-4-(1-methyl-indol-5-yl)-5-hydroxy-[1,2,4]triazole, and
3-(2,4-dihydroxy-5-isopropyl-phenyl)-4-(1-isopropyl-indol-4-yl)-5-hydroxy-[1,2,4]triazole, or a tautomer or pharmaceutically acceptable salt thereof.

7. The method of claim 6, wherein said compound is selected from the group consisting of:
3-(2,4-dihydroxy-5-ethyl-phenyl)-4-(1,3-dimethyl-indol-5-yl)-5-hydroxy-[1,2,4]triazole,
3-(2,4-dihydroxy-5-isopropyl-phenyl)-4-(1,3-dimethyl-indol-5-yl)-5-hydroxy-[1,2,4]triazole,
3-(2,4-dihydroxy-5-isopropyl-phenyl)-4-(1-methyl-indol-5-yl)-5-hydroxy-[1,2,4]triazole, and
3-(2,4-dihydroxy-5-isopropyl-phenyl)-4-(1-isopropyl-indol-4-yl)-5-hydroxy-[1,2,4]triazole, or a tautomer or a pharmaceutically acceptable salt thereof.

8. The method of claim 6, wherein said compound is 3-(2,4-dihydroxy-5-ethyl-phenyl)-4-(1,3-dimethyl-indol-5-yl)-5-hydroxy-[1,2,4]triazole or a tautomer or a pharmaceutically acceptable salt thereof.

9. The method of claim 6, wherein said compound is 3-(2,4-dihydroxy-5-isopropyl-phenyl)-4-(1,3-dimethyl-indol-5-yl)-5-hydroxy-[1,2,4]triazole or a tautomer or a pharmaceutically acceptable salt thereof.

10. The method of claim 6, wherein said compound is 3-(2,4-dihydroxy-5-isopropyl-phenyl)-4-(1-methyl-indol-5-yl)-5-hydroxy-[1,2,4]triazole or a tautomer or a pharmaceutically acceptable salt thereof.

11. The method of claim 6, wherein said compound is 3-(2,4-dihydroxy-5-isopropyl-phenyl)-4-(1-isopropyl-indol-4-yl)-5-hydroxy-[1,2,4]triazole or a tautomer or a pharmaceutically acceptable salt thereof.

* * * * *